US007630838B2

(12) United States Patent
Chopra et al.

(10) Patent No.: US 7,630,838 B2
(45) Date of Patent: Dec. 8, 2009

(54) METHOD FOR IDENTIFYING AGENTS THAT INTERACT WITH BETA-SITE APP CLEAVING ENZYME (BACE)

(75) Inventors: Rajiv Chopra, Belmont, MA (US); Kristine Svenson, Andover, MA (US); Bethany Annis Freeman, Belmont, MA (US); Tatos N. Akopian, West Roxbury, MA (US); Jonathan Bard, Doylestown, PA (US); Mark Lloyd Stahl, Lexington, MA (US); William S. Somers, Cambridge, MA (US)

(73) Assignee: American Home Products Corporation, Madison, NJ (US)

( * ) Notice: Subject to any disclaimer, the term of this patent is extended or adjusted under 35 U.S.C. 154(b) by 774 days.

(21) Appl. No.: 09/955,737

(22) Filed: Sep. 19, 2001

(65) Prior Publication Data

US 2002/0055459 A1 May 9, 2002

Related U.S. Application Data

(60) Provisional application No. 60/234,576, filed on Sep. 22, 2000.

(51) Int. Cl.
*G01N 31/00* (2006.01)
*C12Q 1/37* (2006.01)
*C30B 29/58* (2006.01)

(52) U.S. Cl. .............................. 702/27; 435/23; 117/70

(58) Field of Classification Search .................. 435/7.1, 435/23, 24, 212, 219, 226; 436/4; 702/27
See application file for complete search history.

(56) References Cited

U.S. PATENT DOCUMENTS

| 5,579,250 | A | * | 11/1996 | Balaji et al. .................... 702/19 |
| 5,942,400 | A | * | 8/1999 | Anderson et al. ............ 435/7.1 |
| 6,025,180 | A | | 2/2000 | Powell et al. |
| 6,162,630 | A | | 12/2000 | Powell et al. |
| 6,313,268 | B1 | | 11/2001 | Hook |
| 6,319,689 | B1 | | 11/2001 | Powell et al. |
| 6,545,127 | B1 | | 4/2003 | Tang et al. |
| 2004/0137518 | A1 | * | 7/2004 | Lambert et al. .............. 435/7.1 |

OTHER PUBLICATIONS

Hegyi et al. (1999) J Mol Biol 288:147-164.*
"Drug Design, Cutting Edge Approaches," Flower, Royal Society of Chemistry, Cambridge, UK, 2002.*
Witkowski et al. Biochemistry 38:11643-11650, 1999.*
"Introduction to Protein Structure Second Edition," Branden and Tooze, Garland Publishing Inc., New York, 1999, pp. 374-375.*
"Principles of X-ray Crystallography," Drenth, Springer, New York, 1995, p. 1.*
Kierzek et al. Biophys Chem 91:1-20, 2001.*
Bridges et al., "A novel approach to identifying beta-secretase inhibitors: Bis-statine peptide mimetics discovered using structure and spot synthesis", Peptides 27:1877-1885, 2006.*
Lemaire, "A4 amyloid Protein Precursor (*Homo sapiens*)," Swiss Prot Accession No. CAA31830, Jun. 20, 1995.
Vassar et al., "Beta-secretase cleavage of Alzheimer's amyloid precursor protein by the transmembrane aspartic protease BACE," Science 286:735-741, 1999.
Vassar et al., "Aspartic proteinase (EC 3.4.23.-) BACE precursor —human," GenBank Accession No. A59090, May 11, 2000.
Vassar et al., "Beta-Secretase Precursor (Beta-Site APP Cleaving Enzyme) (Beta-Site Amyloid . . . Precursor Protein Cleaving Enzyme) (Aspartyl Protease 2) (Asp2)," Swiss Prot Accession No. P56817, May 30, 2000.
Hong, et al., Structure of the Protease Domain of Memapsin 2 (Beta-Secretase) Complexed with Inhibitor, Science 290 (5489):150., 2000.
Sauder, et at, Modeling of Substrate Specificity of the Alzheimer's Disease Amyloid Precursor Protein Beta-Secretase, J. Mol.-Bio. (2000) 300(2):241-248.
Vassar, et al., Beta-Secretase Cleavage of Alzheimer's Amyloid Precursor Protein by the Transmembrance Aspartic Protease BACE, Science, 286:735-741, Oct. 22, 1999.
Scheidig, et al., Crystal Structures of Bovine Chymotrypsin and Trypsin Complexed to the Inhibitor Domain of Alzheimer's Amyloid Beta-Protein Precursor (APPI) and Basic Pancreatic Trypsin Inhibitor (BPTI): Engineering of Inhibitors with Altered Specificities, Protein Science Sep. 1997, 6:1806-1824.
Kohno, et al., Three-Dimensional Structures of the Amyloid Beta Peptide (25-35) in Membrane-Mimicking Environment, Biochemistry 1996, 35:16094-16104.
Bailey, et al, X-ray-crystallographic Studies of Complexes of Pepstatin A and a Statine-Containing Human Renin Inhibitor with Endothiapepsin, Biochem.J. (1993) 289:363-371.
Hynes, et al., X-ray Crystal Structure of the Protease Inhibitor Domain of Alzheimer's Amyloid Beta-Protein Precursor, Biochemistry 1990, 29:10018-10023.
Zhang, et al., Sequence-specific Recognition of the Internalization Motif of the Alzheimer's Amyloid Precursor Protein by the X11 PTB Domain, The EMBO Journal, vol. 61, No. 20:6141-6150, 1997.
Marchinkeviciene, et al., Mechanism of Inhibition of Beta-Site Amyloid Precursor Protein-cleaving Enzyme (BASE) by a Satine-based Peptide, The Journal of Biological Chemistry, vol. 276, No. 26, Issue of Jun. 29, 2001, 23790-23794.
Rossjohn, et al., Crystal Structure of the N-terminal, Growth Factor-like Domain of Alzheimer Amyloid Precursor Protein, Nature Structural Biology, vol. 6, No. 4, Apr. 1999.

* cited by examiner

*Primary Examiner*—David J Steadman
(74) *Attorney, Agent, or Firm*—Lando & Anastasi, LLP

(57) ABSTRACT

This invention is directed to the three dimensional crystal structure of Beta-site APP Cleaving Enzyme (BACE), and to the use of this structure in rational drug design methods to identify agents that may interact with active sites of BACE. Such agents may represent new therapeutics in the treatment and/or prevention of Alzheimer's Disease.

16 Claims, 57 Drawing Sheets

|      |   | Atom Type | Res. |   | X | Y | Z | | |
|------|---|------|-----|----|--------|--------|--------|------|-------|
| ATOM | 1 | N    | GLY | A 58 | 31.563 | 49.775 | 16.324 | 1.00 | 59.33 |
| ATOM | 2 | CA   | GLY | A 58 | 32.861 | 50.358 | 16.764 | 1.00 | 58.44 |
| ATOM | 3 | C    | GLY | A 58 | 33.594 | 49.446 | 17.727 | 1.00 | 57.81 |
| ATOM | 4 | O    | GLY | A 58 | 34.067 | 48.331 | 17.333 | 1.00 | 56.66 |
| ATOM | 5 | N    | SER | A 59 | 33.712 | 49.888 | 18.975 | 1.00 | 56.66 |
| ATOM | 6 | CA   | SER | A 59 | 34.391 | 49.094 | 20.015 | 1.00 | 55.45 |
| ATOM | 7 | C    | SER | A 59 | 33.560 | 49.088 | 21.293 | 1.00 | 53.77 |
| ATOM | 8 | O    | SER | A 59 | 32.978 | 50.147 | 21.704 | 1.00 | 54.40 |
| ATOM | 9 | CB   | SER | A 59 | 35.781 | 49.668 | 20.309 | 1.00 | 55.79 |
| ATOM | 10 | OG  | SER | A 59 | 35.690 | 50.952 | 20.899 | 1.00 | 57.07 |
| ATOM | 11 | N   | PHE | A 60 | 33.480 | 47.924 | 21.927 | 1.00 | 49.96 |
| ATOM | 12 | CA  | PHE | A 60 | 32.719 | 47.772 | 23.181 | 1.00 | 45.72 |
| ATOM | 13 | C   | PHE | A 60 | 33.681 | 47.269 | 24.247 | 1.00 | 44.79 |
| ATOM | 14 | O   | PHE | A 60 | 33.495 | 46.160 | 24.831 | 1.00 | 45.45 |
| ATOM | 15 | CB  | PHE | A 60 | 31.564 | 46.790 | 22.976 | 1.00 | 43.28 |
| ATOM | 16 | CG  | PHE | A 60 | 30.557 | 47.249 | 21.957 | 1.00 | 41.00 |
| ATOM | 17 | CD1 | PHE | A 60 | 30.875 | 47.267 | 20.602 | 1.00 | 40.54 |
| ATOM | 18 | CD2 | PHE | A 60 | 29.301 | 47.701 | 22.355 | 1.00 | 40.58 |
| ATOM | 19 | CE1 | PHE | A 60 | 29.954 | 47.731 | 19.658 | 1.00 | 39.88 |
| ATOM | 20 | CE2 | PHE | A 60 | 28.375 | 48.166 | 21.419 | 1.00 | 39.50 |
| ATOM | 21 | CZ  | PHE | A 60 | 28.704 | 48.182 | 20.070 | 1.00 | 39.23 |
| ATOM | 22 | N   | VAL | A 61 | 34.709 | 48.073 | 24.500 | 1.00 | 43.29 |
| ATOM | 23 | CA  | VAL | A 61 | 35.763 | 47.756 | 25.483 | 1.00 | 43.19 |
| ATOM | 24 | C   | VAL | A 61 | 35.243 | 47.069 | 26.738 | 1.00 | 41.81 |
| ATOM | 25 | O   | VAL | A 61 | 35.876 | 46.099 | 27.247 | 1.00 | 42.54 |
| ATOM | 26 | CB  | VAL | A 61 | 36.532 | 49.035 | 25.895 | 1.00 | 43.62 |
| ATOM | 27 | CG1 | VAL | A 61 | 37.069 | 49.730 | 24.655 | 1.00 | 44.38 |
| ATOM | 28 | CG2 | VAL | A 61 | 35.621 | 49.975 | 26.676 | 1.00 | 44.28 |
| ATOM | 29 | N   | GLU | A 62 | 34.114 | 47.542 | 27.252 | 1.00 | 40.86 |
| ATOM | 30 | CA  | GLU | A 62 | 33.517 | 46.959 | 28.470 | 1.00 | 40.02 |
| ATOM | 31 | C   | GLU | A 62 | 33.208 | 45.473 | 28.320 | 1.00 | 36.45 |
| ATOM | 32 | O   | GLU | A 62 | 33.366 | 44.685 | 29.301 | 1.00 | 36.49 |
| ATOM | 33 | CB  | GLU | A 62 | 32.226 | 47.700 | 28.832 | 1.00 | 43.76 |
| ATOM | 34 | CG  | GLU | A 62 | 32.399 | 48.895 | 29.764 | 1.00 | 48.74 |
| ATOM | 35 | CD  | GLU | A 62 | 32.743 | 48.486 | 31.188 | 1.00 | 51.91 |
| ATOM | 36 | OE1 | GLU | A 62 | 32.317 | 47.387 | 31.612 | 1.00 | 53.41 |
| ATOM | 37 | OE2 | GLU | A 62 | 33.423 | 49.271 | 31.890 | 1.00 | 53.64 |
| ATOM | 38 | N   | MET | A 63 | 32.780 | 45.062 | 27.129 | 1.00 | 30.86 |
| ATOM | 39 | CA  | MET | A 63 | 32.421 | 43.643 | 26.896 | 1.00 | 27.79 |
| ATOM | 40 | C   | MET | A 63 | 33.491 | 42.741 | 26.279 | 1.00 | 26.02 |
| ATOM | 41 | O   | MET | A 63 | 33.354 | 41.476 | 26.310 | 1.00 | 25.25 |
| ATOM | 42 | CB  | MET | A 63 | 31.130 | 43.578 | 26.078 | 1.00 | 25.63 |
| ATOM | 43 | CG  | MET | A 63 | 29.942 | 44.133 | 26.858 | 1.00 | 24.89 |
| ATOM | 44 | SD  | MET | A 63 | 28.392 | 44.180 | 25.960 | 1.00 | 23.85 |
| ATOM | 45 | CE  | MET | A 63 | 28.431 | 45.848 | 25.316 | 1.00 | 24.18 |
| ATOM | 46 | N   | VAL | A 64 | 34.551 | 43.330 | 25.736 | 1.00 | 23.39 |
| ATOM | 47 | CA  | VAL | A 64 | 35.639 | 42.516 | 25.143 | 1.00 | 20.76 |
| ATOM | 48 | C   | VAL | A 64 | 36.263 | 41.634 | 26.216 | 1.00 | 20.06 |
| ATOM | 49 | O   | VAL | A 64 | 36.531 | 42.095 | 27.370 | 1.00 | 18.87 |
| ATOM | 50 | CB  | VAL | A 64 | 36.740 | 43.407 | 24.517 | 1.00 | 21.16 |
| ATOM | 51 | CG1 | VAL | A 64 | 37.958 | 42.567 | 24.151 | 1.00 | 18.99 |
| ATOM | 52 | CG2 | VAL | A 64 | 36.193 | 44.092 | 23.266 | 1.00 | 21.01 |
| ATOM | 53 | N   | ASP | A 65 | 36.487 | 40.373 | 25.869 | 1.00 | 18.21 |
| ATOM | 54 | CA  | ASP | A 65 | 37.091 | 39.397 | 26.800 | 1.00 | 18.56 |
| ATOM | 55 | C   | ASP | A 65 | 36.280 | 39.174 | 28.071 | 1.00 | 17.80 |
| ATOM | 56 | O   | ASP | A 65 | 36.869 | 38.964 | 29.165 | 1.00 | 16.29 |
| ATOM | 57 | CB  | ASP | A 65 | 38.508 | 39.829 | 27.194 | 1.00 | 21.53 |
| ATOM | 58 | CG  | ASP | A 65 | 39.409 | 40.055 | 25.993 | 1.00 | 22.65 |

FIG. 1A

```
ATOM    59  OD1 ASP A  65      39.162  39.451  24.930  1.00 23.75
ATOM    60  OD2 ASP A  65      40.375  40.831  26.117  1.00 24.72
ATOM    61  N   ASN A  66      34.955  39.209  27.969  1.00 16.59
ATOM    62  CA  ASN A  66      34.090  38.987  29.156  1.00 16.58
ATOM    63  C   ASN A  66      33.719  37.508  29.274  1.00 17.20
ATOM    64  O   ASN A  66      32.815  37.125  30.070  1.00 19.23
ATOM    65  CB  ASN A  66      32.817  39.845  29.059  1.00 14.62
ATOM    66  CG  ASN A  66      31.967  39.516  27.835  1.00 15.57
ATOM    67  OD1 ASN A  66      32.381  38.714  26.937  1.00 16.31
ATOM    68  ND2 ASN A  66      30.788  40.120  27.760  1.00 14.85
ATOM    69  N   LEU A  67      34.409  36.664  28.515  1.00 17.73
ATOM    70  CA  LEU A  67      34.134  35.206  28.529  1.00 17.36
ATOM    71  C   LEU A  67      35.295  34.328  28.985  1.00 16.04
ATOM    72  O   LEU A  67      36.499  34.701  28.842  1.00 16.38
ATOM    73  CB  LEU A  67      33.707  34.757  27.128  1.00 17.19
ATOM    74  CG  LEU A  67      32.226  34.504  26.839  1.00 18.63
ATOM    75  CD1 LEU A  67      31.349  35.604  27.407  1.00 16.94
ATOM    76  CD2 LEU A  67      32.049  34.375  25.330  1.00 18.67
ATOM    77  N   ARG A  68      34.956  33.166  29.531  1.00 14.58
ATOM    78  CA  ARG A  68      35.961  32.173  29.973  1.00 16.73
ATOM    79  C   ARG A  68      35.394  30.775  29.717  1.00 15.78
ATOM    80  O   ARG A  68      34.154  30.610  29.500  1.00 13.85
ATOM    81  CB  ARG A  68      36.299  32.349  31.459  1.00 18.19
ATOM    82  CG  ARG A  68      37.086  33.623  31.766  1.00 21.67
ATOM    83  CD  ARG A  68      37.571  33.646  33.213  1.00 23.25
ATOM    84  NE  ARG A  68      36.462  33.653  34.165  1.00 26.34
ATOM    85  CZ  ARG A  68      36.598  33.500  35.482  1.00 27.29
ATOM    86  NH1 ARG A  68      37.802  33.324  36.015  1.00 25.91
ATOM    87  NH2 ARG A  68      35.530  33.527  36.271  1.00 26.77
ATOM    88  N   GLY A  69      36.262  29.769  29.726  1.00 14.89
ATOM    89  CA  GLY A  69      35.816  28.409  29.486  1.00 15.62
ATOM    90  C   GLY A  69      36.505  27.806  28.277  1.00 16.66
ATOM    91  O   GLY A  69      37.526  28.367  27.771  1.00 15.60
ATOM    92  N   LYS A  70      35.989  26.676  27.804  1.00 17.25
ATOM    93  CA  LYS A  70      36.556  25.973  26.629  1.00 16.95
ATOM    94  C   LYS A  70      35.472  25.138  25.949  1.00 16.87
ATOM    95  O   LYS A  70      34.394  24.864  26.562  1.00 17.19
ATOM    96  CB  LYS A  70      37.737  25.092  27.058  1.00 18.62
ATOM    97  CG  LYS A  70      37.518  24.303  28.348  1.00 19.97
ATOM    98  CD  LYS A  70      38.737  23.446  28.667  1.00 22.43
ATOM    99  CE  LYS A  70      38.538  22.611  29.926  1.00 23.77
ATOM   100  NZ  LYS A  70      39.660  21.638  30.129  1.00 22.43
ATOM   101  N   SER A  71      35.714  24.729  24.706  1.00 15.11
ATOM   102  CA  SER A  71      34.706  23.950  23.940  1.00 14.34
ATOM   103  C   SER A  71      34.155  22.730  24.667  1.00 14.36
ATOM   104  O   SER A  71      32.918  22.446  24.600  1.00 13.81
ATOM   105  CB  SER A  71      35.281  23.523  22.581  1.00 14.97
ATOM   106  OG  SER A  71      36.456  22.743  22.732  1.00 15.41
ATOM   107  N   GLY A  72      35.024  22.005  25.362  1.00 14.38
ATOM   108  CA  GLY A  72      34.588  20.815  26.072  1.00 14.63
ATOM   109  C   GLY A  72      33.661  21.022  27.262  1.00 16.49
ATOM   110  O   GLY A  72      32.772  20.159  27.537  1.00 16.20
ATOM   111  N   GLN A  73      33.814  22.129  27.979  1.00 16.78
ATOM   112  CA  GLN A  73      32.965  22.369  29.167  1.00 18.67
ATOM   113  C   GLN A  73      32.040  23.570  29.038  1.00 18.70
ATOM   114  O   GLN A  73      31.223  23.858  29.967  1.00 19.81
ATOM   115  CB  GLN A  73      33.852  22.522  30.401  1.00 20.09
ATOM   116  CG  GLN A  73      34.924  21.433  30.493  1.00 24.21
ATOM   117  CD  GLN A  73      35.624  21.400  31.837  1.00 24.83
ATOM   118  OE1 GLN A  73      36.048  22.467  32.380  1.00 26.53
ATOM   119  NE2 GLN A  73      35.769  20.206  32.395  1.00 25.73
ATOM   120  N   GLY A  74      32.138  24.274  27.914  1.00 17.65
```

FIG. 1B

| ATOM | 121 | CA  | GLY A | 74 | 31.292 | 25.429 | 27.688 | 1.00 | 15.83 |
| ATOM | 122 | C   | GLY A | 74 | 31.939 | 26.746 | 28.068 | 1.00 | 15.56 |
| ATOM | 123 | O   | GLY A | 74 | 32.837 | 26.799 | 28.962 | 1.00 | 17.53 |
| ATOM | 124 | N   | TYR A | 75 | 31.517 | 27.814 | 27.403 | 1.00 | 13.96 |
| ATOM | 125 | CA  | TYR A | 75 | 32.041 | 29.164 | 27.686 | 1.00 | 16.12 |
| ATOM | 126 | C   | TYR A | 75 | 30.991 | 29.903 | 28.502 | 1.00 | 14.92 |
| ATOM | 127 | O   | TYR A | 75 | 29.758 | 29.793 | 28.217 | 1.00 | 14.71 |
| ATOM | 128 | CB  | TYR A | 75 | 32.324 | 29.918 | 26.385 | 1.00 | 17.79 |
| ATOM | 129 | CG  | TYR A | 75 | 33.490 | 29.354 | 25.605 | 1.00 | 18.92 |
| ATOM | 130 | CD1 | TYR A | 75 | 33.326 | 28.271 | 24.742 | 1.00 | 19.83 |
| ATOM | 131 | CD2 | TYR A | 75 | 34.763 | 29.909 | 25.735 | 1.00 | 20.43 |
| ATOM | 132 | CE1 | TYR A | 75 | 34.409 | 27.757 | 24.020 | 1.00 | 21.98 |
| ATOM | 133 | CE2 | TYR A | 75 | 35.847 | 29.407 | 25.025 | 1.00 | 21.04 |
| ATOM | 134 | CZ  | TYR A | 75 | 35.666 | 28.339 | 24.170 | 1.00 | 22.04 |
| ATOM | 135 | OH  | TYR A | 75 | 36.746 | 27.882 | 23.456 | 1.00 | 22.86 |
| ATOM | 136 | N   | TYR A | 76 | 31.432 | 30.653 | 29.507 | 1.00 | 13.66 |
| ATOM | 137 | CA  | TYR A | 76 | 30.478 | 31.360 | 30.368 | 1.00 | 12.95 |
| ATOM | 138 | C   | TYR A | 76 | 30.753 | 32.837 | 30.593 | 1.00 | 13.47 |
| ATOM | 139 | O   | TYR A | 76 | 31.901 | 33.345 | 30.391 | 1.00 | 13.77 |
| ATOM | 140 | CB  | TYR A | 76 | 30.395 | 30.662 | 31.725 | 1.00 | 13.31 |
| ATOM | 141 | CG  | TYR A | 76 | 31.723 | 30.548 | 32.446 | 1.00 | 14.55 |
| ATOM | 142 | CD1 | TYR A | 76 | 32.601 | 29.497 | 32.174 | 1.00 | 16.16 |
| ATOM | 143 | CD2 | TYR A | 76 | 32.105 | 31.495 | 33.392 | 1.00 | 15.68 |
| ATOM | 144 | CE1 | TYR A | 76 | 33.829 | 29.392 | 32.832 | 1.00 | 17.64 |
| ATOM | 145 | CE2 | TYR A | 76 | 33.329 | 31.402 | 34.055 | 1.00 | 18.14 |
| ATOM | 146 | CZ  | TYR A | 76 | 34.183 | 30.348 | 33.770 | 1.00 | 18.24 |
| ATOM | 147 | OH  | TYR A | 76 | 35.390 | 30.252 | 34.428 | 1.00 | 21.79 |
| ATOM | 148 | N   | VAL A | 77 | 29.716 | 33.546 | 31.017 | 1.00 | 12.55 |
| ATOM | 149 | CA  | VAL A | 77 | 29.844 | 34.980 | 31.298 | 1.00 | 14.17 |
| ATOM | 150 | C   | VAL A | 77 | 29.390 | 35.225 | 32.727 | 1.00 | 15.16 |
| ATOM | 151 | O   | VAL A | 77 | 28.564 | 34.439 | 33.283 | 1.00 | 16.09 |
| ATOM | 152 | CB  | VAL A | 77 | 28.975 | 35.821 | 30.336 | 1.00 | 13.43 |
| ATOM | 153 | CG1 | VAL A | 77 | 27.495 | 35.528 | 30.567 | 1.00 | 11.59 |
| ATOM | 154 | CG2 | VAL A | 77 | 29.281 | 37.305 | 30.524 | 1.00 | 10.74 |
| ATOM | 155 | N   | GLU A | 78 | 29.905 | 36.276 | 33.352 | 1.00 | 16.88 |
| ATOM | 156 | CA  | GLU A | 78 | 29.486 | 36.571 | 34.731 | 1.00 | 17.45 |
| ATOM | 157 | C   | GLU A | 78 | 28.178 | 37.345 | 34.706 | 1.00 | 16.89 |
| ATOM | 158 | O   | GLU A | 78 | 27.961 | 38.239 | 33.826 | 1.00 | 14.65 |
| ATOM | 159 | CB  | GLU A | 78 | 30.538 | 37.392 | 35.479 | 1.00 | 19.11 |
| ATOM | 160 | CG  | GLU A | 78 | 30.222 | 37.503 | 36.974 | 1.00 | 24.70 |
| ATOM | 161 | CD  | GLU A | 78 | 31.225 | 38.342 | 37.757 | 1.00 | 26.24 |
| ATOM | 162 | OE1 | GLU A | 78 | 31.162 | 39.584 | 37.679 | 1.00 | 27.53 |
| ATOM | 163 | OE2 | GLU A | 78 | 32.076 | 37.755 | 38.452 | 1.00 | 29.49 |
| ATOM | 164 | N   | MET A | 79 | 27.296 | 37.012 | 35.641 | 1.00 | 16.65 |
| ATOM | 165 | CA  | MET A | 79 | 25.992 | 37.684 | 35.761 | 1.00 | 17.22 |
| ATOM | 166 | C   | MET A | 79 | 25.610 | 37.768 | 37.232 | 1.00 | 17.77 |
| ATOM | 167 | O   | MET A | 79 | 26.208 | 37.066 | 38.100 | 1.00 | 18.29 |
| ATOM | 168 | CB  | MET A | 79 | 24.908 | 36.899 | 35.007 | 1.00 | 16.88 |
| ATOM | 169 | CG  | MET A | 79 | 25.070 | 36.874 | 33.492 | 1.00 | 16.65 |
| ATOM | 170 | SD  | MET A | 79 | 23.798 | 35.865 | 32.673 | 1.00 | 17.43 |
| ATOM | 171 | CE  | MET A | 79 | 22.442 | 37.003 | 32.577 | 1.00 | 15.55 |
| ATOM | 172 | N   | THR A | 80 | 24.637 | 38.617 | 37.539 | 1.00 | 17.73 |
| ATOM | 173 | CA  | THR A | 80 | 24.146 | 38.741 | 38.917 | 1.00 | 17.50 |
| ATOM | 174 | C   | THR A | 80 | 22.632 | 38.630 | 38.853 | 1.00 | 17.85 |
| ATOM | 175 | O   | THR A | 80 | 21.995 | 39.075 | 37.851 | 1.00 | 17.14 |
| ATOM | 176 | CB  | THR A | 80 | 24.524 | 40.100 | 39.550 | 1.00 | 18.12 |
| ATOM | 177 | OG1 | THR A | 80 | 23.851 | 41.158 | 38.857 | 1.00 | 18.55 |
| ATOM | 178 | CG2 | THR A | 80 | 26.031 | 40.328 | 39.474 | 1.00 | 16.48 |
| ATOM | 179 | N   | VAL A | 81 | 22.042 | 38.020 | 39.874 | 1.00 | 18.24 |
| ATOM | 180 | CA  | VAL A | 81 | 20.573 | 37.882 | 39.959 | 1.00 | 20.23 |
| ATOM | 181 | C   | VAL A | 81 | 20.145 | 38.274 | 41.375 | 1.00 | 21.18 |
| ATOM | 182 | O   | VAL A | 81 | 20.929 | 38.093 | 42.362 | 1.00 | 20.31 |

FIG. 1C

| | | | | | | | | | |
|---|---|---|---|---|---|---|---|---|---|
| ATOM | 183 | CB | VAL | A | 81 | 20.105 | 36.429 | 39.700 | 1.00 20.43 |
| ATOM | 184 | CG1 | VAL | A | 81 | 20.566 | 35.959 | 38.334 | 1.00 21.49 |
| ATOM | 185 | CG2 | VAL | A | 81 | 20.639 | 35.518 | 40.777 | 1.00 21.78 |
| ATOM | 186 | N | GLY | A | 82 | 18.938 | 38.817 | 41.497 | 1.00 21.84 |
| ATOM | 187 | CA | GLY | A | 82 | 18.421 | 39.200 | 42.799 | 1.00 21.10 |
| ATOM | 188 | C | GLY | A | 82 | 18.973 | 40.475 | 43.404 | 1.00 21.47 |
| ATOM | 189 | O | GLY | A | 82 | 19.864 | 41.159 | 42.814 | 1.00 21.97 |
| ATOM | 190 | N | SER | A | 83 | 18.454 | 40.808 | 44.581 | 1.00 22.27 |
| ATOM | 191 | CA | SER | A | 83 | 18.869 | 42.012 | 45.335 | 1.00 22.02 |
| ATOM | 192 | C | SER | A | 83 | 18.996 | 41.607 | 46.795 | 1.00 20.16 |
| ATOM | 193 | O | SER | A | 83 | 18.002 | 41.120 | 47.410 | 1.00 20.07 |
| ATOM | 194 | CB | SER | A | 83 | 17.804 | 43.104 | 45.213 | 1.00 21.98 |
| ATOM | 195 | OG | SER | A | 83 | 17.356 | 43.229 | 43.874 | 1.00 23.70 |
| ATOM | 196 | N | PRO | A | 84 | 20.198 | 41.734 | 47.380 | 1.00 21.14 |
| ATOM | 197 | CA | PRO | A | 84 | 21.454 | 42.221 | 46.785 | 1.00 20.45 |
| ATOM | 198 | C | PRO | A | 84 | 21.911 | 41.288 | 45.656 | 1.00 20.37 |
| ATOM | 199 | O | PRO | A | 84 | 21.508 | 40.086 | 45.606 | 1.00 18.46 |
| ATOM | 200 | CB | PRO | A | 84 | 22.434 | 42.193 | 47.962 | 1.00 19.74 |
| ATOM | 201 | CG | PRO | A | 84 | 21.548 | 42.320 | 49.166 | 1.00 20.71 |
| ATOM | 202 | CD | PRO | A | 84 | 20.377 | 41.447 | 48.815 | 1.00 19.44 |
| ATOM | 203 | N | PRO | A | 85 | 22.754 | 41.790 | 44.741 | 1.00 20.53 |
| ATOM | 204 | CA | PRO | A | 85 | 23.258 | 40.997 | 43.616 | 1.00 20.58 |
| ATOM | 205 | C | PRO | A | 85 | 23.949 | 39.706 | 44.046 | 1.00 20.81 |
| ATOM | 206 | O | PRO | A | 85 | 24.854 | 39.720 | 44.936 | 1.00 21.15 |
| ATOM | 207 | CB | PRO | A | 85 | 24.240 | 41.947 | 42.932 | 1.00 20.87 |
| ATOM | 208 | CG | PRO | A | 85 | 23.732 | 43.294 | 43.282 | 1.00 22.23 |
| ATOM | 209 | CD | PRO | A | 85 | 23.340 | 43.141 | 44.724 | 1.00 21.41 |
| ATOM | 210 | N | GLN | A | 86 | 23.541 | 38.590 | 43.453 | 1.00 20.05 |
| ATOM | 211 | CA | GLN | A | 86 | 24.174 | 37.289 | 43.752 | 1.00 19.63 |
| ATOM | 212 | C | GLN | A | 86 | 24.904 | 36.923 | 42.472 | 1.00 20.50 |
| ATOM | 213 | O | GLN | A | 86 | 24.263 | 36.622 | 41.412 | 1.00 19.85 |
| ATOM | 214 | CB | GLN | A | 86 | 23.127 | 36.227 | 44.097 | 1.00 19.82 |
| ATOM | 215 | CG | GLN | A | 86 | 22.283 | 36.586 | 45.314 | 1.00 18.97 |
| ATOM | 216 | CD | GLN | A | 86 | 21.292 | 35.506 | 45.693 | 1.00 19.84 |
| ATOM | 217 | OE1 | GLN | A | 86 | 20.226 | 35.801 | 46.316 | 1.00 21.21 |
| ATOM | 218 | NE2 | GLN | A | 86 | 21.603 | 34.259 | 45.354 | 1.00 17.54 |
| ATOM | 219 | N | THR | A | 87 | 26.229 | 36.969 | 42.527 | 1.00 19.61 |
| ATOM | 220 | CA | THR | A | 87 | 27.057 | 36.669 | 41.346 | 1.00 19.61 |
| ATOM | 221 | C | THR | A | 87 | 27.088 | 35.188 | 40.994 | 1.00 18.63 |
| ATOM | 222 | O | THR | A | 87 | 27.220 | 34.302 | 41.892 | 1.00 18.56 |
| ATOM | 223 | CB | THR | A | 87 | 28.501 | 37.164 | 41.549 | 1.00 19.88 |
| ATOM | 224 | OG1 | THR | A | 87 | 28.486 | 38.558 | 41.887 | 1.00 20.57 |
| ATOM | 225 | CG2 | THR | A | 87 | 29.304 | 36.977 | 40.278 | 1.00 18.65 |
| ATOM | 226 | N | LEU | A | 88 | 26.972 | 34.907 | 39.701 | 1.00 18.38 |
| ATOM | 227 | CA | LEU | A | 88 | 26.991 | 33.522 | 39.193 | 1.00 18.18 |
| ATOM | 228 | C | LEU | A | 88 | 27.572 | 33.496 | 37.781 | 1.00 18.11 |
| ATOM | 229 | O | LEU | A | 88 | 27.353 | 34.457 | 36.974 | 1.00 18.86 |
| ATOM | 230 | CB | LEU | A | 88 | 25.568 | 32.952 | 39.159 | 1.00 16.21 |
| ATOM | 231 | CG | LEU | A | 88 | 24.825 | 32.828 | 40.495 | 1.00 18.20 |
| ATOM | 232 | CD1 | LEU | A | 88 | 23.366 | 32.474 | 40.226 | 1.00 18.10 |
| ATOM | 233 | CD2 | LEU | A | 88 | 25.484 | 31.766 | 41.379 | 1.00 16.56 |
| ATOM | 234 | N | ASN | A | 89 | 28.317 | 32.443 | 37.459 | 1.00 15.84 |
| ATOM | 235 | CA | ASN | A | 89 | 28.876 | 32.312 | 36.101 | 1.00 16.22 |
| ATOM | 236 | C | ASN | A | 89 | 27.841 | 31.544 | 35.300 | 1.00 16.03 |
| ATOM | 237 | O | ASN | A | 89 | 27.363 | 30.450 | 35.735 | 1.00 15.05 |
| ATOM | 238 | CB | ASN | A | 89 | 30.208 | 31.565 | 36.114 | 1.00 15.71 |
| ATOM | 239 | CG | ASN | A | 89 | 31.324 | 32.396 | 36.700 | 1.00 16.10 |
| ATOM | 240 | OD1 | ASN | A | 89 | 31.390 | 33.650 | 36.477 | 1.00 15.48 |
| ATOM | 241 | ND2 | ASN | A | 89 | 32.217 | 31.750 | 37.439 | 1.00 14.07 |
| ATOM | 242 | N | ILE | A | 90 | 27.485 | 32.091 | 34.145 | 1.00 15.55 |
| ATOM | 243 | CA | ILE | A | 90 | 26.445 | 31.494 | 33.292 | 1.00 14.59 |
| ATOM | 244 | C | ILE | A | 90 | 26.960 | 31.052 | 31.930 | 1.00 15.07 |

FIG. 1D

| | | | | | | | | |
|---|---|---|---|---|---|---|---|---|
| ATOM | 245 | O | ILE | A | 90 | 27.578 | 31.867 | 31.173 | 1.00 | 13.01 |
| ATOM | 246 | CB | ILE | A | 90 | 25.301 | 32.512 | 33.084 | 1.00 | 14.44 |
| ATOM | 247 | CG1 | ILE | A | 90 | 24.884 | 33.098 | 34.437 | 1.00 | 14.15 |
| ATOM | 248 | CG2 | ILE | A | 90 | 24.114 | 31.847 | 32.407 | 1.00 | 14.29 |
| ATOM | 249 | CD1 | ILE | A | 90 | 24.356 | 32.062 | 35.426 | 1.00 | 13.44 |
| ATOM | 250 | N | LEU | A | 91 | 26.714 | 29.790 | 31.590 | 1.00 | 15.08 |
| ATOM | 251 | CA | LEU | A | 91 | 27.153 | 29.249 | 30.284 | 1.00 | 15.63 |
| ATOM | 252 | C | LEU | A | 91 | 26.313 | 29.878 | 29.174 | 1.00 | 16.04 |
| ATOM | 253 | O | LEU | A | 91 | 25.041 | 29.904 | 29.250 | 1.00 | 16.72 |
| ATOM | 254 | CB | LEU | A | 91 | 27.008 | 27.721 | 30.265 | 1.00 | 14.67 |
| ATOM | 255 | CG | LEU | A | 91 | 27.450 | 26.945 | 29.012 | 1.00 | 15.49 |
| ATOM | 256 | CD1 | LEU | A | 91 | 27.692 | 25.485 | 29.364 | 1.00 | 15.10 |
| ATOM | 257 | CD2 | LEU | A | 91 | 26.393 | 27.052 | 27.925 | 1.00 | 15.54 |
| ATOM | 258 | N | VAL | A | 92 | 26.995 | 30.408 | 28.164 | 1.00 | 16.13 |
| ATOM | 259 | CA | VAL | A | 92 | 26.336 | 31.051 | 27.003 | 1.00 | 15.39 |
| ATOM | 260 | C | VAL | A | 92 | 25.901 | 29.960 | 26.038 | 1.00 | 15.51 |
| ATOM | 261 | O | VAL | A | 92 | 26.761 | 29.243 | 25.440 | 1.00 | 16.92 |
| ATOM | 262 | CB | VAL | A | 92 | 27.306 | 32.008 | 26.278 | 1.00 | 15.40 |
| ATOM | 263 | CG1 | VAL | A | 92 | 26.668 | 32.523 | 24.994 | 1.00 | 16.99 |
| ATOM | 264 | CG2 | VAL | A | 92 | 27.671 | 33.172 | 27.200 | 1.00 | 13.64 |
| ATOM | 265 | N | ASP | A | 93 | 24.594 | 29.824 | 25.845 | 1.00 | 16.41 |
| ATOM | 266 | CA | ASP | A | 93 | 24.069 | 28.762 | 24.974 | 1.00 | 14.41 |
| ATOM | 267 | C | ASP | A | 93 | 23.090 | 29.226 | 23.903 | 1.00 | 15.40 |
| ATOM | 268 | O | ASP | A | 93 | 21.889 | 29.494 | 24.206 | 1.00 | 15.81 |
| ATOM | 269 | CB | ASP | A | 93 | 23.411 | 27.701 | 25.861 | 1.00 | 16.00 |
| ATOM | 270 | CG | ASP | A | 93 | 22.897 | 26.512 | 25.078 | 1.00 | 16.45 |
| ATOM | 271 | OD1 | ASP | A | 93 | 23.536 | 26.133 | 24.076 | 1.00 | 17.23 |
| ATOM | 272 | OD2 | ASP | A | 93 | 21.863 | 25.938 | 25.481 | 1.00 | 16.68 |
| ATOM | 273 | N | THR | A | 94 | 23.550 | 29.326 | 22.657 | 1.00 | 13.38 |
| ATOM | 274 | CA | THR | A | 94 | 22.636 | 29.745 | 21.574 | 1.00 | 13.70 |
| ATOM | 275 | C | THR | A | 94 | 21.811 | 28.549 | 21.109 | 1.00 | 13.68 |
| ATOM | 276 | O | THR | A | 94 | 20.941 | 28.671 | 20.190 | 1.00 | 14.18 |
| ATOM | 277 | CB | THR | A | 94 | 23.397 | 30.349 | 20.362 | 1.00 | 14.99 |
| ATOM | 278 | OG1 | THR | A | 94 | 24.279 | 29.370 | 19.798 | 1.00 | 14.96 |
| ATOM | 279 | CG2 | THR | A | 94 | 24.201 | 31.568 | 20.794 | 1.00 | 14.04 |
| ATOM | 280 | N | GLY | A | 95 | 22.053 | 27.392 | 21.719 | 1.00 | 14.90 |
| ATOM | 281 | CA | GLY | A | 95 | 21.309 | 26.199 | 21.351 | 1.00 | 15.51 |
| ATOM | 282 | C | GLY | A | 95 | 20.108 | 25.969 | 22.255 | 1.00 | 16.96 |
| ATOM | 283 | O | GLY | A | 95 | 19.516 | 24.850 | 22.275 | 1.00 | 16.90 |
| ATOM | 284 | N | SER | A | 96 | 19.721 | 26.987 | 23.011 | 1.00 | 17.38 |
| ATOM | 285 | CA | SER | A | 96 | 18.562 | 26.851 | 23.922 | 1.00 | 17.95 |
| ATOM | 286 | C | SER | A | 96 | 17.990 | 28.231 | 24.226 | 1.00 | 17.07 |
| ATOM | 287 | O | SER | A | 96 | 18.573 | 29.269 | 23.803 | 1.00 | 14.94 |
| ATOM | 288 | CB | SER | A | 96 | 19.005 | 26.174 | 25.219 | 1.00 | 18.55 |
| ATOM | 289 | OG | SER | A | 96 | 19.640 | 26.894 | 26.276 | 1.00 | 26.99 |
| ATOM | 290 | N | SER | A | 97 | 16.869 | 28.292 | 24.936 | 1.00 | 16.25 |
| ATOM | 291 | CA | SER | A | 97 | 16.290 | 29.614 | 25.258 | 1.00 | 18.39 |
| ATOM | 292 | C | SER | A | 97 | 15.740 | 29.776 | 26.670 | 1.00 | 17.83 |
| ATOM | 293 | O | SER | A | 97 | 14.866 | 30.653 | 26.932 | 1.00 | 18.75 |
| ATOM | 294 | CB | SER | A | 97 | 15.224 | 29.993 | 24.227 | 1.00 | 18.88 |
| ATOM | 295 | OG | SER | A | 97 | 14.633 | 28.850 | 23.651 | 1.00 | 23.68 |
| ATOM | 296 | N | ASN | A | 98 | 16.229 | 28.959 | 27.592 | 1.00 | 17.57 |
| ATOM | 297 | CA | ASN | A | 98 | 15.809 | 29.073 | 28.993 | 1.00 | 16.01 |
| ATOM | 298 | C | ASN | A | 98 | 16.963 | 29.611 | 29.821 | 1.00 | 16.51 |
| ATOM | 299 | O | ASN | A | 98 | 18.127 | 29.109 | 29.709 | 1.00 | 16.69 |
| ATOM | 300 | CB | ASN | A | 98 | 15.401 | 27.720 | 29.566 | 1.00 | 13.74 |
| ATOM | 301 | CG | ASN | A | 98 | 13.969 | 27.359 | 29.241 | 1.00 | 16.04 |
| ATOM | 302 | OD1 | ASN | A | 98 | 13.669 | 26.795 | 28.139 | 1.00 | 13.27 |
| ATOM | 303 | ND2 | ASN | A | 98 | 13.058 | 27.680 | 30.158 | 1.00 | 13.26 |
| ATOM | 304 | N | PHE | A | 99 | 16.688 | 30.640 | 30.614 | 1.00 | 14.45 |
| ATOM | 305 | CA | PHE | A | 99 | 17.710 | 31.196 | 31.519 | 1.00 | 13.19 |
| ATOM | 306 | C | PHE | A | 99 | 17.453 | 30.424 | 32.812 | 1.00 | 13.23 |

FIG. 1E

| | | | | | | | | |
|---|---|---|---|---|---|---|---|---|
| ATOM | 307 | O | PHE | A | 99 | 16.319 | 30.466 | 33.384 | 1.00 | 11.00 |
| ATOM | 308 | CB | PHE | A | 99 | 17.491 | 32.699 | 31.722 | 1.00 | 13.54 |
| ATOM | 309 | CG | PHE | A | 99 | 18.390 | 33.318 | 32.761 | 1.00 | 14.79 |
| ATOM | 310 | CD1 | PHE | A | 99 | 19.741 | 32.978 | 32.836 | 1.00 | 15.02 |
| ATOM | 311 | CD2 | PHE | A | 99 | 17.889 | 34.258 | 33.657 | 1.00 | 16.17 |
| ATOM | 312 | CE1 | PHE | A | 99 | 20.576 | 33.564 | 33.784 | 1.00 | 14.99 |
| ATOM | 313 | CE2 | PHE | A | 99 | 18.718 | 34.852 | 34.610 | 1.00 | 16.36 |
| ATOM | 314 | CZ | PHE | A | 99 | 20.064 | 34.503 | 34.674 | 1.00 | 14.33 |
| ATOM | 315 | N | ALA | A | 100 | 18.457 | 29.691 | 33.274 | 1.00 | 11.83 |
| ATOM | 316 | CA | ALA | A | 100 | 18.298 | 28.889 | 34.497 | 1.00 | 12.34 |
| ATOM | 317 | C | ALA | A | 100 | 19.594 | 28.836 | 35.277 | 1.00 | 14.53 |
| ATOM | 318 | O | ALA | A | 100 | 20.722 | 28.896 | 34.684 | 1.00 | 15.19 |
| ATOM | 319 | CB | ALA | A | 100 | 17.849 | 27.486 | 34.138 | 1.00 | 13.09 |
| ATOM | 320 | N | VAL | A | 101 | 19.467 | 28.727 | 36.595 | 1.00 | 13.51 |
| ATOM | 321 | CA | VAL | A | 101 | 20.640 | 28.686 | 37.473 | 1.00 | 13.80 |
| ATOM | 322 | C | VAL | A | 101 | 20.429 | 27.693 | 38.610 | 1.00 | 15.86 |
| ATOM | 323 | O | VAL | A | 101 | 19.253 | 27.424 | 39.031 | 1.00 | 13.90 |
| ATOM | 324 | CB | VAL | A | 101 | 20.912 | 30.082 | 38.075 | 1.00 | 14.68 |
| ATOM | 325 | CG1 | VAL | A | 101 | 21.126 | 31.098 | 36.962 | 1.00 | 12.49 |
| ATOM | 326 | CG2 | VAL | A | 101 | 19.743 | 30.509 | 38.953 | 1.00 | 13.11 |
| ATOM | 327 | N | GLY | A | 102 | 21.528 | 27.120 | 39.098 | 1.00 | 16.51 |
| ATOM | 328 | CA | GLY | A | 102 | 21.437 | 26.189 | 40.207 | 1.00 | 17.46 |
| ATOM | 329 | C | GLY | A | 102 | 20.858 | 26.966 | 41.375 | 1.00 | 19.61 |
| ATOM | 330 | O | GLY | A | 102 | 21.303 | 28.128 | 41.641 | 1.00 | 19.12 |
| ATOM | 331 | N | ALA | A | 103 | 19.875 | 26.395 | 42.065 | 1.00 | 19.81 |
| ATOM | 332 | CA | ALA | A | 103 | 19.241 | 27.092 | 43.212 | 1.00 | 22.41 |
| ATOM | 333 | C | ALA | A | 103 | 19.098 | 26.169 | 44.414 | 1.00 | 23.71 |
| ATOM | 334 | O | ALA | A | 103 | 18.196 | 26.366 | 45.293 | 1.00 | 24.50 |
| ATOM | 335 | CB | ALA | A | 103 | 17.880 | 27.627 | 42.807 | 1.00 | 21.12 |
| ATOM | 336 | N | ALA | A | 104 | 19.967 | 25.168 | 44.470 | 1.00 | 23.53 |
| ATOM | 337 | CA | ALA | A | 104 | 19.979 | 24.180 | 45.566 | 1.00 | 24.47 |
| ATOM | 338 | C | ALA | A | 104 | 21.341 | 23.505 | 45.517 | 1.00 | 24.98 |
| ATOM | 339 | O | ALA | A | 104 | 21.974 | 23.413 | 44.419 | 1.00 | 26.65 |
| ATOM | 340 | CB | ALA | A | 104 | 18.869 | 23.150 | 45.367 | 1.00 | 23.55 |
| ATOM | 341 | N | PRO | A | 105 | 21.836 | 23.026 | 46.668 | 1.00 | 25.27 |
| ATOM | 342 | CA | PRO | A | 105 | 23.140 | 22.361 | 46.733 | 1.00 | 24.87 |
| ATOM | 343 | C | PRO | A | 105 | 23.328 | 21.286 | 45.672 | 1.00 | 24.16 |
| ATOM | 344 | O | PRO | A | 105 | 22.350 | 20.594 | 45.251 | 1.00 | 24.35 |
| ATOM | 345 | CB | PRO | A | 105 | 23.159 | 21.778 | 48.143 | 1.00 | 25.36 |
| ATOM | 346 | CG | PRO | A | 105 | 22.347 | 22.763 | 48.920 | 1.00 | 25.71 |
| ATOM | 347 | CD | PRO | A | 105 | 21.183 | 23.020 | 47.990 | 1.00 | 25.99 |
| ATOM | 348 | N | HIS | A | 106 | 24.566 | 21.135 | 45.227 | 1.00 | 24.93 |
| ATOM | 349 | CA | HIS | A | 106 | 24.918 | 20.119 | 44.223 | 1.00 | 23.63 |
| ATOM | 350 | C | HIS | A | 106 | 26.402 | 19.843 | 44.367 | 1.00 | 24.29 |
| ATOM | 351 | O | HIS | A | 106 | 27.207 | 20.790 | 44.596 | 1.00 | 24.19 |
| ATOM | 352 | CB | HIS | A | 106 | 24.646 | 20.622 | 42.807 | 1.00 | 24.15 |
| ATOM | 353 | CG | HIS | A | 106 | 24.887 | 19.587 | 41.756 | 1.00 | 24.43 |
| ATOM | 354 | ND1 | HIS | A | 106 | 23.912 | 18.702 | 41.348 | 1.00 | 25.53 |
| ATOM | 355 | CD2 | HIS | A | 106 | 26.012 | 19.244 | 41.084 | 1.00 | 23.79 |
| ATOM | 356 | CE1 | HIS | A | 106 | 24.426 | 17.857 | 40.471 | 1.00 | 25.66 |
| ATOM | 357 | NE2 | HIS | A | 106 | 25.699 | 18.164 | 40.294 | 1.00 | 24.92 |
| ATOM | 358 | N | PRO | A | 107 | 26.811 | 18.572 | 44.236 | 1.00 | 25.36 |
| ATOM | 359 | CA | PRO | A | 107 | 28.224 | 18.200 | 44.358 | 1.00 | 26.23 |
| ATOM | 360 | C | PRO | A | 107 | 29.164 | 19.025 | 43.474 | 1.00 | 26.26 |
| ATOM | 361 | O | PRO | A | 107 | 30.335 | 19.296 | 43.866 | 1.00 | 28.01 |
| ATOM | 362 | CB | PRO | A | 107 | 28.225 | 16.722 | 43.972 | 1.00 | 26.21 |
| ATOM | 363 | CG | PRO | A | 107 | 26.875 | 16.259 | 44.418 | 1.00 | 26.75 |
| ATOM | 364 | CD | PRO | A | 107 | 25.977 | 17.384 | 43.971 | 1.00 | 25.04 |
| ATOM | 365 | N | PHE | A | 108 | 28.695 | 19.435 | 42.299 | 1.00 | 25.94 |
| ATOM | 366 | CA | PHE | A | 108 | 29.556 | 20.218 | 41.384 | 1.00 | 26.76 |
| ATOM | 367 | C | PHE | A | 108 | 29.358 | 21.726 | 41.450 | 1.00 | 26.66 |
| ATOM | 368 | O | PHE | A | 108 | 30.103 | 22.494 | 40.778 | 1.00 | 26.81 |

FIG. 1F

| ATOM | 369 | CB  | PHE A 108 | 29.368 | 19.754 | 39.936 | 1.00 | 26.67 |
| ATOM | 370 | CG  | PHE A 108 | 29.665 | 18.300 | 39.720 | 1.00 | 26.80 |
| ATOM | 371 | CD1 | PHE A 108 | 30.531 | 17.614 | 40.569 | 1.00 | 27.67 |
| ATOM | 372 | CD2 | PHE A 108 | 29.090 | 17.615 | 38.655 | 1.00 | 27.12 |
| ATOM | 373 | CE1 | PHE A 108 | 30.819 | 16.262 | 40.359 | 1.00 | 27.99 |
| ATOM | 374 | CE2 | PHE A 108 | 29.369 | 16.267 | 38.433 | 1.00 | 26.65 |
| ATOM | 375 | CZ  | PHE A 108 | 30.235 | 15.587 | 39.286 | 1.00 | 26.94 |
| ATOM | 376 | N   | LEU A 109 | 28.386 | 22.180 | 42.231 | 1.00 | 26.14 |
| ATOM | 377 | CA  | LEU A 109 | 28.144 | 23.629 | 42.346 | 1.00 | 27.17 |
| ATOM | 378 | C   | LEU A 109 | 28.914 | 24.248 | 43.510 | 1.00 | 29.20 |
| ATOM | 379 | O   | LEU A 109 | 28.861 | 23.743 | 44.669 | 1.00 | 26.91 |
| ATOM | 380 | CB  | LEU A 109 | 26.647 | 23.911 | 42.498 | 1.00 | 25.73 |
| ATOM | 381 | CG  | LEU A 109 | 25.811 | 23.714 | 41.230 | 1.00 | 25.94 |
| ATOM | 382 | CD1 | LEU A 109 | 24.343 | 23.983 | 41.530 | 1.00 | 24.99 |
| ATOM | 383 | CD2 | LEU A 109 | 26.310 | 24.657 | 40.136 | 1.00 | 24.26 |
| ATOM | 384 | N   | HIS A 110 | 29.632 | 25.328 | 43.213 | 1.00 | 32.94 |
| ATOM | 385 | CA  | HIS A 110 | 30.442 | 26.077 | 44.207 | 1.00 | 35.82 |
| ATOM | 386 | C   | HIS A 110 | 29.533 | 27.015 | 44.983 | 1.00 | 33.93 |
| ATOM | 387 | O   | HIS A 110 | 29.732 | 27.265 | 46.209 | 1.00 | 34.20 |
| ATOM | 388 | CB  | HIS A 110 | 31.501 | 26.915 | 43.485 | 1.00 | 42.49 |
| ATOM | 389 | CG  | HIS A 110 | 32.907 | 26.469 | 43.732 | 1.00 | 47.84 |
| ATOM | 390 | ND1 | HIS A 110 | 33.509 | 26.558 | 44.969 | 1.00 | 50.74 |
| ATOM | 391 | CD2 | HIS A 110 | 33.834 | 25.934 | 42.899 | 1.00 | 49.74 |
| ATOM | 392 | CE1 | HIS A 110 | 34.746 | 26.098 | 44.888 | 1.00 | 51.83 |
| ATOM | 393 | NE2 | HIS A 110 | 34.968 | 25.713 | 43.644 | 1.00 | 51.38 |
| ATOM | 394 | N   | ARG A 111 | 28.547 | 27.553 | 44.279 | 1.00 | 31.13 |
| ATOM | 395 | CA  | ARG A 111 | 27.579 | 28.494 | 44.857 | 1.00 | 28.72 |
| ATOM | 396 | C   | ARG A 111 | 26.287 | 28.331 | 44.072 | 1.00 | 28.16 |
| ATOM | 397 | O   | ARG A 111 | 26.267 | 27.652 | 43.000 | 1.00 | 27.40 |
| ATOM | 398 | CB  | ARG A 111 | 28.108 | 29.924 | 44.717 | 1.00 | 28.09 |
| ATOM | 399 | CG  | ARG A 111 | 28.550 | 30.255 | 43.305 | 1.00 | 26.48 |
| ATOM | 400 | CD  | ARG A 111 | 29.216 | 31.616 | 43.201 | 1.00 | 25.86 |
| ATOM | 401 | NE  | ARG A 111 | 29.723 | 31.831 | 41.849 | 1.00 | 25.21 |
| ATOM | 402 | CZ  | ARG A 111 | 30.423 | 32.892 | 41.465 | 1.00 | 24.44 |
| ATOM | 403 | NH1 | ARG A 111 | 30.708 | 33.850 | 42.337 | 1.00 | 25.08 |
| ATOM | 404 | NH2 | ARG A 111 | 30.828 | 32.995 | 40.205 | 1.00 | 22.62 |
| ATOM | 405 | N   | TYR A 112 | 25.207 | 28.922 | 44.566 | 1.00 | 26.27 |
| ATOM | 406 | CA  | TYR A 112 | 23.922 | 28.814 | 43.866 | 1.00 | 23.70 |
| ATOM | 407 | C   | TYR A 112 | 22.955 | 29.916 | 44.250 | 1.00 | 22.77 |
| ATOM | 408 | O   | TYR A 112 | 23.140 | 30.633 | 45.283 | 1.00 | 21.10 |
| ATOM | 409 | CB  | TYR A 112 | 23.295 | 27.437 | 44.119 | 1.00 | 25.47 |
| ATOM | 410 | CG  | TYR A 112 | 23.036 | 27.111 | 45.575 | 1.00 | 27.20 |
| ATOM | 411 | CD1 | TYR A 112 | 21.885 | 27.569 | 46.222 | 1.00 | 28.51 |
| ATOM | 412 | CD2 | TYR A 112 | 23.946 | 26.353 | 46.309 | 1.00 | 27.51 |
| ATOM | 413 | CE1 | TYR A 112 | 21.647 | 27.276 | 47.565 | 1.00 | 27.78 |
| ATOM | 414 | CE2 | TYR A 112 | 23.720 | 26.058 | 47.651 | 1.00 | 28.63 |
| ATOM | 415 | CZ  | TYR A 112 | 22.570 | 26.522 | 48.270 | 1.00 | 28.98 |
| ATOM | 416 | OH  | TYR A 112 | 22.352 | 26.228 | 49.591 | 1.00 | 30.28 |
| ATOM | 417 | N   | TYR A 113 | 21.927 | 30.069 | 43.428 | 1.00 | 19.32 |
| ATOM | 418 | CA  | TYR A 113 | 20.896 | 31.090 | 43.624 | 1.00 | 18.94 |
| ATOM | 419 | C   | TYR A 113 | 20.047 | 30.807 | 44.857 | 1.00 | 17.90 |
| ATOM | 420 | O   | TYR A 113 | 19.480 | 29.688 | 45.011 | 1.00 | 19.37 |
| ATOM | 421 | CB  | TYR A 113 | 20.027 | 31.141 | 42.369 | 1.00 | 17.76 |
| ATOM | 422 | CG  | TYR A 113 | 18.887 | 32.135 | 42.378 | 1.00 | 17.68 |
| ATOM | 423 | CD1 | TYR A 113 | 19.024 | 33.397 | 42.963 | 1.00 | 16.86 |
| ATOM | 424 | CD2 | TYR A 113 | 17.709 | 31.854 | 41.688 | 1.00 | 16.79 |
| ATOM | 425 | CE1 | TYR A 113 | 18.020 | 34.349 | 42.848 | 1.00 | 17.05 |
| ATOM | 426 | CE2 | TYR A 113 | 16.704 | 32.796 | 41.563 | 1.00 | 16.02 |
| ATOM | 427 | CZ  | TYR A 113 | 16.858 | 34.038 | 42.138 | 1.00 | 17.36 |
| ATOM | 428 | OH  | TYR A 113 | 15.848 | 34.963 | 41.984 | 1.00 | 16.62 |
| ATOM | 429 | N   | GLN A 114 | 19.967 | 31.790 | 45.746 | 1.00 | 18.68 |
| ATOM | 430 | CA  | GLN A 114 | 19.156 | 31.673 | 46.983 | 1.00 | 20.28 |

FIG. 1G

| | | | | | | | | |
|---|---|---|---|---|---|---|---|---|
| ATOM | 431 | C | GLN | A | 114 | 18.057 | 32.719 | 46.897 | 1.00 19.59 |
| ATOM | 432 | O | GLN | A | 114 | 18.285 | 33.933 | 47.192 | 1.00 20.34 |
| ATOM | 433 | CB | GLN | A | 114 | 20.028 | 31.912 | 48.216 | 1.00 19.79 |
| ATOM | 434 | CG | GLN | A | 114 | 21.048 | 30.814 | 48.434 | 1.00 22.79 |
| ATOM | 435 | CD | GLN | A | 114 | 21.942 | 31.063 | 49.626 | 1.00 24.34 |
| ATOM | 436 | OE1 | GLN | A | 114 | 22.708 | 32.073 | 49.668 | 1.00 26.47 |
| ATOM | 437 | NE2 | GLN | A | 114 | 21.876 | 30.173 | 50.606 | 1.00 24.49 |
| ATOM | 438 | N | ARG | A | 115 | 16.876 | 32.275 | 46.479 | 1.00 20.48 |
| ATOM | 439 | CA | ARG | A | 115 | 15.703 | 33.159 | 46.305 | 1.00 21.24 |
| ATOM | 440 | C | ARG | A | 115 | 15.234 | 33.837 | 47.583 | 1.00 21.94 |
| ATOM | 441 | O | ARG | A | 115 | 14.784 | 35.022 | 47.546 | 1.00 21.40 |
| ATOM | 442 | CB | ARG | A | 115 | 14.550 | 32.366 | 45.686 | 1.00 20.21 |
| ATOM | 443 | CG | ARG | A | 115 | 14.807 | 31.953 | 44.240 | 1.00 20.95 |
| ATOM | 444 | CD | ARG | A | 115 | 13.917 | 30.796 | 43.824 | 1.00 20.32 |
| ATOM | 445 | NE | ARG | A | 115 | 14.305 | 29.567 | 44.508 | 1.00 20.45 |
| ATOM | 446 | CZ | ARG | A | 115 | 13.626 | 28.428 | 44.448 | 1.00 19.47 |
| ATOM | 447 | NH1 | ARG | A | 115 | 12.514 | 28.352 | 43.732 | 1.00 20.02 |
| ATOM | 448 | NH2 | ARG | A | 115 | 14.061 | 27.366 | 45.106 | 1.00 21.63 |
| ATOM | 449 | N | GLN | A | 116 | 15.323 | 33.138 | 48.710 | 1.00 22.93 |
| ATOM | 450 | CA | GLN | A | 116 | 14.880 | 33.723 | 49.993 | 1.00 24.99 |
| ATOM | 451 | C | GLN | A | 116 | 15.718 | 34.953 | 50.343 | 1.00 23.86 |
| ATOM | 452 | O | GLN | A | 116 | 15.242 | 35.873 | 51.080 | 1.00 24.27 |
| ATOM | 453 | CB | GLN | A | 116 | 14.972 | 32.691 | 51.123 | 1.00 27.81 |
| ATOM | 454 | CG | GLN | A | 116 | 16.391 | 32.280 | 51.502 | 1.00 32.89 |
| ATOM | 455 | CD | GLN | A | 116 | 16.999 | 31.257 | 50.550 | 1.00 36.05 |
| ATOM | 456 | OE1 | GLN | A | 116 | 16.955 | 31.423 | 49.295 | 1.00 36.88 |
| ATOM | 457 | NE2 | GLN | A | 116 | 17.577 | 30.199 | 51.112 | 1.00 37.21 |
| ATOM | 458 | N | LEU | A | 117 | 16.944 | 35.006 | 49.833 | 1.00 20.91 |
| ATOM | 459 | CA | LEU | A | 117 | 17.831 | 36.153 | 50.112 | 1.00 20.59 |
| ATOM | 460 | C | LEU | A | 117 | 17.673 | 37.296 | 49.124 | 1.00 19.96 |
| ATOM | 461 | O | LEU | A | 117 | 18.440 | 38.301 | 49.191 | 1.00 18.93 |
| ATOM | 462 | CB | LEU | A | 117 | 19.296 | 35.707 | 50.128 | 1.00 21.68 |
| ATOM | 463 | CG | LEU | A | 117 | 19.887 | 35.224 | 51.454 | 1.00 22.49 |
| ATOM | 464 | CD1 | LEU | A | 117 | 19.001 | 34.175 | 52.074 | 1.00 22.63 |
| ATOM | 465 | CD2 | LEU | A | 117 | 21.286 | 34.675 | 51.210 | 1.00 22.12 |
| ATOM | 466 | N | SER | A | 118 | 16.714 | 37.183 | 48.210 | 1.00 18.14 |
| ATOM | 467 | CA | SER | A | 118 | 16.484 | 38.252 | 47.208 | 1.00 17.08 |
| ATOM | 468 | C | SER | A | 118 | 15.150 | 38.953 | 47.436 | 1.00 16.25 |
| ATOM | 469 | O | SER | A | 118 | 14.055 | 38.316 | 47.347 | 1.00 16.00 |
| ATOM | 470 | CB | SER | A | 118 | 16.519 | 37.679 | 45.787 | 1.00 15.12 |
| ATOM | 471 | OG | SER | A | 118 | 16.301 | 38.708 | 44.835 | 1.00 16.81 |
| ATOM | 472 | N | SER | A | 119 | 15.210 | 40.250 | 47.711 | 1.00 15.31 |
| ATOM | 473 | CA | SER | A | 119 | 13.991 | 41.044 | 47.973 | 1.00 18.09 |
| ATOM | 474 | C | SER | A | 119 | 13.169 | 41.307 | 46.714 | 1.00 17.35 |
| ATOM | 475 | O | SER | A | 119 | 11.964 | 41.669 | 46.800 | 1.00 17.62 |
| ATOM | 476 | CB | SER | A | 119 | 14.371 | 42.380 | 48.618 | 1.00 16.85 |
| ATOM | 477 | OG | SER | A | 119 | 15.158 | 43.160 | 47.727 | 1.00 18.71 |
| ATOM | 478 | N | THR | A | 120 | 13.781 | 41.137 | 45.546 | 1.00 18.90 |
| ATOM | 479 | CA | THR | A | 120 | 13.075 | 41.381 | 44.263 | 1.00 17.26 |
| ATOM | 480 | C | THR | A | 120 | 12.587 | 40.104 | 43.594 | 1.00 17.17 |
| ATOM | 481 | O | THR | A | 120 | 12.004 | 40.139 | 42.466 | 1.00 18.70 |
| ATOM | 482 | CB | THR | A | 120 | 13.980 | 42.143 | 43.283 | 1.00 17.78 |
| ATOM | 483 | OG1 | THR | A | 120 | 15.305 | 41.609 | 43.355 | 1.00 17.35 |
| ATOM | 484 | CG2 | THR | A | 120 | 14.012 | 43.630 | 43.624 | 1.00 17.37 |
| ATOM | 485 | N | TYR | A | 121 | 12.800 | 38.977 | 44.257 | 1.00 18.03 |
| ATOM | 486 | CA | TYR | A | 121 | 12.364 | 37.676 | 43.715 | 1.00 18.53 |
| ATOM | 487 | C | TYR | A | 121 | 10.841 | 37.584 | 43.606 | 1.00 18.12 |
| ATOM | 488 | O | TYR | A | 121 | 10.088 | 38.028 | 44.531 | 1.00 19.29 |
| ATOM | 489 | CB | TYR | A | 121 | 12.878 | 36.547 | 44.607 | 1.00 18.32 |
| ATOM | 490 | CG | TYR | A | 121 | 12.187 | 35.225 | 44.368 | 1.00 22.03 |
| ATOM | 491 | CD1 | TYR | A | 121 | 12.429 | 34.484 | 43.209 | 1.00 21.48 |
| ATOM | 492 | CD2 | TYR | A | 121 | 11.268 | 34.725 | 45.291 | 1.00 21.95 |

FIG. 1H

```
ATOM   493  CE1 TYR A 121      11.776  33.280  42.977  1.00 21.33
ATOM   494  CE2 TYR A 121      10.608  33.523  45.067  1.00 22.77
ATOM   495  CZ  TYR A 121      10.867  32.807  43.908  1.00 23.35
ATOM   496  OH  TYR A 121      10.206  31.622  43.682  1.00 23.63
ATOM   497  N   ARG A 122      10.365  37.039  42.492  1.00 16.86
ATOM   498  CA  ARG A 122       8.909  36.851  42.281  1.00 16.79
ATOM   499  C   ARG A 122       8.703  35.397  41.890  1.00 17.46
ATOM   500  O   ARG A 122       9.348  34.884  40.924  1.00 17.88
ATOM   501  CB  ARG A 122       8.384  37.764  41.174  1.00 14.87
ATOM   502  CG  ARG A 122       8.335  39.230  41.548  1.00 14.83
ATOM   503  CD  ARG A 122       7.895  40.067  40.369  1.00 14.98
ATOM   504  NE  ARG A 122       7.822  41.481  40.706  1.00 16.19
ATOM   505  CZ  ARG A 122       7.546  42.442  39.833  1.00 16.67
ATOM   506  NH1 ARG A 122       7.316  42.142  38.559  1.00 15.67
ATOM   507  NH2 ARG A 122       7.505  43.704  40.233  1.00 16.38
ATOM   508  N   ASP A 123       7.836  34.720  42.628  1.00 18.52
ATOM   509  CA  ASP A 123       7.538  33.296  42.388  1.00 19.00
ATOM   510  C   ASP A 123       6.435  33.147  41.347  1.00 19.87
ATOM   511  O   ASP A 123       5.342  33.757  41.490  1.00 17.59
ATOM   512  CB  ASP A 123       7.090  32.657  43.702  1.00 19.80
ATOM   513  CG  ASP A 123       6.841  31.171  43.582  1.00 20.76
ATOM   514  OD1 ASP A 123       6.933  30.615  42.463  1.00 20.41
ATOM   515  OD2 ASP A 123       6.549  30.559  44.629  1.00 22.50
ATOM   516  N   LEU A 124       6.689  32.359  40.305  1.00 20.70
ATOM   517  CA  LEU A 124       5.672  32.139  39.255  1.00 21.20
ATOM   518  C   LEU A 124       4.790  30.929  39.562  1.00 21.64
ATOM   519  O   LEU A 124       3.832  30.601  38.786  1.00 21.17
ATOM   520  CB  LEU A 124       6.343  31.978  37.888  1.00 21.51
ATOM   521  CG  LEU A 124       6.850  33.288  37.270  1.00 22.05
ATOM   522  CD1 LEU A 124       7.617  32.994  35.997  1.00 22.23
ATOM   523  CD2 LEU A 124       5.678  34.217  36.983  1.00 21.49
ATOM   524  N   ARG A 125       5.083  30.252  40.666  1.00 22.67
ATOM   525  CA  ARG A 125       4.286  29.078  41.085  1.00 25.58
ATOM   526  C   ARG A 125       4.106  28.081  39.944  1.00 26.39
ATOM   527  O   ARG A 125       2.974  27.552  39.719  1.00 26.83
ATOM   528  CB  ARG A 125       2.918  29.553  41.593  1.00 26.62
ATOM   529  CG  ARG A 125       3.016  30.511  42.783  1.00 30.02
ATOM   530  CD  ARG A 125       1.733  31.311  43.002  1.00 32.48
ATOM   531  NE  ARG A 125       1.910  32.334  44.034  1.00 36.63
ATOM   532  CZ  ARG A 125       1.049  33.323  44.282  1.00 38.12
ATOM   533  NH1 ARG A 125      -0.070  33.441  43.575  1.00 37.55
ATOM   534  NH2 ARG A 125       1.307  34.202  45.240  1.00 38.11
ATOM   535  N   LYS A 126       5.189  27.810  39.221  1.00 26.62
ATOM   536  CA  LYS A 126       5.162  26.861  38.079  1.00 26.41
ATOM   537  C   LYS A 126       6.453  26.063  37.986  1.00 24.61
ATOM   538  O   LYS A 126       7.577  26.624  38.141  1.00 22.46
ATOM   539  CB  LYS A 126       4.971  27.605  36.756  1.00 28.55
ATOM   540  CG  LYS A 126       3.539  27.804  36.326  1.00 32.76
ATOM   541  CD  LYS A 126       3.486  28.380  34.917  1.00 36.53
ATOM   542  CE  LYS A 126       2.048  28.607  34.456  1.00 38.52
ATOM   543  NZ  LYS A 126       1.234  27.355  34.550  1.00 40.78
ATOM   544  N   GLY A 127       6.326  24.770  37.731  1.00 23.25
ATOM   545  CA  GLY A 127       7.504  23.941  37.598  1.00 22.82
ATOM   546  C   GLY A 127       7.970  23.995  36.157  1.00 22.77
ATOM   547  O   GLY A 127       7.220  24.487  35.252  1.00 22.00
ATOM   548  N   VAL A 128       9.184  23.521  35.909  1.00 21.58
ATOM   549  CA  VAL A 128       9.731  23.511  34.541  1.00 22.39
ATOM   550  C   VAL A 128      10.736  22.388  34.390  1.00 21.31
ATOM   551  O   VAL A 128      11.547  22.101  35.323  1.00 21.59
ATOM   552  CB  VAL A 128      10.416  24.851  34.180  1.00 21.77
ATOM   553  CG1 VAL A 128      11.572  25.120  35.122  1.00 22.15
ATOM   554  CG2 VAL A 128      10.903  24.809  32.740  1.00 23.66
```

FIG. 1I

| ATOM | 555 | N   | TYR | A | 129 | 10.700 | 21.744 | 33.233 | 1.00 | 21.64 |
|------|-----|-----|-----|---|-----|--------|--------|--------|------|-------|
| ATOM | 556 | CA  | TYR | A | 129 | 11.598 | 20.624 | 32.933 | 1.00 | 21.55 |
| ATOM | 557 | C   | TYR | A | 129 | 12.298 | 20.882 | 31.609 | 1.00 | 20.25 |
| ATOM | 558 | O   | TYR | A | 129 | 11.635 | 21.188 | 30.573 | 1.00 | 20.01 |
| ATOM | 559 | CB  | TYR | A | 129 | 10.785 | 19.333 | 32.841 | 1.00 | 23.37 |
| ATOM | 560 | CG  | TYR | A | 129 | 11.545 | 18.164 | 32.271 | 1.00 | 26.64 |
| ATOM | 561 | CD1 | TYR | A | 129 | 12.628 | 17.613 | 32.956 | 1.00 | 27.70 |
| ATOM | 562 | CD2 | TYR | A | 129 | 11.178 | 17.598 | 31.048 | 1.00 | 27.27 |
| ATOM | 563 | CE1 | TYR | A | 129 | 13.323 | 16.529 | 32.443 | 1.00 | 29.33 |
| ATOM | 564 | CE2 | TYR | A | 129 | 11.872 | 16.507 | 30.524 | 1.00 | 28.75 |
| ATOM | 565 | CZ  | TYR | A | 129 | 12.942 | 15.980 | 31.231 | 1.00 | 28.91 |
| ATOM | 566 | OH  | TYR | A | 129 | 13.634 | 14.896 | 30.751 | 1.00 | 30.21 |
| ATOM | 567 | N   | VAL | A | 130 | 13.620 | 20.782 | 31.602 | 1.00 | 19.35 |
| ATOM | 568 | CA  | VAL | A | 130 | 14.353 | 21.003 | 30.350 | 1.00 | 17.21 |
| ATOM | 569 | C   | VAL | A | 130 | 15.308 | 19.872 | 30.022 | 1.00 | 16.02 |
| ATOM | 570 | O   | VAL | A | 130 | 16.319 | 19.628 | 30.748 | 1.00 | 16.89 |
| ATOM | 571 | CB  | VAL | A | 130 | 15.136 | 22.334 | 30.370 | 1.00 | 17.86 |
| ATOM | 572 | CG1 | VAL | A | 130 | 15.934 | 22.485 | 29.075 | 1.00 | 15.31 |
| ATOM | 573 | CG2 | VAL | A | 130 | 14.163 | 23.505 | 30.525 | 1.00 | 15.67 |
| ATOM | 574 | N   | PRO | A | 131 | 15.013 | 19.136 | 28.945 | 1.00 | 14.83 |
| ATOM | 575 | CA  | PRO | A | 131 | 15.868 | 18.028 | 28.529 | 1.00 | 14.77 |
| ATOM | 576 | C   | PRO | A | 131 | 16.743 | 18.516 | 27.372 | 1.00 | 15.00 |
| ATOM | 577 | O   | PRO | A | 131 | 16.234 | 19.154 | 26.402 | 1.00 | 15.43 |
| ATOM | 578 | CB  | PRO | A | 131 | 14.857 | 16.971 | 28.106 | 1.00 | 13.57 |
| ATOM | 579 | CG  | PRO | A | 131 | 13.809 | 17.806 | 27.421 | 1.00 | 13.44 |
| ATOM | 580 | CD  | PRO | A | 131 | 13.706 | 19.078 | 28.262 | 1.00 | 13.99 |
| ATOM | 581 | N   | TYR | A | 132 | 18.043 | 18.268 | 27.465 | 1.00 | 14.75 |
| ATOM | 582 | CA  | TYR | A | 132 | 18.989 | 18.679 | 26.404 | 1.00 | 17.37 |
| ATOM | 583 | C   | TYR | A | 132 | 19.438 | 17.415 | 25.676 | 1.00 | 17.52 |
| ATOM | 584 | O   | TYR | A | 132 | 19.100 | 16.274 | 26.105 | 1.00 | 17.41 |
| ATOM | 585 | CB  | TYR | A | 132 | 20.211 | 19.369 | 27.020 | 1.00 | 16.93 |
| ATOM | 586 | CG  | TYR | A | 132 | 19.909 | 20.665 | 27.742 | 1.00 | 18.63 |
| ATOM | 587 | CD1 | TYR | A | 132 | 19.834 | 21.881 | 27.051 | 1.00 | 17.88 |
| ATOM | 588 | CD2 | TYR | A | 132 | 19.706 | 20.681 | 29.122 | 1.00 | 19.01 |
| ATOM | 589 | CE1 | TYR | A | 132 | 19.564 | 23.080 | 27.722 | 1.00 | 16.57 |
| ATOM | 590 | CE2 | TYR | A | 132 | 19.435 | 21.867 | 29.799 | 1.00 | 17.74 |
| ATOM | 591 | CZ  | TYR | A | 132 | 19.365 | 23.062 | 29.098 | 1.00 | 19.02 |
| ATOM | 592 | OH  | TYR | A | 132 | 19.083 | 24.229 | 29.782 | 1.00 | 18.23 |
| ATOM | 593 | N   | THR | A | 133 | 20.188 | 17.574 | 24.592 | 1.00 | 18.46 |
| ATOM | 594 | CA  | THR | A | 133 | 20.686 | 16.403 | 23.842 | 1.00 | 18.54 |
| ATOM | 595 | C   | THR | A | 133 | 21.525 | 15.580 | 24.812 | 1.00 | 20.42 |
| ATOM | 596 | O   | THR | A | 133 | 21.667 | 14.325 | 24.672 | 1.00 | 19.49 |
| ATOM | 597 | CB  | THR | A | 133 | 21.546 | 16.846 | 22.653 | 1.00 | 18.40 |
| ATOM | 598 | OG1 | THR | A | 133 | 20.720 | 17.539 | 21.708 | 1.00 | 20.46 |
| ATOM | 599 | CG2 | THR | A | 133 | 22.194 | 15.645 | 21.976 | 1.00 | 18.37 |
| ATOM | 600 | N   | GLN | A | 134 | 22.064 | 16.265 | 25.810 | 1.00 | 22.23 |
| ATOM | 601 | CA  | GLN | A | 134 | 22.890 | 15.624 | 26.842 | 1.00 | 24.27 |
| ATOM | 602 | C   | GLN | A | 134 | 22.723 | 16.406 | 28.140 | 1.00 | 23.32 |
| ATOM | 603 | O   | GLN | A | 134 | 23.179 | 17.580 | 28.252 | 1.00 | 21.03 |
| ATOM | 604 | CB  | GLN | A | 134 | 24.352 | 15.633 | 26.405 | 1.00 | 28.22 |
| ATOM | 605 | CG  | GLN | A | 134 | 25.140 | 14.412 | 26.808 | 1.00 | 32.76 |
| ATOM | 606 | CD  | GLN | A | 134 | 25.020 | 13.296 | 25.781 | 1.00 | 36.63 |
| ATOM | 607 | OE1 | GLN | A | 134 | 26.052 | 12.680 | 25.356 | 1.00 | 37.34 |
| ATOM | 608 | NE2 | GLN | A | 134 | 23.791 | 13.018 | 25.352 | 1.00 | 38.92 |
| ATOM | 609 | N   | GLY | A | 135 | 22.080 | 15.789 | 29.124 | 1.00 | 23.28 |
| ATOM | 610 | CA  | GLY | A | 135 | 21.863 | 16.460 | 30.391 | 1.00 | 21.50 |
| ATOM | 611 | C   | GLY | A | 135 | 20.432 | 16.946 | 30.483 | 1.00 | 22.11 |
| ATOM | 612 | O   | GLY | A | 135 | 19.735 | 17.111 | 29.435 | 1.00 | 20.68 |
| ATOM | 613 | N   | LYS | A | 136 | 19.968 | 17.190 | 31.703 | 1.00 | 22.97 |
| ATOM | 614 | CA  | LYS | A | 136 | 18.584 | 17.654 | 31.923 | 1.00 | 23.80 |
| ATOM | 615 | C   | LYS | A | 136 | 18.429 | 18.147 | 33.353 | 1.00 | 22.33 |
| ATOM | 616 | O   | LYS | A | 136 | 19.196 | 17.719 | 34.269 | 1.00 | 21.42 |

FIG. 1J

```
ATOM    617  CB   LYS A 136      17.606  16.501  31.677  1.00 25.37
ATOM    618  CG   LYS A 136      17.823  15.310  32.607  1.00 28.29
ATOM    619  CD   LYS A 136      16.804  14.196  32.374  1.00 31.54
ATOM    620  CE   LYS A 136      16.955  13.570  31.000  1.00 34.21
ATOM    621  NZ   LYS A 136      15.996  12.444  30.789  1.00 37.76
ATOM    622  N    TRP A 137      17.470  19.040  33.573  1.00 21.02
ATOM    623  CA   TRP A 137      17.214  19.562  34.928  1.00 20.75
ATOM    624  C    TRP A 137      15.750  19.907  35.133  1.00 20.62
ATOM    625  O    TRP A 137      14.951  19.978  34.153  1.00 20.05
ATOM    626  CB   TRP A 137      18.077  20.800  35.231  1.00 18.46
ATOM    627  CG   TRP A 137      17.960  21.937  34.248  1.00 18.02
ATOM    628  CD1  TRP A 137      18.865  22.276  33.281  1.00 18.12
ATOM    629  CD2  TRP A 137      16.881  22.879  34.134  1.00 17.27
ATOM    630  NE1  TRP A 137      18.419  23.369  32.574  1.00 17.78
ATOM    631  CE2  TRP A 137      17.204  23.758  33.074  1.00 17.40
ATOM    632  CE3  TRP A 137      15.675  23.067  34.823  1.00 17.08
ATOM    633  CZ2  TRP A 137      16.363  24.807  32.684  1.00 15.50
ATOM    634  CZ3  TRP A 137      14.836  24.113  34.434  1.00 17.23
ATOM    635  CH2  TRP A 137      15.188  24.968  33.373  1.00 17.46
ATOM    636  N    GLU A 138      15.385  20.098  36.395  1.00 21.53
ATOM    637  CA   GLU A 138      14.014  20.472  36.789  1.00 24.94
ATOM    638  C    GLU A 138      14.166  21.642  37.745  1.00 23.18
ATOM    639  O    GLU A 138      15.168  21.719  38.526  1.00 21.21
ATOM    640  CB   GLU A 138      13.320  19.320  37.515  1.00 28.46
ATOM    641  CG   GLU A 138      13.053  18.101  36.656  1.00 34.91
ATOM    642  CD   GLU A 138      12.562  16.919  37.472  1.00 37.93
ATOM    643  OE1  GLU A 138      12.175  15.897  36.864  1.00 40.28
ATOM    644  OE2  GLU A 138      12.570  17.009  38.722  1.00 40.20
ATOM    645  N    GLY A 139      13.214  22.559  37.711  1.00 22.13
ATOM    646  CA   GLY A 139      13.298  23.693  38.604  1.00 22.60
ATOM    647  C    GLY A 139      11.975  24.402  38.713  1.00 21.54
ATOM    648  O    GLY A 139      10.949  23.953  38.116  1.00 23.29
ATOM    649  N    GLU A 140      11.962  25.494  39.465  1.00 21.74
ATOM    650  CA   GLU A 140      10.733  26.284  39.648  1.00 21.81
ATOM    651  C    GLU A 140      10.900  27.646  38.998  1.00 19.04
ATOM    652  O    GLU A 140      11.975  28.304  39.125  1.00 18.42
ATOM    653  CB   GLU A 140      10.404  26.425  41.139  1.00 24.39
ATOM    654  CG   GLU A 140      11.479  25.887  42.065  1.00 28.61
ATOM    655  CD   GLU A 140      10.922  25.385  43.383  1.00 29.72
ATOM    656  OE1  GLU A 140      10.311  24.297  43.389  1.00 31.43
ATOM    657  OE2  GLU A 140      11.091  26.077  44.410  1.00 30.48
ATOM    658  N    LEU A 141       9.870  28.071  38.278  1.00 16.35
ATOM    659  CA   LEU A 141       9.901  29.360  37.585  1.00 15.48
ATOM    660  C    LEU A 141       9.674  30.546  38.511  1.00 15.68
ATOM    661  O    LEU A 141       8.832  30.499  39.466  1.00 13.45
ATOM    662  CB   LEU A 141       8.864  29.376  36.460  1.00 15.23
ATOM    663  CG   LEU A 141       9.145  28.412  35.300  1.00 16.27
ATOM    664  CD1  LEU A 141       8.008  28.461  34.300  1.00 15.60
ATOM    665  CD2  LEU A 141      10.458  28.785  34.627  1.00 16.48
ATOM    666  N    GLY A 142      10.424  31.608  38.241  1.00 15.15
ATOM    667  CA   GLY A 142      10.323  32.819  39.015  1.00 12.33
ATOM    668  C    GLY A 142      10.845  33.953  38.167  1.00 14.67
ATOM    669  O    GLY A 142      11.242  33.758  36.971  1.00 13.75
ATOM    670  N    THR A 143      10.877  35.137  38.754  1.00 14.88
ATOM    671  CA   THR A 143      11.354  36.324  38.050  1.00 15.26
ATOM    672  C    THR A 143      12.262  37.103  39.008  1.00 14.53
ATOM    673  O    THR A 143      12.119  36.991  40.269  1.00 13.46
ATOM    674  CB   THR A 143      10.131  37.154  37.600  1.00 16.18
ATOM    675  OG1  THR A 143      10.192  37.362  36.187  1.00 20.69
ATOM    676  CG2  THR A 143      10.058  38.465  38.325  1.00 12.43
ATOM    677  N    ASP A 144      13.202  37.866  38.466  1.00 14.22
ATOM    678  CA   ASP A 144      14.117  38.652  39.321  1.00 15.38
```

FIG. 1K

| ATOM | 679 | C   | ASP | A | 144 | 14.942 | 39.609 | 38.479 | 1.00 | 15.67 |
| ATOM | 680 | O   | ASP | A | 144 | 14.984 | 39.496 | 37.208 | 1.00 | 16.83 |
| ATOM | 681 | CB  | ASP | A | 144 | 15.063 | 37.721 | 40.086 | 1.00 | 15.20 |
| ATOM | 682 | CG  | ASP | A | 144 | 15.367 | 38.218 | 41.496 | 1.00 | 17.84 |
| ATOM | 683 | OD1 | ASP | A | 144 | 15.359 | 39.447 | 41.724 | 1.00 | 16.62 |
| ATOM | 684 | OD2 | ASP | A | 144 | 15.630 | 37.373 | 42.379 | 1.00 | 16.33 |
| ATOM | 685 | N   | LEU | A | 145 | 15.596 | 40.551 | 39.147 | 1.00 | 16.74 |
| ATOM | 686 | CA  | LEU | A | 145 | 16.442 | 41.537 | 38.454 | 1.00 | 18.66 |
| ATOM | 687 | C   | LEU | A | 145 | 17.757 | 40.854 | 38.101 | 1.00 | 20.21 |
| ATOM | 688 | O   | LEU | A | 145 | 18.381 | 40.147 | 38.961 | 1.00 | 21.75 |
| ATOM | 689 | CB  | LEU | A | 145 | 16.697 | 42.746 | 39.351 | 1.00 | 18.43 |
| ATOM | 690 | CG  | LEU | A | 145 | 15.452 | 43.522 | 39.786 | 1.00 | 19.69 |
| ATOM | 691 | CD1 | LEU | A | 145 | 15.878 | 44.720 | 40.628 | 1.00 | 19.11 |
| ATOM | 692 | CD2 | LEU | A | 145 | 14.660 | 43.971 | 38.557 | 1.00 | 18.50 |
| ATOM | 693 | N   | VAL | A | 146 | 18.186 | 41.030 | 36.858 | 1.00 | 20.48 |
| ATOM | 694 | CA  | VAL | A | 146 | 19.426 | 40.402 | 36.387 | 1.00 | 21.21 |
| ATOM | 695 | C   | VAL | A | 146 | 20.331 | 41.426 | 35.725 | 1.00 | 22.80 |
| ATOM | 696 | O   | VAL | A | 146 | 19.849 | 42.386 | 35.045 | 1.00 | 22.16 |
| ATOM | 697 | CB  | VAL | A | 146 | 19.118 | 39.265 | 35.373 | 1.00 | 20.39 |
| ATOM | 698 | CG1 | VAL | A | 146 | 20.405 | 38.575 | 34.941 | 1.00 | 20.39 |
| ATOM | 699 | CG2 | VAL | A | 146 | 18.163 | 38.261 | 35.998 | 1.00 | 17.90 |
| ATOM | 700 | N   | SER | A | 147 | 21.633 | 41.251 | 35.913 | 1.00 | 22.35 |
| ATOM | 701 | CA  | SER | A | 147 | 22.615 | 42.158 | 35.309 | 1.00 | 23.39 |
| ATOM | 702 | C   | SER | A | 147 | 23.829 | 41.383 | 34.833 | 1.00 | 21.77 |
| ATOM | 703 | O   | SER | A | 147 | 24.119 | 40.242 | 35.321 | 1.00 | 20.08 |
| ATOM | 704 | CB  | SER | A | 147 | 23.059 | 43.225 | 36.316 | 1.00 | 25.41 |
| ATOM | 705 | OG  | SER | A | 147 | 21.993 | 44.107 | 36.627 | 1.00 | 31.97 |
| ATOM | 706 | N   | ILE | A | 148 | 24.534 | 41.972 | 33.878 | 1.00 | 19.69 |
| ATOM | 707 | CA  | ILE | A | 148 | 25.757 | 41.377 | 33.329 | 1.00 | 19.14 |
| ATOM | 708 | C   | ILE | A | 148 | 26.853 | 42.405 | 33.614 | 1.00 | 18.85 |
| ATOM | 709 | O   | ILE | A | 148 | 27.021 | 43.408 | 32.853 | 1.00 | 17.87 |
| ATOM | 710 | CB  | ILE | A | 148 | 25.618 | 41.137 | 31.817 | 1.00 | 18.61 |
| ATOM | 711 | CG1 | ILE | A | 148 | 24.449 | 40.181 | 31.559 | 1.00 | 19.01 |
| ATOM | 712 | CG2 | ILE | A | 148 | 26.909 | 40.564 | 31.255 | 1.00 | 17.68 |
| ATOM | 713 | CD1 | ILE | A | 148 | 24.221 | 39.864 | 30.097 | 1.00 | 19.61 |
| ATOM | 714 | N   | PRO | A | 149 | 27.601 | 42.214 | 34.711 | 1.00 | 17.99 |
| ATOM | 715 | CA  | PRO | A | 149 | 28.679 | 43.134 | 35.095 | 1.00 | 21.17 |
| ATOM | 716 | C   | PRO | A | 149 | 29.523 | 43.638 | 33.926 | 1.00 | 22.18 |
| ATOM | 717 | O   | PRO | A | 149 | 29.800 | 44.869 | 33.823 | 1.00 | 24.08 |
| ATOM | 718 | CB  | PRO | A | 149 | 29.485 | 42.317 | 36.103 | 1.00 | 19.87 |
| ATOM | 719 | CG  | PRO | A | 149 | 28.404 | 41.529 | 36.797 | 1.00 | 19.57 |
| ATOM | 720 | CD  | PRO | A | 149 | 27.542 | 41.061 | 35.628 | 1.00 | 17.55 |
| ATOM | 721 | N   | HIS | A | 150 | 29.930 | 42.733 | 33.041 | 1.00 | 23.43 |
| ATOM | 722 | CA  | HIS | A | 150 | 30.748 | 43.119 | 31.869 | 1.00 | 23.84 |
| ATOM | 723 | C   | HIS | A | 150 | 29.933 | 43.067 | 30.588 | 1.00 | 24.47 |
| ATOM | 724 | O   | HIS | A | 150 | 30.334 | 42.431 | 29.566 | 1.00 | 25.89 |
| ATOM | 725 | CB  | HIS | A | 150 | 31.968 | 42.211 | 31.765 | 1.00 | 23.54 |
| ATOM | 726 | CG  | HIS | A | 150 | 32.880 | 42.313 | 32.945 | 1.00 | 26.15 |
| ATOM | 727 | ND1 | HIS | A | 150 | 33.619 | 43.446 | 33.216 | 1.00 | 27.28 |
| ATOM | 728 | CD2 | HIS | A | 150 | 33.149 | 41.439 | 33.943 | 1.00 | 26.32 |
| ATOM | 729 | CE1 | HIS | A | 150 | 34.305 | 43.264 | 34.330 | 1.00 | 27.48 |
| ATOM | 730 | NE2 | HIS | A | 150 | 34.038 | 42.055 | 34.791 | 1.00 | 28.01 |
| ATOM | 731 | N   | GLY | A | 151 | 28.785 | 43.727 | 30.630 | 1.00 | 25.49 |
| ATOM | 732 | CA  | GLY | A | 151 | 27.906 | 43.784 | 29.485 | 1.00 | 26.41 |
| ATOM | 733 | C   | GLY | A | 151 | 27.325 | 45.179 | 29.468 | 1.00 | 27.16 |
| ATOM | 734 | O   | GLY | A | 151 | 27.981 | 46.136 | 29.983 | 1.00 | 26.97 |
| ATOM | 735 | N   | PRO | A | 152 | 26.125 | 45.370 | 28.903 | 1.00 | 28.12 |
| ATOM | 736 | CA  | PRO | A | 152 | 25.540 | 46.712 | 28.880 | 1.00 | 28.75 |
| ATOM | 737 | C   | PRO | A | 152 | 25.219 | 47.165 | 30.304 | 1.00 | 30.53 |
| ATOM | 738 | O   | PRO | A | 152 | 24.844 | 46.331 | 31.182 | 1.00 | 28.62 |
| ATOM | 739 | CB  | PRO | A | 152 | 24.294 | 46.528 | 28.017 | 1.00 | 29.49 |
| ATOM | 740 | CG  | PRO | A | 152 | 23.897 | 45.105 | 28.303 | 1.00 | 29.85 |

FIG. 1L

| | | | | | | | | | |
|---|---|---|---|---|---|---|---|---|---|
| ATOM | 741 | CD | PRO | A | 152 | 25.227 | 44.385 | 28.277 | 1.00 28.15 |
| ATOM | 742 | N | ASN | A | 153 | 25.375 | 48.457 | 30.560 | 1.00 33.03 |
| ATOM | 743 | CA | ASN | A | 153 | 25.111 | 49.016 | 31.902 | 1.00 34.39 |
| ATOM | 744 | C | ASN | A | 153 | 23.604 | 49.096 | 32.144 | 1.00 33.81 |
| ATOM | 745 | O | ASN | A | 153 | 23.009 | 50.218 | 32.222 | 1.00 33.63 |
| ATOM | 746 | CB | ASN | A | 153 | 25.755 | 50.401 | 32.009 | 1.00 37.16 |
| ATOM | 747 | CG | ASN | A | 153 | 25.680 | 50.978 | 33.406 | 1.00 38.88 |
| ATOM | 748 | OD1 | ASN | A | 153 | 25.974 | 50.272 | 34.416 | 1.00 40.17 |
| ATOM | 749 | ND2 | ASN | A | 153 | 25.309 | 52.251 | 33.504 | 1.00 39.91 |
| ATOM | 750 | N | VAL | A | 154 | 22.971 | 47.934 | 32.265 | 1.00 31.55 |
| ATOM | 751 | CA | VAL | A | 154 | 21.514 | 47.872 | 32.486 | 1.00 29.59 |
| ATOM | 752 | C | VAL | A | 154 | 21.113 | 46.739 | 33.418 | 1.00 29.47 |
| ATOM | 753 | O | VAL | A | 154 | 21.924 | 45.809 | 33.718 | 1.00 30.24 |
| ATOM | 754 | CB | VAL | A | 154 | 20.755 | 47.681 | 31.154 | 1.00 29.95 |
| ATOM | 755 | CG1 | VAL | A | 154 | 20.990 | 48.875 | 30.242 | 1.00 29.70 |
| ATOM | 756 | CG2 | VAL | A | 154 | 21.216 | 46.397 | 30.474 | 1.00 28.94 |
| ATOM | 757 | N | THR | A | 155 | 19.874 | 46.799 | 33.882 | 1.00 27.83 |
| ATOM | 758 | CA | THR | A | 155 | 19.323 | 45.773 | 34.779 | 1.00 27.61 |
| ATOM | 759 | C | THR | A | 155 | 17.918 | 45.472 | 34.296 | 1.00 26.01 |
| ATOM | 760 | O | THR | A | 155 | 17.114 | 46.413 | 34.041 | 1.00 27.70 |
| ATOM | 761 | CB | THR | A | 155 | 19.268 | 46.280 | 36.229 | 1.00 27.24 |
| ATOM | 762 | OG1 | THR | A | 155 | 20.603 | 46.486 | 36.703 | 1.00 29.54 |
| ATOM | 763 | CG2 | THR | A | 155 | 18.573 | 45.270 | 37.129 | 1.00 27.37 |
| ATOM | 764 | N | VAL | A | 156 | 17.592 | 44.197 | 34.143 | 1.00 24.69 |
| ATOM | 765 | CA | VAL | A | 156 | 16.241 | 43.847 | 33.672 | 1.00 24.32 |
| ATOM | 766 | C | VAL | A | 156 | 15.631 | 42.736 | 34.504 | 1.00 23.23 |
| ATOM | 767 | O | VAL | A | 156 | 16.364 | 41.920 | 35.154 | 1.00 23.57 |
| ATOM | 768 | CB | VAL | A | 156 | 16.253 | 43.402 | 32.184 | 1.00 25.34 |
| ATOM | 769 | CG1 | VAL | A | 156 | 17.178 | 44.302 | 31.379 | 1.00 26.63 |
| ATOM | 770 | CG2 | VAL | A | 156 | 16.684 | 41.960 | 32.063 | 1.00 24.89 |
| ATOM | 771 | N | ARG | A | 157 | 14.306 | 42.687 | 34.521 | 1.00 21.44 |
| ATOM | 772 | CA | ARG | A | 157 | 13.613 | 41.626 | 35.262 | 1.00 20.90 |
| ATOM | 773 | C | ARG | A | 157 | 13.374 | 40.560 | 34.215 | 1.00 20.13 |
| ATOM | 774 | O | ARG | A | 157 | 12.746 | 40.836 | 33.152 | 1.00 19.99 |
| ATOM | 775 | CB | ARG | A | 157 | 12.280 | 42.121 | 35.830 | 1.00 20.03 |
| ATOM | 776 | CG | ARG | A | 157 | 11.528 | 41.053 | 36.621 | 1.00 18.95 |
| ATOM | 777 | CD | ARG | A | 157 | 10.271 | 41.616 | 37.260 | 1.00 18.99 |
| ATOM | 778 | NE | ARG | A | 157 | 10.554 | 42.408 | 38.456 | 1.00 18.47 |
| ATOM | 779 | CZ | ARG | A | 157 | 10.973 | 41.902 | 39.613 | 1.00 19.19 |
| ATOM | 780 | NH1 | ARG | A | 157 | 11.167 | 40.596 | 39.747 | 1.00 18.30 |
| ATOM | 781 | NH2 | ARG | A | 157 | 11.178 | 42.703 | 40.650 | 1.00 15.82 |
| ATOM | 782 | N | ALA | A | 158 | 13.878 | 39.359 | 34.463 | 1.00 20.27 |
| ATOM | 783 | CA | ALA | A | 158 | 13.713 | 38.266 | 33.496 | 1.00 19.08 |
| ATOM | 784 | C | ALA | A | 158 | 13.279 | 36.986 | 34.175 | 1.00 19.45 |
| ATOM | 785 | O | ALA | A | 158 | 13.379 | 36.845 | 35.432 | 1.00 19.64 |
| ATOM | 786 | CB | ALA | A | 158 | 15.017 | 38.031 | 32.756 | 1.00 18.56 |
| ATOM | 787 | N | ASN | A | 159 | 12.792 | 36.053 | 33.370 | 1.00 18.08 |
| ATOM | 788 | CA | ASN | A | 159 | 12.363 | 34.756 | 33.876 | 1.00 18.21 |
| ATOM | 789 | C | ASN | A | 159 | 13.607 | 33.992 | 34.282 | 1.00 18.60 |
| ATOM | 790 | O | ASN | A | 159 | 14.666 | 34.033 | 33.577 | 1.00 19.42 |
| ATOM | 791 | CB | ASN | A | 159 | 11.601 | 33.992 | 32.797 | 1.00 16.91 |
| ATOM | 792 | CG | ASN | A | 159 | 10.282 | 34.647 | 32.459 | 1.00 18.46 |
| ATOM | 793 | OD1 | ASN | A | 159 | 9.479 | 34.978 | 33.381 | 1.00 19.46 |
| ATOM | 794 | ND2 | ASN | A | 159 | 10.020 | 34.848 | 31.174 | 1.00 16.51 |
| ATOM | 795 | N | ILE | A | 160 | 13.518 | 33.311 | 35.412 | 1.00 18.73 |
| ATOM | 796 | CA | ILE | A | 160 | 14.643 | 32.529 | 35.916 | 1.00 17.64 |
| ATOM | 797 | C | ILE | A | 160 | 14.112 | 31.191 | 36.373 | 1.00 19.09 |
| ATOM | 798 | O | ILE | A | 160 | 13.122 | 31.125 | 37.176 | 1.00 18.38 |
| ATOM | 799 | CB | ILE | A | 160 | 15.319 | 33.212 | 37.128 | 1.00 18.36 |
| ATOM | 800 | CG1 | ILE | A | 160 | 15.764 | 34.629 | 36.758 | 1.00 17.90 |
| ATOM | 801 | CG2 | ILE | A | 160 | 16.521 | 32.394 | 37.585 | 1.00 17.16 |
| ATOM | 802 | CD1 | ILE | A | 160 | 16.521 | 35.336 | 37.875 | 1.00 18.56 |

FIG. 1M

```
ATOM    803  N   ALA A 161      14.717  30.123  35.871  1.00 17.55
ATOM    804  CA  ALA A 161      14.314  28.778  36.275  1.00 18.11
ATOM    805  C   ALA A 161      15.267  28.394  37.399  1.00 18.26
ATOM    806  O   ALA A 161      16.507  28.223  37.166  1.00 17.61
ATOM    807  CB  ALA A 161      14.447  27.805  35.105  1.00 17.28
ATOM    808  N   ALA A 162      14.737  28.283  38.614  1.00 17.99
ATOM    809  CA  ALA A 162      15.567  27.901  39.775  1.00 18.02
ATOM    810  C   ALA A 162      15.746  26.382  39.774  1.00 18.52
ATOM    811  O   ALA A 162      14.835  25.619  40.207  1.00 18.43
ATOM    812  CB  ALA A 162      14.897  28.359  41.067  1.00 17.36
ATOM    813  N   ILE A 163      16.900  25.928  39.300  1.00 19.89
ATOM    814  CA  ILE A 163      17.204  24.480  39.215  1.00 18.56
ATOM    815  C   ILE A 163      17.314  23.802  40.577  1.00 20.34
ATOM    816  O   ILE A 163      18.238  24.122  41.402  1.00 19.83
ATOM    817  CB  ILE A 163      18.512  24.245  38.430  1.00 17.19
ATOM    818  CG1 ILE A 163      18.347  24.753  36.994  1.00 16.02
ATOM    819  CG2 ILE A 163      18.874  22.761  38.445  1.00 14.93
ATOM    820  CD1 ILE A 163      19.628  24.735  36.174  1.00 16.24
ATOM    821  N   THR A 164      16.409  22.860  40.826  1.00 20.42
ATOM    822  CA  THR A 164      16.379  22.122  42.112  1.00 23.01
ATOM    823  C   THR A 164      16.817  20.665  41.958  1.00 24.30
ATOM    824  O   THR A 164      17.119  19.966  42.973  1.00 26.25
ATOM    825  CB  THR A 164      14.966  22.173  42.735  1.00 22.01
ATOM    826  OG1 THR A 164      13.990  21.799  41.754  1.00 22.15
ATOM    827  CG2 THR A 164      14.656  23.584  43.214  1.00 22.73
ATOM    828  N   GLU A 165      16.858  20.187  40.721  1.00 25.84
ATOM    829  CA  GLU A 165      17.281  18.804  40.444  1.00 27.82
ATOM    830  C   GLU A 165      17.800  18.693  39.024  1.00 26.80
ATOM    831  O   GLU A 165      17.246  19.323  38.072  1.00 26.59
ATOM    832  CB  GLU A 165      16.121  17.834  40.678  1.00 31.67
ATOM    833  CG  GLU A 165      16.233  17.118  42.020  1.00 38.94
ATOM    834  CD  GLU A 165      14.913  16.568  42.519  1.00 41.54
ATOM    835  OE1 GLU A 165      14.282  15.765  41.796  1.00 44.35
ATOM    836  OE2 GLU A 165      14.510  16.940  43.644  1.00 43.84
ATOM    837  N   SER A 166      18.861  17.919  38.852  1.00 24.81
ATOM    838  CA  SER A 166      19.455  17.765  37.525  1.00 25.32
ATOM    839  C   SER A 166      20.213  16.459  37.397  1.00 25.44
ATOM    840  O   SER A 166      20.551  15.795  38.427  1.00 24.00
ATOM    841  CB  SER A 166      20.405  18.928  37.255  1.00 23.13
ATOM    842  OG  SER A 166      21.444  18.939  38.217  1.00 21.22
ATOM    843  N   ASP A 167      20.490  16.079  36.155  1.00 26.01
ATOM    844  CA  ASP A 167      21.227  14.842  35.871  1.00 26.62
ATOM    845  C   ASP A 167      22.138  15.038  34.671  1.00 25.62
ATOM    846  O   ASP A 167      21.656  15.300  33.528  1.00 24.35
ATOM    847  CB  ASP A 167      20.253  13.691  35.601  1.00 30.53
ATOM    848  CG  ASP A 167      20.966  12.370  35.387  1.00 32.67
ATOM    849  OD1 ASP A 167      21.912  12.083  36.152  1.00 36.14
ATOM    850  OD2 ASP A 167      20.586  11.615  34.469  1.00 34.63
ATOM    851  N   LYS A 168      23.440  14.930  34.910  1.00 25.32
ATOM    852  CA  LYS A 168      24.461  15.078  33.847  1.00 25.94
ATOM    853  C   LYS A 168      24.416  16.445  33.175  1.00 25.49
ATOM    854  O   LYS A 168      24.742  16.580  31.955  1.00 25.50
ATOM    855  CB  LYS A 168      24.282  13.979  32.800  1.00 27.68
ATOM    856  CG  LYS A 168      24.408  12.570  33.362  1.00 30.33
ATOM    857  CD  LYS A 168      24.117  11.532  32.292  1.00 32.36
ATOM    858  CE  LYS A 168      24.205  10.126  32.855  1.00 34.37
ATOM    859  NZ  LYS A 168      23.889   9.101  31.821  1.00 36.50
ATOM    860  N   PHE A 169      24.024  17.460  33.937  1.00 22.87
ATOM    861  CA  PHE A 169      23.942  18.835  33.418  1.00 20.96
ATOM    862  C   PHE A 169      25.158  19.616  33.897  1.00 22.06
ATOM    863  O   PHE A 169      25.983  20.119  33.069  1.00 20.71
ATOM    864  CB  PHE A 169      22.668  19.506  33.919  1.00 19.76
```

FIG. 1N

| | | | | | | | | |
|---|---|---|---|---|---|---|---|---|
| ATOM | 865 | CG | PHE | A | 169 | 22.526 | 20.931 | 33.479 | 1.00 18.95 |
| ATOM | 866 | CD1 | PHE | A | 169 | 22.400 | 21.248 | 32.130 | 1.00 18.27 |
| ATOM | 867 | CD2 | PHE | A | 169 | 22.525 | 21.963 | 34.416 | 1.00 18.36 |
| ATOM | 868 | CE1 | PHE | A | 169 | 22.275 | 22.571 | 31.720 | 1.00 16.94 |
| ATOM | 869 | CE2 | PHE | A | 169 | 22.401 | 23.287 | 34.013 | 1.00 17.25 |
| ATOM | 870 | CZ | PHE | A | 169 | 22.275 | 23.590 | 32.661 | 1.00 16.89 |
| ATOM | 871 | N | PHE | A | 170 | 25.292 | 19.738 | 35.212 | 1.00 20.46 |
| ATOM | 872 | CA | PHE | A | 170 | 26.438 | 20.452 | 35.788 | 1.00 21.45 |
| ATOM | 873 | C | PHE | A | 170 | 27.702 | 19.620 | 35.574 | 1.00 22.40 |
| ATOM | 874 | O | PHE | A | 170 | 27.675 | 18.355 | 35.665 | 1.00 22.55 |
| ATOM | 875 | CB | PHE | A | 170 | 26.205 | 20.705 | 37.281 | 1.00 19.44 |
| ATOM | 876 | CG | PHE | A | 170 | 25.079 | 21.663 | 37.559 | 1.00 18.44 |
| ATOM | 877 | CD1 | PHE | A | 170 | 23.988 | 21.276 | 38.330 | 1.00 18.45 |
| ATOM | 878 | CD2 | PHE | A | 170 | 25.098 | 22.948 | 37.025 | 1.00 16.73 |
| ATOM | 879 | CE1 | PHE | A | 170 | 22.932 | 22.154 | 38.563 | 1.00 17.50 |
| ATOM | 880 | CE2 | PHE | A | 170 | 24.046 | 23.832 | 37.253 | 1.00 17.78 |
| ATOM | 881 | CZ | PHE | A | 170 | 22.963 | 23.432 | 38.023 | 1.00 16.39 |
| ATOM | 882 | N | ILE | A | 171 | 28.805 | 20.297 | 35.272 | 1.00 23.10 |
| ATOM | 883 | CA | ILE | A | 171 | 30.095 | 19.615 | 35.043 | 1.00 22.87 |
| ATOM | 884 | C | ILE | A | 171 | 31.057 | 19.962 | 36.163 | 1.00 24.02 |
| ATOM | 885 | O | ILE | A | 171 | 31.222 | 21.162 | 36.537 | 1.00 22.48 |
| ATOM | 886 | CB | ILE | A | 171 | 30.729 | 20.048 | 33.704 | 1.00 24.70 |
| ATOM | 887 | CG1 | ILE | A | 171 | 29.823 | 19.632 | 32.544 | 1.00 22.57 |
| ATOM | 888 | CG2 | ILE | A | 171 | 32.123 | 19.434 | 33.558 | 1.00 22.35 |
| ATOM | 889 | CD1 | ILE | A | 171 | 30.319 | 20.100 | 31.192 | 1.00 23.46 |
| ATOM | 890 | N | ASN | A | 172 | 31.702 | 18.942 | 36.709 | 1.00 27.12 |
| ATOM | 891 | CA | ASN | A | 172 | 32.657 | 19.143 | 37.809 | 1.00 30.01 |
| ATOM | 892 | C | ASN | A | 172 | 33.864 | 19.975 | 37.359 | 1.00 29.57 |
| ATOM | 893 | O | ASN | A | 172 | 34.616 | 19.574 | 36.418 | 1.00 29.20 |
| ATOM | 894 | CB | ASN | A | 172 | 33.105 | 17.779 | 38.337 | 1.00 31.92 |
| ATOM | 895 | CG | ASN | A | 172 | 33.913 | 17.885 | 39.608 | 1.00 34.74 |
| ATOM | 896 | OD1 | ASN | A | 172 | 33.615 | 18.737 | 40.504 | 1.00 36.04 |
| ATOM | 897 | ND2 | ASN | A | 172 | 34.927 | 17.034 | 39.734 | 1.00 36.14 |
| ATOM | 898 | N | GLY | A | 173 | 34.049 | 21.132 | 37.991 | 1.00 28.24 |
| ATOM | 899 | CA | GLY | A | 173 | 35.166 | 22.001 | 37.659 | 1.00 27.99 |
| ATOM | 900 | C | GLY | A | 173 | 34.973 | 22.938 | 36.476 | 1.00 28.87 |
| ATOM | 901 | O | GLY | A | 173 | 35.944 | 23.644 | 36.063 | 1.00 29.20 |
| ATOM | 902 | N | SER | A | 174 | 33.769 | 22.988 | 35.914 | 1.00 28.95 |
| ATOM | 903 | CA | SER | A | 174 | 33.498 | 23.880 | 34.748 | 1.00 29.13 |
| ATOM | 904 | C | SER | A | 174 | 33.524 | 25.348 | 35.168 | 1.00 27.92 |
| ATOM | 905 | O | SER | A | 174 | 33.878 | 26.255 | 34.354 | 1.00 29.51 |
| ATOM | 906 | CB | SER | A | 174 | 32.130 | 23.562 | 34.148 | 1.00 28.90 |
| ATOM | 907 | OG | SER | A | 174 | 31.102 | 23.922 | 35.054 | 1.00 30.49 |
| ATOM | 908 | N | ASN | A | 175 | 33.140 | 25.593 | 36.416 | 1.00 25.45 |
| ATOM | 909 | CA | ASN | A | 175 | 33.095 | 26.951 | 37.011 | 1.00 23.59 |
| ATOM | 910 | C | ASN | A | 175 | 31.855 | 27.767 | 36.647 | 1.00 21.71 |
| ATOM | 911 | O | ASN | A | 175 | 31.828 | 29.019 | 36.853 | 1.00 20.11 |
| ATOM | 912 | CB | ASN | A | 175 | 34.354 | 27.754 | 36.662 | 1.00 27.01 |
| ATOM | 913 | CG | ASN | A | 175 | 34.548 | 28.950 | 37.582 | 1.00 29.09 |
| ATOM | 914 | OD1 | ASN | A | 175 | 34.648 | 28.794 | 38.840 | 1.00 30.19 |
| ATOM | 915 | ND2 | ASN | A | 175 | 34.600 | 30.144 | 37.004 | 1.00 30.01 |
| ATOM | 916 | N | TRP | A | 176 | 30.841 | 27.121 | 36.078 | 1.00 16.70 |
| ATOM | 917 | CA | TRP | A | 176 | 29.590 | 27.847 | 35.790 | 1.00 18.41 |
| ATOM | 918 | C | TRP | A | 176 | 28.482 | 27.170 | 36.580 | 1.00 17.87 |
| ATOM | 919 | O | TRP | A | 176 | 28.534 | 25.927 | 36.838 | 1.00 15.45 |
| ATOM | 920 | CB | TRP | A | 176 | 29.248 | 27.888 | 34.292 | 1.00 16.48 |
| ATOM | 921 | CG | TRP | A | 176 | 29.257 | 26.588 | 33.563 | 1.00 17.63 |
| ATOM | 922 | CD1 | TRP | A | 176 | 30.291 | 26.063 | 32.842 | 1.00 17.33 |
| ATOM | 923 | CD2 | TRP | A | 176 | 28.165 | 25.668 | 33.425 | 1.00 17.78 |
| ATOM | 924 | NE1 | TRP | A | 176 | 29.911 | 24.881 | 32.258 | 1.00 16.01 |
| ATOM | 925 | CE2 | TRP | A | 176 | 28.612 | 24.613 | 32.599 | 1.00 16.95 |
| ATOM | 926 | CE3 | TRP | A | 176 | 26.852 | 25.635 | 33.918 | 1.00 18.29 |

FIG. 10

| ATOM | 927 | CZ2 | TRP A 176 | 27.794 | 23.532 | 32.252 | 1.00 | 17.40 |
|------|-----|-----|-----------|--------|--------|--------|------|-------|
| ATOM | 928 | CZ3 | TRP A 176 | 26.034 | 24.557 | 33.573 | 1.00 | 19.02 |
| ATOM | 929 | CH2 | TRP A 176 | 26.512 | 23.521 | 32.747 | 1.00 | 19.06 |
| ATOM | 930 | N | GLU A 177 | 27.496 | 27.950 | 37.005 | 1.00 | 18.68 |
| ATOM | 931 | CA | GLU A 177 | 26.387 | 27.385 | 37.797 | 1.00 | 21.01 |
| ATOM | 932 | C | GLU A 177 | 25.024 | 27.700 | 37.224 | 1.00 | 20.81 |
| ATOM | 933 | O | GLU A 177 | 23.977 | 27.582 | 37.938 | 1.00 | 21.08 |
| ATOM | 934 | CB | GLU A 177 | 26.461 | 27.869 | 39.250 | 1.00 | 22.84 |
| ATOM | 935 | CG | GLU A 177 | 26.865 | 29.322 | 39.443 | 1.00 | 26.63 |
| ATOM | 936 | CD | GLU A 177 | 28.377 | 29.531 | 39.446 | 1.00 | 27.90 |
| ATOM | 937 | OE1 | GLU A 177 | 29.121 | 28.568 | 39.726 | 1.00 | 28.44 |
| ATOM | 938 | OE2 | GLU A 177 | 28.818 | 30.670 | 39.186 | 1.00 | 28.24 |
| ATOM | 939 | N | GLY A 178 | 25.007 | 28.088 | 35.953 | 1.00 | 18.48 |
| ATOM | 940 | CA | GLY A 178 | 23.759 | 28.411 | 35.295 | 1.00 | 16.82 |
| ATOM | 941 | C | GLY A 178 | 23.929 | 28.406 | 33.791 | 1.00 | 15.90 |
| ATOM | 942 | O | GLY A 178 | 25.070 | 28.248 | 33.264 | 1.00 | 15.75 |
| ATOM | 943 | N | ILE A 179 | 22.831 | 28.589 | 33.076 | 1.00 | 14.53 |
| ATOM | 944 | CA | ILE A 179 | 22.882 | 28.588 | 31.610 | 1.00 | 14.26 |
| ATOM | 945 | C | ILE A 179 | 22.007 | 29.701 | 31.057 | 1.00 | 14.53 |
| ATOM | 946 | O | ILE A 179 | 20.896 | 29.980 | 31.603 | 1.00 | 15.23 |
| ATOM | 947 | CB | ILE A 179 | 22.428 | 27.217 | 31.069 | 1.00 | 14.45 |
| ATOM | 948 | CG1 | ILE A 179 | 22.535 | 27.183 | 29.548 | 1.00 | 14.28 |
| ATOM | 949 | CG2 | ILE A 179 | 21.002 | 26.921 | 31.525 | 1.00 | 13.41 |
| ATOM | 950 | CD1 | ILE A 179 | 22.359 | 25.788 | 28.974 | 1.00 | 13.85 |
| ATOM | 951 | N | LEU A 180 | 22.489 | 30.350 | 29.998 | 1.00 | 14.91 |
| ATOM | 952 | CA | LEU A 180 | 21.763 | 31.464 | 29.353 | 1.00 | 14.24 |
| ATOM | 953 | C | LEU A 180 | 21.311 | 31.050 | 27.961 | 1.00 | 15.19 |
| ATOM | 954 | O | LEU A 180 | 22.117 | 31.115 | 26.973 | 1.00 | 15.79 |
| ATOM | 955 | CB | LEU A 180 | 22.675 | 32.690 | 29.223 | 1.00 | 14.83 |
| ATOM | 956 | CG | LEU A 180 | 22.078 | 34.107 | 29.257 | 1.00 | 16.59 |
| ATOM | 957 | CD1 | LEU A 180 | 22.902 | 34.996 | 28.351 | 1.00 | 15.04 |
| ATOM | 958 | CD2 | LEU A 180 | 20.622 | 34.120 | 28.818 | 1.00 | 17.08 |
| ATOM | 959 | N | GLY A 181 | 20.057 | 30.621 | 27.851 | 1.00 | 15.40 |
| ATOM | 960 | CA | GLY A 181 | 19.525 | 30.227 | 26.561 | 1.00 | 13.68 |
| ATOM | 961 | C | GLY A 181 | 19.276 | 31.481 | 25.741 | 1.00 | 15.03 |
| ATOM | 962 | O | GLY A 181 | 18.402 | 32.330 | 26.107 | 1.00 | 14.58 |
| ATOM | 963 | N | LEU A 182 | 20.002 | 31.629 | 24.638 | 1.00 | 12.84 |
| ATOM | 964 | CA | LEU A 182 | 19.859 | 32.831 | 23.787 | 1.00 | 13.53 |
| ATOM | 965 | C | LEU A 182 | 19.029 | 32.646 | 22.521 | 1.00 | 14.25 |
| ATOM | 966 | O | LEU A 182 | 18.883 | 33.607 | 21.701 | 1.00 | 13.52 |
| ATOM | 967 | CB | LEU A 182 | 21.250 | 33.352 | 23.418 | 1.00 | 13.44 |
| ATOM | 968 | CG | LEU A 182 | 22.036 | 33.949 | 24.583 | 1.00 | 11.84 |
| ATOM | 969 | CD1 | LEU A 182 | 23.506 | 34.067 | 24.211 | 1.00 | 11.17 |
| ATOM | 970 | CD2 | LEU A 182 | 21.450 | 35.311 | 24.936 | 1.00 | 12.14 |
| ATOM | 971 | N | ALA A 183 | 18.491 | 31.449 | 22.322 | 1.00 | 15.12 |
| ATOM | 972 | CA | ALA A 183 | 17.660 | 31.183 | 21.131 | 1.00 | 15.16 |
| ATOM | 973 | C | ALA A 183 | 16.276 | 31.788 | 21.361 | 1.00 | 17.66 |
| ATOM | 974 | O | ALA A 183 | 16.053 | 32.526 | 22.377 | 1.00 | 16.26 |
| ATOM | 975 | CB | ALA A 183 | 17.557 | 29.684 | 20.875 | 1.00 | 14.23 |
| ATOM | 976 | N | TYR A 184 | 15.338 | 31.487 | 20.466 | 1.00 | 18.41 |
| ATOM | 977 | CA | TYR A 184 | 13.976 | 32.060 | 20.550 | 1.00 | 17.40 |
| ATOM | 978 | C | TYR A 184 | 12.953 | 31.334 | 21.424 | 1.00 | 18.41 |
| ATOM | 979 | O | TYR A 184 | 13.131 | 30.135 | 21.807 | 1.00 | 14.95 |
| ATOM | 980 | CB | TYR A 184 | 13.411 | 32.237 | 19.138 | 1.00 | 18.07 |
| ATOM | 981 | CG | TYR A 184 | 14.327 | 33.017 | 18.216 | 1.00 | 19.50 |
| ATOM | 982 | CD1 | TYR A 184 | 15.295 | 32.367 | 17.446 | 1.00 | 19.23 |
| ATOM | 983 | CD2 | TYR A 184 | 14.233 | 34.408 | 18.119 | 1.00 | 19.65 |
| ATOM | 984 | CE1 | TYR A 184 | 16.144 | 33.083 | 16.599 | 1.00 | 19.22 |
| ATOM | 985 | CE2 | TYR A 184 | 15.079 | 35.134 | 17.279 | 1.00 | 19.50 |
| ATOM | 986 | CZ | TYR A 184 | 16.027 | 34.466 | 16.521 | 1.00 | 19.86 |
| ATOM | 987 | OH | TYR A 184 | 16.842 | 35.185 | 15.670 | 1.00 | 20.69 |
| ATOM | 988 | N | ALA A 185 | 11.873 | 32.046 | 21.734 | 1.00 | 16.29 |

FIG. 1P

```
ATOM    989  CA   ALA A 185      10.784  31.519  22.592  1.00 17.90
ATOM    990  C    ALA A 185      10.185  30.221  22.068  1.00 17.38
ATOM    991  O    ALA A 185       9.682  29.372  22.869  1.00 15.41
ATOM    992  CB   ALA A 185       9.690  32.579  22.742  1.00 15.99
ATOM    993  N    GLU A 186      10.232  30.046  20.751  1.00 20.56
ATOM    994  CA   GLU A 186       9.679  28.846  20.086  1.00 23.43
ATOM    995  C    GLU A 186      10.169  27.533  20.690  1.00 23.87
ATOM    996  O    GLU A 186       9.448  26.486  20.619  1.00 24.67
ATOM    997  CB   GLU A 186      10.009  28.887  18.591  1.00 27.60
ATOM    998  CG   GLU A 186       9.447  27.729  17.786  1.00 32.42
ATOM    999  CD   GLU A 186       7.941  27.593  17.923  1.00 36.08
ATOM   1000  OE1  GLU A 186       7.255  28.633  18.041  1.00 39.03
ATOM   1001  OE2  GLU A 186       7.439  26.448  17.900  1.00 37.05
ATOM   1002  N    ILE A 187      11.363  27.540  21.283  1.00 22.31
ATOM   1003  CA   ILE A 187      11.904  26.302  21.900  1.00 19.35
ATOM   1004  C    ILE A 187      12.113  26.441  23.403  1.00 20.13
ATOM   1005  O    ILE A 187      12.887  25.654  24.034  1.00 19.35
ATOM   1006  CB   ILE A 187      13.241  25.872  21.248  1.00 19.03
ATOM   1007  CG1  ILE A 187      14.270  26.998  21.355  1.00 18.36
ATOM   1008  CG2  ILE A 187      13.008  25.488  19.795  1.00 19.03
ATOM   1009  CD1  ILE A 187      15.627  26.635  20.780  1.00 17.45
ATOM   1010  N    ALA A 188      11.441  27.416  23.999  1.00 19.82
ATOM   1011  CA   ALA A 188      11.551  27.636  25.454  1.00 20.35
ATOM   1012  C    ALA A 188      10.622  26.661  26.171  1.00 19.60
ATOM   1013  O    ALA A 188       9.554  26.277  25.618  1.00 19.52
ATOM   1014  CB   ALA A 188      11.160  29.083  25.793  1.00 17.16
ATOM   1015  N    ARG A 189      11.004  26.231  27.372  1.00 20.77
ATOM   1016  CA   ARG A 189      10.142  25.324  28.164  1.00 21.43
ATOM   1017  C    ARG A 189       9.577  26.162  29.303  1.00 22.80
ATOM   1018  O    ARG A 189      10.274  27.099  29.817  1.00 23.68
ATOM   1019  CB   ARG A 189      10.949  24.151  28.753  1.00 22.36
ATOM   1020  CG   ARG A 189      11.689  23.285  27.729  1.00 23.90
ATOM   1021  CD   ARG A 189      10.765  22.818  26.624  1.00 24.33
ATOM   1022  NE   ARG A 189      11.419  21.914  25.681  1.00 25.35
ATOM   1023  CZ   ARG A 189      11.336  20.586  25.724  1.00 27.35
ATOM   1024  NH1  ARG A 189      10.620  19.991  26.673  1.00 24.73
ATOM   1025  NH2  ARG A 189      11.959  19.849  24.807  1.00 25.42
ATOM   1026  N    PRO A 190       8.325  25.890  29.725  1.00 23.27
ATOM   1027  CA   PRO A 190       7.442  24.830  29.216  1.00 23.21
ATOM   1028  C    PRO A 190       6.826  25.110  27.849  1.00 23.72
ATOM   1029  O    PRO A 190       6.458  24.157  27.101  1.00 23.77
ATOM   1030  CB   PRO A 190       6.377  24.713  30.305  1.00 22.63
ATOM   1031  CG   PRO A 190       6.285  26.115  30.830  1.00 24.33
ATOM   1032  CD   PRO A 190       7.745  26.527  30.921  1.00 22.73
ATOM   1033  N    ASP A 191       6.681  26.383  27.508  1.00 25.20
ATOM   1034  CA   ASP A 191       6.107  26.754  26.202  1.00 25.89
ATOM   1035  C    ASP A 191       6.653  28.106  25.770  1.00 25.76
ATOM   1036  O    ASP A 191       7.488  28.716  26.498  1.00 24.40
ATOM   1037  CB   ASP A 191       4.569  26.757  26.269  1.00 28.36
ATOM   1038  CG   ASP A 191       4.024  27.697  27.323  1.00 30.16
ATOM   1039  OD1  ASP A 191       2.887  27.468  27.783  1.00 33.88
ATOM   1040  OD2  ASP A 191       4.714  28.669  27.686  1.00 30.53
ATOM   1041  N    ASP A 192       6.214  28.596  24.617  1.00 26.01
ATOM   1042  CA   ASP A 192       6.724  29.877  24.088  1.00 26.22
ATOM   1043  C    ASP A 192       6.236  31.123  24.813  1.00 26.52
ATOM   1044  O    ASP A 192       6.567  32.275  24.395  1.00 26.27
ATOM   1045  CB   ASP A 192       6.419  29.985  22.589  1.00 27.69
ATOM   1046  CG   ASP A 192       4.940  30.161  22.296  1.00 29.61
ATOM   1047  OD1  ASP A 192       4.102  29.647  23.066  1.00 31.87
ATOM   1048  OD2  ASP A 192       4.618  30.805  21.279  1.00 30.31
ATOM   1049  N    SER A 193       5.470  30.947  25.885  1.00 24.46
ATOM   1050  CA   SER A 193       4.988  32.117  26.645  1.00 24.21
```

FIG. 1Q

| | | | | | | | | | |
|---|---|---|---|---|---|---|---|---|---|
| ATOM | 1051 | C | SER | A | 193 | 6.078 | 32.565 | 27.614 | 1.00 22.68 |
| ATOM | 1052 | O | SER | A | 193 | 6.082 | 33.740 | 28.082 | 1.00 22.41 |
| ATOM | 1053 | CB | SER | A | 193 | 3.701 | 31.787 | 27.415 | 1.00 25.67 |
| ATOM | 1054 | OG | SER | A | 193 | 3.910 | 30.774 | 28.386 | 1.00 27.13 |
| ATOM | 1055 | N | LEU | A | 194 | 7.009 | 31.670 | 27.932 | 1.00 20.84 |
| ATOM | 1056 | CA | LEU | A | 194 | 8.107 | 32.044 | 28.852 | 1.00 18.87 |
| ATOM | 1057 | C | LEU | A | 194 | 9.149 | 32.830 | 28.065 | 1.00 18.82 |
| ATOM | 1058 | O | LEU | A | 194 | 10.066 | 32.240 | 27.419 | 1.00 19.19 |
| ATOM | 1059 | CB | LEU | A | 194 | 8.758 | 30.809 | 29.469 | 1.00 17.48 |
| ATOM | 1060 | CG | LEU | A | 194 | 9.680 | 31.201 | 30.631 | 1.00 19.18 |
| ATOM | 1061 | CD1 | LEU | A | 194 | 8.825 | 31.633 | 31.825 | 1.00 16.80 |
| ATOM | 1062 | CD2 | LEU | A | 194 | 10.585 | 30.044 | 31.014 | 1.00 16.32 |
| ATOM | 1063 | N | GLU | A | 195 | 9.025 | 34.150 | 28.095 | 1.00 18.44 |
| ATOM | 1064 | CA | GLU | A | 195 | 9.949 | 35.029 | 27.369 | 1.00 18.80 |
| ATOM | 1065 | C | GLU | A | 195 | 11.415 | 34.777 | 27.733 | 1.00 19.02 |
| ATOM | 1066 | O | GLU | A | 195 | 11.791 | 34.754 | 28.953 | 1.00 17.72 |
| ATOM | 1067 | CB | GLU | A | 195 | 9.575 | 36.485 | 27.644 | 1.00 20.83 |
| ATOM | 1068 | CG | GLU | A | 195 | 10.514 | 37.512 | 27.047 | 1.00 23.03 |
| ATOM | 1069 | CD | GLU | A | 195 | 9.989 | 38.926 | 27.204 | 1.00 24.10 |
| ATOM | 1070 | OE1 | GLU | A | 195 | 9.211 | 39.373 | 26.337 | 1.00 25.77 |
| ATOM | 1071 | OE2 | GLU | A | 195 | 10.343 | 39.585 | 28.203 | 1.00 24.06 |
| ATOM | 1072 | N | PRO | A | 196 | 12.272 | 34.559 | 26.714 | 1.00 18.43 |
| ATOM | 1073 | CA | PRO | A | 196 | 13.702 | 34.311 | 26.935 | 1.00 18.17 |
| ATOM | 1074 | C | PRO | A | 196 | 14.385 | 35.571 | 27.447 | 1.00 16.90 |
| ATOM | 1075 | O | PRO | A | 196 | 13.845 | 36.715 | 27.297 | 1.00 17.67 |
| ATOM | 1076 | CB | PRO | A | 196 | 14.210 | 33.914 | 25.546 | 1.00 17.79 |
| ATOM | 1077 | CG | PRO | A | 196 | 12.992 | 33.305 | 24.892 | 1.00 19.11 |
| ATOM | 1078 | CD | PRO | A | 196 | 11.911 | 34.287 | 25.310 | 1.00 18.58 |
| ATOM | 1079 | N | PHE | A | 197 | 15.558 | 35.405 | 28.039 | 1.00 15.80 |
| ATOM | 1080 | CA | PHE | A | 197 | 16.290 | 36.550 | 28.574 | 1.00 14.47 |
| ATOM | 1081 | C | PHE | A | 197 | 16.597 | 37.663 | 27.576 | 1.00 16.31 |
| ATOM | 1082 | O | PHE | A | 197 | 16.392 | 38.873 | 27.894 | 1.00 14.87 |
| ATOM | 1083 | CB | PHE | A | 197 | 17.595 | 36.093 | 29.217 | 1.00 12.99 |
| ATOM | 1084 | CG | PHE | A | 197 | 18.472 | 37.227 | 29.652 | 1.00 13.09 |
| ATOM | 1085 | CD1 | PHE | A | 197 | 19.376 | 37.806 | 28.767 | 1.00 12.33 |
| ATOM | 1086 | CD2 | PHE | A | 197 | 18.347 | 37.766 | 30.926 | 1.00 14.29 |
| ATOM | 1087 | CE1 | PHE | A | 197 | 20.139 | 38.907 | 29.143 | 1.00 12.22 |
| ATOM | 1088 | CE2 | PHE | A | 197 | 19.108 | 38.873 | 31.310 | 1.00 14.64 |
| ATOM | 1089 | CZ | PHE | A | 197 | 20.002 | 39.441 | 30.415 | 1.00 13.26 |
| ATOM | 1090 | N | PHE | A | 198 | 17.089 | 37.319 | 26.390 | 1.00 16.71 |
| ATOM | 1091 | CA | PHE | A | 198 | 17.427 | 38.384 | 25.431 | 1.00 17.60 |
| ATOM | 1092 | C | PHE | A | 198 | 16.212 | 39.192 | 25.001 | 1.00 17.52 |
| ATOM | 1093 | O | PHE | A | 198 | 16.317 | 40.434 | 24.774 | 1.00 16.03 |
| ATOM | 1094 | CB | PHE | A | 198 | 18.133 | 37.829 | 24.196 | 1.00 17.77 |
| ATOM | 1095 | CG | PHE | A | 198 | 19.051 | 38.826 | 23.549 | 1.00 17.92 |
| ATOM | 1096 | CD1 | PHE | A | 198 | 20.310 | 39.075 | 24.087 | 1.00 18.66 |
| ATOM | 1097 | CD2 | PHE | A | 198 | 18.633 | 39.569 | 22.455 | 1.00 16.90 |
| ATOM | 1098 | CE1 | PHE | A | 198 | 21.139 | 40.053 | 23.546 | 1.00 18.55 |
| ATOM | 1099 | CE2 | PHE | A | 198 | 19.454 | 40.551 | 21.904 | 1.00 17.96 |
| ATOM | 1100 | CZ | PHE | A | 198 | 20.708 | 40.795 | 22.451 | 1.00 18.52 |
| ATOM | 1101 | N | ASP | A | 199 | 15.066 | 38.530 | 24.879 | 1.00 17.52 |
| ATOM | 1102 | CA | ASP | A | 199 | 13.819 | 39.225 | 24.491 | 1.00 19.54 |
| ATOM | 1103 | C | ASP | A | 199 | 13.464 | 40.261 | 25.561 | 1.00 18.83 |
| ATOM | 1104 | O | ASP | A | 199 | 13.134 | 41.444 | 25.233 | 1.00 20.48 |
| ATOM | 1105 | CB | ASP | A | 199 | 12.685 | 38.210 | 24.338 | 1.00 21.95 |
| ATOM | 1106 | CG | ASP | A | 199 | 12.868 | 37.312 | 23.126 | 1.00 24.77 |
| ATOM | 1107 | OD1 | ASP | A | 199 | 12.408 | 37.687 | 22.028 | 1.00 27.27 |
| ATOM | 1108 | OD2 | ASP | A | 199 | 13.481 | 36.234 | 23.261 | 1.00 27.11 |
| ATOM | 1109 | N | SER | A | 200 | 13.530 | 39.858 | 26.829 | 1.00 17.89 |
| ATOM | 1110 | CA | SER | A | 200 | 13.223 | 40.784 | 27.947 | 1.00 16.17 |
| ATOM | 1111 | C | SER | A | 200 | 14.211 | 41.943 | 27.915 | 1.00 16.77 |
| ATOM | 1112 | O | SER | A | 200 | 13.823 | 43.140 | 28.072 | 1.00 17.20 |

FIG. 1R

| | | | | | | | | | |
|---|---|---|---|---|---|---|---|---|---|
| ATOM | 1113 | CB | SER | A | 200 | 13.336 | 40.062 | 29.292 | 1.00 14.55 |
| ATOM | 1114 | OG | SER | A | 200 | 12.386 | 39.017 | 29.400 | 1.00 14.16 |
| ATOM | 1115 | N | LEU | A | 201 | 15.481 | 41.617 | 27.711 | 1.00 16.47 |
| ATOM | 1116 | CA | LEU | A | 201 | 16.553 | 42.638 | 27.654 | 1.00 18.93 |
| ATOM | 1117 | C | LEU | A | 201 | 16.237 | 43.684 | 26.586 | 1.00 18.88 |
| ATOM | 1118 | O | LEU | A | 201 | 16.274 | 44.917 | 26.852 | 1.00 18.26 |
| ATOM | 1119 | CB | LEU | A | 201 | 17.884 | 41.953 | 27.337 | 1.00 18.68 |
| ATOM | 1120 | CG | LEU | A | 201 | 19.244 | 42.637 | 27.523 | 1.00 20.59 |
| ATOM | 1121 | CD1 | LEU | A | 201 | 19.973 | 42.616 | 26.194 | 1.00 20.98 |
| ATOM | 1122 | CD2 | LEU | A | 201 | 19.100 | 44.053 | 28.045 | 1.00 20.13 |
| ATOM | 1123 | N | VAL | A | 202 | 15.919 | 43.222 | 25.383 | 1.00 20.38 |
| ATOM | 1124 | CA | VAL | A | 202 | 15.600 | 44.130 | 24.264 | 1.00 20.23 |
| ATOM | 1125 | C | VAL | A | 202 | 14.335 | 44.938 | 24.532 | 1.00 23.13 |
| ATOM | 1126 | O | VAL | A | 202 | 14.284 | 46.175 | 24.255 | 1.00 23.36 |
| ATOM | 1127 | CB | VAL | A | 202 | 15.433 | 43.337 | 22.948 | 1.00 19.84 |
| ATOM | 1128 | CG1 | VAL | A | 202 | 14.830 | 44.228 | 21.855 | 1.00 17.60 |
| ATOM | 1129 | CG2 | VAL | A | 202 | 16.792 | 42.804 | 22.502 | 1.00 16.36 |
| ATOM | 1130 | N | LYS | A | 203 | 13.315 | 44.285 | 25.074 | 1.00 24.15 |
| ATOM | 1131 | CA | LYS | A | 203 | 12.050 | 44.985 | 25.360 | 1.00 27.77 |
| ATOM | 1132 | C | LYS | A | 203 | 12.178 | 46.049 | 26.452 | 1.00 27.47 |
| ATOM | 1133 | O | LYS | A | 203 | 11.753 | 47.223 | 26.252 | 1.00 26.63 |
| ATOM | 1134 | CB | LYS | A | 203 | 10.970 | 43.973 | 25.746 | 1.00 29.55 |
| ATOM | 1135 | CG | LYS | A | 203 | 9.609 | 44.594 | 26.008 | 1.00 34.08 |
| ATOM | 1136 | CD | LYS | A | 203 | 8.497 | 43.798 | 25.335 | 1.00 36.82 |
| ATOM | 1137 | CE | LYS | A | 203 | 8.504 | 42.342 | 25.774 | 1.00 38.97 |
| ATOM | 1138 | NZ | LYS | A | 203 | 7.512 | 41.533 | 25.012 | 1.00 40.86 |
| ATOM | 1139 | N | GLN | A | 204 | 12.771 | 45.687 | 27.585 | 1.00 26.46 |
| ATOM | 1140 | CA | GLN | A | 204 | 12.910 | 46.632 | 28.721 | 1.00 26.94 |
| ATOM | 1141 | C | GLN | A | 204 | 14.125 | 47.542 | 28.614 | 1.00 28.51 |
| ATOM | 1142 | O | GLN | A | 204 | 14.479 | 48.264 | 29.600 | 1.00 30.36 |
| ATOM | 1143 | CB | GLN | A | 204 | 13.007 | 45.848 | 30.032 | 1.00 24.17 |
| ATOM | 1144 | CG | GLN | A | 204 | 11.980 | 44.739 | 30.170 | 1.00 20.78 |
| ATOM | 1145 | CD | GLN | A | 204 | 12.270 | 43.821 | 31.342 | 1.00 20.14 |
| ATOM | 1146 | OE1 | GLN | A | 204 | 11.725 | 42.676 | 31.420 | 1.00 19.72 |
| ATOM | 1147 | NE2 | GLN | A | 204 | 13.107 | 44.279 | 32.265 | 1.00 16.56 |
| ATOM | 1148 | N | THR | A | 205 | 14.762 | 47.568 | 27.453 | 1.00 28.58 |
| ATOM | 1149 | CA | THR | A | 205 | 15.979 | 48.375 | 27.306 | 1.00 29.06 |
| ATOM | 1150 | C | THR | A | 205 | 16.186 | 48.905 | 25.885 | 1.00 30.58 |
| ATOM | 1151 | O | THR | A | 205 | 15.427 | 48.525 | 24.940 | 1.00 30.23 |
| ATOM | 1152 | CB | THR | A | 205 | 17.175 | 47.501 | 27.772 | 1.00 29.85 |
| ATOM | 1153 | OG1 | THR | A | 205 | 17.572 | 47.899 | 29.088 | 1.00 29.62 |
| ATOM | 1154 | CG2 | THR | A | 205 | 18.328 | 47.576 | 26.823 | 1.00 29.03 |
| ATOM | 1155 | N | HIS | A | 206 | 17.175 | 49.784 | 25.711 | 1.00 31.92 |
| ATOM | 1156 | CA | HIS | A | 206 | 17.488 | 50.350 | 24.372 | 1.00 33.38 |
| ATOM | 1157 | C | HIS | A | 206 | 18.548 | 49.530 | 23.637 | 1.00 32.31 |
| ATOM | 1158 | O | HIS | A | 206 | 18.905 | 49.845 | 22.460 | 1.00 31.08 |
| ATOM | 1159 | CB | HIS | A | 206 | 17.975 | 51.799 | 24.487 | 1.00 36.39 |
| ATOM | 1160 | CG | HIS | A | 206 | 16.898 | 52.773 | 24.848 | 1.00 39.92 |
| ATOM | 1161 | ND1 | HIS | A | 206 | 15.696 | 52.836 | 24.177 | 1.00 40.95 |
| ATOM | 1162 | CD2 | HIS | A | 206 | 16.849 | 53.736 | 25.800 | 1.00 40.35 |
| ATOM | 1163 | CE1 | HIS | A | 206 | 14.951 | 53.794 | 24.699 | 1.00 41.58 |
| ATOM | 1164 | NE2 | HIS | A | 206 | 15.627 | 54.356 | 25.685 | 1.00 41.65 |
| ATOM | 1165 | N | VAL | A | 207 | 19.075 | 48.501 | 24.291 | 1.00 29.55 |
| ATOM | 1166 | CA | VAL | A | 207 | 20.097 | 47.639 | 23.651 | 1.00 28.49 |
| ATOM | 1167 | C | VAL | A | 207 | 19.511 | 47.083 | 22.354 | 1.00 26.27 |
| ATOM | 1168 | O | VAL | A | 207 | 18.415 | 46.441 | 22.358 | 1.00 26.26 |
| ATOM | 1169 | CB | VAL | A | 207 | 20.498 | 46.462 | 24.572 | 1.00 28.77 |
| ATOM | 1170 | CG1 | VAL | A | 207 | 21.399 | 45.491 | 23.825 | 1.00 29.45 |
| ATOM | 1171 | CG2 | VAL | A | 207 | 21.219 | 46.987 | 25.805 | 1.00 28.52 |
| ATOM | 1172 | N | PRO | A | 208 | 20.192 | 47.311 | 21.220 | 1.00 24.42 |
| ATOM | 1173 | CA | PRO | A | 208 | 19.683 | 46.804 | 19.944 | 1.00 23.82 |
| ATOM | 1174 | C | PRO | A | 208 | 19.547 | 45.284 | 19.914 | 1.00 22.81 |

FIG. 1S

```
ATOM   1175  O    PRO A 208      20.290  44.545  20.630  1.00 21.12
ATOM   1176  CB   PRO A 208      20.689  47.343  18.926  1.00 24.65
ATOM   1177  CG   PRO A 208      21.927  47.510  19.711  1.00 25.77
ATOM   1178  CD   PRO A 208      21.441  48.062  21.025  1.00 24.39
ATOM   1179  N    ASN A 209      18.605  44.806  19.109  1.00 21.59
ATOM   1180  CA   ASN A 209      18.322  43.362  18.995  1.00 20.43
ATOM   1181  C    ASN A 209      19.390  42.599  18.222  1.00 20.52
ATOM   1182  O    ASN A 209      19.190  42.217  17.026  1.00 21.39
ATOM   1183  CB   ASN A 209      16.957  43.159  18.340  1.00 18.52
ATOM   1184  CG   ASN A 209      16.501  41.728  18.402  1.00 18.12
ATOM   1185  OD1  ASN A 209      16.968  40.948  19.281  1.00 18.32
ATOM   1186  ND2  ASN A 209      15.594  41.348  17.513  1.00 15.63
ATOM   1187  N    LEU A 210      20.514  42.346  18.883  1.00 19.53
ATOM   1188  CA   LEU A 210      21.631  41.634  18.243  1.00 19.83
ATOM   1189  C    LEU A 210      22.765  41.421  19.226  1.00 19.02
ATOM   1190  O    LEU A 210      22.958  42.238  20.176  1.00 18.52
ATOM   1191  CB   LEU A 210      22.120  42.451  17.035  1.00 21.93
ATOM   1192  CG   LEU A 210      23.534  42.305  16.456  1.00 22.75
ATOM   1193  CD1  LEU A 210      23.612  43.009  15.102  1.00 23.20
ATOM   1194  CD2  LEU A 210      24.548  42.910  17.409  1.00 24.60
ATOM   1195  N    PHE A 211      23.509  40.334  19.044  1.00 16.48
ATOM   1196  CA   PHE A 211      24.671  40.055  19.909  1.00 16.70
ATOM   1197  C    PHE A 211      25.722  39.310  19.095  1.00 16.08
ATOM   1198  O    PHE A 211      25.392  38.653  18.063  1.00 17.22
ATOM   1199  CB   PHE A 211      24.251  39.280  21.173  1.00 14.67
ATOM   1200  CG   PHE A 211      23.813  37.863  20.924  1.00 16.01
ATOM   1201  CD1  PHE A 211      24.748  36.837  20.835  1.00 14.91
ATOM   1202  CD2  PHE A 211      22.465  37.546  20.824  1.00 14.62
ATOM   1203  CE1  PHE A 211      24.344  35.515  20.653  1.00 15.05
ATOM   1204  CE2  PHE A 211      22.054  36.224  20.641  1.00 15.47
ATOM   1205  CZ   PHE A 211      22.996  35.207  20.558  1.00 12.73
ATOM   1206  N    SER A 212      26.977  39.424  19.520  1.00 17.19
ATOM   1207  CA   SER A 212      28.126  38.803  18.818  1.00 16.98
ATOM   1208  C    SER A 212      28.894  37.862  19.725  1.00 16.10
ATOM   1209  O    SER A 212      29.036  38.122  20.955  1.00 14.22
ATOM   1210  CB   SER A 212      29.094  39.888  18.349  1.00 16.89
ATOM   1211  OG   SER A 212      28.431  40.869  17.593  1.00 26.70
ATOM   1212  N    LEU A 213      29.430  36.797  19.144  1.00 14.76
ATOM   1213  CA   LEU A 213      30.194  35.819  19.930  1.00 14.81
ATOM   1214  C    LEU A 213      31.563  35.509  19.352  1.00 14.32
ATOM   1215  O    LEU A 213      31.702  35.162  18.137  1.00 12.74
ATOM   1216  CB   LEU A 213      29.394  34.522  20.060  1.00 15.67
ATOM   1217  CG   LEU A 213      28.735  34.210  21.408  1.00 18.95
ATOM   1218  CD1  LEU A 213      28.196  35.475  22.050  1.00 18.65
ATOM   1219  CD2  LEU A 213      27.627  33.185  21.192  1.00 16.46
ATOM   1220  N    GLN A 214      32.581  35.656  20.191  1.00 14.19
ATOM   1221  CA   GLN A 214      33.954  35.324  19.797  1.00 15.89
ATOM   1222  C    GLN A 214      34.407  34.258  20.778  1.00 15.04
ATOM   1223  O    GLN A 214      34.848  34.582  21.917  1.00 16.01
ATOM   1224  CB   GLN A 214      34.903  36.523  19.914  1.00 17.92
ATOM   1225  CG   GLN A 214      36.290  36.231  19.341  1.00 20.63
ATOM   1226  CD   GLN A 214      37.397  37.099  19.932  1.00 23.22
ATOM   1227  OE1  GLN A 214      38.459  37.332  19.273  1.00 24.79
ATOM   1228  NE2  GLN A 214      37.199  37.571  21.156  1.00 24.53
ATOM   1229  N    LEU A 215      34.284  32.997  20.390  1.00 14.37
ATOM   1230  CA   LEU A 215      34.729  31.890  21.262  1.00 13.74
ATOM   1231  C    LEU A 215      36.193  31.625  20.925  1.00 14.40
ATOM   1232  O    LEU A 215      36.541  31.357  19.737  1.00 14.39
ATOM   1233  CB   LEU A 215      33.872  30.644  21.005  1.00 13.94
ATOM   1234  CG   LEU A 215      32.636  30.429  21.893  1.00 14.78
ATOM   1235  CD1  LEU A 215      31.900  31.734  22.143  1.00 13.31
ATOM   1236  CD2  LEU A 215      31.723  29.407  21.240  1.00 12.97
```

FIG. 1T

```
ATOM   1237  N    CYS A 216      37.066  31.706  21.922  1.00 14.83
ATOM   1238  CA   CYS A 216      38.504  31.486  21.682  1.00 16.37
ATOM   1239  C    CYS A 216      39.066  30.196  22.263  1.00 17.20
ATOM   1240  O    CYS A 216      39.174  30.046  23.519  1.00 16.79
ATOM   1241  CB   CYS A 216      39.314  32.668  22.227  1.00 19.03
ATOM   1242  SG   CYS A 216      38.852  34.278  21.505  1.00 23.75
ATOM   1243  N    GLY A 217      39.415  29.257  21.387  1.00 15.43
ATOM   1244  CA   GLY A 217      40.018  28.021  21.843  1.00 16.40
ATOM   1245  C    GLY A 217      41.483  28.371  22.064  1.00 17.87
ATOM   1246  O    GLY A 217      42.057  29.204  21.303  1.00 17.53
ATOM   1247  N    ALA A 218      42.119  27.785  23.069  1.00 17.79
ATOM   1248  CA   ALA A 218      43.539  28.108  23.349  1.00 16.33
ATOM   1249  C    ALA A 218      44.486  27.408  22.379  1.00 17.71
ATOM   1250  O    ALA A 218      45.602  27.927  22.069  1.00 16.46
ATOM   1251  CB   ALA A 218      43.884  27.731  24.779  1.00 14.95
ATOM   1252  N    GLY A 219      44.073  26.245  21.890  1.00 16.19
ATOM   1253  CA   GLY A 219      44.909  25.505  20.970  1.00 17.57
ATOM   1254  C    GLY A 219      45.696  24.439  21.703  1.00 17.52
ATOM   1255  O    GLY A 219      46.490  23.675  21.076  1.00 16.29
ATOM   1256  N    PHE A 220      45.502  24.375  23.018  1.00 17.13
ATOM   1257  CA   PHE A 220      46.190  23.381  23.873  1.00 18.29
ATOM   1258  C    PHE A 220      45.381  23.185  25.153  1.00 19.24
ATOM   1259  O    PHE A 220      44.477  24.012  25.475  1.00 19.69
ATOM   1260  CB   PHE A 220      47.616  23.854  24.187  1.00 18.72
ATOM   1261  CG   PHE A 220      47.689  25.253  24.731  1.00 20.07
ATOM   1262  CD1  PHE A 220      47.448  25.507  26.077  1.00 20.91
ATOM   1263  CD2  PHE A 220      47.984  26.320  23.890  1.00 19.91
ATOM   1264  CE1  PHE A 220      47.505  26.809  26.576  1.00 21.79
ATOM   1265  CE2  PHE A 220      48.043  27.620  24.374  1.00 20.35
ATOM   1266  CZ   PHE A 220      47.802  27.866  25.721  1.00 21.77
ATOM   1267  N    PRO A 221      45.659  22.110  25.907  1.00 20.17
ATOM   1268  CA   PRO A 221      44.922  21.846  27.147  1.00 21.27
ATOM   1269  C    PRO A 221      45.014  22.959  28.180  1.00 23.04
ATOM   1270  O    PRO A 221      46.065  23.666  28.292  1.00 23.99
ATOM   1271  CB   PRO A 221      45.545  20.543  27.648  1.00 20.22
ATOM   1272  CG   PRO A 221      45.946  19.855  26.390  1.00 20.63
ATOM   1273  CD   PRO A 221      46.571  20.994  25.602  1.00 20.45
ATOM   1274  N    LEU A 222      43.934  23.132  28.933  1.00 25.72
ATOM   1275  CA   LEU A 222      43.873  24.158  29.991  1.00 28.32
ATOM   1276  C    LEU A 222      43.425  23.516  31.291  1.00 30.88
ATOM   1277  O    LEU A 222      42.248  23.042  31.403  1.00 31.71
ATOM   1278  CB   LEU A 222      42.880  25.261  29.620  1.00 27.52
ATOM   1279  CG   LEU A 222      43.264  26.233  28.506  1.00 27.30
ATOM   1280  CD1  LEU A 222      42.040  27.042  28.096  1.00 26.79
ATOM   1281  CD2  LEU A 222      44.382  27.143  28.983  1.00 27.13
ATOM   1282  N    ASN A 223      44.320  23.470  32.273  1.00 34.15
ATOM   1283  CA   ASN A 223      43.959  22.893  33.583  1.00 37.64
ATOM   1284  C    ASN A 223      43.014  23.882  34.254  1.00 38.54
ATOM   1285  O    ASN A 223      42.864  25.056  33.785  1.00 36.72
ATOM   1286  CB   ASN A 223      45.204  22.663  34.457  1.00 38.54
ATOM   1287  CG   ASN A 223      45.905  23.952  34.839  1.00 39.09
ATOM   1288  OD1  ASN A 223      45.268  24.903  35.375  1.00 41.39
ATOM   1289  ND2  ASN A 223      47.208  24.013  34.595  1.00 40.09
ATOM   1290  N    GLN A 224      42.380  23.444  35.335  1.00 41.79
ATOM   1291  CA   GLN A 224      41.415  24.278  36.073  1.00 43.58
ATOM   1292  C    GLN A 224      41.898  25.708  36.359  1.00 42.52
ATOM   1293  O    GLN A 224      41.138  26.705  36.126  1.00 42.75
ATOM   1294  CB   GLN A 224      41.021  23.572  37.378  1.00 46.22
ATOM   1295  CG   GLN A 224      39.629  23.956  37.827  1.00 49.86
ATOM   1296  CD   GLN A 224      39.085  23.160  38.990  1.00 51.40
ATOM   1297  OE1  GLN A 224      37.923  23.406  39.443  1.00 52.42
ATOM   1298  NE2  GLN A 224      39.866  22.215  39.496  1.00 52.75
```

FIG. 1U

```
ATOM  1299  N    SER A 225      43.133  25.852  36.831  1.00 40.27
ATOM  1300  CA   SER A 225      43.669  27.200  37.138  1.00 39.30
ATOM  1301  C    SER A 225      43.989  28.028  35.893  1.00 36.57
ATOM  1302  O    SER A 225      43.920  29.292  35.930  1.00 36.27
ATOM  1303  CB   SER A 225      44.917  27.094  38.027  1.00 40.27
ATOM  1304  OG   SER A 225      45.974  26.411  37.376  1.00 42.21
ATOM  1305  N    GLU A 226      44.339  27.364  34.796  1.00 34.29
ATOM  1306  CA   GLU A 226      44.654  28.083  33.542  1.00 32.79
ATOM  1307  C    GLU A 226      43.375  28.651  32.954  1.00 31.17
ATOM  1308  O    GLU A 226      43.354  29.815  32.454  1.00 29.09
ATOM  1309  CB   GLU A 226      45.307  27.144  32.526  1.00 33.69
ATOM  1310  CG   GLU A 226      46.708  26.696  32.902  1.00 36.40
ATOM  1311  CD   GLU A 226      47.251  25.619  31.972  1.00 37.70
ATOM  1312  OE1  GLU A 226      46.585  24.567  31.830  1.00 37.54
ATOM  1313  OE2  GLU A 226      48.340  25.823  31.389  1.00 37.14
ATOM  1314  N    VAL A 227      42.305  27.867  33.007  1.00 29.89
ATOM  1315  CA   VAL A 227      41.013  28.312  32.458  1.00 30.15
ATOM  1316  C    VAL A 227      40.512  29.547  33.203  1.00 29.84
ATOM  1317  O    VAL A 227      39.922  30.484  32.582  1.00 30.30
ATOM  1318  CB   VAL A 227      39.940  27.210  32.558  1.00 30.93
ATOM  1319  CG1  VAL A 227      38.800  27.538  31.637  1.00 32.67
ATOM  1320  CG2  VAL A 227      40.516  25.867  32.183  1.00 32.31
ATOM  1321  N    LEU A 228      40.731  29.581  34.513  1.00 28.88
ATOM  1322  CA   LEU A 228      40.292  30.726  35.336  1.00 27.31
ATOM  1323  C    LEU A 228      41.059  31.992  34.975  1.00 27.59
ATOM  1324  O    LEU A 228      40.491  33.129  35.020  1.00 27.84
ATOM  1325  CB   LEU A 228      40.496  30.420  36.819  1.00 27.50
ATOM  1326  CG   LEU A 228      39.700  29.259  37.419  1.00 29.32
ATOM  1327  CD1  LEU A 228      40.129  29.053  38.867  1.00 28.16
ATOM  1328  CD2  LEU A 228      38.205  29.549  37.339  1.00 28.58
ATOM  1329  N    ALA A 229      42.327  31.835  34.610  1.00 27.12
ATOM  1330  CA   ALA A 229      43.176  32.998  34.257  1.00 27.64
ATOM  1331  C    ALA A 229      43.134  33.347  32.776  1.00 27.65
ATOM  1332  O    ALA A 229      43.460  34.504  32.375  1.00 29.94
ATOM  1333  CB   ALA A 229      44.617  32.736  34.682  1.00 27.52
ATOM  1334  N    SER A 230      42.736  32.393  31.947  1.00 26.68
ATOM  1335  CA   SER A 230      42.692  32.635  30.498  1.00 26.33
ATOM  1336  C    SER A 230      41.438  33.360  30.032  1.00 26.22
ATOM  1337  O    SER A 230      40.356  33.302  30.695  1.00 25.70
ATOM  1338  CB   SER A 230      42.815  31.310  29.746  1.00 26.07
ATOM  1339  OG   SER A 230      42.759  31.519  28.344  1.00 26.54
ATOM  1340  N    VAL A 231      41.562  34.056  28.909  1.00 25.03
ATOM  1341  CA   VAL A 231      40.415  34.764  28.320  1.00 24.89
ATOM  1342  C    VAL A 231      39.785  33.776  27.346  1.00 24.75
ATOM  1343  O    VAL A 231      40.453  33.310  26.371  1.00 25.97
ATOM  1344  CB   VAL A 231      40.859  36.043  27.568  1.00 24.38
ATOM  1345  CG1  VAL A 231      39.729  36.554  26.678  1.00 22.98
ATOM  1346  CG2  VAL A 231      41.244  37.119  28.577  1.00 23.20
ATOM  1347  N    GLY A 232      38.526  33.433  27.588  1.00 23.26
ATOM  1348  CA   GLY A 232      37.846  32.481  26.729  1.00 22.77
ATOM  1349  C    GLY A 232      37.125  33.081  25.538  1.00 21.57
ATOM  1350  O    GLY A 232      36.590  32.324  24.666  1.00 20.69
ATOM  1351  N    GLY A 233      37.078  34.408  25.468  1.00 19.21
ATOM  1352  CA   GLY A 233      36.410  35.050  24.353  1.00 17.96
ATOM  1353  C    GLY A 233      35.599  36.275  24.731  1.00 18.25
ATOM  1354  O    GLY A 233      35.778  36.866  25.851  1.00 15.19
ATOM  1355  N    SER A 234      34.708  36.677  23.828  1.00 16.58
ATOM  1356  CA   SER A 234      33.864  37.864  24.053  1.00 16.83
ATOM  1357  C    SER A 234      32.423  37.667  23.599  1.00 17.82
ATOM  1358  O    SER A 234      32.134  36.995  22.552  1.00 17.90
ATOM  1359  CB   SER A 234      34.426  39.072  23.291  1.00 16.36
ATOM  1360  OG   SER A 234      35.816  39.253  23.508  1.00 18.23
```

FIG. 1V

| ATOM | 1361 | N | MET | A | 235 | 31.506 | 38.227 | 24.372 | 1.00 | 18.00 |
| ATOM | 1362 | CA | MET | A | 235 | 30.091 | 38.201 | 24.010 | 1.00 | 17.58 |
| ATOM | 1363 | C | MET | A | 235 | 29.732 | 39.677 | 23.996 | 1.00 | 18.27 |
| ATOM | 1364 | O | MET | A | 235 | 29.594 | 40.322 | 25.087 | 1.00 | 19.03 |
| ATOM | 1365 | CB | MET | A | 235 | 29.232 | 37.475 | 25.046 | 1.00 | 16.91 |
| ATOM | 1366 | CG | MET | A | 235 | 27.759 | 37.455 | 24.634 | 1.00 | 17.60 |
| ATOM | 1367 | SD | MET | A | 235 | 26.597 | 36.751 | 25.819 | 1.00 | 20.56 |
| ATOM | 1368 | CE | MET | A | 235 | 25.105 | 36.803 | 24.857 | 1.00 | 21.69 |
| ATOM | 1369 | N | ILE | A | 236 | 29.629 | 40.248 | 22.801 | 1.00 | 19.70 |
| ATOM | 1370 | CA | ILE | A | 236 | 29.271 | 41.669 | 22.674 | 1.00 | 19.40 |
| ATOM | 1371 | C | ILE | A | 236 | 27.764 | 41.758 | 22.522 | 1.00 | 20.06 |
| ATOM | 1372 | O | ILE | A | 236 | 27.175 | 41.365 | 21.467 | 1.00 | 16.87 |
| ATOM | 1373 | CB | ILE | A | 236 | 29.985 | 42.341 | 21.470 | 1.00 | 21.41 |
| ATOM | 1374 | CG1 | ILE | A | 236 | 31.452 | 42.625 | 21.821 | 1.00 | 22.57 |
| ATOM | 1375 | CG2 | ILE | A | 236 | 29.329 | 43.672 | 21.149 | 1.00 | 21.72 |
| ATOM | 1376 | CD1 | ILE | A | 236 | 32.243 | 41.426 | 22.228 | 1.00 | 25.65 |
| ATOM | 1377 | N | ILE | A | 237 | 27.122 | 42.246 | 23.575 | 1.00 | 20.16 |
| ATOM | 1378 | CA | ILE | A | 237 | 25.663 | 42.382 | 23.599 | 1.00 | 21.01 |
| ATOM | 1379 | C | ILE | A | 237 | 25.215 | 43.710 | 22.996 | 1.00 | 22.16 |
| ATOM | 1380 | O | ILE | A | 237 | 25.620 | 44.812 | 23.472 | 1.00 | 22.96 |
| ATOM | 1381 | CB | ILE | A | 237 | 25.153 | 42.241 | 25.050 | 1.00 | 21.36 |
| ATOM | 1382 | CG1 | ILE | A | 237 | 25.346 | 40.791 | 25.498 | 1.00 | 22.29 |
| ATOM | 1383 | CG2 | ILE | A | 237 | 23.694 | 42.660 | 25.156 | 1.00 | 20.45 |
| ATOM | 1384 | CD1 | ILE | A | 237 | 25.002 | 40.529 | 26.939 | 1.00 | 24.84 |
| ATOM | 1385 | N | GLY | A | 238 | 24.404 | 43.626 | 21.946 | 1.00 | 23.30 |
| ATOM | 1386 | CA | GLY | A | 238 | 23.903 | 44.820 | 21.288 | 1.00 | 25.11 |
| ATOM | 1387 | C | GLY | A | 238 | 24.821 | 45.437 | 20.244 | 1.00 | 26.35 |
| ATOM | 1388 | O | GLY | A | 238 | 24.644 | 46.640 | 19.874 | 1.00 | 27.08 |
| ATOM | 1389 | N | GLY | A | 239 | 25.792 | 44.681 | 19.743 | 1.00 | 25.50 |
| ATOM | 1390 | CA | GLY | A | 239 | 26.679 | 45.251 | 18.747 | 1.00 | 24.81 |
| ATOM | 1391 | C | GLY | A | 239 | 27.807 | 44.371 | 18.242 | 1.00 | 26.38 |
| ATOM | 1392 | O | GLY | A | 239 | 27.942 | 43.167 | 18.632 | 1.00 | 23.61 |
| ATOM | 1393 | N | ILE | A | 240 | 28.632 | 44.960 | 17.383 | 1.00 | 26.33 |
| ATOM | 1394 | CA | ILE | A | 240 | 29.780 | 44.273 | 16.758 | 1.00 | 25.87 |
| ATOM | 1395 | C | ILE | A | 240 | 31.067 | 45.033 | 17.055 | 1.00 | 26.95 |
| ATOM | 1396 | O | ILE | A | 240 | 31.121 | 46.287 | 16.882 | 1.00 | 28.86 |
| ATOM | 1397 | CB | ILE | A | 240 | 29.607 | 44.226 | 15.226 | 1.00 | 25.88 |
| ATOM | 1398 | CG1 | ILE | A | 240 | 28.298 | 43.519 | 14.871 | 1.00 | 25.12 |
| ATOM | 1399 | CG2 | ILE | A | 240 | 30.806 | 43.541 | 14.581 | 1.00 | 26.56 |
| ATOM | 1400 | CD1 | ILE | A | 240 | 27.939 | 43.599 | 13.396 | 1.00 | 24.59 |
| ATOM | 1401 | N | ASP | A | 241 | 32.100 | 44.323 | 17.498 | 1.00 | 25.24 |
| ATOM | 1402 | CA | ASP | A | 241 | 33.395 | 44.973 | 17.781 | 1.00 | 25.13 |
| ATOM | 1403 | C | ASP | A | 241 | 34.383 | 44.548 | 16.698 | 1.00 | 26.31 |
| ATOM | 1404 | O | ASP | A | 241 | 34.676 | 43.326 | 16.536 | 1.00 | 26.89 |
| ATOM | 1405 | CB | ASP | A | 241 | 33.922 | 44.561 | 19.153 | 1.00 | 24.85 |
| ATOM | 1406 | CG | ASP | A | 241 | 35.171 | 45.325 | 19.541 | 1.00 | 24.81 |
| ATOM | 1407 | OD1 | ASP | A | 241 | 35.144 | 46.032 | 20.567 | 1.00 | 27.86 |
| ATOM | 1408 | OD2 | ASP | A | 241 | 36.180 | 45.226 | 18.817 | 1.00 | 25.69 |
| ATOM | 1409 | N | HIS | A | 242 | 34.913 | 45.517 | 15.960 | 1.00 | 26.86 |
| ATOM | 1410 | CA | HIS | A | 242 | 35.853 | 45.222 | 14.852 | 1.00 | 27.45 |
| ATOM | 1411 | C | HIS | A | 242 | 37.197 | 44.613 | 15.221 | 1.00 | 25.41 |
| ATOM | 1412 | O | HIS | A | 242 | 37.871 | 43.998 | 14.347 | 1.00 | 23.94 |
| ATOM | 1413 | CB | HIS | A | 242 | 36.085 | 46.481 | 14.013 | 1.00 | 32.38 |
| ATOM | 1414 | CG | HIS | A | 242 | 34.858 | 46.957 | 13.304 | 1.00 | 37.46 |
| ATOM | 1415 | ND1 | HIS | A | 242 | 33.822 | 47.591 | 13.956 | 1.00 | 39.65 |
| ATOM | 1416 | CD2 | HIS | A | 242 | 34.472 | 46.837 | 12.011 | 1.00 | 39.29 |
| ATOM | 1417 | CE1 | HIS | A | 242 | 32.850 | 47.840 | 13.096 | 1.00 | 40.56 |
| ATOM | 1418 | NE2 | HIS | A | 242 | 33.219 | 47.392 | 11.909 | 1.00 | 40.36 |
| ATOM | 1419 | N | SER | A | 243 | 37.615 | 44.751 | 16.471 | 1.00 | 22.23 |
| ATOM | 1420 | CA | SER | A | 243 | 38.915 | 44.184 | 16.877 | 1.00 | 22.06 |
| ATOM | 1421 | C | SER | A | 243 | 38.843 | 42.667 | 17.011 | 1.00 | 20.51 |
| ATOM | 1422 | O | SER | A | 243 | 39.897 | 41.986 | 17.130 | 1.00 | 23.23 |

FIG. 1W

| ATOM | 1423 | CB  | SER | A | 243 | 39.368 | 44.785 | 18.211 | 1.00 | 22.47 |
| ATOM | 1424 | OG  | SER | A | 243 | 38.515 | 44.386 | 19.274 | 1.00 | 23.32 |
| ATOM | 1425 | N   | LEU | A | 244 | 37.635 | 42.115 | 16.979 | 1.00 | 20.52 |
| ATOM | 1426 | CA  | LEU | A | 244 | 37.454 | 40.649 | 17.145 | 1.00 | 18.32 |
| ATOM | 1427 | C   | LEU | A | 244 | 37.535 | 39.844 | 15.860 | 1.00 | 18.66 |
| ATOM | 1428 | O   | LEU | A | 244 | 37.482 | 38.576 | 15.892 | 1.00 | 18.25 |
| ATOM | 1429 | CB  | LEU | A | 244 | 36.120 | 40.368 | 17.843 | 1.00 | 18.01 |
| ATOM | 1430 | CG  | LEU | A | 244 | 35.998 | 41.054 | 19.206 | 1.00 | 17.93 |
| ATOM | 1431 | CD1 | LEU | A | 244 | 34.689 | 40.666 | 19.885 | 1.00 | 17.04 |
| ATOM | 1432 | CD2 | LEU | A | 244 | 37.189 | 40.661 | 20.063 | 1.00 | 19.23 |
| ATOM | 1433 | N   | TYR | A | 245 | 37.666 | 40.522 | 14.729 | 1.00 | 18.73 |
| ATOM | 1434 | CA  | TYR | A | 245 | 37.756 | 39.795 | 13.459 | 1.00 | 19.72 |
| ATOM | 1435 | C   | TYR | A | 245 | 38.536 | 40.545 | 12.398 | 1.00 | 20.55 |
| ATOM | 1436 | O   | TYR | A | 245 | 38.819 | 41.771 | 12.542 | 1.00 | 21.10 |
| ATOM | 1437 | CB  | TYR | A | 245 | 36.357 | 39.494 | 12.924 | 1.00 | 19.56 |
| ATOM | 1438 | CG  | TYR | A | 245 | 35.606 | 40.708 | 12.421 | 1.00 | 20.40 |
| ATOM | 1439 | CD1 | TYR | A | 245 | 34.977 | 41.586 | 13.302 | 1.00 | 20.11 |
| ATOM | 1440 | CD2 | TYR | A | 245 | 35.512 | 40.966 | 11.055 | 1.00 | 20.70 |
| ATOM | 1441 | CE1 | TYR | A | 245 | 34.265 | 42.689 | 12.834 | 1.00 | 21.90 |
| ATOM | 1442 | CE2 | TYR | A | 245 | 34.809 | 42.060 | 10.573 | 1.00 | 22.10 |
| ATOM | 1443 | CZ  | TYR | A | 245 | 34.184 | 42.919 | 11.466 | 1.00 | 23.05 |
| ATOM | 1444 | OH  | TYR | A | 245 | 33.476 | 43.993 | 10.979 | 1.00 | 22.53 |
| ATOM | 1445 | N   | THR | A | 246 | 38.902 | 39.829 | 11.340 | 1.00 | 20.48 |
| ATOM | 1446 | CA  | THR | A | 246 | 39.621 | 40.429 | 10.195 | 1.00 | 19.46 |
| ATOM | 1447 | C   | THR | A | 246 | 38.811 | 40.054 | 8.964  | 1.00 | 19.29 |
| ATOM | 1448 | O   | THR | A | 246 | 37.999 | 39.085 | 9.000  | 1.00 | 16.84 |
| ATOM | 1449 | CB  | THR | A | 246 | 41.049 | 39.865 | 10.031 | 1.00 | 19.69 |
| ATOM | 1450 | OG1 | THR | A | 246 | 40.997 | 38.434 | 9.953  | 1.00 | 20.05 |
| ATOM | 1451 | CG2 | THR | A | 246 | 41.929 | 40.294 | 11.194 | 1.00 | 19.01 |
| ATOM | 1452 | N   | GLY | A | 247 | 38.996 | 40.793 | 7.879  | 1.00 | 19.48 |
| ATOM | 1453 | CA  | GLY | A | 247 | 38.259 | 40.490 | 6.668  | 1.00 | 19.61 |
| ATOM | 1454 | C   | GLY | A | 247 | 36.812 | 40.927 | 6.747  | 1.00 | 20.26 |
| ATOM | 1455 | O   | GLY | A | 247 | 36.412 | 41.712 | 7.660  | 1.00 | 21.64 |
| ATOM | 1456 | N   | SER | A | 248 | 36.006 | 40.437 | 5.816  | 1.00 | 21.23 |
| ATOM | 1457 | CA  | SER | A | 248 | 34.580 | 40.806 | 5.765  | 1.00 | 23.54 |
| ATOM | 1458 | C   | SER | A | 248 | 33.649 | 39.836 | 6.484  | 1.00 | 23.00 |
| ATOM | 1459 | O   | SER | A | 248 | 33.978 | 38.625 | 6.684  | 1.00 | 21.96 |
| ATOM | 1460 | CB  | SER | A | 248 | 34.135 | 40.936 | 4.304  | 1.00 | 24.06 |
| ATOM | 1461 | OG  | SER | A | 248 | 34.814 | 41.999 | 3.656  | 1.00 | 28.27 |
| ATOM | 1462 | N   | LEU | A | 249 | 32.494 | 40.355 | 6.881  | 1.00 | 23.33 |
| ATOM | 1463 | CA  | LEU | A | 249 | 31.453 | 39.551 | 7.550  | 1.00 | 23.71 |
| ATOM | 1464 | C   | LEU | A | 249 | 30.478 | 39.103 | 6.468  | 1.00 | 23.26 |
| ATOM | 1465 | O   | LEU | A | 249 | 29.913 | 39.958 | 5.721  | 1.00 | 24.66 |
| ATOM | 1466 | CB  | LEU | A | 249 | 30.687 | 40.392 | 8.576  | 1.00 | 22.83 |
| ATOM | 1467 | CG  | LEU | A | 249 | 31.234 | 40.585 | 9.992  | 1.00 | 23.68 |
| ATOM | 1468 | CD1 | LEU | A | 249 | 30.483 | 41.728 | 10.659 | 1.00 | 23.07 |
| ATOM | 1469 | CD2 | LEU | A | 249 | 31.077 | 39.299 | 10.802 | 1.00 | 22.16 |
| ATOM | 1470 | N   | TRP | A | 250 | 30.285 | 37.797 | 6.335  | 1.00 | 21.28 |
| ATOM | 1471 | CA  | TRP | A | 250 | 29.328 | 37.282 | 5.348  | 1.00 | 18.03 |
| ATOM | 1472 | C   | TRP | A | 250 | 28.115 | 36.810 | 6.115  | 1.00 | 18.51 |
| ATOM | 1473 | O   | TRP | A | 250 | 28.242 | 36.079 | 7.153  | 1.00 | 18.65 |
| ATOM | 1474 | CB  | TRP | A | 250 | 29.925 | 36.128 | 4.550  | 1.00 | 19.15 |
| ATOM | 1475 | CG  | TRP | A | 250 | 30.759 | 36.597 | 3.411  | 1.00 | 19.10 |
| ATOM | 1476 | CD1 | TRP | A | 250 | 32.061 | 36.998 | 3.456  | 1.00 | 18.51 |
| ATOM | 1477 | CD2 | TRP | A | 250 | 30.328 | 36.777 | 2.058  | 1.00 | 18.74 |
| ATOM | 1478 | NE1 | TRP | A | 250 | 32.470 | 37.418 | 2.214  | 1.00 | 18.41 |
| ATOM | 1479 | CE2 | TRP | A | 250 | 31.425 | 37.294 | 1.336  | 1.00 | 18.71 |
| ATOM | 1480 | CE3 | TRP | A | 250 | 29.118 | 36.554 | 1.386  | 1.00 | 19.61 |
| ATOM | 1481 | CZ2 | TRP | A | 250 | 31.352 | 37.594 | -0.029 | 1.00 | 18.57 |
| ATOM | 1482 | CZ3 | TRP | A | 250 | 29.043 | 36.853 | 0.026  | 1.00 | 20.92 |
| ATOM | 1483 | CH2 | TRP | A | 250 | 30.158 | 37.369 | -0.666 | 1.00 | 17.98 |
| ATOM | 1484 | N   | TYR | A | 251 | 26.939 | 37.203 | 5.644  | 1.00 | 17.22 |

FIG. 1X

```
ATOM   1485  CA   TYR A 251      25.699  36.825   6.328  1.00 16.85
ATOM   1486  C    TYR A 251      24.875  35.751   5.642  1.00 16.82
ATOM   1487  O    TYR A 251      24.668  35.782   4.397  1.00 17.05
ATOM   1488  CB   TYR A 251      24.814  38.059   6.536  1.00 17.46
ATOM   1489  CG   TYR A 251      25.389  39.070   7.493  1.00 17.27
ATOM   1490  CD1  TYR A 251      26.265  40.065   7.055  1.00 18.34
ATOM   1491  CD2  TYR A 251      25.076  39.018   8.852  1.00 16.39
ATOM   1492  CE1  TYR A 251      26.819  40.984   7.955  1.00 18.20
ATOM   1493  CE2  TYR A 251      25.622  39.925   9.753  1.00 17.81
ATOM   1494  CZ   TYR A 251      26.487  40.900   9.302  1.00 17.43
ATOM   1495  OH   TYR A 251      27.014  41.779  10.215  1.00 20.25
ATOM   1496  N    THR A 252      24.395  34.803   6.436  1.00 15.07
ATOM   1497  CA   THR A 252      23.525  33.725   5.933  1.00 14.48
ATOM   1498  C    THR A 252      22.204  33.996   6.646  1.00 16.15
ATOM   1499  O    THR A 252      22.193  34.429   7.845  1.00 16.66
ATOM   1500  CB   THR A 252      24.056  32.325   6.330  1.00 14.69
ATOM   1501  OG1  THR A 252      23.273  31.316   5.684  1.00 13.97
ATOM   1502  CG2  THR A 252      23.974  32.118   7.839  1.00 14.05
ATOM   1503  N    PRO A 253      21.070  33.774   5.972  1.00 15.93
ATOM   1504  CA   PRO A 253      19.826  34.054   6.694  1.00 17.09
ATOM   1505  C    PRO A 253      19.418  33.029   7.741  1.00 18.67
ATOM   1506  O    PRO A 253      19.782  31.813   7.653  1.00 17.11
ATOM   1507  CB   PRO A 253      18.789  34.161   5.572  1.00 17.20
ATOM   1508  CG   PRO A 253      19.304  33.207   4.545  1.00 17.18
ATOM   1509  CD   PRO A 253      20.809  33.468   4.553  1.00 17.14
ATOM   1510  N    ILE A 254      18.692  33.501   8.750  1.00 18.82
ATOM   1511  CA   ILE A 254      18.165  32.604   9.792  1.00 20.14
ATOM   1512  C    ILE A 254      16.885  32.091   9.137  1.00 21.33
ATOM   1513  O    ILE A 254      15.911  32.875   8.914  1.00 21.52
ATOM   1514  CB   ILE A 254      17.827  33.368  11.091  1.00 20.62
ATOM   1515  CG1  ILE A 254      19.124  33.752  11.806  1.00 20.82
ATOM   1516  CG2  ILE A 254      16.935  32.509  11.994  1.00 19.41
ATOM   1517  CD1  ILE A 254      18.920  34.458  13.127  1.00 22.19
ATOM   1518  N    ARG A 255      16.868  30.810   8.795  1.00 22.06
ATOM   1519  CA   ARG A 255      15.702  30.211   8.115  1.00 23.47
ATOM   1520  C    ARG A 255      14.398  30.343   8.880  1.00 24.68
ATOM   1521  O    ARG A 255      13.334  30.719   8.299  1.00 25.49
ATOM   1522  CB   ARG A 255      15.951  28.735   7.852  1.00 22.62
ATOM   1523  CG   ARG A 255      14.843  28.093   7.053  1.00 22.10
ATOM   1524  CD   ARG A 255      14.985  26.598   7.069  1.00 22.76
ATOM   1525  NE   ARG A 255      14.031  25.958   6.176  1.00 22.51
ATOM   1526  CZ   ARG A 255      13.692  24.679   6.256  1.00 22.37
ATOM   1527  NH1  ARG A 255      14.232  23.914   7.195  1.00 20.91
ATOM   1528  NH2  ARG A 255      12.819  24.166   5.396  1.00 23.78
ATOM   1529  N    ARG A 256      14.451  30.023  10.165  1.00 24.98
ATOM   1530  CA   ARG A 256      13.264  30.085  11.029  1.00 25.56
ATOM   1531  C    ARG A 256      13.723  30.441  12.438  1.00 24.84
ATOM   1532  O    ARG A 256      14.829  30.013  12.893  1.00 22.14
ATOM   1533  CB   ARG A 256      12.561  28.729  11.009  1.00 27.37
ATOM   1534  CG   ARG A 256      11.350  28.599  11.914  1.00 29.24
ATOM   1535  CD   ARG A 256      10.878  27.150  11.899  1.00 29.60
ATOM   1536  NE   ARG A 256      10.180  26.788  13.126  1.00 31.29
ATOM   1537  CZ   ARG A 256      10.043  25.543  13.563  1.00 31.25
ATOM   1538  NH1  ARG A 256      10.559  24.535  12.870  1.00 31.19
ATOM   1539  NH2  ARG A 256       9.398  25.307  14.698  1.00 32.97
ATOM   1540  N    GLU A 257      12.914  31.219  13.141  1.00 24.01
ATOM   1541  CA   GLU A 257      13.270  31.650  14.500  1.00 23.46
ATOM   1542  C    GLU A 257      12.829  30.739  15.636  1.00 23.02
ATOM   1543  O    GLU A 257      11.749  30.947  16.264  1.00 26.15
ATOM   1544  CB   GLU A 257      12.739  33.055  14.748  1.00 23.25
ATOM   1545  CG   GLU A 257      13.439  34.123  13.930  1.00 26.24
ATOM   1546  CD   GLU A 257      12.572  35.353  13.746  1.00 27.27
```

FIG. 1Y

```
ATOM  1547  OE1  GLU  A  257    13.124  36.470  13.673  1.00  27.35
ATOM  1548  OE2  GLU  A  257    11.334  35.197  13.665  1.00  30.46
ATOM  1549  N    TRP  A  258    13.632  29.719  15.898  1.00  19.64
ATOM  1550  CA   TRP  A  258    13.390  28.798  17.016  1.00  19.75
ATOM  1551  C    TRP  A  258    14.812  28.548  17.495  1.00  19.46
ATOM  1552  O    TRP  A  258    15.267  29.190  18.500  1.00  20.47
ATOM  1553  CB   TRP  A  258    12.632  27.537  16.561  1.00  18.27
ATOM  1554  CG   TRP  A  258    13.203  26.710  15.455  1.00  17.96
ATOM  1555  CD1  TRP  A  258    13.898  27.143  14.364  1.00  18.43
ATOM  1556  CD2  TRP  A  258    13.051  25.293  15.298  1.00  17.87
ATOM  1557  NE1  TRP  A  258    14.187  26.082  13.537  1.00  18.62
ATOM  1558  CE2  TRP  A  258    13.678  24.935  14.088  1.00  17.86
ATOM  1559  CE3  TRP  A  258    12.441  24.291  16.067  1.00  17.50
ATOM  1560  CZ2  TRP  A  258    13.717  23.614  13.624  1.00  19.19
ATOM  1561  CZ3  TRP  A  258    12.477  22.976  15.608  1.00  19.16
ATOM  1562  CH2  TRP  A  258    13.113  22.650  14.396  1.00  18.86
ATOM  1563  N    TYR  A  259    15.538  27.670  16.814  1.00  18.33
ATOM  1564  CA   TYR  A  259    16.965  27.458  17.126  1.00  15.42
ATOM  1565  C    TYR  A  259    17.550  28.474  16.157  1.00  16.46
ATOM  1566  O    TYR  A  259    16.789  29.066  15.323  1.00  15.71
ATOM  1567  CB   TYR  A  259    17.439  26.078  16.671  1.00  13.86
ATOM  1568  CG   TYR  A  259    17.056  24.927  17.564  1.00  13.98
ATOM  1569  CD1  TYR  A  259    17.876  24.539  18.627  1.00  13.32
ATOM  1570  CD2  TYR  A  259    15.875  24.224  17.346  1.00  12.14
ATOM  1571  CE1  TYR  A  259    17.520  23.467  19.450  1.00  15.06
ATOM  1572  CE2  TYR  A  259    15.510  23.167  18.155  1.00  14.24
ATOM  1573  CZ   TYR  A  259    16.329  22.789  19.200  1.00  14.26
ATOM  1574  OH   TYR  A  259    15.940  21.719  19.955  1.00  12.92
ATOM  1575  N    TYR  A  260    18.851  28.725  16.224  1.00  14.50
ATOM  1576  CA   TYR  A  260    19.440  29.630  15.232  1.00  15.21
ATOM  1577  C    TYR  A  260    19.716  28.718  14.037  1.00  15.90
ATOM  1578  O    TYR  A  260    20.866  28.210  13.836  1.00  16.76
ATOM  1579  CB   TYR  A  260    20.722  30.269  15.759  1.00  13.84
ATOM  1580  CG   TYR  A  260    20.426  31.416  16.690  1.00  14.32
ATOM  1581  CD1  TYR  A  260    20.534  31.270  18.078  1.00  13.41
ATOM  1582  CD2  TYR  A  260    19.996  32.642  16.187  1.00  13.45
ATOM  1583  CE1  TYR  A  260    20.224  32.320  18.933  1.00  13.15
ATOM  1584  CE2  TYR  A  260    19.680  33.699  17.037  1.00  12.56
ATOM  1585  CZ   TYR  A  260    19.801  33.530  18.404  1.00  13.22
ATOM  1586  OH   TYR  A  260    19.531  34.582  19.239  1.00  12.88
ATOM  1587  N    GLU  A  261    18.664  28.476  13.260  1.00  15.81
ATOM  1588  CA   GLU  A  261    18.741  27.586  12.081  1.00  17.54
ATOM  1589  C    GLU  A  261    19.191  28.266  10.791  1.00  17.31
ATOM  1590  O    GLU  A  261    18.665  29.355  10.402  1.00  16.63
ATOM  1591  CB   GLU  A  261    17.382  26.914  11.842  1.00  16.53
ATOM  1592  CG   GLU  A  261    17.326  26.076  10.573  1.00  19.47
ATOM  1593  CD   GLU  A  261    15.965  25.454  10.326  1.00  20.18
ATOM  1594  OE1  GLU  A  261    14.956  26.037  10.766  1.00  21.27
ATOM  1595  OE2  GLU  A  261    15.902  24.390   9.673  1.00  20.94
ATOM  1596  N    VAL  A  262    20.153  27.640  10.122  1.00  16.45
ATOM  1597  CA   VAL  A  262    20.679  28.147   8.842  1.00  16.13
ATOM  1598  C    VAL  A  262    20.620  27.006   7.831  1.00  17.33
ATOM  1599  O    VAL  A  262    20.168  25.863   8.166  1.00  17.30
ATOM  1600  CB   VAL  A  262    22.131  28.624   8.982  1.00  14.58
ATOM  1601  CG1  VAL  A  262    22.218  29.690  10.064  1.00  14.84
ATOM  1602  CG2  VAL  A  262    23.039  27.449   9.306  1.00  14.53
ATOM  1603  N    ILE  A  263    21.064  27.271   6.608  1.00  17.34
ATOM  1604  CA   ILE  A  263    21.044  26.245   5.554  1.00  16.67
ATOM  1605  C    ILE  A  263    22.419  26.042   4.931  1.00  16.64
ATOM  1606  O    ILE  A  263    23.054  27.016   4.418  1.00  17.50
ATOM  1607  CB   ILE  A  263    20.031  26.619   4.445  1.00  18.45
ATOM  1608  CG1  ILE  A  263    18.608  26.522   4.996  1.00  18.90
```

FIG. 1Z

| ATOM | 1609 | CG2 | ILE A 263 | 20.192 | 25.694 | 3.243 | 1.00 | 18.17 |
| ATOM | 1610 | CD1 | ILE A 263 | 17.541 | 26.974 | 4.023 | 1.00 | 23.31 |
| ATOM | 1611 | N | ILE A 264 | 22.897 | 24.802 | 4.988 | 1.00 | 16.67 |
| ATOM | 1612 | CA | ILE A 264 | 24.199 | 24.413 | 4.409 | 1.00 | 14.63 |
| ATOM | 1613 | C | ILE A 264 | 23.882 | 23.836 | 3.031 | 1.00 | 16.44 |
| ATOM | 1614 | O | ILE A 264 | 23.019 | 22.915 | 2.908 | 1.00 | 13.53 |
| ATOM | 1615 | CB | ILE A 264 | 24.877 | 23.320 | 5.253 | 1.00 | 14.79 |
| ATOM | 1616 | CG1 | ILE A 264 | 25.174 | 23.855 | 6.657 | 1.00 | 12.53 |
| ATOM | 1617 | CG2 | ILE A 264 | 26.154 | 22.846 | 4.563 | 1.00 | 12.07 |
| ATOM | 1618 | CD1 | ILE A 264 | 25.685 | 22.799 | 7.615 | 1.00 | 12.69 |
| ATOM | 1619 | N | VAL A 265 | 24.546 | 24.334 | 1.992 | 1.00 | 17.37 |
| ATOM | 1620 | CA | VAL A 265 | 24.258 | 23.841 | 0.627 | 1.00 | 18.64 |
| ATOM | 1621 | C | VAL A 265 | 25.368 | 23.004 | 0.006 | 1.00 | 19.95 |
| ATOM | 1622 | O | VAL A 265 | 25.202 | 22.455 | -1.127 | 1.00 | 19.29 |
| ATOM | 1623 | CB | VAL A 265 | 23.956 | 25.011 | -0.322 | 1.00 | 18.56 |
| ATOM | 1624 | CG1 | VAL A 265 | 22.874 | 25.901 | 0.287 | 1.00 | 16.70 |
| ATOM | 1625 | CG2 | VAL A 265 | 25.227 | 25.802 | -0.590 | 1.00 | 17.47 |
| ATOM | 1626 | N | ARG A 266 | 26.486 | 22.872 | 0.707 | 1.00 | 20.42 |
| ATOM | 1627 | CA | ARG A 266 | 27.617 | 22.098 | 0.165 | 1.00 | 20.48 |
| ATOM | 1628 | C | ARG A 266 | 28.752 | 22.044 | 1.162 | 1.00 | 19.59 |
| ATOM | 1629 | O | ARG A 266 | 29.030 | 23.055 | 1.885 | 1.00 | 19.51 |
| ATOM | 1630 | CB | ARG A 266 | 28.112 | 22.763 | -1.129 | 1.00 | 22.33 |
| ATOM | 1631 | CG | ARG A 266 | 29.417 | 22.218 | -1.713 | 1.00 | 22.40 |
| ATOM | 1632 | CD | ARG A 266 | 29.939 | 23.170 | -2.789 | 1.00 | 24.49 |
| ATOM | 1633 | NE | ARG A 266 | 31.244 | 22.785 | -3.322 | 1.00 | 24.49 |
| ATOM | 1634 | CZ | ARG A 266 | 31.444 | 22.266 | -4.528 | 1.00 | 26.46 |
| ATOM | 1635 | NH1 | ARG A 266 | 30.426 | 22.061 | -5.349 | 1.00 | 25.31 |
| ATOM | 1636 | NH2 | ARG A 266 | 32.672 | 21.956 | -4.920 | 1.00 | 27.88 |
| ATOM | 1637 | N | VAL A 267 | 29.404 | 20.891 | 1.246 | 1.00 | 18.31 |
| ATOM | 1638 | CA | VAL A 267 | 30.561 | 20.766 | 2.136 | 1.00 | 18.32 |
| ATOM | 1639 | C | VAL A 267 | 31.671 | 20.072 | 1.369 | 1.00 | 18.25 |
| ATOM | 1640 | O | VAL A 267 | 31.409 | 19.192 | 0.489 | 1.00 | 19.14 |
| ATOM | 1641 | CB | VAL A 267 | 30.248 | 19.974 | 3.456 | 1.00 | 18.72 |
| ATOM | 1642 | CG1 | VAL A 267 | 28.784 | 19.645 | 3.547 | 1.00 | 18.30 |
| ATOM | 1643 | CG2 | VAL A 267 | 31.112 | 18.728 | 3.554 | 1.00 | 17.65 |
| ATOM | 1644 | N | GLU A 268 | 32.903 | 20.471 | 1.647 | 1.00 | 16.18 |
| ATOM | 1645 | CA | GLU A 268 | 34.046 | 19.848 | 0.990 | 1.00 | 17.71 |
| ATOM | 1646 | C | GLU A 268 | 35.169 | 19.546 | 1.970 | 1.00 | 16.08 |
| ATOM | 1647 | O | GLU A 268 | 35.293 | 20.191 | 3.064 | 1.00 | 13.62 |
| ATOM | 1648 | CB | GLU A 268 | 34.550 | 20.717 | -0.177 | 1.00 | 18.50 |
| ATOM | 1649 | CG | GLU A 268 | 34.430 | 22.207 | 0.030 | 1.00 | 22.46 |
| ATOM | 1650 | CD | GLU A 268 | 34.888 | 23.016 | -1.181 | 1.00 | 22.13 |
| ATOM | 1651 | OE1 | GLU A 268 | 34.216 | 22.970 | -2.237 | 1.00 | 20.91 |
| ATOM | 1652 | OE2 | GLU A 268 | 35.927 | 23.703 | -1.067 | 1.00 | 22.44 |
| ATOM | 1653 | N | ILE A 269 | 35.948 | 18.531 | 1.623 | 1.00 | 13.57 |
| ATOM | 1654 | CA | ILE A 269 | 37.103 | 18.112 | 2.418 | 1.00 | 13.89 |
| ATOM | 1655 | C | ILE A 269 | 38.259 | 18.448 | 1.485 | 1.00 | 14.06 |
| ATOM | 1656 | O | ILE A 269 | 38.396 | 17.832 | 0.386 | 1.00 | 14.03 |
| ATOM | 1657 | CB | ILE A 269 | 37.051 | 16.596 | 2.703 | 1.00 | 14.48 |
| ATOM | 1658 | CG1 | ILE A 269 | 35.697 | 16.239 | 3.327 | 1.00 | 14.59 |
| ATOM | 1659 | CG2 | ILE A 269 | 38.180 | 16.193 | 3.645 | 1.00 | 12.12 |
| ATOM | 1660 | CD1 | ILE A 269 | 35.358 | 17.022 | 4.592 | 1.00 | 13.16 |
| ATOM | 1661 | N | ASN A 270 | 39.067 | 19.431 | 1.872 | 1.00 | 14.16 |
| ATOM | 1662 | CA | ASN A 270 | 40.205 | 19.886 | 1.038 | 1.00 | 13.20 |
| ATOM | 1663 | C | ASN A 270 | 39.774 | 20.177 | -0.399 | 1.00 | 13.24 |
| ATOM | 1664 | O | ASN A 270 | 40.427 | 19.714 | -1.385 | 1.00 | 13.72 |
| ATOM | 1665 | CB | ASN A 270 | 41.336 | 18.852 | 1.047 | 1.00 | 11.19 |
| ATOM | 1666 | CG | ASN A 270 | 42.424 | 19.186 | 2.054 | 1.00 | 13.23 |
| ATOM | 1667 | OD1 | ASN A 270 | 42.339 | 20.224 | 2.790 | 1.00 | 13.62 |
| ATOM | 1668 | ND2 | ASN A 270 | 43.454 | 18.348 | 2.117 | 1.00 | 11.67 |
| ATOM | 1669 | N | GLY A 271 | 38.691 | 20.932 | -0.540 | 1.00 | 13.07 |
| ATOM | 1670 | CA | GLY A 271 | 38.210 | 21.302 | -1.858 | 1.00 | 13.58 |

FIG. 1AA

| ATOM | 1671 | C | GLY | A | 271 | 37.393 | 20.241 | -2.564 | 1.00 | 14.87 |
| ATOM | 1672 | O | GLY | A | 271 | 36.704 | 20.545 | -3.581 | 1.00 | 13.70 |
| ATOM | 1673 | N | GLN | A | 272 | 37.447 | 19.005 | -2.076 | 1.00 | 14.64 |
| ATOM | 1674 | CA | GLN | A | 272 | 36.674 | 17.914 | -2.705 | 1.00 | 14.45 |
| ATOM | 1675 | C | GLN | A | 272 | 35.261 | 17.870 | -2.140 | 1.00 | 15.83 |
| ATOM | 1676 | O | GLN | A | 272 | 35.050 | 17.717 | -0.902 | 1.00 | 15.81 |
| ATOM | 1677 | CB | GLN | A | 272 | 37.357 | 16.561 | -2.486 | 1.00 | 14.85 |
| ATOM | 1678 | CG | GLN | A | 272 | 36.692 | 15.421 | -3.250 | 1.00 | 14.45 |
| ATOM | 1679 | CD | GLN | A | 272 | 37.499 | 14.135 | -3.211 | 1.00 | 16.34 |
| ATOM | 1680 | OE1 | GLN | A | 272 | 37.097 | 13.134 | -2.535 | 1.00 | 20.05 |
| ATOM | 1681 | NE2 | GLN | A | 272 | 38.633 | 14.121 | -3.909 | 1.00 | 13.09 |
| ATOM | 1682 | N | ASP | A | 273 | 34.291 | 17.995 | -3.035 | 1.00 | 16.17 |
| ATOM | 1683 | CA | ASP | A | 273 | 32.857 | 17.987 | -2.686 | 1.00 | 17.89 |
| ATOM | 1684 | C | ASP | A | 273 | 32.388 | 16.612 | -2.201 | 1.00 | 16.92 |
| ATOM | 1685 | O | ASP | A | 273 | 32.713 | 15.566 | -2.831 | 1.00 | 16.53 |
| ATOM | 1686 | CB | ASP | A | 273 | 32.060 | 18.395 | -3.930 | 1.00 | 20.38 |
| ATOM | 1687 | CG | ASP | A | 273 | 30.576 | 18.526 | -3.665 | 1.00 | 20.89 |
| ATOM | 1688 | OD1 | ASP | A | 273 | 29.827 | 18.788 | -4.630 | 1.00 | 21.98 |
| ATOM | 1689 | OD2 | ASP | A | 273 | 30.155 | 18.378 | -2.503 | 1.00 | 22.40 |
| ATOM | 1690 | N | LEU | A | 274 | 31.639 | 16.576 | -1.101 | 1.00 | 17.95 |
| ATOM | 1691 | CA | LEU | A | 274 | 31.117 | 15.285 | -0.587 | 1.00 | 19.37 |
| ATOM | 1692 | C | LEU | A | 274 | 30.092 | 14.805 | -1.598 | 1.00 | 21.18 |
| ATOM | 1693 | O | LEU | A | 274 | 29.702 | 13.603 | -1.623 | 1.00 | 20.08 |
| ATOM | 1694 | CB | LEU | A | 274 | 30.451 | 15.455 | 0.783 | 1.00 | 18.46 |
| ATOM | 1695 | CG | LEU | A | 274 | 31.356 | 15.595 | 2.011 | 1.00 | 19.89 |
| ATOM | 1696 | CD1 | LEU | A | 274 | 30.489 | 15.558 | 3.267 | 1.00 | 17.23 |
| ATOM | 1697 | CD2 | LEU | A | 274 | 32.392 | 14.463 | 2.050 | 1.00 | 17.76 |
| ATOM | 1698 | N | LYS | A | 275 | 29.646 | 15.736 | -2.431 | 1.00 | 24.29 |
| ATOM | 1699 | CA | LYS | A | 275 | 28.676 | 15.452 | -3.501 | 1.00 | 29.08 |
| ATOM | 1700 | C | LYS | A | 275 | 27.439 | 14.715 | -3.000 | 1.00 | 28.92 |
| ATOM | 1701 | O | LYS | A | 275 | 27.119 | 13.586 | -3.464 | 1.00 | 30.50 |
| ATOM | 1702 | CB | LYS | A | 275 | 29.360 | 14.642 | -4.608 | 1.00 | 30.50 |
| ATOM | 1703 | CG | LYS | A | 275 | 28.720 | 14.818 | -5.970 | 1.00 | 33.82 |
| ATOM | 1704 | CD | LYS | A | 275 | 29.476 | 14.059 | -7.042 | 1.00 | 36.63 |
| ATOM | 1705 | CE | LYS | A | 275 | 28.848 | 14.297 | -8.408 | 1.00 | 38.29 |
| ATOM | 1706 | NZ | LYS | A | 275 | 28.742 | 15.759 | -8.702 | 1.00 | 39.43 |
| ATOM | 1707 | N | MET | A | 276 | 26.734 | 15.329 | -2.063 | 1.00 | 30.55 |
| ATOM | 1708 | CA | MET | A | 276 | 25.519 | 14.722 | -1.505 | 1.00 | 30.03 |
| ATOM | 1709 | C | MET | A | 276 | 24.319 | 15.592 | -1.815 | 1.00 | 30.11 |
| ATOM | 1710 | O | MET | A | 276 | 24.465 | 16.818 | -2.117 | 1.00 | 28.94 |
| ATOM | 1711 | CB | MET | A | 276 | 25.641 | 14.576 | 0.011 | 1.00 | 30.29 |
| ATOM | 1712 | CG | MET | A | 276 | 26.706 | 13.605 | 0.469 | 1.00 | 30.69 |
| ATOM | 1713 | SD | MET | A | 276 | 26.687 | 13.418 | 2.261 | 1.00 | 32.94 |
| ATOM | 1714 | CE | MET | A | 276 | 25.174 | 12.457 | 2.477 | 1.00 | 31.04 |
| ATOM | 1715 | N | ASP | A | 277 | 23.136 | 14.994 | -1.756 | 1.00 | 31.37 |
| ATOM | 1716 | CA | ASP | A | 277 | 21.906 | 15.750 | -1.994 | 1.00 | 33.34 |
| ATOM | 1717 | C | ASP | A | 277 | 21.903 | 16.864 | -0.955 | 1.00 | 33.96 |
| ATOM | 1718 | O | ASP | A | 277 | 22.070 | 16.608 | 0.278 | 1.00 | 30.80 |
| ATOM | 1719 | CB | ASP | A | 277 | 20.682 | 14.851 | -1.818 | 1.00 | 36.24 |
| ATOM | 1720 | CG | ASP | A | 277 | 19.377 | 15.595 | -2.029 | 1.00 | 38.93 |
| ATOM | 1721 | OD1 | ASP | A | 277 | 18.332 | 14.925 | -2.168 | 1.00 | 42.69 |
| ATOM | 1722 | OD2 | ASP | A | 277 | 19.386 | 16.844 | -2.049 | 1.00 | 39.38 |
| ATOM | 1723 | N | CYS | A | 278 | 21.732 | 18.089 | -1.432 | 1.00 | 34.50 |
| ATOM | 1724 | CA | CYS | A | 278 | 21.725 | 19.294 | -0.581 | 1.00 | 37.44 |
| ATOM | 1725 | C | CYS | A | 278 | 20.988 | 19.126 | 0.749 | 1.00 | 35.96 |
| ATOM | 1726 | O | CYS | A | 278 | 21.503 | 19.540 | 1.834 | 1.00 | 34.38 |
| ATOM | 1727 | CB | CYS | A | 278 | 21.108 | 20.460 | -1.362 | 1.00 | 39.86 |
| ATOM | 1728 | SG | CYS | A | 278 | 21.760 | 22.075 | -0.852 | 1.00 | 50.09 |
| ATOM | 1729 | N | LYS | A | 279 | 19.802 | 18.529 | 0.705 | 1.00 | 33.76 |
| ATOM | 1730 | CA | LYS | A | 279 | 19.003 | 18.359 | 1.931 | 1.00 | 32.65 |
| ATOM | 1731 | C | LYS | A | 279 | 19.584 | 17.430 | 2.996 | 1.00 | 30.06 |
| ATOM | 1732 | O | LYS | A | 279 | 19.173 | 17.501 | 4.189 | 1.00 | 27.89 |

FIG. 1BB

| | | | | | | | | |
|---|---|---|---|---|---|---|---|---|
| ATOM | 1733 | CB | LYS | A | 279 | 17.574 | 17.939 | 1.567 | 1.00 | 34.74 |
| ATOM | 1734 | CG | LYS | A | 279 | 17.459 | 16.765 | 0.612 | 1.00 | 39.08 |
| ATOM | 1735 | CD | LYS | A | 279 | 17.576 | 15.429 | 1.326 | 1.00 | 41.32 |
| ATOM | 1736 | CE | LYS | A | 279 | 17.185 | 14.289 | 0.393 | 1.00 | 42.86 |
| ATOM | 1737 | NZ | LYS | A | 279 | 17.118 | 12.978 | 1.099 | 1.00 | 45.07 |
| ATOM | 1738 | N | GLU | A | 280 | 20.525 | 16.570 | 2.621 | 1.00 | 27.06 |
| ATOM | 1739 | CA | GLU | A | 280 | 21.141 | 15.659 | 3.612 | 1.00 | 26.22 |
| ATOM | 1740 | C | GLU | A | 280 | 21.900 | 16.458 | 4.673 | 1.00 | 25.34 |
| ATOM | 1741 | O | GLU | A | 280 | 21.920 | 16.074 | 5.886 | 1.00 | 23.01 |
| ATOM | 1742 | CB | GLU | A | 280 | 22.109 | 14.693 | 2.928 | 1.00 | 27.98 |
| ATOM | 1743 | CG | GLU | A | 280 | 21.459 | 13.725 | 1.946 | 1.00 | 31.24 |
| ATOM | 1744 | CD | GLU | A | 280 | 20.486 | 12.765 | 2.610 | 1.00 | 32.55 |
| ATOM | 1745 | OE1 | GLU | A | 280 | 20.447 | 12.704 | 3.857 | 1.00 | 33.21 |
| ATOM | 1746 | OE2 | GLU | A | 280 | 19.763 | 12.058 | 1.878 | 1.00 | 34.72 |
| ATOM | 1747 | N | TYR | A | 281 | 22.515 | 17.562 | 4.255 | 1.00 | 23.32 |
| ATOM | 1748 | CA | TYR | A | 281 | 23.295 | 18.420 | 5.176 | 1.00 | 22.69 |
| ATOM | 1749 | C | TYR | A | 281 | 22.415 | 19.082 | 6.219 | 1.00 | 23.40 |
| ATOM | 1750 | O | TYR | A | 281 | 22.904 | 19.470 | 7.327 | 1.00 | 23.11 |
| ATOM | 1751 | CB | TYR | A | 281 | 24.035 | 19.515 | 4.400 | 1.00 | 20.26 |
| ATOM | 1752 | CG | TYR | A | 281 | 24.958 | 18.993 | 3.328 | 1.00 | 19.39 |
| ATOM | 1753 | CD1 | TYR | A | 281 | 25.858 | 17.961 | 3.601 | 1.00 | 17.78 |
| ATOM | 1754 | CD2 | TYR | A | 281 | 24.943 | 19.534 | 2.042 | 1.00 | 18.55 |
| ATOM | 1755 | CE1 | TYR | A | 281 | 26.719 | 17.478 | 2.623 | 1.00 | 17.05 |
| ATOM | 1756 | CE2 | TYR | A | 281 | 25.808 | 19.058 | 1.051 | 1.00 | 18.53 |
| ATOM | 1757 | CZ | TYR | A | 281 | 26.692 | 18.028 | 1.355 | 1.00 | 17.87 |
| ATOM | 1758 | OH | TYR | A | 281 | 27.558 | 17.533 | 0.407 | 1.00 | 18.13 |
| ATOM | 1759 | N | ASN | A | 282 | 21.136 | 19.232 | 5.899 | 1.00 | 22.82 |
| ATOM | 1760 | CA | ASN | A | 282 | 20.194 | 19.881 | 6.820 | 1.00 | 23.17 |
| ATOM | 1761 | C | ASN | A | 282 | 19.089 | 18.922 | 7.238 | 1.00 | 23.84 |
| ATOM | 1762 | O | ASN | A | 282 | 17.987 | 19.366 | 7.685 | 1.00 | 21.83 |
| ATOM | 1763 | CB | ASN | A | 282 | 19.598 | 21.111 | 6.137 | 1.00 | 22.42 |
| ATOM | 1764 | CG | ASN | A | 282 | 20.665 | 22.018 | 5.549 | 1.00 | 23.90 |
| ATOM | 1765 | OD1 | ASN | A | 282 | 21.426 | 22.693 | 6.298 | 1.00 | 23.87 |
| ATOM | 1766 | ND2 | ASN | A | 282 | 20.760 | 22.044 | 4.224 | 1.00 | 23.36 |
| ATOM | 1767 | N | TYR | A | 283 | 19.343 | 17.623 | 7.102 | 1.00 | 25.74 |
| ATOM | 1768 | CA | TYR | A | 283 | 18.322 | 16.633 | 7.472 | 1.00 | 28.01 |
| ATOM | 1769 | C | TYR | A | 283 | 17.905 | 16.843 | 8.912 | 1.00 | 29.29 |
| ATOM | 1770 | O | TYR | A | 283 | 18.686 | 16.572 | 9.881 | 1.00 | 27.50 |
| ATOM | 1771 | CB | TYR | A | 283 | 18.810 | 15.200 | 7.280 | 1.00 | 29.52 |
| ATOM | 1772 | CG | TYR | A | 283 | 17.783 | 14.200 | 7.756 | 1.00 | 31.64 |
| ATOM | 1773 | CD1 | TYR | A | 283 | 16.428 | 14.374 | 7.460 | 1.00 | 32.38 |
| ATOM | 1774 | CD2 | TYR | A | 283 | 18.153 | 13.098 | 8.523 | 1.00 | 33.44 |
| ATOM | 1775 | CE1 | TYR | A | 283 | 15.468 | 13.479 | 7.919 | 1.00 | 33.96 |
| ATOM | 1776 | CE2 | TYR | A | 283 | 17.201 | 12.194 | 8.987 | 1.00 | 35.48 |
| ATOM | 1777 | CZ | TYR | A | 283 | 15.860 | 12.392 | 8.683 | 1.00 | 35.35 |
| ATOM | 1778 | OH | TYR | A | 283 | 14.918 | 11.504 | 9.149 | 1.00 | 36.54 |
| ATOM | 1779 | N | ASP | A | 284 | 16.665 | 17.299 | 9.043 | 1.00 | 30.23 |
| ATOM | 1780 | CA | ASP | A | 284 | 16.026 | 17.638 | 10.312 | 1.00 | 28.41 |
| ATOM | 1781 | C | ASP | A | 284 | 16.273 | 19.129 | 10.409 | 1.00 | 27.12 |
| ATOM | 1782 | O | ASP | A | 284 | 15.309 | 19.953 | 10.305 | 1.00 | 25.19 |
| ATOM | 1783 | CB | ASP | A | 284 | 16.684 | 16.928 | 11.494 | 1.00 | 33.07 |
| ATOM | 1784 | CG | ASP | A | 284 | 16.035 | 17.283 | 12.813 | 1.00 | 33.49 |
| ATOM | 1785 | OD1 | ASP | A | 284 | 16.520 | 16.815 | 13.860 | 1.00 | 37.38 |
| ATOM | 1786 | OD2 | ASP | A | 284 | 15.035 | 18.031 | 12.802 | 1.00 | 35.95 |
| ATOM | 1787 | N | LYS | A | 285 | 17.542 | 19.499 | 10.563 | 1.00 | 22.62 |
| ATOM | 1788 | CA | LYS | A | 285 | 17.914 | 20.927 | 10.678 | 1.00 | 20.42 |
| ATOM | 1789 | C | LYS | A | 285 | 19.420 | 21.145 | 10.812 | 1.00 | 19.89 |
| ATOM | 1790 | O | LYS | A | 285 | 20.209 | 20.174 | 11.037 | 1.00 | 19.63 |
| ATOM | 1791 | CB | LYS | A | 285 | 17.230 | 21.540 | 11.903 | 1.00 | 18.63 |
| ATOM | 1792 | CG | LYS | A | 285 | 17.753 | 20.987 | 13.232 | 1.00 | 16.63 |
| ATOM | 1793 | CD | LYS | A | 285 | 16.966 | 21.538 | 14.421 | 1.00 | 14.93 |
| ATOM | 1794 | CE | LYS | A | 285 | 17.551 | 21.088 | 15.754 | 1.00 | 15.57 |

FIG. 1CC

| ATOM | 1795 | NZ | LYS | A | 285 | 17.482 | 19.606 | 15.974 | 1.00 | 13.50 |
|---|---|---|---|---|---|---|---|---|---|---|
| ATOM | 1796 | N | SER | A | 286 | 19.827 | 22.402 | 10.678 | 1.00 | 17.19 |
| ATOM | 1797 | CA | SER | A | 286 | 21.241 | 22.808 | 10.827 | 1.00 | 16.52 |
| ATOM | 1798 | C | SER | A | 286 | 21.228 | 24.034 | 11.727 | 1.00 | 15.74 |
| ATOM | 1799 | O | SER | A | 286 | 20.592 | 25.080 | 11.377 | 1.00 | 14.46 |
| ATOM | 1800 | CB | SER | A | 286 | 21.862 | 23.179 | 9.475 | 1.00 | 16.90 |
| ATOM | 1801 | OG | SER | A | 286 | 22.064 | 22.036 | 8.671 | 1.00 | 16.60 |
| ATOM | 1802 | N | ILE | A | 287 | 21.900 | 23.946 | 12.870 | 1.00 | 13.25 |
| ATOM | 1803 | CA | ILE | A | 287 | 21.933 | 25.079 | 13.805 | 1.00 | 13.97 |
| ATOM | 1804 | C | ILE | A | 287 | 23.342 | 25.511 | 14.206 | 1.00 | 15.14 |
| ATOM | 1805 | O | ILE | A | 287 | 24.346 | 24.750 | 14.024 | 1.00 | 14.63 |
| ATOM | 1806 | CB | ILE | A | 287 | 21.145 | 24.757 | 15.102 | 1.00 | 13.55 |
| ATOM | 1807 | CG1 | ILE | A | 287 | 21.898 | 23.717 | 15.929 | 1.00 | 12.52 |
| ATOM | 1808 | CG2 | ILE | A | 287 | 19.758 | 24.214 | 14.754 | 1.00 | 12.10 |
| ATOM | 1809 | CD1 | ILE | A | 287 | 21.274 | 23.455 | 17.283 | 1.00 | 14.43 |
| ATOM | 1810 | N | VAL | A | 288 | 23.431 | 26.728 | 14.732 | 1.00 | 14.78 |
| ATOM | 1811 | CA | VAL | A | 288 | 24.701 | 27.292 | 15.223 | 1.00 | 15.54 |
| ATOM | 1812 | C | VAL | A | 288 | 24.510 | 27.262 | 16.733 | 1.00 | 16.05 |
| ATOM | 1813 | O | VAL | A | 288 | 23.571 | 27.930 | 17.278 | 1.00 | 15.61 |
| ATOM | 1814 | CB | VAL | A | 288 | 24.896 | 28.751 | 14.767 | 1.00 | 15.19 |
| ATOM | 1815 | CG1 | VAL | A | 288 | 26.248 | 29.259 | 15.239 | 1.00 | 14.78 |
| ATOM | 1816 | CG2 | VAL | A | 288 | 24.791 | 28.842 | 13.246 | 1.00 | 15.19 |
| ATOM | 1817 | N | ASP | A | 289 | 25.355 | 26.512 | 17.430 | 1.00 | 15.91 |
| ATOM | 1818 | CA | ASP | A | 289 | 25.194 | 26.373 | 18.891 | 1.00 | 14.81 |
| ATOM | 1819 | C | ASP | A | 289 | 26.467 | 26.444 | 19.724 | 1.00 | 15.27 |
| ATOM | 1820 | O | ASP | A | 289 | 27.322 | 25.504 | 19.700 | 1.00 | 15.75 |
| ATOM | 1821 | CB | ASP | A | 289 | 24.467 | 25.060 | 19.168 | 1.00 | 12.65 |
| ATOM | 1822 | CG | ASP | A | 289 | 24.264 | 24.806 | 20.634 | 1.00 | 13.29 |
| ATOM | 1823 | OD1 | ASP | A | 289 | 24.372 | 25.768 | 21.426 | 1.00 | 11.88 |
| ATOM | 1824 | OD2 | ASP | A | 289 | 23.981 | 23.639 | 20.988 | 1.00 | 10.63 |
| ATOM | 1825 | N | SER | A | 290 | 26.604 | 27.529 | 20.479 | 1.00 | 15.19 |
| ATOM | 1826 | CA | SER | A | 290 | 27.782 | 27.730 | 21.346 | 1.00 | 14.55 |
| ATOM | 1827 | C | SER | A | 290 | 27.770 | 26.748 | 22.510 | 1.00 | 15.43 |
| ATOM | 1828 | O | SER | A | 290 | 28.823 | 26.539 | 23.186 | 1.00 | 13.77 |
| ATOM | 1829 | CB | SER | A | 290 | 27.795 | 29.165 | 21.888 | 1.00 | 15.33 |
| ATOM | 1830 | OG | SER | A | 290 | 26.614 | 29.442 | 22.620 | 1.00 | 12.79 |
| ATOM | 1831 | N | GLY | A | 291 | 26.612 | 26.137 | 22.759 | 1.00 | 14.34 |
| ATOM | 1832 | CA | GLY | A | 291 | 26.486 | 25.192 | 23.856 | 1.00 | 14.93 |
| ATOM | 1833 | C | GLY | A | 291 | 26.779 | 23.751 | 23.479 | 1.00 | 16.64 |
| ATOM | 1834 | O | GLY | A | 291 | 26.502 | 22.792 | 24.277 | 1.00 | 14.49 |
| ATOM | 1835 | N | THR | A | 292 | 27.305 | 23.556 | 22.277 | 1.00 | 16.47 |
| ATOM | 1836 | CA | THR | A | 292 | 27.674 | 22.202 | 21.812 | 1.00 | 15.30 |
| ATOM | 1837 | C | THR | A | 292 | 29.159 | 22.215 | 21.482 | 1.00 | 14.67 |
| ATOM | 1838 | O | THR | A | 292 | 29.653 | 23.102 | 20.725 | 1.00 | 13.26 |
| ATOM | 1839 | CB | THR | A | 292 | 26.889 | 21.784 | 20.550 | 1.00 | 15.29 |
| ATOM | 1840 | OG1 | THR | A | 292 | 25.522 | 21.521 | 20.895 | 1.00 | 13.88 |
| ATOM | 1841 | CG2 | THR | A | 292 | 27.514 | 20.527 | 19.932 | 1.00 | 13.59 |
| ATOM | 1842 | N | THR | A | 293 | 29.887 | 21.253 | 22.027 | 1.00 | 14.43 |
| ATOM | 1843 | CA | THR | A | 293 | 31.343 | 21.162 | 21.801 | 1.00 | 12.76 |
| ATOM | 1844 | C | THR | A | 293 | 31.749 | 20.906 | 20.348 | 1.00 | 14.47 |
| ATOM | 1845 | O | THR | A | 293 | 32.478 | 21.735 | 19.712 | 1.00 | 14.61 |
| ATOM | 1846 | CB | THR | A | 293 | 31.949 | 20.035 | 22.650 | 1.00 | 12.36 |
| ATOM | 1847 | OG1 | THR | A | 293 | 31.726 | 20.304 | 24.041 | 1.00 | 10.79 |
| ATOM | 1848 | CG2 | THR | A | 293 | 33.437 | 19.916 | 22.382 | 1.00 | 9.56 |
| ATOM | 1849 | N | ASN | A | 294 | 31.286 | 19.783 | 19.810 | 1.00 | 13.53 |
| ATOM | 1850 | CA | ASN | A | 294 | 31.648 | 19.349 | 18.440 | 1.00 | 15.26 |
| ATOM | 1851 | C | ASN | A | 294 | 30.871 | 19.917 | 17.276 | 1.00 | 15.45 |
| ATOM | 1852 | O | ASN | A | 294 | 29.851 | 20.662 | 17.431 | 1.00 | 13.68 |
| ATOM | 1853 | CB | ASN | A | 294 | 31.494 | 17.832 | 18.307 | 1.00 | 14.81 |
| ATOM | 1854 | CG | ASN | A | 294 | 32.351 | 17.051 | 19.270 | 1.00 | 14.13 |
| ATOM | 1855 | OD1 | ASN | A | 294 | 32.264 | 15.791 | 19.304 | 1.00 | 19.85 |
| ATOM | 1856 | ND2 | ASN | A | 294 | 33.174 | 17.734 | 20.051 | 1.00 | 13.25 |

FIG. 1DD

```
ATOM   1857  N    LEU A 295      31.365  19.556  16.096  1.00 15.21
ATOM   1858  CA   LEU A 295      30.689  19.866  14.835  1.00 15.29
ATOM   1859  C    LEU A 295      29.924  18.548  14.719  1.00 16.43
ATOM   1860  O    LEU A 295      30.556  17.452  14.575  1.00 16.34
ATOM   1861  CB   LEU A 295      31.674  19.963  13.671  1.00 13.54
ATOM   1862  CG   LEU A 295      31.017  19.837  12.287  1.00 14.74
ATOM   1863  CD1  LEU A 295      29.991  20.947  12.109  1.00 14.37
ATOM   1864  CD2  LEU A 295      32.073  19.903  11.179  1.00 13.91
ATOM   1865  N    ARG A 296      28.606  18.591  14.831  1.00 16.08
ATOM   1866  CA   ARG A 296      27.827  17.349  14.719  1.00 17.47
ATOM   1867  C    ARG A 296      27.180  17.300  13.343  1.00 17.04
ATOM   1868  O    ARG A 296      26.655  18.339  12.840  1.00 15.28
ATOM   1869  CB   ARG A 296      26.785  17.290  15.834  1.00 18.37
ATOM   1870  CG   ARG A 296      27.421  17.444  17.208  1.00 19.73
ATOM   1871  CD   ARG A 296      26.425  17.262  18.324  1.00 22.63
ATOM   1872  NE   ARG A 296      26.292  15.867  18.722  1.00 25.23
ATOM   1873  CZ   ARG A 296      25.135  15.223  18.776  1.00 26.52
ATOM   1874  NH1  ARG A 296      24.011  15.851  18.446  1.00 27.11
ATOM   1875  NH2  ARG A 296      25.100  13.961  19.179  1.00 27.00
ATOM   1876  N    LEU A 297      27.211  16.123  12.722  1.00 15.65
ATOM   1877  CA   LEU A 297      26.660  15.945  11.356  1.00 15.33
ATOM   1878  C    LEU A 297      25.657  14.800  11.246  1.00 17.46
ATOM   1879  O    LEU A 297      25.795  13.743  11.938  1.00 16.37
ATOM   1880  CB   LEU A 297      27.806  15.681  10.371  1.00 12.00
ATOM   1881  CG   LEU A 297      28.925  16.729  10.277  1.00 11.84
ATOM   1882  CD1  LEU A 297      30.136  16.148   9.561  1.00  8.16
ATOM   1883  CD2  LEU A 297      28.410  17.962   9.559  1.00  8.99
ATOM   1884  N    PRO A 298      24.636  14.960  10.386  1.00 19.11
ATOM   1885  CA   PRO A 298      23.636  13.901  10.217  1.00 20.53
ATOM   1886  C    PRO A 298      24.387  12.619   9.868  1.00 21.03
ATOM   1887  O    PRO A 298      25.419  12.668   9.131  1.00 21.77
ATOM   1888  CB   PRO A 298      22.788  14.411   9.054  1.00 19.18
ATOM   1889  CG   PRO A 298      22.861  15.897   9.209  1.00 20.46
ATOM   1890  CD   PRO A 298      24.335  16.111   9.517  1.00 19.69
ATOM   1891  N    LYS A 299      23.911  11.487  10.376  1.00 22.77
ATOM   1892  CA   LYS A 299      24.562  10.169  10.137  1.00 25.34
ATOM   1893  C    LYS A 299      25.169   9.979   8.753  1.00 24.56
ATOM   1894  O    LYS A 299      26.393   9.681   8.617  1.00 22.24
ATOM   1895  CB   LYS A 299      23.566   9.034  10.387  1.00 29.05
ATOM   1896  CG   LYS A 299      24.156   7.650  10.146  1.00 33.27
ATOM   1897  CD   LYS A 299      23.144   6.547  10.408  1.00 37.10
ATOM   1898  CE   LYS A 299      23.758   5.178  10.151  1.00 38.78
ATOM   1899  NZ   LYS A 299      22.775   4.077  10.380  1.00 42.51
ATOM   1900  N    LYS A 300      24.340  10.127   7.729  1.00 24.24
ATOM   1901  CA   LYS A 300      24.774   9.955   6.333  1.00 25.41
ATOM   1902  C    LYS A 300      25.901  10.916   5.952  1.00 24.12
ATOM   1903  O    LYS A 300      26.889  10.515   5.262  1.00 23.67
ATOM   1904  CB   LYS A 300      23.576  10.154   5.403  1.00 28.77
ATOM   1905  CG   LYS A 300      23.788   9.660   3.990  1.00 33.37
ATOM   1906  CD   LYS A 300      22.661   8.718   3.569  1.00 38.01
ATOM   1907  CE   LYS A 300      21.298   9.393   3.652  1.00 40.18
ATOM   1908  NZ   LYS A 300      20.191   8.455   3.291  1.00 42.69
ATOM   1909  N    VAL A 301      25.784  12.172   6.368  1.00 20.46
ATOM   1910  CA   VAL A 301      26.832  13.169   6.058  1.00 18.21
ATOM   1911  C    VAL A 301      28.083  12.842   6.867  1.00 17.93
ATOM   1912  O    VAL A 301      29.241  12.929   6.343  1.00 16.84
ATOM   1913  CB   VAL A 301      26.358  14.601   6.391  1.00 17.29
ATOM   1914  CG1  VAL A 301      27.468  15.605   6.105  1.00 15.43
ATOM   1915  CG2  VAL A 301      25.118  14.935   5.565  1.00 16.34
ATOM   1916  N    PHE A 302      27.887  12.448   8.122  1.00 17.43
ATOM   1917  CA   PHE A 302      29.032  12.099   8.990  1.00 18.16
ATOM   1918  C    PHE A 302      29.854  10.957   8.399  1.00 18.95
```

FIG. 1EE

| | | | | | | | | | |
|---|---|---|---|---|---|---|---|---|---|
| ATOM | 1919 | O | PHE | A | 302 | 31.121 | 11.004 | 8.399 | 1.00 18.60 |
| ATOM | 1920 | CB | PHE | A | 302 | 28.550 | 11.713 | 10.391 | 1.00 17.38 |
| ATOM | 1921 | CG | PHE | A | 302 | 29.639 | 11.180 | 11.265 | 1.00 19.16 |
| ATOM | 1922 | CD1 | PHE | A | 302 | 29.866 | 9.810 | 11.362 | 1.00 17.81 |
| ATOM | 1923 | CD2 | PHE | A | 302 | 30.498 | 12.051 | 11.923 | 1.00 18.89 |
| ATOM | 1924 | CE1 | PHE | A | 302 | 30.934 | 9.320 | 12.096 | 1.00 19.63 |
| ATOM | 1925 | CE2 | PHE | A | 302 | 31.573 | 11.569 | 12.660 | 1.00 19.90 |
| ATOM | 1926 | CZ | PHE | A | 302 | 31.793 | 10.201 | 12.747 | 1.00 19.13 |
| ATOM | 1927 | N | GLU | A | 303 | 29.172 | 9.931 | 7.901 | 1.00 19.20 |
| ATOM | 1928 | CA | GLU | A | 303 | 29.859 | 8.769 | 7.295 | 1.00 21.56 |
| ATOM | 1929 | C | GLU | A | 303 | 30.679 | 9.189 | 6.083 | 1.00 19.19 |
| ATOM | 1930 | O | GLU | A | 303 | 31.865 | 8.777 | 5.929 | 1.00 18.04 |
| ATOM | 1931 | CB | GLU | A | 303 | 28.836 | 7.704 | 6.888 | 1.00 24.72 |
| ATOM | 1932 | CG | GLU | A | 303 | 28.246 | 6.939 | 8.069 | 1.00 29.90 |
| ATOM | 1933 | CD | GLU | A | 303 | 27.051 | 6.076 | 7.683 | 1.00 33.77 |
| ATOM | 1934 | OE1 | GLU | A | 303 | 26.585 | 5.294 | 8.541 | 1.00 36.31 |
| ATOM | 1935 | OE2 | GLU | A | 303 | 26.572 | 6.183 | 6.528 | 1.00 36.51 |
| ATOM | 1936 | N | ALA | A | 304 | 30.088 | 9.998 | 5.216 | 1.00 17.86 |
| ATOM | 1937 | CA | ALA | A | 304 | 30.805 | 10.472 | 4.007 | 1.00 18.11 |
| ATOM | 1938 | C | ALA | A | 304 | 31.999 | 11.354 | 4.386 | 1.00 17.49 |
| ATOM | 1939 | O | ALA | A | 304 | 33.102 | 11.242 | 3.777 | 1.00 17.76 |
| ATOM | 1940 | CB | ALA | A | 304 | 29.849 | 11.244 | 3.102 | 1.00 17.14 |
| ATOM | 1941 | N | ALA | A | 305 | 31.812 | 12.221 | 5.377 | 1.00 17.06 |
| ATOM | 1942 | CA | ALA | A | 305 | 32.900 | 13.128 | 5.829 | 1.00 16.43 |
| ATOM | 1943 | C | ALA | A | 305 | 34.092 | 12.387 | 6.440 | 1.00 16.39 |
| ATOM | 1944 | O | ALA | A | 305 | 35.272 | 12.644 | 6.054 | 1.00 17.78 |
| ATOM | 1945 | CB | ALA | A | 305 | 32.351 | 14.140 | 6.833 | 1.00 15.92 |
| ATOM | 1946 | N | VAL | A | 306 | 33.842 | 11.476 | 7.375 | 1.00 15.50 |
| ATOM | 1947 | CA | VAL | A | 306 | 34.971 | 10.756 | 8.004 | 1.00 17.31 |
| ATOM | 1948 | C | VAL | A | 306 | 35.719 | 9.920 | 6.987 | 1.00 16.95 |
| ATOM | 1949 | O | VAL | A | 306 | 36.983 | 9.829 | 7.029 | 1.00 16.21 |
| ATOM | 1950 | CB | VAL | A | 306 | 34.514 | 9.845 | 9.162 | 1.00 17.93 |
| ATOM | 1951 | CG1 | VAL | A | 306 | 33.954 | 10.693 | 10.280 | 1.00 19.37 |
| ATOM | 1952 | CG2 | VAL | A | 306 | 33.477 | 8.851 | 8.669 | 1.00 19.63 |
| ATOM | 1953 | N | LYS | A | 307 | 34.987 | 9.307 | 6.065 | 1.00 17.11 |
| ATOM | 1954 | CA | LYS | A | 307 | 35.641 | 8.488 | 5.032 | 1.00 18.39 |
| ATOM | 1955 | C | LYS | A | 307 | 36.654 | 9.350 | 4.279 | 1.00 17.59 |
| ATOM | 1956 | O | LYS | A | 307 | 37.848 | 8.959 | 4.107 | 1.00 18.09 |
| ATOM | 1957 | CB | LYS | A | 307 | 34.602 | 7.940 | 4.052 | 1.00 19.72 |
| ATOM | 1958 | CG | LYS | A | 307 | 35.212 | 7.112 | 2.930 | 1.00 24.02 |
| ATOM | 1959 | CD | LYS | A | 307 | 34.147 | 6.415 | 2.102 | 1.00 26.72 |
| ATOM | 1960 | CE | LYS | A | 307 | 34.779 | 5.505 | 1.058 | 1.00 29.36 |
| ATOM | 1961 | NZ | LYS | A | 307 | 33.745 | 4.869 | 0.193 | 1.00 31.68 |
| ATOM | 1962 | N | SER | A | 308 | 36.205 | 10.520 | 3.842 | 1.00 16.75 |
| ATOM | 1963 | CA | SER | A | 308 | 37.059 | 11.460 | 3.091 | 1.00 17.46 |
| ATOM | 1964 | C | SER | A | 308 | 38.198 | 12.000 | 3.953 | 1.00 16.11 |
| ATOM | 1965 | O | SER | A | 308 | 39.378 | 12.056 | 3.501 | 1.00 17.12 |
| ATOM | 1966 | CB | SER | A | 308 | 36.208 | 12.620 | 2.560 | 1.00 17.51 |
| ATOM | 1967 | OG | SER | A | 308 | 36.982 | 13.505 | 1.774 | 1.00 19.76 |
| ATOM | 1968 | N | ILE | A | 309 | 37.886 | 12.400 | 5.180 | 1.00 16.07 |
| ATOM | 1969 | CA | ILE | A | 309 | 38.926 | 12.927 | 6.083 | 1.00 14.41 |
| ATOM | 1970 | C | ILE | A | 309 | 39.945 | 11.831 | 6.378 | 1.00 14.93 |
| ATOM | 1971 | O | ILE | A | 309 | 41.171 | 12.112 | 6.505 | 1.00 14.90 |
| ATOM | 1972 | CB | ILE | A | 309 | 38.310 | 13.439 | 7.401 | 1.00 13.88 |
| ATOM | 1973 | CG1 | ILE | A | 309 | 37.346 | 14.595 | 7.099 | 1.00 13.08 |
| ATOM | 1974 | CG2 | ILE | A | 309 | 39.404 | 13.887 | 8.350 | 1.00 11.40 |
| ATOM | 1975 | CD1 | ILE | A | 309 | 36.575 | 15.084 | 8.315 | 1.00 12.70 |
| ATOM | 1976 | N | LYS | A | 310 | 39.475 | 10.592 | 6.485 | 1.00 15.62 |
| ATOM | 1977 | CA | LYS | A | 310 | 40.375 | 9.437 | 6.752 | 1.00 17.74 |
| ATOM | 1978 | C | LYS | A | 310 | 41.289 | 9.223 | 5.559 | 1.00 17.22 |
| ATOM | 1979 | O | LYS | A | 310 | 42.532 | 9.061 | 5.715 | 1.00 16.87 |
| ATOM | 1980 | CB | LYS | A | 310 | 39.577 | 8.149 | 6.976 | 1.00 18.35 |

FIG. 1FF

```
ATOM   1981  CG   LYS A 310      39.003   7.953   8.373  1.00 20.85
ATOM   1982  CD   LYS A 310      38.269   6.617   8.432  1.00 22.02
ATOM   1983  CE   LYS A 310      37.584   6.404   9.757  1.00 25.26
ATOM   1984  NZ   LYS A 310      36.808   5.129   9.752  1.00 26.15
ATOM   1985  N    ALA A 311      40.698   9.211   4.370  1.00 15.56
ATOM   1986  CA   ALA A 311      41.466   9.007   3.124  1.00 17.77
ATOM   1987  C    ALA A 311      42.549  10.071   2.990  1.00 17.36
ATOM   1988  O    ALA A 311      43.708   9.768   2.578  1.00 20.71
ATOM   1989  CB   ALA A 311      40.524   9.047   1.908  1.00 14.11
ATOM   1990  N    ALA A 312      42.210  11.309   3.330  1.00 16.63
ATOM   1991  CA   ALA A 312      43.184  12.418   3.235  1.00 15.73
ATOM   1992  C    ALA A 312      44.247  12.342   4.333  1.00 15.59
ATOM   1993  O    ALA A 312      45.348  12.958   4.207  1.00 13.09
ATOM   1994  CB   ALA A 312      42.449  13.758   3.301  1.00 13.50
ATOM   1995  N    SER A 313      43.950  11.593   5.393  1.00 17.05
ATOM   1996  CA   SER A 313      44.867  11.432   6.560  1.00 19.05
ATOM   1997  C    SER A 313      45.579  10.085   6.593  1.00 19.49
ATOM   1998  O    SER A 313      46.332   9.787   7.568  1.00 21.95
ATOM   1999  CB   SER A 313      44.075  11.555   7.865  1.00 17.23
ATOM   2000  OG   SER A 313      43.501  12.834   8.003  1.00 23.58
ATOM   2001  N    SER A 314      45.368   9.270   5.570  1.00 20.76
ATOM   2002  CA   SER A 314      45.952   7.909   5.513  1.00 22.73
ATOM   2003  C    SER A 314      47.436   7.725   5.838  1.00 21.90
ATOM   2004  O    SER A 314      47.825   6.639   6.359  1.00 20.76
ATOM   2005  CB   SER A 314      45.650   7.271   4.150  1.00 22.50
ATOM   2006  OG   SER A 314      46.207   8.032   3.093  1.00 27.94
ATOM   2007  N    THR A 315      48.285   8.714   5.570  1.00 20.90
ATOM   2008  CA   THR A 315      49.732   8.523   5.868  1.00 23.78
ATOM   2009  C    THR A 315      50.020   8.454   7.361  1.00 25.42
ATOM   2010  O    THR A 315      51.191   8.219   7.784  1.00 26.24
ATOM   2011  CB   THR A 315      50.616   9.634   5.257  1.00 23.59
ATOM   2012  OG1  THR A 315      50.256  10.901   5.818  1.00 22.73
ATOM   2013  CG2  THR A 315      50.456   9.668   3.745  1.00 22.59
ATOM   2014  N    GLU A 316      48.994   8.655   8.176  1.00 27.46
ATOM   2015  CA   GLU A 316      49.170   8.589   9.638  1.00 29.81
ATOM   2016  C    GLU A 316      48.258   7.503  10.201  1.00 30.55
ATOM   2017  O    GLU A 316      47.110   7.314   9.710  1.00 29.51
ATOM   2018  CB   GLU A 316      48.819   9.931  10.279  1.00 32.51
ATOM   2019  CG   GLU A 316      49.277  10.039  11.725  1.00 36.72
ATOM   2020  CD   GLU A 316      50.571  10.818  11.879  1.00 36.99
ATOM   2021  OE1  GLU A 316      51.456  10.728  11.003  1.00 37.39
ATOM   2022  OE2  GLU A 316      50.704  11.522  12.893  1.00 41.14
ATOM   2023  N    LYS A 317      48.736   6.775  11.205  1.00 32.69
ATOM   2024  CA   LYS A 317      47.928   5.702  11.828  1.00 35.09
ATOM   2025  C    LYS A 317      47.216   6.223  13.071  1.00 33.44
ATOM   2026  O    LYS A 317      47.804   7.005  13.883  1.00 34.13
ATOM   2027  CB   LYS A 317      48.809   4.505  12.202  1.00 38.52
ATOM   2028  CG   LYS A 317      49.980   4.844  13.106  1.00 43.41
ATOM   2029  CD   LYS A 317      50.665   3.588  13.638  1.00 46.99
ATOM   2030  CE   LYS A 317      51.165   2.686  12.514  1.00 48.65
ATOM   2031  NZ   LYS A 317      51.731   1.410  13.043  1.00 49.49
ATOM   2032  N    PHE A 318      45.965   5.818  13.245  1.00 31.00
ATOM   2033  CA   PHE A 318      45.188   6.272  14.408  1.00 30.33
ATOM   2034  C    PHE A 318      44.683   5.120  15.263  1.00 30.57
ATOM   2035  O    PHE A 318      44.171   4.088  14.732  1.00 29.80
ATOM   2036  CB   PHE A 318      44.014   7.135  13.944  1.00 28.83
ATOM   2037  CG   PHE A 318      44.436   8.367  13.197  1.00 28.31
ATOM   2038  CD1  PHE A 318      44.625   8.333  11.817  1.00 27.09
ATOM   2039  CD2  PHE A 318      44.686   9.554  13.879  1.00 27.59
ATOM   2040  CE1  PHE A 318      45.060   9.466  11.130  1.00 27.37
ATOM   2041  CE2  PHE A 318      45.122  10.691  13.200  1.00 26.98
ATOM   2042  CZ   PHE A 318      45.309  10.648  11.826  1.00 27.12
```

FIG. 1GG

```
ATOM   2043  N    PRO A 319      44.805    5.252   16.591  1.00 30.02
ATOM   2044  CA   PRO A 319      44.361    4.222   17.535  1.00 30.20
ATOM   2045  C    PRO A 319      42.864    3.977   17.460  1.00 29.88
ATOM   2046  O    PRO A 319      42.087    4.882   17.040  1.00 29.27
ATOM   2047  CB   PRO A 319      44.777    4.793   18.890  1.00 30.49
ATOM   2048  CG   PRO A 319      44.667    6.276   18.674  1.00 31.99
ATOM   2049  CD   PRO A 319      45.308    6.437   17.309  1.00 30.77
ATOM   2050  N    ASP A 320      42.449    2.779   17.860  1.00 30.08
ATOM   2051  CA   ASP A 320      41.018    2.389   17.867  1.00 29.79
ATOM   2052  C    ASP A 320      40.183    3.406   18.652  1.00 28.71
ATOM   2053  O    ASP A 320      40.560    3.804   19.804  1.00 27.90
ATOM   2054  CB   ASP A 320      40.855    1.009   18.520  1.00 31.81
ATOM   2055  CG   ASP A 320      41.545   -0.104   17.740  1.00 34.27
ATOM   2056  OD1  ASP A 320      41.787   -1.182   18.331  1.00 34.13
ATOM   2057  OD2  ASP A 320      41.833    0.092   16.538  1.00 35.41
ATOM   2058  N    GLY A 321      39.067    3.837   18.068  1.00 26.34
ATOM   2059  CA   GLY A 321      38.193    4.781   18.745  1.00 24.91
ATOM   2060  C    GLY A 321      38.439    6.259   18.490  1.00 23.96
ATOM   2061  O    GLY A 321      37.632    7.129   18.941  1.00 23.66
ATOM   2062  N    PHE A 322      39.519    6.591   17.793  1.00 22.07
ATOM   2063  CA   PHE A 322      39.810    8.011   17.507  1.00 20.41
ATOM   2064  C    PHE A 322      38.705    8.670   16.684  1.00 20.53
ATOM   2065  O    PHE A 322      38.157    9.743   17.078  1.00 20.75
ATOM   2066  CB   PHE A 322      41.126    8.157   16.747  1.00 19.07
ATOM   2067  CG   PHE A 322      41.405    9.567   16.306  1.00 19.05
ATOM   2068  CD1  PHE A 322      41.701   10.555   17.240  1.00 17.04
ATOM   2069  CD2  PHE A 322      41.326    9.918   14.960  1.00 17.20
ATOM   2070  CE1  PHE A 322      41.912   11.872   16.840  1.00 18.99
ATOM   2071  CE2  PHE A 322      41.535   11.229   14.552  1.00 17.99
ATOM   2072  CZ   PHE A 322      41.829   12.210   15.494  1.00 16.28
ATOM   2073  N    TRP A 323      38.367    8.063   15.552  1.00 20.75
ATOM   2074  CA   TRP A 323      37.330    8.622   14.664  1.00 22.37
ATOM   2075  C    TRP A 323      35.940    8.626   15.273  1.00 23.50
ATOM   2076  O    TRP A 323      35.036    9.379   14.804  1.00 22.84
ATOM   2077  CB   TRP A 323      37.322    7.872   13.335  1.00 21.45
ATOM   2078  CG   TRP A 323      38.643    7.924   12.664  1.00 20.71
ATOM   2079  CD1  TRP A 323      39.566    6.921   12.594  1.00 20.50
ATOM   2080  CD2  TRP A 323      39.217    9.049   11.986  1.00 20.31
ATOM   2081  NE1  TRP A 323      40.679    7.349   11.913  1.00 20.18
ATOM   2082  CE2  TRP A 323      40.492    8.651   11.527  1.00 20.95
ATOM   2083  CE3  TRP A 323      38.778   10.354   11.722  1.00 20.80
ATOM   2084  CZ2  TRP A 323      41.337    9.511   10.816  1.00 20.49
ATOM   2085  CZ3  TRP A 323      39.618   11.212   11.013  1.00 21.58
ATOM   2086  CH2  TRP A 323      40.885   10.784   10.569  1.00 21.15
ATOM   2087  N    LEU A 324      35.734    7.810   16.300  1.00 26.13
ATOM   2088  CA   LEU A 324      34.428    7.772   16.983  1.00 27.96
ATOM   2089  C    LEU A 324      34.417    8.877   18.040  1.00 29.09
ATOM   2090  O    LEU A 324      33.413    9.044   18.799  1.00 29.23
ATOM   2091  CB   LEU A 324      34.202    6.408   17.642  1.00 29.11
ATOM   2092  CG   LEU A 324      33.910    5.236   16.697  1.00 30.04
ATOM   2093  CD1  LEU A 324      33.791    3.948   17.501  1.00 30.31
ATOM   2094  CD2  LEU A 324      32.625    5.499   15.924  1.00 29.47
ATOM   2095  N    GLY A 325      35.513    9.634   18.098  1.00 29.34
ATOM   2096  CA   GLY A 325      35.632   10.728   19.048  1.00 30.68
ATOM   2097  C    GLY A 325      35.794   10.280   20.489  1.00 31.19
ATOM   2098  O    GLY A 325      35.687   11.109   21.442  1.00 31.53
ATOM   2099  N    GLU A 326      36.067    8.995   20.683  1.00 32.22
ATOM   2100  CA   GLU A 326      36.225    8.436   22.042  1.00 34.09
ATOM   2101  C    GLU A 326      37.655    8.482   22.563  1.00 33.56
ATOM   2102  O    GLU A 326      37.907    8.933   23.720  1.00 34.19
ATOM   2103  CB   GLU A 326      35.728    6.992   22.062  1.00 35.56
ATOM   2104  CG   GLU A 326      34.267    6.847   21.683  1.00 38.03
```

FIG. 1HH

| | | | | | | | | | |
|---|---|---|---|---|---|---|---|---|---|
| ATOM | 2105 | CD | GLU | A | 326 | 33.855 | 5.401 | 21.494 | 1.00 40.36 |
| ATOM | 2106 | OE1 | GLU | A | 326 | 32.662 | 5.162 | 21.207 | 1.00 41.84 |
| ATOM | 2107 | OE2 | GLU | A | 326 | 34.720 | 4.506 | 21.626 | 1.00 42.10 |
| ATOM | 2108 | N | GLN | A | 327 | 38.602 | 8.031 | 21.750 | 1.00 32.81 |
| ATOM | 2109 | CA | GLN | A | 327 | 40.009 | 8.017 | 22.178 | 1.00 31.36 |
| ATOM | 2110 | C | GLN | A | 327 | 40.844 | 9.142 | 21.608 | 1.00 30.14 |
| ATOM | 2111 | O | GLN | A | 327 | 40.612 | 9.626 | 20.458 | 1.00 28.97 |
| ATOM | 2112 | CB | GLN | A | 327 | 40.650 | 6.667 | 21.842 | 1.00 34.41 |
| ATOM | 2113 | CG | GLN | A | 327 | 40.770 | 5.749 | 23.060 | 1.00 38.96 |
| ATOM | 2114 | CD | GLN | A | 327 | 39.443 | 5.546 | 23.778 | 1.00 40.61 |
| ATOM | 2115 | OE1 | GLN | A | 327 | 39.410 | 5.223 | 25.002 | 1.00 42.73 |
| ATOM | 2116 | NE2 | GLN | A | 327 | 38.344 | 5.714 | 23.053 | 1.00 42.75 |
| ATOM | 2117 | N | LEU | A | 328 | 41.814 | 9.581 | 22.394 | 1.00 28.01 |
| ATOM | 2118 | CA | LEU | A | 328 | 42.695 | 10.663 | 21.964 | 1.00 28.64 |
| ATOM | 2119 | C | LEU | A | 328 | 43.889 | 10.100 | 21.219 | 1.00 27.50 |
| ATOM | 2120 | O | LEU | A | 328 | 44.207 | 8.873 | 21.317 | 1.00 27.23 |
| ATOM | 2121 | CB | LEU | A | 328 | 43.177 | 11.467 | 23.180 | 1.00 29.39 |
| ATOM | 2122 | CG | LEU | A | 328 | 43.924 | 10.735 | 24.304 | 1.00 31.09 |
| ATOM | 2123 | CD1 | LEU | A | 328 | 45.298 | 10.283 | 23.831 | 1.00 31.75 |
| ATOM | 2124 | CD2 | LEU | A | 328 | 44.074 | 11.669 | 25.498 | 1.00 31.12 |
| ATOM | 2125 | N | VAL | A | 329 | 44.539 | 10.961 | 20.449 | 1.00 25.26 |
| ATOM | 2126 | CA | VAL | A | 329 | 45.748 | 10.583 | 19.722 | 1.00 23.64 |
| ATOM | 2127 | C | VAL | A | 329 | 46.779 | 11.593 | 20.203 | 1.00 23.76 |
| ATOM | 2128 | O | VAL | A | 329 | 46.431 | 12.786 | 20.476 | 1.00 21.96 |
| ATOM | 2129 | CB | VAL | A | 329 | 45.560 | 10.675 | 18.194 | 1.00 23.82 |
| ATOM | 2130 | CG1 | VAL | A | 329 | 45.100 | 12.070 | 17.794 | 1.00 23.64 |
| ATOM | 2131 | CG2 | VAL | A | 329 | 46.866 | 10.317 | 17.501 | 1.00 23.70 |
| ATOM | 2132 | N | CYS | A | 330 | 48.025 | 11.157 | 20.344 | 1.00 23.69 |
| ATOM | 2133 | CA | CYS | A | 330 | 49.088 | 12.046 | 20.830 | 1.00 24.17 |
| ATOM | 2134 | C | CYS | A | 330 | 50.315 | 12.060 | 19.937 | 1.00 23.87 |
| ATOM | 2135 | O | CYS | A | 330 | 50.592 | 11.089 | 19.165 | 1.00 24.32 |
| ATOM | 2136 | CB | CYS | A | 330 | 49.548 | 11.633 | 22.228 | 1.00 24.93 |
| ATOM | 2137 | SG | CYS | A | 330 | 48.353 | 11.638 | 23.608 | 1.00 29.07 |
| ATOM | 2138 | N | TRP | A | 331 | 51.069 | 13.144 | 20.047 | 1.00 22.66 |
| ATOM | 2139 | CA | TRP | A | 331 | 52.306 | 13.318 | 19.281 | 1.00 22.40 |
| ATOM | 2140 | C | TRP | A | 331 | 53.333 | 13.972 | 20.177 | 1.00 22.22 |
| ATOM | 2141 | O | TRP | A | 331 | 52.979 | 14.698 | 21.154 | 1.00 21.57 |
| ATOM | 2142 | CB | TRP | A | 331 | 52.069 | 14.207 | 18.064 | 1.00 21.16 |
| ATOM | 2143 | CG | TRP | A | 331 | 51.345 | 13.524 | 16.959 | 1.00 19.61 |
| ATOM | 2144 | CD1 | TRP | A | 331 | 51.868 | 12.634 | 16.067 | 1.00 18.33 |
| ATOM | 2145 | CD2 | TRP | A | 331 | 49.966 | 13.684 | 16.606 | 1.00 18.42 |
| ATOM | 2146 | NE1 | TRP | A | 331 | 50.902 | 12.233 | 15.177 | 1.00 17.37 |
| ATOM | 2147 | CE2 | TRP | A | 331 | 49.721 | 12.862 | 15.488 | 1.00 18.60 |
| ATOM | 2148 | CE3 | TRP | A | 331 | 48.911 | 14.446 | 17.130 | 1.00 19.20 |
| ATOM | 2149 | CZ2 | TRP | A | 331 | 48.467 | 12.778 | 14.874 | 1.00 17.86 |
| ATOM | 2150 | CZ3 | TRP | A | 331 | 47.659 | 14.364 | 16.521 | 1.00 19.94 |
| ATOM | 2151 | CH2 | TRP | A | 331 | 47.450 | 13.535 | 15.406 | 1.00 19.08 |
| ATOM | 2152 | N | GLN | A | 332 | 54.598 | 13.730 | 19.873 | 1.00 23.04 |
| ATOM | 2153 | CA | GLN | A | 332 | 55.689 | 14.321 | 20.648 | 1.00 25.14 |
| ATOM | 2154 | C | GLN | A | 332 | 55.490 | 15.836 | 20.594 | 1.00 23.64 |
| ATOM | 2155 | O | GLN | A | 332 | 55.066 | 16.397 | 19.533 | 1.00 23.11 |
| ATOM | 2156 | CB | GLN | A | 332 | 57.020 | 13.937 | 20.015 | 1.00 27.80 |
| ATOM | 2157 | CG | GLN | A | 332 | 58.171 | 13.877 | 20.982 | 1.00 33.30 |
| ATOM | 2158 | CD | GLN | A | 332 | 59.450 | 13.445 | 20.305 | 1.00 35.55 |
| ATOM | 2159 | OE1 | GLN | A | 332 | 60.060 | 14.224 | 19.507 | 1.00 36.94 |
| ATOM | 2160 | NE2 | GLN | A | 332 | 59.879 | 12.217 | 20.579 | 1.00 36.57 |
| ATOM | 2161 | N | ALA | A | 333 | 55.778 | 16.506 | 21.704 | 1.00 22.79 |
| ATOM | 2162 | CA | ALA | A | 333 | 55.618 | 17.977 | 21.820 | 1.00 21.04 |
| ATOM | 2163 | C | ALA | A | 333 | 55.936 | 18.759 | 20.552 | 1.00 19.77 |
| ATOM | 2164 | O | ALA | A | 333 | 57.076 | 18.671 | 19.997 | 1.00 19.85 |
| ATOM | 2165 | CB | ALA | A | 333 | 56.475 | 18.499 | 22.971 | 1.00 21.00 |
| ATOM | 2166 | N | GLY | A | 334 | 54.949 | 19.515 | 20.083 | 1.00 17.64 |

FIG. 1II

| | | | | | | | | |
|---|---|---|---|---|---|---|---|---|
| ATOM | 2167 | CA | GLY | A | 334 | 55.123 | 20.340 | 18.903 | 1.00 16.89 |
| ATOM | 2168 | C | GLY | A | 334 | 55.205 | 19.663 | 17.548 | 1.00 17.61 |
| ATOM | 2169 | O | GLY | A | 334 | 55.403 | 20.370 | 16.512 | 1.00 17.50 |
| ATOM | 2170 | N | THR | A | 335 | 55.060 | 18.343 | 17.490 | 1.00 16.55 |
| ATOM | 2171 | CA | THR | A | 335 | 55.146 | 17.648 | 16.182 | 1.00 17.58 |
| ATOM | 2172 | C | THR | A | 335 | 53.802 | 17.260 | 15.557 | 1.00 16.83 |
| ATOM | 2173 | O | THR | A | 335 | 53.761 | 16.408 | 14.618 | 1.00 17.71 |
| ATOM | 2174 | CB | THR | A | 335 | 56.017 | 16.377 | 16.275 | 1.00 17.76 |
| ATOM | 2175 | OG1 | THR | A | 335 | 55.361 | 15.401 | 17.095 | 1.00 17.56 |
| ATOM | 2176 | CG2 | THR | A | 335 | 57.373 | 16.710 | 16.884 | 1.00 17.23 |
| ATOM | 2177 | N | THR | A | 336 | 52.707 | 17.842 | 16.037 | 1.00 16.75 |
| ATOM | 2178 | CA | THR | A | 336 | 51.373 | 17.527 | 15.460 | 1.00 16.56 |
| ATOM | 2179 | C | THR | A | 336 | 51.473 | 17.752 | 13.952 | 1.00 16.24 |
| ATOM | 2180 | O | THR | A | 336 | 51.821 | 18.868 | 13.487 | 1.00 16.30 |
| ATOM | 2181 | CB | THR | A | 336 | 50.267 | 18.437 | 16.030 | 1.00 17.05 |
| ATOM | 2182 | OG1 | THR | A | 336 | 50.181 | 18.255 | 17.451 | 1.00 17.15 |
| ATOM | 2183 | CG2 | THR | A | 336 | 48.917 | 18.096 | 15.401 | 1.00 16.72 |
| ATOM | 2184 | N | PRO | A | 337 | 51.182 | 16.718 | 13.157 | 1.00 15.50 |
| ATOM | 2185 | CA | PRO | A | 337 | 51.254 | 16.820 | 11.699 | 1.00 14.87 |
| ATOM | 2186 | C | PRO | A | 337 | 50.006 | 17.444 | 11.082 | 1.00 14.56 |
| ATOM | 2187 | O | PRO | A | 337 | 49.310 | 16.800 | 10.249 | 1.00 14.49 |
| ATOM | 2188 | CB | PRO | A | 337 | 51.448 | 15.369 | 11.281 | 1.00 15.18 |
| ATOM | 2189 | CG | PRO | A | 337 | 50.520 | 14.657 | 12.238 | 1.00 16.05 |
| ATOM | 2190 | CD | PRO | A | 337 | 50.784 | 15.359 | 13.572 | 1.00 15.54 |
| ATOM | 2191 | N | TRP | A | 338 | 49.713 | 18.682 | 11.470 | 1.00 14.89 |
| ATOM | 2192 | CA | TRP | A | 338 | 48.535 | 19.415 | 10.956 | 1.00 14.85 |
| ATOM | 2193 | C | TRP | A | 338 | 48.339 | 19.304 | 9.445 | 1.00 14.87 |
| ATOM | 2194 | O | TRP | A | 338 | 47.194 | 19.048 | 8.966 | 1.00 17.13 |
| ATOM | 2195 | CB | TRP | A | 338 | 48.639 | 20.899 | 11.313 | 1.00 13.77 |
| ATOM | 2196 | CG | TRP | A | 338 | 48.784 | 21.176 | 12.767 | 1.00 15.11 |
| ATOM | 2197 | CD1 | TRP | A | 338 | 49.897 | 21.652 | 13.411 | 1.00 14.78 |
| ATOM | 2198 | CD2 | TRP | A | 338 | 47.780 | 21.011 | 13.771 | 1.00 14.17 |
| ATOM | 2199 | NE1 | TRP | A | 338 | 49.641 | 21.794 | 14.756 | 1.00 14.64 |
| ATOM | 2200 | CE2 | TRP | A | 338 | 48.348 | 21.407 | 15.003 | 1.00 14.35 |
| ATOM | 2201 | CE3 | TRP | A | 338 | 46.451 | 20.566 | 13.751 | 1.00 14.31 |
| ATOM | 2202 | CZ2 | TRP | A | 338 | 47.635 | 21.371 | 16.202 | 1.00 14.86 |
| ATOM | 2203 | CZ3 | TRP | A | 338 | 45.744 | 20.530 | 14.945 | 1.00 16.02 |
| ATOM | 2204 | CH2 | TRP | A | 338 | 46.339 | 20.932 | 16.154 | 1.00 14.77 |
| ATOM | 2205 | N | ASN | A | 339 | 49.414 | 19.486 | 8.682 | 1.00 13.22 |
| ATOM | 2206 | CA | ASN | A | 339 | 49.319 | 19.449 | 7.203 | 1.00 12.87 |
| ATOM | 2207 | C | ASN | A | 339 | 48.674 | 18.208 | 6.608 | 1.00 12.01 |
| ATOM | 2208 | O | ASN | A | 339 | 48.061 | 18.288 | 5.508 | 1.00 13.99 |
| ATOM | 2209 | CB | ASN | A | 339 | 50.699 | 19.649 | 6.552 | 1.00 12.61 |
| ATOM | 2210 | CG | ASN | A | 339 | 51.576 | 18.404 | 6.627 | 1.00 15.28 |
| ATOM | 2211 | OD1 | ASN | A | 339 | 52.290 | 18.174 | 7.648 | 1.00 16.29 |
| ATOM | 2212 | ND2 | ASN | A | 339 | 51.541 | 17.584 | 5.578 | 1.00 12.93 |
| ATOM | 2213 | N | ILE | A | 340 | 48.774 | 17.064 | 7.276 | 1.00 12.88 |
| ATOM | 2214 | CA | ILE | A | 340 | 48.171 | 15.831 | 6.698 | 1.00 12.98 |
| ATOM | 2215 | C | ILE | A | 340 | 46.655 | 15.864 | 6.794 | 1.00 12.80 |
| ATOM | 2216 | O | ILE | A | 340 | 45.944 | 15.237 | 5.959 | 1.00 12.80 |
| ATOM | 2217 | CB | ILE | A | 340 | 48.667 | 14.545 | 7.400 | 1.00 14.79 |
| ATOM | 2218 | CG1 | ILE | A | 340 | 48.142 | 14.512 | 8.833 | 1.00 14.91 |
| ATOM | 2219 | CG2 | ILE | A | 340 | 50.194 | 14.483 | 7.372 | 1.00 12.38 |
| ATOM | 2220 | CD1 | ILE | A | 340 | 48.177 | 13.142 | 9.454 | 1.00 17.42 |
| ATOM | 2221 | N | PHE | A | 341 | 46.138 | 16.577 | 7.790 | 1.00 13.19 |
| ATOM | 2222 | CA | PHE | A | 341 | 44.677 | 16.689 | 7.972 | 1.00 13.87 |
| ATOM | 2223 | C | PHE | A | 341 | 44.143 | 17.741 | 7.006 | 1.00 13.37 |
| ATOM | 2224 | O | PHE | A | 341 | 44.787 | 18.812 | 6.798 | 1.00 12.72 |
| ATOM | 2225 | CB | PHE | A | 341 | 44.354 | 17.087 | 9.410 | 1.00 13.10 |
| ATOM | 2226 | CG | PHE | A | 341 | 44.685 | 16.027 | 10.429 | 1.00 13.55 |
| ATOM | 2227 | CD1 | PHE | A | 341 | 43.817 | 14.960 | 10.654 | 1.00 13.48 |
| ATOM | 2228 | CD2 | PHE | A | 341 | 45.861 | 16.104 | 11.171 | 1.00 12.12 |

FIG. 1JJ

| | | | | | | | | |
|---|---|---|---|---|---|---|---|---|
| ATOM | 2229 | CE1 | PHE | A | 341 | 44.115 | 13.984 | 11.607 | 1.00 | 13.44 |
| ATOM | 2230 | CE2 | PHE | A | 341 | 46.172 | 15.136 | 12.127 | 1.00 | 14.31 |
| ATOM | 2231 | CZ | PHE | A | 341 | 45.298 | 14.074 | 12.346 | 1.00 | 13.92 |
| ATOM | 2232 | N | PRO | A | 342 | 42.975 | 17.484 | 6.402 | 1.00 | 12.78 |
| ATOM | 2233 | CA | PRO | A | 342 | 42.357 | 18.413 | 5.448 | 1.00 | 12.17 |
| ATOM | 2234 | C | PRO | A | 342 | 41.565 | 19.544 | 6.100 | 1.00 | 12.90 |
| ATOM | 2235 | O | PRO | A | 342 | 41.168 | 19.465 | 7.309 | 1.00 | 12.52 |
| ATOM | 2236 | CB | PRO | A | 342 | 41.447 | 17.502 | 4.638 | 1.00 | 10.18 |
| ATOM | 2237 | CG | PRO | A | 342 | 40.920 | 16.570 | 5.714 | 1.00 | 11.48 |
| ATOM | 2238 | CD | PRO | A | 342 | 42.180 | 16.244 | 6.523 | 1.00 | 12.10 |
| ATOM | 2239 | N | VAL | A | 343 | 41.342 | 20.609 | 5.342 | 1.00 | 12.27 |
| ATOM | 2240 | CA | VAL | A | 343 | 40.528 | 21.712 | 5.851 | 1.00 | 10.51 |
| ATOM | 2241 | C | VAL | A | 343 | 39.101 | 21.281 | 5.521 | 1.00 | 12.41 |
| ATOM | 2242 | O | VAL | A | 343 | 38.878 | 20.401 | 4.632 | 1.00 | 10.45 |
| ATOM | 2243 | CB | VAL | A | 343 | 40.838 | 23.054 | 5.143 | 1.00 | 10.23 |
| ATOM | 2244 | CG1 | VAL | A | 343 | 42.247 | 23.507 | 5.488 | 1.00 | 8.58 |
| ATOM | 2245 | CG2 | VAL | A | 343 | 40.672 | 22.914 | 3.636 | 1.00 | 8.08 |
| ATOM | 2246 | N | ILE | A | 344 | 38.132 | 21.848 | 6.224 | 1.00 | 13.49 |
| ATOM | 2247 | CA | ILE | A | 344 | 36.725 | 21.507 | 5.991 | 1.00 | 13.17 |
| ATOM | 2248 | C | ILE | A | 344 | 35.989 | 22.789 | 5.664 | 1.00 | 13.33 |
| ATOM | 2249 | O | ILE | A | 344 | 36.067 | 23.795 | 6.427 | 1.00 | 13.12 |
| ATOM | 2250 | CB | ILE | A | 344 | 36.099 | 20.859 | 7.246 | 1.00 | 14.77 |
| ATOM | 2251 | CG1 | ILE | A | 344 | 36.776 | 19.512 | 7.517 | 1.00 | 14.50 |
| ATOM | 2252 | CG2 | ILE | A | 344 | 34.585 | 20.702 | 7.060 | 1.00 | 13.14 |
| ATOM | 2253 | CD1 | ILE | A | 344 | 36.374 | 18.875 | 8.825 | 1.00 | 17.73 |
| ATOM | 2254 | N | SER | A | 345 | 35.292 | 22.794 | 4.537 | 1.00 | 12.41 |
| ATOM | 2255 | CA | SER | A | 345 | 34.547 | 23.982 | 4.136 | 1.00 | 13.41 |
| ATOM | 2256 | C | SER | A | 345 | 33.051 | 23.723 | 4.172 | 1.00 | 14.94 |
| ATOM | 2257 | O | SER | A | 345 | 32.555 | 22.641 | 3.721 | 1.00 | 14.55 |
| ATOM | 2258 | CB | SER | A | 345 | 34.967 | 24.430 | 2.728 | 1.00 | 14.23 |
| ATOM | 2259 | OG | SER | A | 345 | 36.329 | 24.834 | 2.703 | 1.00 | 13.57 |
| ATOM | 2260 | N | LEU | A | 346 | 32.320 | 24.682 | 4.725 | 1.00 | 13.42 |
| ATOM | 2261 | CA | LEU | A | 346 | 30.859 | 24.594 | 4.796 | 1.00 | 14.08 |
| ATOM | 2262 | C | LEU | A | 346 | 30.320 | 25.772 | 4.003 | 1.00 | 13.86 |
| ATOM | 2263 | O | LEU | A | 346 | 30.681 | 26.956 | 4.286 | 1.00 | 13.52 |
| ATOM | 2264 | CB | LEU | A | 346 | 30.383 | 24.674 | 6.252 | 1.00 | 15.83 |
| ATOM | 2265 | CG | LEU | A | 346 | 30.239 | 23.372 | 7.051 | 1.00 | 17.74 |
| ATOM | 2266 | CD1 | LEU | A | 346 | 31.455 | 22.492 | 6.875 | 1.00 | 18.92 |
| ATOM | 2267 | CD2 | LEU | A | 346 | 30.028 | 23.711 | 8.521 | 1.00 | 19.69 |
| ATOM | 2268 | N | TYR | A | 347 | 29.496 | 25.485 | 3.000 | 1.00 | 13.48 |
| ATOM | 2269 | CA | TYR | A | 347 | 28.894 | 26.543 | 2.176 | 1.00 | 13.76 |
| ATOM | 2270 | C | TYR | A | 347 | 27.525 | 26.864 | 2.745 | 1.00 | 14.58 |
| ATOM | 2271 | O | TYR | A | 347 | 26.676 | 25.948 | 2.979 | 1.00 | 13.16 |
| ATOM | 2272 | CB | TYR | A | 347 | 28.757 | 26.101 | 0.716 | 1.00 | 14.82 |
| ATOM | 2273 | CG | TYR | A | 347 | 30.066 | 26.051 | -0.034 | 1.00 | 15.10 |
| ATOM | 2274 | CD1 | TYR | A | 347 | 31.022 | 25.074 | 0.252 | 1.00 | 13.97 |
| ATOM | 2275 | CD2 | TYR | A | 347 | 30.349 | 26.977 | -1.038 | 1.00 | 13.98 |
| ATOM | 2276 | CE1 | TYR | A | 347 | 32.228 | 25.018 | -0.447 | 1.00 | 14.47 |
| ATOM | 2277 | CE2 | TYR | A | 347 | 31.556 | 26.930 | -1.746 | 1.00 | 15.69 |
| ATOM | 2278 | CZ | TYR | A | 347 | 32.487 | 25.949 | -1.445 | 1.00 | 15.09 |
| ATOM | 2279 | OH | TYR | A | 347 | 33.672 | 25.895 | -2.141 | 1.00 | 16.72 |
| ATOM | 2280 | N | LEU | A | 348 | 27.288 | 28.145 | 2.971 | 1.00 | 13.86 |
| ATOM | 2281 | CA | LEU | A | 348 | 26.018 | 28.593 | 3.545 | 1.00 | 16.70 |
| ATOM | 2282 | C | LEU | A | 348 | 25.246 | 29.445 | 2.559 | 1.00 | 17.37 |
| ATOM | 2283 | O | LEU | A | 348 | 25.856 | 30.183 | 1.722 | 1.00 | 16.05 |
| ATOM | 2284 | CB | LEU | A | 348 | 26.292 | 29.401 | 4.814 | 1.00 | 15.57 |
| ATOM | 2285 | CG | LEU | A | 348 | 27.019 | 28.620 | 5.908 | 1.00 | 17.10 |
| ATOM | 2286 | CD1 | LEU | A | 348 | 27.518 | 29.565 | 6.985 | 1.00 | 15.71 |
| ATOM | 2287 | CD2 | LEU | A | 348 | 26.078 | 27.580 | 6.495 | 1.00 | 16.92 |
| ATOM | 2288 | N | MET | A | 349 | 23.922 | 29.352 | 2.617 | 1.00 | 19.68 |
| ATOM | 2289 | CA | MET | A | 349 | 23.073 | 30.167 | 1.734 | 1.00 | 22.78 |
| ATOM | 2290 | C | MET | A | 349 | 23.384 | 31.629 | 2.024 | 1.00 | 22.03 |

FIG. 1KK

| | | | | | | | | |
|---|---|---|---|---|---|---|---|---|
| ATOM | 2291 | O | MET | A 349 | 23.478 | 32.049 | 3.222 | 1.00 20.70 |
| ATOM | 2292 | CB | MET | A 349 | 21.594 | 29.897 | 2.008 | 1.00 25.40 |
| ATOM | 2293 | CG | MET | A 349 | 20.931 | 28.954 | 1.012 | 1.00 31.18 |
| ATOM | 2294 | SD | MET | A 349 | 19.139 | 28.833 | 1.272 | 1.00 37.43 |
| ATOM | 2295 | CE | MET | A 349 | 18.697 | 30.583 | 1.318 | 1.00 32.73 |
| ATOM | 2296 | N | GLY | A 350 | 23.573 | 32.414 | 0.972 | 1.00 20.81 |
| ATOM | 2297 | CA | GLY | A 350 | 23.857 | 33.824 | 1.167 | 1.00 23.50 |
| ATOM | 2298 | C | GLY | A 350 | 22.565 | 34.612 | 1.280 | 1.00 24.26 |
| ATOM | 2299 | O | GLY | A 350 | 21.450 | 34.042 | 1.091 | 1.00 23.13 |
| ATOM | 2300 | N | GLU | A 351 | 22.662 | 35.899 | 1.591 | 1.00 27.25 |
| ATOM | 2301 | CA | GLU | A 351 | 21.448 | 36.734 | 1.698 | 1.00 32.00 |
| ATOM | 2302 | C | GLU | A 351 | 20.870 | 36.948 | 0.306 | 1.00 33.92 |
| ATOM | 2303 | O | GLU | A 351 | 19.620 | 37.066 | 0.125 | 1.00 34.42 |
| ATOM | 2304 | CB | GLU | A 351 | 21.774 | 38.081 | 2.340 | 1.00 32.31 |
| ATOM | 2305 | CG | GLU | A 351 | 22.012 | 37.996 | 3.831 | 1.00 34.92 |
| ATOM | 2306 | CD | GLU | A 351 | 21.916 | 39.346 | 4.503 | 1.00 35.55 |
| ATOM | 2307 | OE1 | GLU | A 351 | 22.819 | 40.187 | 4.293 | 1.00 36.64 |
| ATOM | 2308 | OE2 | GLU | A 351 | 20.927 | 39.567 | 5.233 | 1.00 36.29 |
| ATOM | 2309 | N | VAL | A 352 | 21.753 | 37.007 | -0.684 | 1.00 36.98 |
| ATOM | 2310 | CA | VAL | A 352 | 21.327 | 37.181 | -2.082 | 1.00 38.72 |
| ATOM | 2311 | C | VAL | A 352 | 20.944 | 35.809 | -2.629 | 1.00 40.47 |
| ATOM | 2312 | O | VAL | A 352 | 21.689 | 34.799 | -2.426 | 1.00 39.68 |
| ATOM | 2313 | CB | VAL | A 352 | 22.456 | 37.767 | -2.939 | 1.00 38.31 |
| ATOM | 2314 | CG1 | VAL | A 352 | 21.999 | 37.892 | -4.382 | 1.00 38.33 |
| ATOM | 2315 | CG2 | VAL | A 352 | 22.866 | 39.123 | -2.391 | 1.00 37.93 |
| ATOM | 2316 | N | THR | A 353 | 19.806 | 35.747 | -3.314 | 1.00 42.33 |
| ATOM | 2317 | CA | THR | A 353 | 19.300 | 34.476 | -3.882 | 1.00 43.97 |
| ATOM | 2318 | C | THR | A 353 | 20.254 | 33.832 | -4.877 | 1.00 43.18 |
| ATOM | 2319 | O | THR | A 353 | 20.941 | 34.536 | -5.688 | 1.00 42.65 |
| ATOM | 2320 | CB | THR | A 353 | 17.929 | 34.672 | -4.578 | 1.00 45.29 |
| ATOM | 2321 | OG1 | THR | A 353 | 18.018 | 35.743 | -5.526 | 1.00 46.63 |
| ATOM | 2322 | CG2 | THR | A 353 | 16.849 | 34.988 | -3.551 | 1.00 46.31 |
| ATOM | 2323 | N | ASN | A 354 | 20.307 | 32.507 | -4.839 | 1.00 42.20 |
| ATOM | 2324 | CA | ASN | A 354 | 21.183 | 31.741 | -5.742 | 1.00 43.39 |
| ATOM | 2325 | C | ASN | A 354 | 22.641 | 32.166 | -5.611 | 1.00 41.22 |
| ATOM | 2326 | O | ASN | A 354 | 23.444 | 32.078 | -6.584 | 1.00 43.04 |
| ATOM | 2327 | CB | ASN | A 354 | 20.698 | 31.887 | -7.187 | 1.00 45.64 |
| ATOM | 2328 | CG | ASN | A 354 | 19.467 | 31.036 | -7.474 | 1.00 47.44 |
| ATOM | 2329 | OD1 | ASN | A 354 | 18.824 | 31.163 | -8.562 | 1.00 48.61 |
| ATOM | 2330 | ND2 | ASN | A 354 | 19.121 | 30.159 | -6.534 | 1.00 47.73 |
| ATOM | 2331 | N | GLN | A 355 | 22.999 | 32.621 | -4.419 | 1.00 37.62 |
| ATOM | 2332 | CA | GLN | A 355 | 24.371 | 33.042 | -4.128 | 1.00 34.85 |
| ATOM | 2333 | C | GLN | A 355 | 24.737 | 32.475 | -2.764 | 1.00 32.57 |
| ATOM | 2334 | O | GLN | A 355 | 23.863 | 32.388 | -1.846 | 1.00 31.25 |
| ATOM | 2335 | CB | GLN | A 355 | 24.459 | 34.563 | -4.105 | 1.00 35.77 |
| ATOM | 2336 | CG | GLN | A 355 | 25.834 | 35.089 | -3.797 | 1.00 38.04 |
| ATOM | 2337 | CD | GLN | A 355 | 25.909 | 36.590 | -3.915 | 1.00 39.05 |
| ATOM | 2338 | OE1 | GLN | A 355 | 25.586 | 37.171 | -4.992 | 1.00 40.57 |
| ATOM | 2339 | NE2 | GLN | A 355 | 26.331 | 37.249 | -2.844 | 1.00 39.68 |
| ATOM | 2340 | N | SER | A 356 | 25.989 | 32.071 | -2.597 | 1.00 29.33 |
| ATOM | 2341 | CA | SER | A 356 | 26.419 | 31.514 | -1.304 | 1.00 25.60 |
| ATOM | 2342 | C | SER | A 356 | 27.850 | 31.897 | -0.981 | 1.00 22.66 |
| ATOM | 2343 | O | SER | A 356 | 28.580 | 32.481 | -1.833 | 1.00 21.99 |
| ATOM | 2344 | CB | SER | A 356 | 26.313 | 29.991 | -1.318 | 1.00 25.71 |
| ATOM | 2345 | OG | SER | A 356 | 27.449 | 29.425 | -1.945 | 1.00 24.59 |
| ATOM | 2346 | N | PHE | A 357 | 28.267 | 31.583 | 0.239 | 1.00 20.53 |
| ATOM | 2347 | CA | PHE | A 357 | 29.639 | 31.865 | 0.676 | 1.00 17.95 |
| ATOM | 2348 | C | PHE | A 357 | 30.104 | 30.643 | 1.437 | 1.00 17.15 |
| ATOM | 2349 | O | PHE | A 357 | 29.279 | 29.750 | 1.784 | 1.00 17.21 |
| ATOM | 2350 | CB | PHE | A 357 | 29.687 | 33.126 | 1.550 | 1.00 17.62 |
| ATOM | 2351 | CG | PHE | A 357 | 28.926 | 33.017 | 2.850 | 1.00 17.61 |
| ATOM | 2352 | CD1 | PHE | A 357 | 29.571 | 32.625 | 4.018 | 1.00 15.09 |

FIG. 1LL

```
ATOM   2353  CD2  PHE A 357      27.577  33.357   2.912  1.00 16.90
ATOM   2354  CE1  PHE A 357      28.887  32.577   5.229  1.00 14.87
ATOM   2355  CE2  PHE A 357      26.881  33.312   4.120  1.00 15.64
ATOM   2356  CZ   PHE A 357      27.538  32.924   5.280  1.00 16.14
ATOM   2357  N    ARG A 358      31.397  30.545   1.687  1.00 16.29
ATOM   2358  CA   ARG A 358      31.891  29.383   2.412  1.00 14.04
ATOM   2359  C    ARG A 358      32.642  29.755   3.664  1.00 14.59
ATOM   2360  O    ARG A 358      33.237  30.869   3.785  1.00 13.01
ATOM   2361  CB   ARG A 358      32.784  28.525   1.516  1.00 14.11
ATOM   2362  CG   ARG A 358      34.084  29.172   1.102  1.00 13.28
ATOM   2363  CD   ARG A 358      34.809  28.275   0.121  1.00 13.06
ATOM   2364  NE   ARG A 358      36.090  28.831  -0.291  1.00 14.39
ATOM   2365  CZ   ARG A 358      36.723  28.489  -1.409  1.00 14.92
ATOM   2366  NH1  ARG A 358      36.188  27.591  -2.232  1.00 13.71
ATOM   2367  NH2  ARG A 358      37.888  29.045  -1.701  1.00 12.88
ATOM   2368  N    ILE A 359      32.612  28.819   4.596  1.00 14.51
ATOM   2369  CA   ILE A 359      33.268  28.935   5.891  1.00 16.36
ATOM   2370  C    ILE A 359      34.242  27.762   5.913  1.00 15.41
ATOM   2371  O    ILE A 359      33.836  26.583   5.675  1.00 15.49
ATOM   2372  CB   ILE A 359      32.197  28.824   7.001  1.00 17.94
ATOM   2373  CG1  ILE A 359      31.543  30.190   7.198  1.00 19.68
ATOM   2374  CG2  ILE A 359      32.766  28.260   8.255  1.00 20.12
ATOM   2375  CD1  ILE A 359      32.515  31.288   7.500  1.00 22.40
ATOM   2376  N    THR A 360      35.513  28.046   6.162  1.00 13.01
ATOM   2377  CA   THR A 360      36.531  26.983   6.167  1.00 14.32
ATOM   2378  C    THR A 360      37.307  26.894   7.470  1.00 14.04
ATOM   2379  O    THR A 360      37.892  27.913   7.938  1.00 13.82
ATOM   2380  CB   THR A 360      37.536  27.202   5.021  1.00 14.49
ATOM   2381  OG1  THR A 360      36.828  27.286   3.774  1.00 15.69
ATOM   2382  CG2  THR A 360      38.532  26.053   4.964  1.00 15.11
ATOM   2383  N    ILE A 361      37.331  25.709   8.074  1.00 13.79
ATOM   2384  CA   ILE A 361      38.091  25.524   9.330  1.00 17.36
ATOM   2385  C    ILE A 361      39.241  24.548   9.122  1.00 16.53
ATOM   2386  O    ILE A 361      39.237  23.717   8.160  1.00 16.37
ATOM   2387  CB   ILE A 361      37.208  24.982  10.476  1.00 18.15
ATOM   2388  CG1  ILE A 361      36.608  23.632  10.077  1.00 18.53
ATOM   2389  CG2  ILE A 361      36.126  25.999  10.830  1.00 18.95
ATOM   2390  CD1  ILE A 361      35.899  22.937  11.208  1.00 18.19
ATOM   2391  N    LEU A 362      40.230  24.614   9.998  1.00 17.82
ATOM   2392  CA   LEU A 362      41.375  23.710   9.876  1.00 18.92
ATOM   2393  C    LEU A 362      41.412  22.659  10.983  1.00 17.87
ATOM   2394  O    LEU A 362      40.533  22.654  11.912  1.00 17.21
ATOM   2395  CB   LEU A 362      42.675  24.525   9.837  1.00 22.47
ATOM   2396  CG   LEU A 362      42.686  25.974  10.320  1.00 25.03
ATOM   2397  CD1  LEU A 362      42.945  25.992  11.802  1.00 28.14
ATOM   2398  CD2  LEU A 362      43.781  26.751   9.623  1.00 25.06
ATOM   2399  N    PRO A 363      42.380  21.729  10.910  1.00 16.12
ATOM   2400  CA   PRO A 363      42.507  20.681  11.925  1.00 14.51
ATOM   2401  C    PRO A 363      42.628  21.325  13.303  1.00 14.50
ATOM   2402  O    PRO A 363      42.234  20.710  14.339  1.00 13.48
ATOM   2403  CB   PRO A 363      43.801  19.971  11.534  1.00 15.57
ATOM   2404  CG   PRO A 363      43.902  20.202  10.076  1.00 16.87
ATOM   2405  CD   PRO A 363      43.450  21.616   9.903  1.00 14.60
ATOM   2406  N    GLN A 364      43.178  22.539  13.337  1.00 12.36
ATOM   2407  CA   GLN A 364      43.357  23.271  14.608  1.00 13.04
ATOM   2408  C    GLN A 364      42.014  23.557  15.254  1.00 13.41
ATOM   2409  O    GLN A 364      41.953  23.895  16.467  1.00 12.73
ATOM   2410  CB   GLN A 364      44.111  24.585  14.392  1.00 12.04
ATOM   2411  CG   GLN A 364      45.637  24.449  14.304  1.00 11.85
ATOM   2412  CD   GLN A 364      46.141  24.079  12.919  1.00 11.11
ATOM   2413  OE1  GLN A 364      47.372  24.211  12.625  1.00 13.65
ATOM   2414  NE2  GLN A 364      45.245  23.621  12.056  1.00  8.04
```

FIG. 1MM

| | | | | | | | | |
|---|---|---|---|---|---|---|---|---|
| ATOM | 2415 | N | GLN | A | 365 | 40.939 | 23.446 | 14.478 | 1.00 13.30 |
| ATOM | 2416 | CA | GLN | A | 365 | 39.580 | 23.657 | 15.023 | 1.00 14.36 |
| ATOM | 2417 | C | GLN | A | 365 | 38.873 | 22.341 | 15.339 | 1.00 14.57 |
| ATOM | 2418 | O | GLN | A | 365 | 38.312 | 22.175 | 16.457 | 1.00 16.56 |
| ATOM | 2419 | CB | GLN | A | 365 | 38.691 | 24.452 | 14.056 | 1.00 14.03 |
| ATOM | 2420 | CG | GLN | A | 365 | 38.816 | 25.962 | 14.167 | 1.00 15.23 |
| ATOM | 2421 | CD | GLN | A | 365 | 40.073 | 26.489 | 13.515 | 1.00 15.81 |
| ATOM | 2422 | OE1 | GLN | A | 365 | 40.290 | 26.292 | 12.282 | 1.00 15.51 |
| ATOM | 2423 | NE2 | GLN | A | 365 | 40.917 | 27.158 | 14.295 | 1.00 15.82 |
| ATOM | 2424 | N | TYR | A | 366 | 38.873 | 21.392 | 14.406 | 1.00 14.93 |
| ATOM | 2425 | CA | TYR | A | 366 | 38.149 | 20.128 | 14.673 | 1.00 15.12 |
| ATOM | 2426 | C | TYR | A | 366 | 38.914 | 19.053 | 15.447 | 1.00 15.66 |
| ATOM | 2427 | O | TYR | A | 366 | 38.378 | 17.930 | 15.703 | 1.00 17.42 |
| ATOM | 2428 | CB | TYR | A | 366 | 37.557 | 19.567 | 13.371 | 1.00 14.28 |
| ATOM | 2429 | CG | TYR | A | 366 | 38.541 | 19.107 | 12.322 | 1.00 13.05 |
| ATOM | 2430 | CD1 | TYR | A | 366 | 39.228 | 17.907 | 12.467 | 1.00 13.67 |
| ATOM | 2431 | CD2 | TYR | A | 366 | 38.721 | 19.835 | 11.145 | 1.00 13.44 |
| ATOM | 2432 | CE1 | TYR | A | 366 | 40.062 | 17.431 | 11.463 | 1.00 12.91 |
| ATOM | 2433 | CE2 | TYR | A | 366 | 39.555 | 19.369 | 10.128 | 1.00 12.63 |
| ATOM | 2434 | CZ | TYR | A | 366 | 40.218 | 18.163 | 10.294 | 1.00 13.86 |
| ATOM | 2435 | OH | TYR | A | 366 | 41.008 | 17.669 | 9.287 | 1.00 12.42 |
| ATOM | 2436 | N | LEU | A | 367 | 40.144 | 19.367 | 15.835 | 1.00 16.84 |
| ATOM | 2437 | CA | LEU | A | 367 | 40.966 | 18.450 | 16.660 | 1.00 16.98 |
| ATOM | 2438 | C | LEU | A | 367 | 40.996 | 19.161 | 18.017 | 1.00 17.50 |
| ATOM | 2439 | O | LEU | A | 367 | 41.662 | 20.224 | 18.172 | 1.00 16.40 |
| ATOM | 2440 | CB | LEU | A | 367 | 42.382 | 18.324 | 16.088 | 1.00 17.44 |
| ATOM | 2441 | CG | LEU | A | 367 | 42.764 | 16.991 | 15.429 | 1.00 18.54 |
| ATOM | 2442 | CD1 | LEU | A | 367 | 41.681 | 16.534 | 14.482 | 1.00 17.60 |
| ATOM | 2443 | CD2 | LEU | A | 367 | 44.091 | 17.143 | 14.700 | 1.00 17.38 |
| ATOM | 2444 | N | ARG | A | 368 | 40.270 | 18.624 | 18.990 | 1.00 17.06 |
| ATOM | 2445 | CA | ARG | A | 368 | 40.192 | 19.253 | 20.326 | 1.00 17.22 |
| ATOM | 2446 | C | ARG | A | 368 | 41.341 | 18.874 | 21.243 | 1.00 16.52 |
| ATOM | 2447 | O | ARG | A | 368 | 41.554 | 17.662 | 21.538 | 1.00 16.19 |
| ATOM | 2448 | CB | ARG | A | 368 | 38.879 | 18.871 | 21.009 | 1.00 16.02 |
| ATOM | 2449 | CG | ARG | A | 368 | 38.050 | 20.055 | 21.444 | 1.00 19.09 |
| ATOM | 2450 | CD | ARG | A | 368 | 37.415 | 19.811 | 22.792 | 1.00 17.88 |
| ATOM | 2451 | NE | ARG | A | 368 | 36.840 | 18.474 | 22.906 | 1.00 17.20 |
| ATOM | 2452 | CZ | ARG | A | 368 | 36.775 | 17.806 | 24.053 | 1.00 18.65 |
| ATOM | 2453 | NH1 | ARG | A | 368 | 37.247 | 18.361 | 25.164 | 1.00 18.77 |
| ATOM | 2454 | NH2 | ARG | A | 368 | 36.258 | 16.584 | 24.095 | 1.00 17.53 |
| ATOM | 2455 | N | PRO | A | 369 | 42.100 | 19.867 | 21.722 | 1.00 17.88 |
| ATOM | 2456 | CA | PRO | A | 369 | 43.220 | 19.558 | 22.615 | 1.00 19.69 |
| ATOM | 2457 | C | PRO | A | 369 | 42.744 | 19.067 | 23.969 | 1.00 22.16 |
| ATOM | 2458 | O | PRO | A | 369 | 41.786 | 19.645 | 24.575 | 1.00 20.49 |
| ATOM | 2459 | CB | PRO | A | 369 | 43.983 | 20.883 | 22.700 | 1.00 20.03 |
| ATOM | 2460 | CG | PRO | A | 369 | 42.932 | 21.911 | 22.429 | 1.00 19.96 |
| ATOM | 2461 | CD | PRO | A | 369 | 42.122 | 21.285 | 21.320 | 1.00 17.42 |
| ATOM | 2462 | N | VAL | A | 370 | 43.376 | 18.001 | 24.444 | 1.00 23.75 |
| ATOM | 2463 | CA | VAL | A | 370 | 43.040 | 17.399 | 25.747 | 1.00 27.84 |
| ATOM | 2464 | C | VAL | A | 370 | 44.332 | 16.921 | 26.394 | 1.00 30.26 |
| ATOM | 2465 | O | VAL | A | 370 | 45.321 | 16.577 | 25.682 | 1.00 30.79 |
| ATOM | 2466 | CB | VAL | A | 370 | 42.093 | 16.197 | 25.577 | 1.00 26.52 |
| ATOM | 2467 | CG1 | VAL | A | 370 | 40.771 | 16.654 | 24.989 | 1.00 26.57 |
| ATOM | 2468 | CG2 | VAL | A | 370 | 42.737 | 15.160 | 24.669 | 1.00 26.53 |
| ATOM | 2469 | N | GLU | A | 371 | 44.361 | 16.891 | 27.719 | 1.00 35.50 |
| ATOM | 2470 | CA | GLU | A | 371 | 45.574 | 16.450 | 28.426 | 1.00 40.60 |
| ATOM | 2471 | C | GLU | A | 371 | 45.800 | 14.963 | 28.235 | 1.00 42.42 |
| ATOM | 2472 | O | GLU | A | 371 | 44.832 | 14.138 | 28.321 | 1.00 41.89 |
| ATOM | 2473 | CB | GLU | A | 371 | 45.472 | 16.758 | 29.921 | 1.00 43.12 |
| ATOM | 2474 | CG | GLU | A | 371 | 46.603 | 17.634 | 30.443 | 1.00 47.33 |
| ATOM | 2475 | CD | GLU | A | 371 | 47.954 | 17.245 | 29.864 | 1.00 49.98 |
| ATOM | 2476 | OE1 | GLU | A | 371 | 48.264 | 16.036 | 29.818 | 1.00 51.63 |

FIG. 1NN

| ATOM | 2477 | OE2 | GLU A 371 | 48.710 | 18.151 | 29.456 | 1.00 | 51.00 |
|------|------|-----|-----------|--------|--------|--------|------|-------|
| ATOM | 2478 | N | ASP A 372 | 47.046 | 14.596 | 27.960 | 1.00 | 45.77 |
| ATOM | 2479 | CA | ASP A 372 | 47.396 | 13.182 | 27.774 | 1.00 | 49.75 |
| ATOM | 2480 | C | ASP A 372 | 46.889 | 12.468 | 29.014 | 1.00 | 52.41 |
| ATOM | 2481 | O | ASP A 372 | 47.090 | 12.966 | 30.165 | 1.00 | 52.32 |
| ATOM | 2482 | CB | ASP A 372 | 48.913 | 13.015 | 27.665 | 1.00 | 50.28 |
| ATOM | 2483 | CG | ASP A 372 | 49.323 | 11.587 | 27.333 | 1.00 | 51.15 |
| ATOM | 2484 | OD1 | ASP A 372 | 50.541 | 11.323 | 27.246 | 1.00 | 51.32 |
| ATOM | 2485 | OD2 | ASP A 372 | 48.429 | 10.729 | 27.156 | 1.00 | 50.76 |
| ATOM | 2486 | N | VAL A 373 | 46.217 | 11.340 | 28.819 | 1.00 | 55.35 |
| ATOM | 2487 | CA | VAL A 373 | 45.688 | 10.570 | 29.956 | 1.00 | 58.73 |
| ATOM | 2488 | C | VAL A 373 | 46.850 | 10.213 | 30.896 | 1.00 | 60.04 |
| ATOM | 2489 | O | VAL A 373 | 47.465 | 9.105 | 30.817 | 1.00 | 60.06 |
| ATOM | 2490 | CB | VAL A 373 | 44.901 | 9.313 | 29.433 | 1.00 | 59.43 |
| ATOM | 2491 | CG1 | VAL A 373 | 45.292 | 8.044 | 30.176 | 1.00 | 59.64 |
| ATOM | 2492 | CG2 | VAL A 373 | 43.402 | 9.556 | 29.597 | 1.00 | 59.89 |
| ATOM | 2493 | N | ALA A 374 | 47.187 | 11.169 | 31.759 | 1.00 | 61.58 |
| ATOM | 2494 | CA | ALA A 374 | 48.277 | 11.020 | 32.755 | 1.00 | 61.52 |
| ATOM | 2495 | C | ALA A 374 | 49.709 | 11.205 | 32.233 | 1.00 | 61.38 |
| ATOM | 2496 | O | ALA A 374 | 50.104 | 10.633 | 31.169 | 1.00 | 60.95 |
| ATOM | 2497 | CB | ALA A 374 | 48.155 | 9.668 | 33.455 | 1.00 | 62.66 |
| ATOM | 2498 | N | THR A 375 | 50.477 | 12.002 | 32.977 | 1.00 | 61.03 |
| ATOM | 2499 | CA | THR A 375 | 51.919 | 12.320 | 32.715 | 1.00 | 60.30 |
| ATOM | 2500 | C | THR A 375 | 52.401 | 12.358 | 31.269 | 1.00 | 58.41 |
| ATOM | 2501 | O | THR A 375 | 52.361 | 11.308 | 30.555 | 1.00 | 59.21 |
| ATOM | 2502 | CB | THR A 375 | 52.838 | 11.327 | 33.455 | 1.00 | 61.35 |
| ATOM | 2503 | OG1 | THR A 375 | 52.302 | 11.049 | 34.756 | 1.00 | 62.26 |
| ATOM | 2504 | CG2 | THR A 375 | 54.237 | 11.912 | 33.599 | 1.00 | 61.47 |
| ATOM | 2505 | N | SER A 376 | 52.892 | 13.520 | 30.833 | 1.00 | 55.18 |
| ATOM | 2506 | CA | SER A 376 | 53.407 | 13.683 | 29.445 | 1.00 | 51.40 |
| ATOM | 2507 | C | SER A 376 | 53.538 | 15.132 | 28.981 | 1.00 | 48.79 |
| ATOM | 2508 | O | SER A 376 | 52.887 | 16.067 | 29.540 | 1.00 | 48.19 |
| ATOM | 2509 | CB | SER A 376 | 52.502 | 12.943 | 28.456 | 1.00 | 51.90 |
| ATOM | 2510 | OG | SER A 376 | 52.880 | 13.193 | 27.115 | 1.00 | 51.94 |
| ATOM | 2511 | N | GLN A 377 | 54.373 | 15.333 | 27.968 | 1.00 | 44.88 |
| ATOM | 2512 | CA | GLN A 377 | 54.576 | 16.664 | 27.367 | 1.00 | 41.28 |
| ATOM | 2513 | C | GLN A 377 | 54.106 | 16.580 | 25.923 | 1.00 | 37.22 |
| ATOM | 2514 | O | GLN A 377 | 54.380 | 17.489 | 25.081 | 1.00 | 35.23 |
| ATOM | 2515 | CB | GLN A 377 | 56.048 | 17.062 | 27.425 | 1.00 | 43.59 |
| ATOM | 2516 | CG | GLN A 377 | 56.468 | 17.585 | 28.789 | 1.00 | 46.22 |
| ATOM | 2517 | CD | GLN A 377 | 57.955 | 17.831 | 28.886 | 1.00 | 47.12 |
| ATOM | 2518 | OE1 | GLN A 377 | 58.710 | 17.710 | 27.867 | 1.00 | 48.44 |
| ATOM | 2519 | NE2 | GLN A 377 | 58.414 | 18.177 | 30.081 | 1.00 | 48.23 |
| ATOM | 2520 | N | ASP A 378 | 53.399 | 15.499 | 25.618 | 1.00 | 31.89 |
| ATOM | 2521 | CA | ASP A 378 | 52.866 | 15.289 | 24.263 | 1.00 | 28.31 |
| ATOM | 2522 | C | ASP A 378 | 51.663 | 16.183 | 24.034 | 1.00 | 25.36 |
| ATOM | 2523 | O | ASP A 378 | 50.958 | 16.590 | 25.004 | 1.00 | 22.58 |
| ATOM | 2524 | CB | ASP A 378 | 52.422 | 13.835 | 24.072 | 1.00 | 28.64 |
| ATOM | 2525 | CG | ASP A 378 | 53.582 | 12.867 | 23.998 | 1.00 | 29.19 |
| ATOM | 2526 | OD1 | ASP A 378 | 54.746 | 13.316 | 23.948 | 1.00 | 30.91 |
| ATOM | 2527 | OD2 | ASP A 378 | 53.323 | 11.647 | 23.981 | 1.00 | 30.50 |
| ATOM | 2528 | N | ASP A 379 | 51.415 | 16.513 | 22.776 | 1.00 | 23.06 |
| ATOM | 2529 | CA | ASP A 379 | 50.236 | 17.317 | 22.436 | 1.00 | 22.51 |
| ATOM | 2530 | C | ASP A 379 | 49.220 | 16.294 | 21.964 | 1.00 | 21.46 |
| ATOM | 2531 | O | ASP A 379 | 49.436 | 15.581 | 20.945 | 1.00 | 19.87 |
| ATOM | 2532 | CB | ASP A 379 | 50.570 | 18.335 | 21.346 | 1.00 | 21.72 |
| ATOM | 2533 | CG | ASP A 379 | 51.557 | 19.377 | 21.829 | 1.00 | 23.29 |
| ATOM | 2534 | OD1 | ASP A 379 | 51.434 | 19.786 | 23.005 | 1.00 | 23.00 |
| ATOM | 2535 | OD2 | ASP A 379 | 52.446 | 19.789 | 21.052 | 1.00 | 23.50 |
| ATOM | 2536 | N | CYS A 380 | 48.128 | 16.182 | 22.706 | 1.00 | 20.99 |
| ATOM | 2537 | CA | CYS A 380 | 47.082 | 15.201 | 22.393 | 1.00 | 20.40 |
| ATOM | 2538 | C | CYS A 380 | 45.769 | 15.865 | 22.013 | 1.00 | 19.94 |

FIG. 100

```
ATOM   2539  O    CYS A 380      45.489  17.038  22.417  1.00 18.77
ATOM   2540  CB   CYS A 380      46.867  14.292  23.596  1.00 23.14
ATOM   2541  SG   CYS A 380      48.368  13.550  24.327  1.00 25.25
ATOM   2542  N    TYR A 381      44.947  15.140  21.255  1.00 18.49
ATOM   2543  CA   TYR A 381      43.656  15.681  20.785  1.00 17.31
ATOM   2544  C    TYR A 381      42.595  14.610  20.602  1.00 17.45
ATOM   2545  O    TYR A 381      42.890  13.376  20.532  1.00 16.46
ATOM   2546  CB   TYR A 381      43.833  16.370  19.427  1.00 15.47
ATOM   2547  CG   TYR A 381      45.034  17.275  19.314  1.00 14.93
ATOM   2548  CD1  TYR A 381      44.899  18.659  19.408  1.00 14.20
ATOM   2549  CD2  TYR A 381      46.311  16.746  19.118  1.00 14.17
ATOM   2550  CE1  TYR A 381      46.009  19.499  19.307  1.00 14.66
ATOM   2551  CE2  TYR A 381      47.431  17.576  19.021  1.00 15.73
ATOM   2552  CZ   TYR A 381      47.272  18.952  19.113  1.00 16.02
ATOM   2553  OH   TYR A 381      48.369  19.785  18.994  1.00 15.32
ATOM   2554  N    LYS A 382      41.356  15.066  20.506  1.00 18.35
ATOM   2555  CA   LYS A 382      40.218  14.174  20.248  1.00 20.26
ATOM   2556  C    LYS A 382      39.555  14.695  18.981  1.00 19.31
ATOM   2557  O    LYS A 382      39.575  15.941  18.704  1.00 19.65
ATOM   2558  CB   LYS A 382      39.221  14.204  21.404  1.00 21.74
ATOM   2559  CG   LYS A 382      39.632  13.348  22.585  1.00 25.42
ATOM   2560  CD   LYS A 382      38.509  13.266  23.602  1.00 27.59
ATOM   2561  CE   LYS A 382      38.878  12.342  24.759  1.00 29.84
ATOM   2562  NZ   LYS A 382      37.779  12.246  25.761  1.00 31.22
ATOM   2563  N    PHE A 383      38.994  13.786  18.192  1.00 18.55
ATOM   2564  CA   PHE A 383      38.298  14.165  16.942  1.00 16.97
ATOM   2565  C    PHE A 383      36.992  14.823  17.375  1.00 16.22
ATOM   2566  O    PHE A 383      36.079  14.138  17.908  1.00 13.73
ATOM   2567  CB   PHE A 383      38.026  12.907  16.110  1.00 16.57
ATOM   2568  CG   PHE A 383      37.447  13.182  14.750  1.00 16.49
ATOM   2569  CD1  PHE A 383      38.052  14.091  13.890  1.00 14.48
ATOM   2570  CD2  PHE A 383      36.319  12.489  14.308  1.00 15.06
ATOM   2571  CE1  PHE A 383      37.542  14.306  12.606  1.00 16.02
ATOM   2572  CE2  PHE A 383      35.807  12.696  13.029  1.00 15.64
ATOM   2573  CZ   PHE A 383      36.419  13.603  12.176  1.00 15.10
ATOM   2574  N    ALA A 384      36.885  16.134  17.173  1.00 16.28
ATOM   2575  CA   ALA A 384      35.675  16.893  17.586  1.00 15.54
ATOM   2576  C    ALA A 384      34.549  16.931  16.559  1.00 15.46
ATOM   2577  O    ALA A 384      33.768  17.931  16.487  1.00 15.60
ATOM   2578  CB   ALA A 384      36.061  18.316  17.987  1.00 14.96
ATOM   2579  N    ILE A 385      34.451  15.888  15.745  1.00 14.66
ATOM   2580  CA   ILE A 385      33.356  15.792  14.763  1.00 13.45
ATOM   2581  C    ILE A 385      32.651  14.487  15.093  1.00 14.39
ATOM   2582  O    ILE A 385      33.303  13.410  15.179  1.00 12.37
ATOM   2583  CB   ILE A 385      33.862  15.724  13.315  1.00 12.54
ATOM   2584  CG1  ILE A 385      34.696  16.959  12.988  1.00 13.08
ATOM   2585  CG2  ILE A 385      32.675  15.655  12.367  1.00 12.56
ATOM   2586  CD1  ILE A 385      35.178  17.003  11.549  1.00 10.74
ATOM   2587  N    SER A 386      31.343  14.543  15.297  1.00 14.95
ATOM   2588  CA   SER A 386      30.605  13.319  15.637  1.00 16.99
ATOM   2589  C    SER A 386      29.275  13.221  14.918  1.00 17.48
ATOM   2590  O    SER A 386      28.795  14.207  14.279  1.00 18.09
ATOM   2591  CB   SER A 386      30.385  13.240  17.151  1.00 16.69
ATOM   2592  OG   SER A 386      29.630  14.345  17.616  1.00 16.81
ATOM   2593  N    GLN A 387      28.673  12.044  15.016  1.00 19.86
ATOM   2594  CA   GLN A 387      27.384  11.748  14.376  1.00 23.09
ATOM   2595  C    GLN A 387      26.209  12.317  15.160  1.00 22.61
ATOM   2596  O    GLN A 387      26.221  12.363  16.427  1.00 22.90
ATOM   2597  CB   GLN A 387      27.222  10.234  14.247  1.00 24.53
ATOM   2598  CG   GLN A 387      26.035   9.795  13.411  1.00 28.94
ATOM   2599  CD   GLN A 387      25.971   8.286  13.272  1.00 30.39
ATOM   2600  OE1  GLN A 387      27.013   7.619  12.999  1.00 31.54
```

FIG. 1PP

| | | | | | | | |
|---|---|---|---|---|---|---|---|
| ATOM | 2601 | NE2 | GLN A 387 | 24.782 | 7.721 | 13.441 | 1.00 32.07 |
| ATOM | 2602 | N | SER A 388 | 25.186 | 12.743 | 14.434 | 1.00 21.60 |
| ATOM | 2603 | CA | SER A 388 | 23.981 | 13.306 | 15.055 | 1.00 21.59 |
| ATOM | 2604 | C | SER A 388 | 22.728 | 12.711 | 14.429 | 1.00 22.68 |
| ATOM | 2605 | O | SER A 388 | 22.707 | 12.380 | 13.203 | 1.00 23.08 |
| ATOM | 2606 | CB | SER A 388 | 23.959 | 14.824 | 14.871 | 1.00 19.88 |
| ATOM | 2607 | OG | SER A 388 | 22.661 | 15.342 | 15.112 | 1.00 19.18 |
| ATOM | 2608 | N | SER A 389 | 21.681 | 12.551 | 15.227 | 1.00 23.51 |
| ATOM | 2609 | CA | SER A 389 | 20.405 | 12.024 | 14.690 | 1.00 24.44 |
| ATOM | 2610 | C | SER A 389 | 19.391 | 13.167 | 14.708 | 1.00 23.83 |
| ATOM | 2611 | O | SER A 389 | 18.181 | 12.973 | 14.385 | 1.00 23.81 |
| ATOM | 2612 | CB | SER A 389 | 19.902 | 10.847 | 15.534 | 1.00 25.63 |
| ATOM | 2613 | OG | SER A 389 | 19.681 | 11.235 | 16.881 | 1.00 27.65 |
| ATOM | 2614 | N | THR A 390 | 19.861 | 14.360 | 15.066 | 1.00 22.66 |
| ATOM | 2615 | CA | THR A 390 | 18.984 | 15.553 | 15.127 | 1.00 22.60 |
| ATOM | 2616 | C | THR A 390 | 19.471 | 16.709 | 14.260 | 1.00 21.12 |
| ATOM | 2617 | O | THR A 390 | 19.272 | 17.910 | 14.608 | 1.00 21.35 |
| ATOM | 2618 | CB | THR A 390 | 18.825 | 16.052 | 16.577 | 1.00 23.02 |
| ATOM | 2619 | OG1 | THR A 390 | 20.117 | 16.288 | 17.150 | 1.00 24.55 |
| ATOM | 2620 | CG2 | THR A 390 | 18.079 | 15.010 | 17.413 | 1.00 23.83 |
| ATOM | 2621 | N | GLY A 391 | 20.093 | 16.381 | 13.136 | 1.00 19.75 |
| ATOM | 2622 | CA | GLY A 391 | 20.573 | 17.410 | 12.237 | 1.00 16.88 |
| ATOM | 2623 | C | GLY A 391 | 21.982 | 17.891 | 12.526 | 1.00 17.24 |
| ATOM | 2624 | O | GLY A 391 | 22.672 | 17.402 | 13.472 | 1.00 16.27 |
| ATOM | 2625 | N | THR A 392 | 22.427 | 18.851 | 11.730 | 1.00 14.99 |
| ATOM | 2626 | CA | THR A 392 | 23.773 | 19.423 | 11.880 | 1.00 14.81 |
| ATOM | 2627 | C | THR A 392 | 23.841 | 20.514 | 12.938 | 1.00 14.47 |
| ATOM | 2628 | O | THR A 392 | 22.949 | 21.409 | 13.012 | 1.00 16.11 |
| ATOM | 2629 | CB | THR A 392 | 24.266 | 20.062 | 10.564 | 1.00 12.95 |
| ATOM | 2630 | OG1 | THR A 392 | 24.494 | 19.043 | 9.588 | 1.00 14.51 |
| ATOM | 2631 | CG2 | THR A 392 | 25.572 | 20.839 | 10.800 | 1.00 14.09 |
| ATOM | 2632 | N | VAL A 393 | 24.857 | 20.458 | 13.779 | 1.00 13.06 |
| ATOM | 2633 | CA | VAL A 393 | 25.027 | 21.534 | 14.746 | 1.00 15.07 |
| ATOM | 2634 | C | VAL A 393 | 26.462 | 22.033 | 14.684 | 1.00 15.47 |
| ATOM | 2635 | O | VAL A 393 | 27.450 | 21.265 | 14.908 | 1.00 16.85 |
| ATOM | 2636 | CB | VAL A 393 | 24.619 | 21.128 | 16.201 | 1.00 16.35 |
| ATOM | 2637 | CG1 | VAL A 393 | 24.559 | 19.624 | 16.348 | 1.00 15.06 |
| ATOM | 2638 | CG2 | VAL A 393 | 25.566 | 21.766 | 17.210 | 1.00 13.79 |
| ATOM | 2639 | N | MET A 394 | 26.592 | 23.298 | 14.312 | 1.00 15.41 |
| ATOM | 2640 | CA | MET A 394 | 27.900 | 23.962 | 14.231 | 1.00 16.55 |
| ATOM | 2641 | C | MET A 394 | 28.188 | 24.442 | 15.647 | 1.00 16.43 |
| ATOM | 2642 | O | MET A 394 | 27.737 | 25.553 | 16.059 | 1.00 14.99 |
| ATOM | 2643 | CB | MET A 394 | 27.822 | 25.143 | 13.264 | 1.00 16.88 |
| ATOM | 2644 | CG | MET A 394 | 27.607 | 24.724 | 11.818 | 1.00 21.12 |
| ATOM | 2645 | SD | MET A 394 | 27.178 | 26.083 | 10.700 | 1.00 27.34 |
| ATOM | 2646 | CE | MET A 394 | 25.475 | 25.768 | 10.522 | 1.00 26.22 |
| ATOM | 2647 | N | GLY A 395 | 28.909 | 23.622 | 16.406 | 1.00 16.28 |
| ATOM | 2648 | CA | GLY A 395 | 29.220 | 23.967 | 17.780 | 1.00 15.87 |
| ATOM | 2649 | C | GLY A 395 | 30.487 | 24.775 | 17.971 | 1.00 16.72 |
| ATOM | 2650 | O | GLY A 395 | 31.011 | 25.408 | 17.005 | 1.00 16.25 |
| ATOM | 2651 | N | ALA A 396 | 30.989 | 24.769 | 19.202 | 1.00 17.29 |
| ATOM | 2652 | CA | ALA A 396 | 32.211 | 25.511 | 19.586 | 1.00 19.21 |
| ATOM | 2653 | C | ALA A 396 | 33.383 | 25.310 | 18.634 | 1.00 19.63 |
| ATOM | 2654 | O | ALA A 396 | 34.050 | 26.303 | 18.223 | 1.00 22.56 |
| ATOM | 2655 | CB | ALA A 396 | 32.626 | 25.128 | 21.013 | 1.00 16.95 |
| ATOM | 2656 | N | VAL A 397 | 33.661 | 24.065 | 18.269 | 1.00 21.31 |
| ATOM | 2657 | CA | VAL A 397 | 34.792 | 23.781 | 17.353 | 1.00 23.40 |
| ATOM | 2658 | C | VAL A 397 | 34.690 | 24.592 | 16.068 | 1.00 21.89 |
| ATOM | 2659 | O | VAL A 397 | 35.731 | 25.029 | 15.496 | 1.00 24.15 |
| ATOM | 2660 | CB | VAL A 397 | 34.874 | 22.274 | 17.012 | 1.00 24.19 |
| ATOM | 2661 | CG1 | VAL A 397 | 35.065 | 21.480 | 18.287 | 1.00 26.91 |
| ATOM | 2662 | CG2 | VAL A 397 | 33.623 | 21.826 | 16.290 | 1.00 25.89 |

FIG. 1QQ

| ATOM | 2663 | N | ILE A 398 | 33.472 | 24.805 | 15.586 | 1.00 | 21.78 |
|------|------|------|-----------|--------|--------|--------|------|-------|
| ATOM | 2664 | CA | ILE A 398 | 33.276 | 25.612 | 14.359 | 1.00 | 21.50 |
| ATOM | 2665 | C | ILE A 398 | 33.403 | 27.086 | 14.735 | 1.00 | 19.91 |
| ATOM | 2666 | O | ILE A 398 | 34.222 | 27.849 | 14.135 | 1.00 | 16.77 |
| ATOM | 2667 | CB | ILE A 398 | 31.872 | 25.390 | 13.749 | 1.00 | 23.48 |
| ATOM | 2668 | CG1 | ILE A 398 | 31.859 | 24.113 | 12.910 | 1.00 | 26.70 |
| ATOM | 2669 | CG2 | ILE A 398 | 31.469 | 26.596 | 12.895 | 1.00 | 24.67 |
| ATOM | 2670 | CD1 | ILE A 398 | 32.656 | 24.223 | 11.620 | 1.00 | 27.64 |
| ATOM | 2671 | N | MET A 399 | 32.614 | 27.492 | 15.726 | 1.00 | 17.64 |
| ATOM | 2672 | CA | MET A 399 | 32.594 | 28.889 | 16.201 | 1.00 | 16.99 |
| ATOM | 2673 | C | MET A 399 | 33.951 | 29.439 | 16.640 | 1.00 | 17.65 |
| ATOM | 2674 | O | MET A 399 | 34.202 | 30.677 | 16.517 | 1.00 | 18.70 |
| ATOM | 2675 | CB | MET A 399 | 31.575 | 29.025 | 17.331 | 1.00 | 15.33 |
| ATOM | 2676 | CG | MET A 399 | 30.138 | 28.800 | 16.866 | 1.00 | 14.30 |
| ATOM | 2677 | SD | MET A 399 | 28.891 | 29.038 | 18.155 | 1.00 | 16.41 |
| ATOM | 2678 | CE | MET A 399 | 28.972 | 30.826 | 18.388 | 1.00 | 10.15 |
| ATOM | 2679 | N | GLU A 400 | 34.835 | 28.579 | 17.143 | 1.00 | 16.09 |
| ATOM | 2680 | CA | GLU A 400 | 36.175 | 29.051 | 17.580 | 1.00 | 16.46 |
| ATOM | 2681 | C | GLU A 400 | 36.968 | 29.576 | 16.389 | 1.00 | 14.50 |
| ATOM | 2682 | O | GLU A 400 | 37.971 | 30.332 | 16.553 | 1.00 | 14.83 |
| ATOM | 2683 | CB | GLU A 400 | 36.957 | 27.919 | 18.257 | 1.00 | 15.95 |
| ATOM | 2684 | CG | GLU A 400 | 36.318 | 27.419 | 19.540 | 1.00 | 18.44 |
| ATOM | 2685 | CD | GLU A 400 | 37.156 | 26.376 | 20.243 | 1.00 | 18.72 |
| ATOM | 2686 | OE1 | GLU A 400 | 37.771 | 25.542 | 19.546 | 1.00 | 20.29 |
| ATOM | 2687 | OE2 | GLU A 400 | 37.186 | 26.383 | 21.493 | 1.00 | 19.60 |
| ATOM | 2688 | N | GLY A 401 | 36.544 | 29.204 | 15.190 | 1.00 | 13.62 |
| ATOM | 2689 | CA | GLY A 401 | 37.246 | 29.662 | 14.010 | 1.00 | 15.09 |
| ATOM | 2690 | C | GLY A 401 | 36.747 | 31.010 | 13.533 | 1.00 | 16.28 |
| ATOM | 2691 | O | GLY A 401 | 37.435 | 31.693 | 12.716 | 1.00 | 16.14 |
| ATOM | 2692 | N | PHE A 402 | 35.591 | 31.438 | 14.033 | 1.00 | 14.90 |
| ATOM | 2693 | CA | PHE A 402 | 35.018 | 32.712 | 13.572 | 1.00 | 15.01 |
| ATOM | 2694 | C | PHE A 402 | 34.378 | 33.605 | 14.615 | 1.00 | 15.52 |
| ATOM | 2695 | O | PHE A 402 | 34.078 | 33.185 | 15.777 | 1.00 | 16.47 |
| ATOM | 2696 | CB | PHE A 402 | 33.966 | 32.424 | 12.495 | 1.00 | 14.48 |
| ATOM | 2697 | CG | PHE A 402 | 34.381 | 31.364 | 11.522 | 1.00 | 15.64 |
| ATOM | 2698 | CD1 | PHE A 402 | 34.126 | 30.021 | 11.785 | 1.00 | 14.91 |
| ATOM | 2699 | CD2 | PHE A 402 | 35.095 | 31.700 | 10.376 | 1.00 | 15.20 |
| ATOM | 2700 | CE1 | PHE A 402 | 34.581 | 29.027 | 10.920 | 1.00 | 15.18 |
| ATOM | 2701 | CE2 | PHE A 402 | 35.555 | 30.717 | 9.507 | 1.00 | 15.72 |
| ATOM | 2702 | CZ | PHE A 402 | 35.298 | 29.376 | 9.782 | 1.00 | 15.12 |
| ATOM | 2703 | N | TYR A 403 | 34.168 | 34.847 | 14.208 | 1.00 | 15.73 |
| ATOM | 2704 | CA | TYR A 403 | 33.474 | 35.837 | 15.039 | 1.00 | 15.81 |
| ATOM | 2705 | C | TYR A 403 | 32.071 | 35.641 | 14.489 | 1.00 | 14.48 |
| ATOM | 2706 | O | TYR A 403 | 31.846 | 35.789 | 13.250 | 1.00 | 15.47 |
| ATOM | 2707 | CB | TYR A 403 | 33.977 | 37.251 | 14.731 | 1.00 | 14.45 |
| ATOM | 2708 | CG | TYR A 403 | 33.265 | 38.340 | 15.499 | 1.00 | 15.22 |
| ATOM | 2709 | CD1 | TYR A 403 | 32.899 | 38.152 | 16.834 | 1.00 | 14.85 |
| ATOM | 2710 | CD2 | TYR A 403 | 33.018 | 39.584 | 14.916 | 1.00 | 14.28 |
| ATOM | 2711 | CE1 | TYR A 403 | 32.311 | 39.175 | 17.569 | 1.00 | 15.25 |
| ATOM | 2712 | CE2 | TYR A 403 | 32.435 | 40.617 | 15.644 | 1.00 | 14.12 |
| ATOM | 2713 | CZ | TYR A 403 | 32.086 | 40.406 | 16.967 | 1.00 | 15.72 |
| ATOM | 2714 | OH | TYR A 403 | 31.525 | 41.427 | 17.697 | 1.00 | 18.09 |
| ATOM | 2715 | N | VAL A 404 | 31.125 | 35.286 | 15.345 | 1.00 | 14.70 |
| ATOM | 2716 | CA | VAL A 404 | 29.753 | 35.040 | 14.854 | 1.00 | 14.44 |
| ATOM | 2717 | C | VAL A 404 | 28.759 | 36.079 | 15.342 | 1.00 | 14.92 |
| ATOM | 2718 | O | VAL A 404 | 28.552 | 36.259 | 16.582 | 1.00 | 15.62 |
| ATOM | 2719 | CB | VAL A 404 | 29.284 | 33.629 | 15.260 | 1.00 | 14.39 |
| ATOM | 2720 | CG1 | VAL A 404 | 27.925 | 33.323 | 14.640 | 1.00 | 11.90 |
| ATOM | 2721 | CG2 | VAL A 404 | 30.327 | 32.603 | 14.819 | 1.00 | 12.73 |
| ATOM | 2722 | N | VAL A 405 | 28.136 | 36.762 | 14.386 | 1.00 | 16.06 |
| ATOM | 2723 | CA | VAL A 405 | 27.153 | 37.822 | 14.676 | 1.00 | 14.31 |
| ATOM | 2724 | C | VAL A 405 | 25.717 | 37.312 | 14.562 | 1.00 | 16.79 |

FIG. 1RR

| | | | | | | | | |
|---|---|---|---|---|---|---|---|---|
| ATOM | 2725 | O   | VAL | A | 405 | 25.238 | 36.955 | 13.443 | 1.00 | 16.14 |
| ATOM | 2726 | CB  | VAL | A | 405 | 27.318 | 39.004 | 13.700 | 1.00 | 13.66 |
| ATOM | 2727 | CG1 | VAL | A | 405 | 26.302 | 40.092 | 14.021 | 1.00 | 12.39 |
| ATOM | 2728 | CG2 | VAL | A | 405 | 28.739 | 39.547 | 13.775 | 1.00 | 10.80 |
| ATOM | 2729 | N   | PHE | A | 406 | 25.019 | 37.260 | 15.691 | 1.00 | 16.73 |
| ATOM | 2730 | CA  | PHE | A | 406 | 23.616 | 36.805 | 15.685 | 1.00 | 16.71 |
| ATOM | 2731 | C   | PHE | A | 406 | 22.755 | 38.049 | 15.531 | 1.00 | 17.47 |
| ATOM | 2732 | O   | PHE | A | 406 | 22.286 | 38.654 | 16.539 | 1.00 | 17.39 |
| ATOM | 2733 | CB  | PHE | A | 406 | 23.287 | 36.053 | 16.979 | 1.00 | 13.96 |
| ATOM | 2734 | CG  | PHE | A | 406 | 24.061 | 34.765 | 17.139 | 1.00 | 13.82 |
| ATOM | 2735 | CD1 | PHE | A | 406 | 25.398 | 34.783 | 17.533 | 1.00 | 13.31 |
| ATOM | 2736 | CD2 | PHE | A | 406 | 23.464 | 33.538 | 16.863 | 1.00 | 12.85 |
| ATOM | 2737 | CE1 | PHE | A | 406 | 26.128 | 33.601 | 17.646 | 1.00 | 13.23 |
| ATOM | 2738 | CE2 | PHE | A | 406 | 24.185 | 32.350 | 16.973 | 1.00 | 12.78 |
| ATOM | 2739 | CZ  | PHE | A | 406 | 25.522 | 32.382 | 17.367 | 1.00 | 12.96 |
| ATOM | 2740 | N   | ASP | A | 407 | 22.566 | 38.449 | 14.278 | 1.00 | 18.08 |
| ATOM | 2741 | CA  | ASP | A | 407 | 21.785 | 39.647 | 13.932 | 1.00 | 19.70 |
| ATOM | 2742 | C   | ASP | A | 407 | 20.297 | 39.316 | 13.927 | 1.00 | 19.73 |
| ATOM | 2743 | O   | ASP | A | 407 | 19.675 | 39.120 | 12.837 | 1.00 | 18.96 |
| ATOM | 2744 | CB  | ASP | A | 407 | 22.221 | 40.153 | 12.552 | 1.00 | 22.61 |
| ATOM | 2745 | CG  | ASP | A | 407 | 21.663 | 41.530 | 12.223 | 1.00 | 24.28 |
| ATOM | 2746 | OD1 | ASP | A | 407 | 20.660 | 41.935 | 12.849 | 1.00 | 24.12 |
| ATOM | 2747 | OD2 | ASP | A | 407 | 22.225 | 42.198 | 11.325 | 1.00 | 23.37 |
| ATOM | 2748 | N   | ARG | A | 408 | 19.709 | 39.245 | 15.116 | 1.00 | 19.72 |
| ATOM | 2749 | CA  | ARG | A | 408 | 18.269 | 38.928 | 15.259 | 1.00 | 22.01 |
| ATOM | 2750 | C   | ARG | A | 408 | 17.393 | 39.967 | 14.557 | 1.00 | 21.56 |
| ATOM | 2751 | O   | ARG | A | 408 | 16.386 | 39.606 | 13.875 | 1.00 | 20.49 |
| ATOM | 2752 | CB  | ARG | A | 408 | 17.909 | 38.835 | 16.748 | 1.00 | 23.44 |
| ATOM | 2753 | CG  | ARG | A | 408 | 18.670 | 37.724 | 17.479 | 1.00 | 25.61 |
| ATOM | 2754 | CD  | ARG | A | 408 | 18.838 | 37.994 | 18.973 | 1.00 | 28.14 |
| ATOM | 2755 | NE  | ARG | A | 408 | 17.843 | 37.328 | 19.814 | 1.00 | 31.17 |
| ATOM | 2756 | CZ  | ARG | A | 408 | 16.567 | 37.679 | 19.887 | 1.00 | 32.24 |
| ATOM | 2757 | NH1 | ARG | A | 408 | 16.127 | 38.693 | 19.163 | 1.00 | 35.70 |
| ATOM | 2758 | NH2 | ARG | A | 408 | 15.735 | 37.029 | 20.687 | 1.00 | 31.13 |
| ATOM | 2759 | N   | ALA | A | 409 | 17.750 | 41.241 | 14.694 | 1.00 | 21.10 |
| ATOM | 2760 | CA  | ALA | A | 409 | 16.978 | 42.329 | 14.056 | 1.00 | 22.43 |
| ATOM | 2761 | C   | ALA | A | 409 | 16.785 | 42.050 | 12.571 | 1.00 | 22.80 |
| ATOM | 2762 | O   | ALA | A | 409 | 15.646 | 42.177 | 12.034 | 1.00 | 24.04 |
| ATOM | 2763 | CB  | ALA | A | 409 | 17.689 | 43.664 | 14.247 | 1.00 | 20.85 |
| ATOM | 2764 | N   | ARG | A | 410 | 17.858 | 41.664 | 11.889 | 1.00 | 23.89 |
| ATOM | 2765 | CA  | ARG | A | 410 | 17.770 | 41.374 | 10.445 | 1.00 | 25.07 |
| ATOM | 2766 | C   | ARG | A | 410 | 17.639 | 39.888 | 10.119 | 1.00 | 24.26 |
| ATOM | 2767 | O   | ARG | A | 410 | 17.908 | 39.461 |  8.956 | 1.00 | 24.63 |
| ATOM | 2768 | CB  | ARG | A | 410 | 18.987 | 41.949 |  9.724 | 1.00 | 26.83 |
| ATOM | 2769 | CG  | ARG | A | 410 | 19.025 | 43.464 |  9.700 | 1.00 | 29.89 |
| ATOM | 2770 | CD  | ARG | A | 410 | 19.326 | 43.944 |  8.295 | 1.00 | 32.69 |
| ATOM | 2771 | NE  | ARG | A | 410 | 20.590 | 44.664 |  8.208 | 1.00 | 33.51 |
| ATOM | 2772 | CZ  | ARG | A | 410 | 21.182 | 44.979 |  7.062 | 1.00 | 34.58 |
| ATOM | 2773 | NH1 | ARG | A | 410 | 20.626 | 44.631 |  5.907 | 1.00 | 33.99 |
| ATOM | 2774 | NH2 | ARG | A | 410 | 22.328 | 45.644 |  7.068 | 1.00 | 35.27 |
| ATOM | 2775 | N   | LYS | A | 411 | 17.223 | 39.091 | 11.097 | 1.00 | 22.77 |
| ATOM | 2776 | CA  | LYS | A | 411 | 17.061 | 37.630 | 10.891 | 1.00 | 22.97 |
| ATOM | 2777 | C   | LYS | A | 411 | 18.227 | 37.031 | 10.104 | 1.00 | 21.80 |
| ATOM | 2778 | O   | LYS | A | 411 | 18.015 | 36.309 |  9.081 | 1.00 | 20.39 |
| ATOM | 2779 | CB  | LYS | A | 411 | 15.761 | 37.335 | 10.138 | 1.00 | 23.53 |
| ATOM | 2780 | CG  | LYS | A | 411 | 14.491 | 37.686 | 10.886 | 1.00 | 27.80 |
| ATOM | 2781 | CD  | LYS | A | 411 | 13.270 | 37.188 | 10.121 | 1.00 | 30.25 |
| ATOM | 2782 | CE  | LYS | A | 411 | 13.337 | 35.678 |  9.890 | 1.00 | 31.18 |
| ATOM | 2783 | NZ  | LYS | A | 411 | 12.153 | 35.163 |  9.142 | 1.00 | 34.08 |
| ATOM | 2784 | N   | ARG | A | 412 | 19.449 | 37.290 | 10.541 | 1.00 | 19.85 |
| ATOM | 2785 | CA  | ARG | A | 412 | 20.607 | 36.748 |  9.815 | 1.00 | 18.29 |
| ATOM | 2786 | C   | ARG | A | 412 | 21.789 | 36.505 | 10.736 | 1.00 | 18.54 |

FIG. 1SS

| ATOM | 2787 | O | ARG A 412 | 21.911 | 37.137 | 11.837 | 1.00 | 18.56 |
| ATOM | 2788 | CB | ARG A 412 | 21.019 | 37.714 | 8.703 | 1.00 | 18.72 |
| ATOM | 2789 | CG | ARG A 412 | 21.571 | 39.027 | 9.239 | 1.00 | 18.66 |
| ATOM | 2790 | CD | ARG A 412 | 21.941 | 39.988 | 8.127 | 1.00 | 18.34 |
| ATOM | 2791 | NE | ARG A 412 | 22.560 | 41.196 | 8.662 | 1.00 | 19.28 |
| ATOM | 2792 | CZ | ARG A 412 | 23.082 | 42.163 | 7.916 | 1.00 | 20.03 |
| ATOM | 2793 | NH1 | ARG A 412 | 23.059 | 42.067 | 6.591 | 1.00 | 19.36 |
| ATOM | 2794 | NH2 | ARG A 412 | 23.635 | 43.219 | 8.496 | 1.00 | 19.27 |
| ATOM | 2795 | N | ILE A 413 | 22.668 | 35.606 | 10.317 | 1.00 | 17.01 |
| ATOM | 2796 | CA | ILE A 413 | 23.865 | 35.285 | 11.103 | 1.00 | 16.43 |
| ATOM | 2797 | C | ILE A 413 | 25.103 | 35.576 | 10.266 | 1.00 | 16.20 |
| ATOM | 2798 | O | ILE A 413 | 25.213 | 35.125 | 9.084 | 1.00 | 17.17 |
| ATOM | 2799 | CB | ILE A 413 | 23.855 | 33.808 | 11.533 | 1.00 | 16.02 |
| ATOM | 2800 | CG1 | ILE A 413 | 22.667 | 33.562 | 12.469 | 1.00 | 13.92 |
| ATOM | 2801 | CG2 | ILE A 413 | 25.168 | 33.458 | 12.218 | 1.00 | 15.95 |
| ATOM | 2802 | CD1 | ILE A 413 | 22.482 | 32.130 | 12.862 | 1.00 | 14.89 |
| ATOM | 2803 | N | GLY A 414 | 26.028 | 36.332 | 10.841 | 1.00 | 15.43 |
| ATOM | 2804 | CA | GLY A 414 | 27.243 | 36.679 | 10.132 | 1.00 | 14.42 |
| ATOM | 2805 | C | GLY A 414 | 28.463 | 35.899 | 10.585 | 1.00 | 14.91 |
| ATOM | 2806 | O | GLY A 414 | 28.569 | 35.463 | 11.779 | 1.00 | 12.74 |
| ATOM | 2807 | N | PHE A 415 | 29.392 | 35.709 | 9.656 | 1.00 | 12.70 |
| ATOM | 2808 | CA | PHE A 415 | 30.638 | 34.977 | 9.932 | 1.00 | 14.84 |
| ATOM | 2809 | C | PHE A 415 | 31.823 | 35.766 | 9.403 | 1.00 | 15.05 |
| ATOM | 2810 | O | PHE A 415 | 31.761 | 36.376 | 8.291 | 1.00 | 17.34 |
| ATOM | 2811 | CB | PHE A 415 | 30.613 | 33.599 | 9.256 | 1.00 | 13.57 |
| ATOM | 2812 | CG | PHE A 415 | 29.628 | 32.640 | 9.860 | 1.00 | 13.35 |
| ATOM | 2813 | CD1 | PHE A 415 | 30.034 | 31.710 | 10.820 | 1.00 | 14.56 |
| ATOM | 2814 | CD2 | PHE A 415 | 28.296 | 32.660 | 9.472 | 1.00 | 11.54 |
| ATOM | 2815 | CE1 | PHE A 415 | 29.117 | 30.809 | 11.383 | 1.00 | 13.74 |
| ATOM | 2816 | CE2 | PHE A 415 | 27.373 | 31.768 | 10.027 | 1.00 | 12.67 |
| ATOM | 2817 | CZ | PHE A 415 | 27.787 | 30.839 | 10.985 | 1.00 | 13.15 |
| ATOM | 2818 | N | ALA A 416 | 32.895 | 35.779 | 10.178 | 1.00 | 15.11 |
| ATOM | 2819 | CA | ALA A 416 | 34.135 | 36.470 | 9.786 | 1.00 | 14.57 |
| ATOM | 2820 | C | ALA A 416 | 35.248 | 35.738 | 10.515 | 1.00 | 14.48 |
| ATOM | 2821 | O | ALA A 416 | 35.027 | 35.186 | 11.639 | 1.00 | 12.56 |
| ATOM | 2822 | CB | ALA A 416 | 34.095 | 37.935 | 10.208 | 1.00 | 11.46 |
| ATOM | 2823 | N | VAL A 417 | 36.425 | 35.692 | 9.906 | 1.00 | 14.71 |
| ATOM | 2824 | CA | VAL A 417 | 37.569 | 35.011 | 10.528 | 1.00 | 16.80 |
| ATOM | 2825 | C | VAL A 417 | 37.835 | 35.634 | 11.892 | 1.00 | 18.08 |
| ATOM | 2826 | O | VAL A 417 | 37.922 | 36.901 | 12.033 | 1.00 | 17.13 |
| ATOM | 2827 | CB | VAL A 417 | 38.824 | 35.126 | 9.642 | 1.00 | 17.67 |
| ATOM | 2828 | CG1 | VAL A 417 | 40.022 | 34.486 | 10.333 | 1.00 | 16.83 |
| ATOM | 2829 | CG2 | VAL A 417 | 38.561 | 34.441 | 8.301 | 1.00 | 18.32 |
| ATOM | 2830 | N | SER A 418 | 37.953 | 34.785 | 12.905 | 1.00 | 17.31 |
| ATOM | 2831 | CA | SER A 418 | 38.201 | 35.271 | 14.272 | 1.00 | 17.62 |
| ATOM | 2832 | C | SER A 418 | 39.637 | 35.712 | 14.455 | 1.00 | 18.36 |
| ATOM | 2833 | O | SER A 418 | 40.591 | 35.038 | 13.963 | 1.00 | 19.44 |
| ATOM | 2834 | CB | SER A 418 | 37.882 | 34.182 | 15.295 | 1.00 | 18.09 |
| ATOM | 2835 | OG | SER A 418 | 38.228 | 34.617 | 16.599 | 1.00 | 17.42 |
| ATOM | 2836 | N | ALA A 419 | 39.821 | 36.827 | 15.150 | 1.00 | 17.60 |
| ATOM | 2837 | CA | ALA A 419 | 41.175 | 37.335 | 15.410 | 1.00 | 18.46 |
| ATOM | 2838 | C | ALA A 419 | 41.877 | 36.423 | 16.423 | 1.00 | 19.09 |
| ATOM | 2839 | O | ALA A 419 | 43.117 | 36.553 | 16.649 | 1.00 | 19.60 |
| ATOM | 2840 | CB | ALA A 419 | 41.106 | 38.772 | 15.943 | 1.00 | 17.70 |
| ATOM | 2841 | N | CYS A 420 | 41.132 | 35.500 | 17.032 | 1.00 | 19.36 |
| ATOM | 2842 | CA | CYS A 420 | 41.736 | 34.575 | 18.029 | 1.00 | 20.89 |
| ATOM | 2843 | C | CYS A 420 | 41.677 | 33.105 | 17.624 | 1.00 | 19.60 |
| ATOM | 2844 | O | CYS A 420 | 41.805 | 32.202 | 18.501 | 1.00 | 22.74 |
| ATOM | 2845 | CB | CYS A 420 | 41.064 | 34.734 | 19.410 | 1.00 | 21.69 |
| ATOM | 2846 | SG | CYS A 420 | 39.353 | 34.096 | 19.526 | 1.00 | 25.02 |
| ATOM | 2847 | N | HIS A 421 | 41.495 | 32.814 | 16.342 | 1.00 | 17.86 |
| ATOM | 2848 | CA | HIS A 421 | 41.435 | 31.393 | 15.933 | 1.00 | 17.71 |

FIG. 1TT

| ATOM | 2849 | C | HIS | A | 421 | 42.834 | 30.798 | 15.799 | 1.00 | 17.18 |
|------|------|------|-----|---|-----|--------|--------|--------|------|-------|
| ATOM | 2850 | O | HIS | A | 421 | 43.801 | 31.495 | 15.356 | 1.00 | 14.17 |
| ATOM | 2851 | CB | HIS | A | 421 | 40.641 | 31.236 | 14.625 | 1.00 | 18.65 |
| ATOM | 2852 | CG | HIS | A | 421 | 41.433 | 31.504 | 13.381 | 1.00 | 18.77 |
| ATOM | 2853 | ND1 | HIS | A | 421 | 42.114 | 30.514 | 12.705 | 1.00 | 18.84 |
| ATOM | 2854 | CD2 | HIS | A | 421 | 41.631 | 32.645 | 12.678 | 1.00 | 18.73 |
| ATOM | 2855 | CE1 | HIS | A | 421 | 42.695 | 31.032 | 11.637 | 1.00 | 17.98 |
| ATOM | 2856 | NE2 | HIS | A | 421 | 42.418 | 32.323 | 11.597 | 1.00 | 20.03 |
| ATOM | 2857 | N | VAL | A | 422 | 42.965 | 29.533 | 16.194 | 1.00 | 16.96 |
| ATOM | 2858 | CA | VAL | A | 422 | 44.260 | 28.816 | 16.132 | 1.00 | 16.89 |
| ATOM | 2859 | C | VAL | A | 422 | 44.571 | 28.334 | 14.719 | 1.00 | 17.53 |
| ATOM | 2860 | O | VAL | A | 422 | 43.678 | 27.764 | 14.021 | 1.00 | 17.13 |
| ATOM | 2861 | CB | VAL | A | 422 | 44.257 | 27.588 | 17.061 | 1.00 | 16.92 |
| ATOM | 2862 | CG1 | VAL | A | 422 | 45.632 | 26.938 | 17.063 | 1.00 | 15.15 |
| ATOM | 2863 | CG2 | VAL | A | 422 | 43.850 | 28.004 | 18.479 | 1.00 | 19.33 |
| ATOM | 2864 | N | HIS | A | 423 | 45.815 | 28.531 | 14.291 | 1.00 | 16.64 |
| ATOM | 2865 | CA | HIS | A | 423 | 46.264 | 28.112 | 12.940 | 1.00 | 16.92 |
| ATOM | 2866 | C | HIS | A | 423 | 47.792 | 28.038 | 12.906 | 1.00 | 17.46 |
| ATOM | 2867 | O | HIS | A | 423 | 48.461 | 28.105 | 13.981 | 1.00 | 17.20 |
| ATOM | 2868 | CB | HIS | A | 423 | 45.755 | 29.111 | 11.889 | 1.00 | 15.85 |
| ATOM | 2869 | CG | HIS | A | 423 | 46.242 | 30.512 | 12.096 | 1.00 | 18.62 |
| ATOM | 2870 | ND1 | HIS | A | 423 | 47.390 | 30.998 | 11.504 | 1.00 | 19.80 |
| ATOM | 2871 | CD2 | HIS | A | 423 | 45.758 | 31.522 | 12.857 | 1.00 | 17.42 |
| ATOM | 2872 | CE1 | HIS | A | 423 | 47.590 | 32.245 | 11.892 | 1.00 | 18.22 |
| ATOM | 2873 | NE2 | HIS | A | 423 | 46.615 | 32.586 | 12.714 | 1.00 | 18.53 |
| ATOM | 2874 | N | ASP | A | 424 | 48.360 | 27.869 | 11.714 | 1.00 | 18.00 |
| ATOM | 2875 | CA | ASP | A | 424 | 49.836 | 27.817 | 11.556 | 1.00 | 17.75 |
| ATOM | 2876 | C | ASP | A | 424 | 50.194 | 28.804 | 10.453 | 1.00 | 18.36 |
| ATOM | 2877 | O | ASP | A | 424 | 49.294 | 29.527 | 9.935 | 1.00 | 20.02 |
| ATOM | 2878 | CB | ASP | A | 424 | 50.305 | 26.396 | 11.206 | 1.00 | 18.00 |
| ATOM | 2879 | CG | ASP | A | 424 | 49.545 | 25.791 | 10.037 | 1.00 | 19.08 |
| ATOM | 2880 | OD1 | ASP | A | 424 | 49.110 | 24.623 | 10.149 | 1.00 | 18.99 |
| ATOM | 2881 | OD2 | ASP | A | 424 | 49.390 | 26.473 | 9.003 | 1.00 | 20.46 |
| ATOM | 2882 | N | GLU | A | 425 | 51.459 | 28.877 | 10.063 | 1.00 | 17.55 |
| ATOM | 2883 | CA | GLU | A | 425 | 51.813 | 29.853 | 9.015 | 1.00 | 18.77 |
| ATOM | 2884 | C | GLU | A | 425 | 51.497 | 29.379 | 7.601 | 1.00 | 16.95 |
| ATOM | 2885 | O | GLU | A | 425 | 51.724 | 30.131 | 6.613 | 1.00 | 17.24 |
| ATOM | 2886 | CB | GLU | A | 425 | 53.289 | 30.239 | 9.112 | 1.00 | 18.65 |
| ATOM | 2887 | CG | GLU | A | 425 | 54.254 | 29.150 | 8.714 | 1.00 | 20.84 |
| ATOM | 2888 | CD | GLU | A | 425 | 55.632 | 29.697 | 8.381 | 1.00 | 21.89 |
| ATOM | 2889 | OE1 | GLU | A | 425 | 56.481 | 28.901 | 7.936 | 1.00 | 22.61 |
| ATOM | 2890 | OE2 | GLU | A | 425 | 55.867 | 30.920 | 8.559 | 1.00 | 22.65 |
| ATOM | 2891 | N | PHE | A | 426 | 50.955 | 28.171 | 7.476 | 1.00 | 14.60 |
| ATOM | 2892 | CA | PHE | A | 426 | 50.619 | 27.606 | 6.150 | 1.00 | 13.51 |
| ATOM | 2893 | C | PHE | A | 426 | 49.157 | 27.767 | 5.763 | 1.00 | 15.14 |
| ATOM | 2894 | O | PHE | A | 426 | 48.826 | 27.822 | 4.540 | 1.00 | 16.10 |
| ATOM | 2895 | CB | PHE | A | 426 | 51.001 | 26.127 | 6.109 | 1.00 | 14.53 |
| ATOM | 2896 | CG | PHE | A | 426 | 52.452 | 25.877 | 6.400 | 1.00 | 14.20 |
| ATOM | 2897 | CD1 | PHE | A | 426 | 53.433 | 26.244 | 5.482 | 1.00 | 13.59 |
| ATOM | 2898 | CD2 | PHE | A | 426 | 52.841 | 25.298 | 7.606 | 1.00 | 14.11 |
| ATOM | 2899 | CE1 | PHE | A | 426 | 54.787 | 26.040 | 5.762 | 1.00 | 14.83 |
| ATOM | 2900 | CE2 | PHE | A | 426 | 54.192 | 25.087 | 7.897 | 1.00 | 15.49 |
| ATOM | 2901 | CZ | PHE | A | 426 | 55.167 | 25.460 | 6.969 | 1.00 | 14.08 |
| ATOM | 2902 | N | ARG | A | 427 | 48.269 | 27.827 | 6.752 | 1.00 | 13.77 |
| ATOM | 2903 | CA | ARG | A | 427 | 46.824 | 27.985 | 6.469 | 1.00 | 14.89 |
| ATOM | 2904 | C | ARG | A | 427 | 46.130 | 28.695 | 7.615 | 1.00 | 15.43 |
| ATOM | 2905 | O | ARG | A | 427 | 46.630 | 28.710 | 8.781 | 1.00 | 14.58 |
| ATOM | 2906 | CB | ARG | A | 427 | 46.132 | 26.632 | 6.301 | 1.00 | 15.33 |
| ATOM | 2907 | CG | ARG | A | 427 | 46.959 | 25.518 | 5.707 | 1.00 | 16.84 |
| ATOM | 2908 | CD | ARG | A | 427 | 46.645 | 24.234 | 6.477 | 1.00 | 17.68 |
| ATOM | 2909 | NE | ARG | A | 427 | 45.994 | 23.230 | 5.655 | 1.00 | 16.69 |
| ATOM | 2910 | CZ | ARG | A | 427 | 45.701 | 21.998 | 6.062 | 1.00 | 15.45 |

FIG. 1UU

```
ATOM   2911  NH1 ARG A 427      45.114  21.159   5.224  1.00 14.20
ATOM   2912  NH2 ARG A 427      45.981  21.603   7.296  1.00 13.31
ATOM   2913  N   THR A 428      44.976  29.269   7.317  1.00 15.28
ATOM   2914  CA  THR A 428      44.180  29.967   8.336  1.00 17.94
ATOM   2915  C   THR A 428      42.731  29.650   8.041  1.00 16.25
ATOM   2916  O   THR A 428      42.400  29.165   6.923  1.00 14.77
ATOM   2917  CB  THR A 428      44.353  31.503   8.249  1.00 18.18
ATOM   2918  OG1 THR A 428      44.043  31.942   6.921  1.00 20.24
ATOM   2919  CG2 THR A 428      45.773  31.901   8.583  1.00 19.84
ATOM   2920  N   ALA A 429      41.860  29.901   9.009  1.00 16.14
ATOM   2921  CA  ALA A 429      40.423  29.677   8.803  1.00 16.03
ATOM   2922  C   ALA A 429      40.048  30.739   7.775  1.00 15.66
ATOM   2923  O   ALA A 429      40.808  31.738   7.574  1.00 14.51
ATOM   2924  CB  ALA A 429      39.656  29.898  10.105  1.00 17.08
ATOM   2925  N   ALA A 430      38.920  30.575   7.107  1.00 14.04
ATOM   2926  CA  ALA A 430      38.556  31.576   6.100  1.00 13.71
ATOM   2927  C   ALA A 430      37.067  31.706   5.883  1.00 11.98
ATOM   2928  O   ALA A 430      36.271  30.754   6.166  1.00 12.33
ATOM   2929  CB  ALA A 430      39.251  31.246   4.762  1.00 12.27
ATOM   2930  N   VAL A 431      36.671  32.874   5.396  1.00 11.01
ATOM   2931  CA  VAL A 431      35.260  33.149   5.076  1.00 13.39
ATOM   2932  C   VAL A 431      35.344  33.773   3.697  1.00 15.69
ATOM   2933  O   VAL A 431      35.857  34.926   3.533  1.00 17.86
ATOM   2934  CB  VAL A 431      34.624  34.145   6.056  1.00 11.50
ATOM   2935  CG1 VAL A 431      33.148  34.294   5.737  1.00 10.61
ATOM   2936  CG2 VAL A 431      34.818  33.659   7.494  1.00 10.71
ATOM   2937  N   GLU A 432      34.874  33.048   2.694  1.00 16.74
ATOM   2938  CA  GLU A 432      34.969  33.544   1.320  1.00 18.65
ATOM   2939  C   GLU A 432      33.681  33.414   0.530  1.00 18.40
ATOM   2940  O   GLU A 432      32.794  32.567   0.852  1.00 16.81
ATOM   2941  CB  GLU A 432      36.097  32.796   0.607  1.00 19.91
ATOM   2942  CG  GLU A 432      37.460  33.031   1.241  1.00 24.66
ATOM   2943  CD  GLU A 432      38.466  31.930   0.935  1.00 27.80
ATOM   2944  OE1 GLU A 432      39.681  32.196   1.051  1.00 30.84
ATOM   2945  OE2 GLU A 432      38.049  30.799   0.595  1.00 28.87
ATOM   2946  N   GLY A 433      33.574  34.243  -0.504  1.00 18.95
ATOM   2947  CA  GLY A 433      32.408  34.244  -1.363  1.00 19.36
ATOM   2948  C   GLY A 433      32.504  35.385  -2.359  1.00 19.59
ATOM   2949  O   GLY A 433      33.489  36.173  -2.328  1.00 18.33
ATOM   2950  N   PRO A 434      31.511  35.539  -3.243  1.00 19.47
ATOM   2951  CA  PRO A 434      30.345  34.655  -3.285  1.00 19.72
ATOM   2952  C   PRO A 434      30.485  33.589  -4.353  1.00 19.98
ATOM   2953  O   PRO A 434      31.382  33.674  -5.235  1.00 22.24
ATOM   2954  CB  PRO A 434      29.215  35.619  -3.595  1.00 19.80
ATOM   2955  CG  PRO A 434      29.869  36.517  -4.616  1.00 19.70
ATOM   2956  CD  PRO A 434      31.261  36.770  -4.018  1.00 19.73
ATOM   2957  N   PHE A 435      29.624  32.583  -4.290  1.00 21.45
ATOM   2958  CA  PHE A 435      29.619  31.502  -5.292  1.00 22.31
ATOM   2959  C   PHE A 435      28.217  31.513  -5.872  1.00 24.39
ATOM   2960  O   PHE A 435      27.207  31.636  -5.110  1.00 24.58
ATOM   2961  CB  PHE A 435      29.924  30.155  -4.636  1.00 22.02
ATOM   2962  CG  PHE A 435      31.215  30.141  -3.876  1.00 20.80
ATOM   2963  CD1 PHE A 435      31.232  30.392  -2.507  1.00 20.70
ATOM   2964  CD2 PHE A 435      32.424  29.945  -4.542  1.00 21.70
ATOM   2965  CE1 PHE A 435      32.432  30.451  -1.809  1.00 20.27
ATOM   2966  CE2 PHE A 435      33.634  30.003  -3.853  1.00 21.68
ATOM   2967  CZ  PHE A 435      33.637  30.259  -2.481  1.00 21.51
ATOM   2968  N   VAL A 436      28.117  31.396  -7.192  1.00 27.02
ATOM   2969  CA  VAL A 436      26.802  31.438  -7.872  1.00 29.79
ATOM   2970  C   VAL A 436      26.526  30.219  -8.739  1.00 32.85
ATOM   2971  O   VAL A 436      25.434  30.120  -9.376  1.00 33.81
ATOM   2972  CB  VAL A 436      26.702  32.677  -8.787  1.00 28.98
```

FIG. 1VV

| ATOM | 2973 | CG1 | VAL | A | 436 | 26.999 | 33.944 | -7.996 | 1.00 | 29.00 |
| ATOM | 2974 | CG2 | VAL | A | 436 | 27.678 | 32.537 | -9.947 | 1.00 | 28.49 |
| ATOM | 2975 | N | THR | A | 437 | 27.473 | 29.292 | -8.795 | 1.00 | 36.05 |
| ATOM | 2976 | CA | THR | A | 437 | 27.305 | 28.089 | -9.638 | 1.00 | 39.30 |
| ATOM | 2977 | C | THR | A | 437 | 26.582 | 26.979 | -8.870 | 1.00 | 41.99 |
| ATOM | 2978 | O | THR | A | 437 | 26.604 | 25.775 | -9.276 | 1.00 | 41.77 |
| ATOM | 2979 | CB | THR | A | 437 | 28.690 | 27.592 | -10.123 | 1.00 | 39.02 |
| ATOM | 2980 | OG1 | THR | A | 437 | 28.552 | 26.981 | -11.408 | 1.00 | 42.51 |
| ATOM | 2981 | CG2 | THR | A | 437 | 29.280 | 26.578 | -9.156 | 1.00 | 38.10 |
| ATOM | 2982 | N | LEU | A | 438 | 25.908 | 27.368 | -7.794 | 1.00 | 45.33 |
| ATOM | 2983 | CA | LEU | A | 438 | 25.199 | 26.417 | -6.901 | 1.00 | 49.22 |
| ATOM | 2984 | C | LEU | A | 438 | 23.753 | 26.016 | -7.165 | 1.00 | 50.49 |
| ATOM | 2985 | O | LEU | A | 438 | 22.869 | 26.878 | -7.466 | 1.00 | 51.99 |
| ATOM | 2986 | CB | LEU | A | 438 | 25.276 | 26.944 | -5.473 | 1.00 | 50.30 |
| ATOM | 2987 | CG | LEU | A | 438 | 26.027 | 28.269 | -5.358 | 1.00 | 50.73 |
| ATOM | 2988 | CD1 | LEU | A | 438 | 25.108 | 29.457 | -5.584 | 1.00 | 50.27 |
| ATOM | 2989 | CD2 | LEU | A | 438 | 26.629 | 28.328 | -4.001 | 1.00 | 51.67 |
| ATOM | 2990 | N | ASP | A | 439 | 23.505 | 24.715 | -7.037 | 1.00 | 52.67 |
| ATOM | 2991 | CA | ASP | A | 439 | 22.149 | 24.128 | -7.172 | 1.00 | 55.74 |
| ATOM | 2992 | C | ASP | A | 439 | 21.690 | 24.224 | -5.722 | 1.00 | 56.96 |
| ATOM | 2993 | O | ASP | A | 439 | 21.757 | 23.221 | -4.945 | 1.00 | 57.33 |
| ATOM | 2994 | CB | ASP | A | 439 | 22.240 | 22.657 | -7.586 | 1.00 | 56.39 |
| ATOM | 2995 | CG | ASP | A | 439 | 20.879 | 21.993 | -7.695 | 1.00 | 57.68 |
| ATOM | 2996 | OD1 | ASP | A | 439 | 20.046 | 22.178 | -6.781 | 1.00 | 57.75 |
| ATOM | 2997 | OD2 | ASP | A | 439 | 20.645 | 21.274 | -8.692 | 1.00 | 58.18 |
| ATOM | 2998 | N | MET | A | 440 | 21.233 | 25.407 | -5.337 | 1.00 | 58.71 |
| ATOM | 2999 | CA | MET | A | 440 | 20.841 | 25.656 | -3.944 | 1.00 | 60.87 |
| ATOM | 3000 | C | MET | A | 440 | 19.435 | 26.215 | -3.713 | 1.00 | 62.52 |
| ATOM | 3001 | O | MET | A | 440 | 19.247 | 27.451 | -3.489 | 1.00 | 63.93 |
| ATOM | 3002 | CB | MET | A | 440 | 21.916 | 26.569 | -3.346 | 1.00 | 60.48 |
| ATOM | 3003 | CG | MET | A | 440 | 21.523 | 27.456 | -2.201 | 1.00 | 60.72 |
| ATOM | 3004 | SD | MET | A | 440 | 22.755 | 28.755 | -2.086 | 1.00 | 59.28 |
| ATOM | 3005 | CE | MET | A | 440 | 22.367 | 29.689 | -3.543 | 1.00 | 59.46 |
| ATOM | 3006 | N | GLU | A | 441 | 18.435 | 25.343 | -3.765 | 1.00 | 63.61 |
| ATOM | 3007 | CA | GLU | A | 441 | 17.042 | 25.774 | -3.514 | 1.00 | 65.54 |
| ATOM | 3008 | C | GLU | A | 441 | 16.356 | 24.847 | -2.518 | 1.00 | 64.49 |
| ATOM | 3009 | O | GLU | A | 441 | 15.998 | 25.285 | -1.375 | 1.00 | 65.36 |
| ATOM | 3010 | CB | GLU | A | 441 | 16.229 | 25.847 | -4.815 | 1.00 | 67.99 |
| ATOM | 3011 | CG | GLU | A | 441 | 16.500 | 24.745 | -5.822 | 1.00 | 70.98 |
| ATOM | 3012 | CD | GLU | A | 441 | 17.353 | 25.228 | -6.981 | 1.00 | 72.23 |
| ATOM | 3013 | OE1 | GLU | A | 441 | 18.507 | 25.646 | -6.742 | 1.00 | 73.24 |
| ATOM | 3014 | OE2 | GLU | A | 441 | 16.867 | 25.194 | -8.132 | 1.00 | 73.30 |
| ATOM | 3015 | N | ASP | A | 442 | 16.170 | 23.585 | -2.896 | 1.00 | 61.29 |
| ATOM | 3016 | CA | ASP | A | 442 | 15.519 | 22.616 | -1.986 | 1.00 | 58.37 |
| ATOM | 3017 | C | ASP | A | 442 | 16.504 | 21.966 | -1.018 | 1.00 | 55.47 |
| ATOM | 3018 | O | ASP | A | 442 | 16.615 | 20.704 | -0.950 | 1.00 | 54.59 |
| ATOM | 3019 | CB | ASP | A | 442 | 14.800 | 21.530 | -2.785 | 1.00 | 59.93 |
| ATOM | 3020 | CG | ASP | A | 442 | 13.298 | 21.616 | -2.646 | 1.00 | 60.90 |
| ATOM | 3021 | OD1 | ASP | A | 442 | 12.689 | 22.478 | -3.312 | 1.00 | 61.34 |
| ATOM | 3022 | OD2 | ASP | A | 442 | 12.729 | 20.832 | -1.854 | 1.00 | 61.81 |
| ATOM | 3023 | N | CYS | A | 443 | 17.207 | 22.790 | -0.252 | 1.00 | 51.31 |
| ATOM | 3024 | CA | CYS | A | 443 | 18.200 | 22.281 | 0.713 | 1.00 | 47.79 |
| ATOM | 3025 | C | CYS | A | 443 | 17.635 | 22.156 | 2.121 | 1.00 | 46.40 |
| ATOM | 3026 | O | CYS | A | 443 | 18.168 | 21.373 | 2.965 | 1.00 | 44.04 |
| ATOM | 3027 | CB | CYS | A | 443 | 19.421 | 23.198 | 0.713 | 1.00 | 48.61 |
| ATOM | 3028 | SG | CYS | A | 443 | 20.176 | 23.339 | -0.939 | 1.00 | 46.95 |
| ATOM | 3029 | N | GLY | A | 444 | 16.566 | 22.895 | 2.395 | 1.00 | 45.40 |
| ATOM | 3030 | CA | GLY | A | 444 | 15.953 | 22.846 | 3.709 | 1.00 | 45.06 |
| ATOM | 3031 | C | GLY | A | 444 | 15.011 | 21.673 | 3.899 | 1.00 | 45.25 |
| ATOM | 3032 | O | GLY | A | 444 | 14.271 | 21.264 | 2.952 | 1.00 | 44.97 |
| ATOM | 3033 | N | TYR | A | 445 | 15.018 | 21.109 | 5.101 | 1.00 | 44.97 |
| ATOM | 3034 | CA | TYR | A | 445 | 14.140 | 19.968 | 5.421 | 1.00 | 44.48 |

FIG. 1WW

| | | | | | | | | | |
|---|---|---|---|---|---|---|---|---|---|
| ATOM | 3035 | C | TYR | A | 445 | 12.778 | 20.467 | 5.882 | 1.00 45.23 |
| ATOM | 3036 | O | TYR | A | 445 | 12.662 | 21.558 | 6.530 | 1.00 44.57 |
| ATOM | 3037 | CB | TYR | A | 445 | 14.801 | 19.172 | 6.531 | 1.00 43.11 |
| ATOM | 3038 | CG | TYR | A | 445 | 13.918 | 17.997 | 6.871 | 1.00 42.75 |
| ATOM | 3039 | CD1 | TYR | A | 445 | 13.846 | 16.905 | 6.010 | 1.00 42.58 |
| ATOM | 3040 | CD2 | TYR | A | 445 | 13.170 | 17.998 | 8.049 | 1.00 42.27 |
| ATOM | 3041 | CE1 | TYR | A | 445 | 13.042 | 15.820 | 6.327 | 1.00 41.99 |
| ATOM | 3042 | CE2 | TYR | A | 445 | 12.358 | 16.917 | 8.360 | 1.00 43.20 |
| ATOM | 3043 | CZ | TYR | A | 445 | 12.289 | 15.835 | 7.503 | 1.00 41.98 |
| ATOM | 3044 | OH | TYR | A | 445 | 11.490 | 14.751 | 7.810 | 1.00 20.00 |
| ATOM | 3045 | N | ASN | A | 446 | 11.746 | 19.699 | 5.550 | 1.00 45.69 |
| ATOM | 3046 | CA | ASN | A | 446 | 10.359 | 20.012 | 5.947 | 1.00 48.64 |
| ATOM | 3047 | C | ASN | A | 446 | 9.776 | 18.726 | 6.524 | 1.00 50.90 |
| ATOM | 3048 | O | ASN | A | 446 | 9.894 | 17.625 | 5.896 | 1.00 51.59 |
| ATOM | 3049 | CB | ASN | A | 446 | 9.537 | 20.470 | 4.738 | 1.00 48.19 |
| ATOM | 3050 | CG | ASN | A | 446 | 9.975 | 21.827 | 4.213 | 1.00 48.18 |
| ATOM | 3051 | OD1 | ASN | A | 446 | 9.926 | 22.858 | 4.950 | 1.00 48.63 |
| ATOM | 3052 | ND2 | ASN | A | 446 | 10.403 | 21.867 | 2.957 | 1.00 48.04 |
| ATOM | 3053 | N | ILE | A | 447 | 9.165 | 18.826 | 7.700 | 1.00 53.94 |
| ATOM | 3054 | CA | ILE | A | 447 | 8.569 | 17.650 | 8.388 | 1.00 55.99 |
| ATOM | 3055 | C | ILE | A | 447 | 7.720 | 16.772 | 7.463 | 1.00 57.01 |
| ATOM | 3056 | O | ILE | A | 447 | 7.449 | 17.195 | 6.318 | 1.00 58.11 |
| ATOM | 3057 | CB | ILE | A | 447 | 7.699 | 18.105 | 9.577 | 1.00 55.86 |
| ATOM | 3058 | CG1 | ILE | A | 447 | 8.488 | 19.086 | 10.450 | 1.00 56.28 |
| ATOM | 3059 | CG2 | ILE | A | 447 | 7.267 | 16.900 | 10.406 | 1.00 56.92 |
| ATOM | 3060 | CD1 | ILE | A | 447 | 9.759 | 18.505 | 11.037 | 1.00 55.79 |
| ATOM | 3061 | OXT | ILE | A | 447 | 7.328 | 15.666 | 7.895 | 1.00 57.55 |
| ATOM | 3062 | N | SER | P | 1 | 35.528 | 15.672 | 28.238 | 1.00 37.61 |
| ATOM | 3063 | CA | SER | P | 1 | 34.172 | 16.082 | 28.590 | 1.00 36.72 |
| ATOM | 3064 | C | SER | P | 1 | 33.508 | 16.863 | 27.450 | 1.00 34.75 |
| ATOM | 3065 | O | SER | P | 1 | 34.132 | 17.643 | 26.742 | 1.00 36.46 |
| ATOM | 3066 | CB | SER | P | 1 | 34.248 | 16.949 | 29.848 | 1.00 37.77 |
| ATOM | 3067 | OG | SER | P | 1 | 33.152 | 17.865 | 29.853 | 1.00 40.82 |
| ATOM | 3068 | N | GLU | P | 2 | 32.203 | 16.601 | 27.257 | 1.00 32.86 |
| ATOM | 3069 | CA | GLU | P | 2 | 31.513 | 17.216 | 26.129 | 1.00 32.80 |
| ATOM | 3070 | C | GLU | P | 2 | 30.218 | 17.906 | 26.552 | 1.00 31.23 |
| ATOM | 3071 | O | GLU | P | 2 | 29.435 | 17.401 | 27.348 | 1.00 31.31 |
| ATOM | 3072 | CB | GLU | P | 2 | 31.275 | 16.167 | 25.027 | 1.00 33.64 |
| ATOM | 3073 | CG | GLU | P | 2 | 31.096 | 17.096 | 23.826 | 1.00 37.41 |
| ATOM | 3074 | CD | GLU | P | 2 | 31.076 | 15.940 | 22.852 | 1.00 38.37 |
| ATOM | 3075 | OE1 | GLU | P | 2 | 31.996 | 15.134 | 22.983 | 1.00 39.04 |
| ATOM | 3076 | OE2 | GLU | P | 2 | 30.175 | 15.798 | 22.037 | 1.00 39.43 |
| ATOM | 3077 | N | VAL | P | 3 | 29.742 | 19.344 | 26.106 | 1.00 27.98 |
| ATOM | 3078 | CA | VAL | P | 3 | 28.367 | 19.820 | 26.101 | 1.00 26.44 |
| ATOM | 3079 | C | VAL | P | 3 | 27.717 | 19.598 | 24.735 | 1.00 26.26 |
| ATOM | 3080 | O | VAL | P | 3 | 28.371 | 19.580 | 23.701 | 1.00 25.48 |
| ATOM | 3081 | CB | VAL | P | 3 | 28.377 | 21.311 | 26.429 | 1.00 25.89 |
| ATOM | 3082 | CG1 | VAL | P | 3 | 28.684 | 21.516 | 27.911 | 1.00 27.07 |
| ATOM | 3083 | CG2 | VAL | P | 3 | 29.431 | 22.012 | 25.594 | 1.00 23.97 |
| ATOM | 3084 | N | ASN | P | 4 | 26.361 | 19.591 | 25.174 | 1.00 25.89 |
| ATOM | 3085 | CA | ASN | P | 4 | 25.421 | 19.254 | 24.075 | 1.00 26.64 |
| ATOM | 3086 | C | ASN | P | 4 | 24.027 | 19.825 | 24.452 | 1.00 26.87 |
| ATOM | 3087 | O | ASN | P | 4 | 23.116 | 19.163 | 25.077 | 1.00 27.10 |
| ATOM | 3088 | CB | ASN | P | 4 | 25.349 | 17.766 | 23.876 | 1.00 27.95 |
| ATOM | 3089 | CG | ASN | P | 4 | 26.498 | 17.245 | 22.971 | 1.00 29.39 |
| ATOM | 3090 | OD1 | ASN | P | 4 | 26.499 | 17.409 | 21.723 | 1.00 31.90 |
| ATOM | 3091 | ND2 | ASN | P | 4 | 27.489 | 16.617 | 23.603 | 1.00 31.97 |
| ATOM | 3092 | N | STA | P | 5 | 24.115 | 21.101 | 24.323 | 1.00 25.26 |
| ATOM | 3093 | CA | STA | P | 5 | 22.965 | 21.865 | 24.929 | 1.00 25.83 |
| ATOM | 3094 | CB | STA | P | 5 | 23.683 | 22.681 | 26.021 | 1.00 27.28 |
| ATOM | 3095 | CG | STA | P | 5 | 24.378 | 22.057 | 27.197 | 1.00 28.07 |
| ATOM | 3096 | CD1 | STA | P | 5 | 25.002 | 23.077 | 28.182 | 1.00 27.46 |

FIG. 1XX

```
ATOM   3097  CD2 STA P   5      23.280  21.130  27.828  1.00 25.47
ATOM   3098  CH  STA P   5      22.223  22.851  23.940  1.00 25.86
ATOM   3099  OH  STA P   5      23.028  23.679  23.298  1.00 25.23
ATOM   3100  CM  STA P   5      21.372  21.980  23.048  1.00 27.11
ATOM   3101  C   STA P   5      20.420  21.340  24.125  1.00 27.81
ATOM   3102  O   STA P   5      20.241  20.065  24.095  1.00 25.70
ATOM   3103  N   VAL P   6      19.339  22.479  23.764  1.00 26.04
ATOM   3104  CA  VAL P   6      18.037  21.953  24.156  1.00 27.12
ATOM   3105  C   VAL P   6      17.496  20.965  23.121  1.00 27.36
ATOM   3106  O   VAL P   6      17.795  21.029  21.936  1.00 26.97
ATOM   3107  CB  VAL P   6      17.073  23.130  24.312  1.00 27.18
ATOM   3108  CG1 VAL P   6      16.433  23.463  22.965  1.00 26.70
ATOM   3109  CG2 VAL P   6      15.985  22.781  25.311  1.00 28.74
ATOM   3110  N   ALA P   7      16.702  19.998  23.617  1.00 28.68
ATOM   3111  CA  ALA P   7      16.158  18.986  22.720  1.00 32.14
ATOM   3112  C   ALA P   7      14.774  19.377  22.197  1.00 32.99
ATOM   3113  O   ALA P   7      14.040  20.149  22.801  1.00 32.08
ATOM   3114  CB  ALA P   7      16.072  17.666  23.489  1.00 31.38
ATOM   3115  N   GLU P   8      14.443  18.843  21.007  1.00 36.10
ATOM   3116  CA  GLU P   8      13.144  19.143  20.418  1.00 39.90
ATOM   3117  C   GLU P   8      12.012  18.425  21.158  1.00 41.72
ATOM   3118  O   GLU P   8      12.189  17.359  21.733  1.00 41.52
ATOM   3119  CB  GLU P   8      13.172  18.705  18.952  1.00 39.88
ATOM   3120  CG  GLU P   8      14.037  19.626  18.090  1.00 41.02
ATOM   3121  CD  GLU P   8      13.896  19.235  16.637  1.00 41.83
ATOM   3122  OE1 GLU P   8      14.911  19.052  15.979  1.00 41.60
ATOM   3123  OE2 GLU P   8      12.765  19.124  16.169  1.00 41.88
ATOM   3124  N   PHE P   9      10.811  18.986  21.162  1.00 45.62
ATOM   3125  CA  PHE P   9       9.677  18.356  21.865  1.00 49.63
ATOM   3126  C   PHE P   9       9.382  16.960  21.337  1.00 50.61
ATOM   3127  O   PHE P   9       9.156  16.839  20.116  1.00 51.38
ATOM   3128  CB  PHE P   9       8.451  19.245  21.670  1.00 50.65
ATOM   3129  CG  PHE P   9       8.607  20.501  22.499  1.00 52.48
ATOM   3130  CD1 PHE P   9       8.278  20.493  23.849  1.00 52.80
ATOM   3131  CD2 PHE P   9       9.073  21.659  21.899  1.00 53.12
ATOM   3132  CE1 PHE P   9       8.420  21.651  24.600  1.00 53.74
ATOM   3133  CE2 PHE P   9       9.215  22.817  22.659  1.00 53.61
ATOM   3134  CZ  PHE P   9       8.890  22.817  24.010  1.00 54.24
ATOM   3135  OXT PHE P   9       9.383  16.011  22.152  1.00 51.56
ATOM   3136  OH2 TIP C   2      37.673   4.149  14.933  1.00 18.73
ATOM   3137  OH2 TIP C   3      37.999  19.019  28.545  1.00 20.36
ATOM   3138  OH2 TIP C  12      46.550  23.555   9.446  1.00 16.05
ATOM   3139  OH2 TIP C  14      18.354  26.505  28.719  1.00 14.14
ATOM   3140  OH2 TIP C  15      33.073  10.884  15.835  1.00 14.30
ATOM   3141  OH2 TIP C  16      15.032  34.698  31.070  1.00 11.96
ATOM   3142  OH2 TIP C  17       7.170  35.908  33.277  1.00 16.70
ATOM   3143  OH2 TIP C  19      16.624  32.704  28.166  1.00 15.10
ATOM   3144  OH2 TIP C  20      35.078  42.552  29.609  1.00 19.72
ATOM   3145  OH2 TIP C  21      40.457  30.360  27.755  1.00 16.31
ATOM   3146  OH2 TIP C  22      52.263  20.430   9.725  1.00 20.11
ATOM   3147  OH2 TIP C  23      20.720  20.412  14.822  1.00 12.68
ATOM   3148  OH2 TIP C  24      33.413  15.317  -5.393  1.00 15.90
ATOM   3149  OH2 TIP C  25      38.275  25.072  23.469  1.00 13.40
ATOM   3150  OH2 TIP C  27      16.591  21.729   7.186  1.00 19.86
ATOM   3151  OH2 TIP C  28      21.798  19.346  19.780  1.00 14.31
ATOM   3152  OH2 TIP C  29      17.533  34.724  25.177  1.00 16.69
ATOM   3153  OH2 TIP C  30      29.162  27.768  25.821  1.00 19.19
ATOM   3154  OH2 TIP C  31      40.631  28.021  16.946  1.00 14.53
ATOM   3155  OH2 TIP C  32      32.428  32.415  17.998  1.00 10.42
ATOM   3156  OH2 TIP C  33      11.884  34.798  21.161  1.00 23.00
ATOM   3157  OH2 TIP C  34      27.837  25.769  -5.173  1.00 33.18
ATOM   3158  OH2 TIP C  35      12.372  31.279  28.339  1.00 16.96
```

FIG. 1YY

```
ATOM   3159  OH2 TIP C   36      39.263  28.648  25.755  1.00  9.84
ATOM   3160  OH2 TIP C   40      38.924  30.840  30.171  1.00 13.35
ATOM   3161  OH2 TIP C   41      18.085  18.989  18.858  1.00 16.60
ATOM   3162  OH2 TIP C   42       7.300  35.692  30.168  1.00 19.22
ATOM   3163  OH2 TIP C   43      14.250  32.017  30.405  1.00 18.32
ATOM   3164  OH2 TIP C   44      37.440  22.761   1.333  1.00 23.96
ATOM   3165  OH2 TIP C   45      29.932  39.949  32.969  1.00 22.64
ATOM   3166  OH2 TIP C   46      29.433  17.902  20.935  1.00 16.15
ATOM   3167  OH2 TIP C   47      53.536  22.468  21.774  1.00 21.62
ATOM   3168  OH2 TIP C   48      40.180  15.699  -0.272  1.00 12.15
ATOM   3169  OH2 TIP C   49      14.955  25.973  25.745  1.00 11.98
ATOM   3170  OH2 TIP C   50      38.595   6.527   3.885  1.00 23.66
ATOM   3171  OH2 TIP C   51      48.551  24.793  17.574  1.00 18.30
ATOM   3172  OH2 TIP C   52      20.747  27.407  17.869  1.00  8.25
ATOM   3173  OH2 TIP C   53      26.489  18.730  30.746  1.00 26.59
ATOM   3174  OH2 TIP C   54      38.723  11.162  19.249  1.00 11.49
ATOM   3175  OH2 TIP C   55      33.881  26.191  31.382  1.00 19.21
ATOM   3176  OH2 TIP C   56      13.322  31.213  40.027  1.00 15.61
ATOM   3177  OH2 TIP C   57      19.497  16.134  41.439  1.00 26.82
ATOM   3178  OH2 TIP C   58      38.469  37.062   5.695  1.00 23.10
ATOM   3179  OH2 TIP C   59      45.575  15.894   3.122  1.00 18.45
ATOM   3180  OH2 TIP C   60      39.615  25.333  -1.743  1.00 20.09
ATOM   3181  OH2 TIP C   61      32.158  37.928  32.431  1.00 12.17
ATOM   3182  OH2 TIP C   62      46.793  19.609  22.823  1.00 19.81
ATOM   3183  OH2 TIP C   63      24.847  37.031  -0.659  1.00 29.98
ATOM   3184  OH2 TIP C   64      45.957  18.715   3.836  1.00 18.88
ATOM   3185  OH2 TIP C   65      36.189  33.100  17.653  1.00 10.63
ATOM   3186  OH2 TIP C   66      31.177  25.020  24.150  1.00 28.40
ATOM   3187  OH2 TIP C   67      46.181  23.210  18.466  1.00 20.41
ATOM   3188  OH2 TIP C   68      21.756  10.923   7.943  1.00 22.80
ATOM   3189  OH2 TIP C   69      12.936  36.695  30.481  1.00 17.63
ATOM   3190  OH2 TIP C   70      33.713  44.843   8.382  1.00 30.49
ATOM   3191  OH2 TIP C   71      21.051  41.550  39.982  1.00 31.15
ATOM   3192  OH2 TIP C   72      26.815  38.732   3.198  1.00 22.61
ATOM   3193  OH2 TIP C   73      41.656  24.820  21.177  1.00 19.69
ATOM   3194  OH2 TIP C   74      25.521  30.139  47.617  1.00 31.08
ATOM   3195  OH2 TIP C   75      20.497  46.537  15.336  1.00 29.67
ATOM   3196  OH2 TIP C   76       7.708  28.422  41.027  1.00 26.00
ATOM   3197  OH2 TIP C   77      25.650  18.585  27.821  1.00 17.30
ATOM   3198  OH2 TIP C   78      35.124  16.582  21.374  1.00 15.44
ATOM   3199  OH2 TIP C   79      16.806  29.258  45.952  1.00 22.64
ATOM   3200  OH2 TIP C   80      29.365   7.305  14.767  1.00 28.00
ATOM   3201  OH2 TIP C   81      36.259   9.577  -0.018  1.00 36.72
ATOM   3202  OH2 TIP C   82       5.598  37.375  35.367  1.00 29.64
ATOM   3203  OH2 TIP C   83      14.256  22.267   9.863  1.00 20.30
ATOM   3204  OH2 TIP C   84      34.533  14.826  41.318  1.00 35.70
ATOM   3205  OH2 TIP C   85      14.253  38.931  17.469  1.00 22.15
ATOM   3206  OH2 TIP C   86      40.762  43.633   8.075  1.00 32.27
ATOM   3207  OH2 TIP C   87      20.139  38.471  47.202  1.00 19.79
ATOM   3208  OH2 TIP C   88      49.003  25.388  14.809  1.00 16.95
ATOM   3209  OH2 TIP C   89      48.376  21.580  21.346  1.00 26.51
ATOM   3210  OH2 TIP C   90      38.281  15.314  27.561  1.00 34.16
ATOM   3211  OH2 TIP C   91       8.631  39.984  34.095  1.00 41.37
ATOM   3212  OH2 TIP C   92      50.906  23.612  20.744  1.00 52.18
ATOM   3213  OH2 TIP C   93      53.785  20.060  24.538  1.00 24.16
ATOM   3214  OH2 TIP C   94      24.823  42.619  11.579  1.00 21.18
ATOM   3215  OH2 TIP C   95      25.075  45.083   6.146  1.00 38.65
ATOM   3216  OH2 TIP C   96      40.830  25.584  18.443  1.00 18.31
ATOM   3217  OH2 TIP C   97      43.416  22.239  18.182  1.00 19.16
ATOM   3218  OH2 TIP C   98      13.417  34.174  40.223  1.00 31.15
ATOM   3219  OH2 TIP C   99      33.278  34.940  35.258  1.00 19.39
ATOM   3220  OH2 TIP C  100      16.214  11.125  16.638  1.00 44.74
```

FIG. 1ZZ

| | | | | | | | |
|---|---|---|---|---|---|---|---|
| ATOM | 3221 | OH2 TIP C | 101 | 53.364 | 20.723 | 14.579 | 1.00 34.15 |
| ATOM | 3222 | OH2 TIP C | 102 | 49.883 | 22.898 | 7.975 | 1.00 17.76 |
| ATOM | 3223 | OH2 TIP C | 103 | 23.025 | 15.361 | 39.364 | 1.00 32.71 |
| ATOM | 3224 | OH2 TIP C | 104 | 9.989 | 41.920 | 29.368 | 1.00 18.54 |
| ATOM | 3225 | OH2 TIP C | 105 | 40.434 | 26.276 | 24.857 | 1.00 17.36 |
| ATOM | 3226 | OH2 TIP C | 106 | 20.997 | 29.964 | 6.095 | 1.00 20.90 |
| ATOM | 3227 | OH2 TIP C | 107 | 27.762 | 47.336 | 16.035 | 1.00 24.48 |
| ATOM | 3228 | OH2 TIP C | 108 | 49.284 | 22.771 | 5.126 | 1.00 18.73 |
| ATOM | 3229 | OH2 TIP C | 109 | 48.838 | 23.239 | 29.592 | 1.00 33.97 |
| ATOM | 3230 | OH2 TIP C | 110 | 28.582 | 23.099 | 35.349 | 1.00 20.25 |
| ATOM | 3231 | OH2 TIP C | 111 | 32.528 | 35.162 | 39.110 | 1.00 29.39 |
| ATOM | 3232 | OH2 TIP C | 112 | 41.404 | 21.066 | 27.696 | 1.00 29.24 |
| ATOM | 3233 | OH2 TIP C | 113 | 41.566 | 30.795 | 24.916 | 1.00 29.04 |
| ATOM | 3234 | OH2 TIP C | 114 | 38.888 | 34.349 | 4.634 | 1.00 19.24 |
| ATOM | 3235 | OH2 TIP C | 115 | 21.524 | 13.318 | 6.181 | 1.00 21.83 |
| ATOM | 3236 | OH2 TIP C | 116 | 20.262 | 44.365 | 41.166 | 1.00 51.68 |
| ATOM | 3237 | OH2 TIP C | 117 | 40.866 | 37.586 | 7.262 | 1.00 26.48 |
| ATOM | 3238 | OH2 TIP C | 118 | 24.269 | 19.013 | 20.381 | 1.00 20.56 |
| ATOM | 3239 | OH2 TIP C | 119 | 14.796 | 40.366 | 21.026 | 1.00 26.21 |
| ATOM | 3240 | OH2 TIP C | 120 | 40.271 | 21.968 | 24.452 | 1.00 22.99 |
| ATOM | 3241 | OH2 TIP C | 121 | 27.256 | 8.206 | 3.568 | 1.00 32.16 |
| ATOM | 3242 | OH2 TIP C | 122 | 38.453 | 23.426 | 21.155 | 1.00 20.65 |
| ATOM | 3243 | OH2 TIP C | 123 | 39.489 | 30.192 | 18.787 | 1.00 19.64 |
| ATOM | 3244 | OH2 TIP C | 124 | 49.479 | 24.877 | 3.120 | 1.00 15.38 |
| ATOM | 3245 | OH2 TIP C | 125 | 23.534 | 17.922 | 36.838 | 1.00 21.55 |
| ATOM | 3246 | OH2 TIP C | 126 | 24.481 | 13.568 | 37.531 | 1.00 33.00 |
| ATOM | 3247 | OH2 TIP C | 127 | 27.515 | 37.075 | 45.132 | 1.00 32.65 |
| ATOM | 3248 | OH2 TIP C | 128 | 20.903 | 11.530 | 10.774 | 1.00 25.13 |
| ATOM | 3249 | OH2 TIP C | 129 | 16.996 | 37.117 | 6.834 | 1.00 26.72 |
| ATOM | 3250 | OH2 TIP C | 130 | 42.280 | 39.848 | 5.806 | 1.00 39.08 |
| ATOM | 3251 | OH2 TIP C | 131 | 15.426 | 37.238 | 14.643 | 1.00 27.36 |
| ATOM | 3252 | OH2 TIP C | 132 | 47.740 | 29.973 | 16.321 | 1.00 27.58 |
| ATOM | 3253 | OH2 TIP C | 133 | 52.162 | 19.864 | 18.278 | 1.00 19.10 |
| ATOM | 3254 | OH2 TIP C | 134 | 47.805 | 11.416 | 4.529 | 1.00 30.40 |
| ATOM | 3255 | OH2 TIP C | 135 | 20.920 | 22.905 | 41.964 | 1.00 23.80 |
| ATOM | 3256 | OH2 TIP C | 136 | 27.784 | 19.013 | -1.506 | 1.00 28.71 |
| ATOM | 3257 | OH2 TIP C | 137 | 25.506 | 36.437 | 2.115 | 1.00 19.53 |
| ATOM | 3258 | OH2 TIP C | 138 | 6.347 | 36.058 | 44.801 | 1.00 30.54 |
| ATOM | 3259 | OH2 TIP C | 139 | 18.428 | 23.862 | 8.397 | 1.00 19.65 |
| ATOM | 3260 | OH2 TIP C | 140 | 56.631 | 14.945 | 24.048 | 1.00 29.26 |
| ATOM | 3261 | OH2 TIP C | 141 | 36.045 | 33.381 | -3.424 | 1.00 39.63 |
| ATOM | 3262 | OH2 TIP C | 142 | 20.242 | 14.180 | 11.802 | 1.00 31.49 |
| ATOM | 3263 | OH2 TIP C | 143 | 8.614 | 22.301 | 31.526 | 1.00 30.94 |
| ATOM | 3264 | OH2 TIP C | 144 | 8.697 | 38.736 | 31.440 | 1.00 44.64 |
| ATOM | 3265 | OH2 TIP C | 145 | 21.002 | 20.115 | 40.621 | 1.00 23.34 |
| ATOM | 3266 | OH2 TIP C | 146 | 36.343 | 37.533 | 7.628 | 1.00 25.43 |
| ATOM | 3267 | OH2 TIP C | 147 | 13.944 | 44.970 | 51.125 | 1.00 40.01 |
| ATOM | 3268 | OH2 TIP C | 148 | 12.509 | 22.964 | 23.735 | 1.00 33.44 |
| ATOM | 3269 | OH2 TIP C | 149 | 32.555 | 6.398 | 6.686 | 1.00 30.50 |
| ATOM | 3270 | OH2 TIP C | 150 | 11.123 | 30.018 | 41.695 | 1.00 29.12 |
| ATOM | 3271 | OH2 TIP C | 151 | 20.406 | 19.454 | 17.419 | 1.00 26.72 |
| ATOM | 3272 | OH2 TIP C | 152 | 37.729 | 21.375 | 25.750 | 1.00 27.16 |
| ATOM | 3273 | OH2 TIP C | 153 | 36.922 | 28.170 | 33.507 | 1.00 42.28 |
| ATOM | 3274 | OH2 TIP C | 154 | 13.904 | 29.766 | 32.277 | 1.00 19.72 |
| ATOM | 3275 | OH2 TIP C | 155 | 54.556 | 19.732 | 11.775 | 1.00 37.67 |
| ATOM | 3276 | OH2 TIP C | 156 | 14.999 | 28.327 | 48.310 | 1.00 40.64 |
| ATOM | 3277 | OH2 TIP C | 157 | 19.001 | 46.759 | 12.106 | 1.00 40.48 |
| ATOM | 3278 | OH2 TIP C | 158 | 22.361 | 9.339 | 13.691 | 1.00 44.57 |
| ATOM | 3279 | OH2 TIP C | 159 | 26.097 | 16.601 | 36.996 | 1.00 27.61 |
| ATOM | 3280 | OH2 TIP C | 160 | 51.862 | 24.669 | 14.501 | 1.00 39.22 |
| ATOM | 3281 | OH2 TIP C | 161 | 42.713 | 33.316 | 38.299 | 1.00 37.21 |
| ATOM | 3282 | OH2 TIP C | 162 | 32.074 | 43.316 | 6.583 | 1.00 32.14 |

FIG. 1AAA

```
ATOM  3283  OH2 TIP C 163    44.434  22.056   2.693  1.00 44.76
ATOM  3284  OH2 TIP C 164    24.074  33.090  45.770  1.00 26.95
ATOM  3285  OH2 TIP C 165    12.289  35.656  48.500  1.00 33.30
ATOM  3286  OH2 TIP C 166    19.499  27.253  51.538  1.00 48.93
ATOM  3287  OH2 TIP C 167    28.896  14.390  20.410  1.00 32.12
ATOM  3288  OH2 TIP C 168     7.799  34.543  25.107  1.00 34.11
ATOM  3289  OH2 TIP C 169    41.359  33.697   5.939  1.00 29.72
ATOM  3290  OH2 TIP C 170    26.378  23.008  46.449  1.00 37.54
ATOM  3291  OH2 TIP C 171    10.530  41.770  49.010  1.00 34.66
ATOM  3292  OH2 TIP C 172    41.154   5.586   4.533  1.00 25.18
ATOM  3293  OH2 TIP C 173    17.462  11.487   4.521  1.00 46.32
ATOM  3294  OH2 TIP C 174     7.600  39.527  37.113  1.00 36.37
ATOM  3295  OH2 TIP C 175     3.552  23.235  37.583  1.00 39.37
ATOM  3296  OH2 TIP C 176    32.818  21.891  40.191  1.00 36.81
ATOM  3297  OH2 TIP C 177    30.404  26.159  40.588  1.00 38.22
ATOM  3298  OH2 TIP C 178    16.691  29.183  54.400  1.00 39.76
ATOM  3299  OH2 TIP C 179    16.247  47.986  22.417  1.00 32.19
ATOM  3300  OH2 TIP C 180    37.394  44.558  11.594  1.00 39.03
ATOM  3301  OH2 TIP C 181    53.552  27.209  11.822  1.00 47.97
ATOM  3302  OH2 TIP C 182    10.503  32.709  12.025  1.00 38.41
ATOM  3303  OH2 TIP C 183    17.985  14.916  28.259  1.00 36.86
ATOM  3304  OH2 TIP C 184    25.047  45.446  12.174  1.00 49.92
ATOM  3305  OH2 TIP C 185    16.402  15.741  36.532  1.00 40.29
ATOM  3306  OH2 TIP C 186    51.364  22.471  17.335  1.00 28.11
ATOM  3307  OH2 TIP C 187    25.633  28.369  50.282  1.00 42.57
ATOM  3308  OH2 TIP C 188    35.183  14.816   0.037  1.00 36.60
ATOM  3309  OH2 TIP C 189     8.318  26.536  23.386  1.00 44.75
ATOM  3310  OH2 TIP C 190    47.893  17.794  24.745  1.00 42.51
ATOM  3311  OH2 TIP C 191     2.728  32.293  36.650  1.00 38.36
ATOM  3312  OH2 TIP C 192    30.315   9.929  15.860  1.00 39.58
ATOM  3313  OH2 TIP C 193    29.613  40.378   2.225  1.00 41.26
ATOM  3314  OH2 TIP C 194    14.241  43.934  16.316  1.00 43.60
ATOM  3315  OH2 TIP C 195    48.673  31.215   7.801  1.00 32.67
ATOM  3316  OH2 TIP C 196    10.948  21.963  18.969  1.00 41.87
ATOM  3317  OH2 TIP C 197    37.378  39.077   3.714  1.00 35.77
ATOM  3318  OH2 TIP C 198    24.488  11.993  21.654  1.00 38.05
ATOM  3319  OH2 TIP C 199    47.986  31.378   4.946  1.00 48.02
ATOM  3320  OH2 TIP C 200    15.373  46.520  15.659  1.00 45.30
ATOM  3321  OH2 TIP C 201    29.464  40.417  40.154  1.00 40.62
ATOM  3322  OH2 TIP C 202    56.018  18.652   7.189  1.00 43.28
ATOM  3323  OH2 TIP C 203    36.508  17.526  41.765  1.00 61.21
ATOM  3324  OH2 TIP C 204    36.132  36.523  -0.637  1.00 43.56
ATOM  3325  OH2 TIP C 205     9.832  29.974  46.230  1.00 47.33
ATOM  3326  OH2 TIP C 206    12.086  37.731  18.949  1.00 44.12
ATOM  3327  OH2 TIP C 207     4.729  26.744  22.711  1.00 40.03
ATOM  3328  OH2 TIP C 208     9.555  36.540  23.357  1.00 46.94
ATOM  3329  OH2 TIP C 209    23.046  47.732   4.343  1.00 48.13
ATOM  3330  OH2 TIP C 210    39.932  44.592   5.460  1.00 64.51
ATOM  3331  OH2 TIP C 211    17.996  41.071   6.267  1.00 48.35
ATOM  3332  OH2 TIP C 212    17.866  46.493  17.139  1.00 39.09
ATOM  3333  OH2 TIP C 213    55.520  11.908  17.658  1.00 43.06
ATOM  3334  OH2 TIP C 214     3.059  35.093  42.826  1.00 38.97
ATOM  3335  OH2 TIP C 215    31.593  14.910  43.677  1.00 44.01
ATOM  3336  OH2 TIP C 216    33.045  23.673  44.607  1.00 45.50
ATOM  3337  OH2 TIP C 217    42.870  35.555   7.510  1.00 29.79
ATOM  3338  OH2 TIP C 218     4.112  25.648  42.564  1.00 56.65
ATOM  3339  OH2 TIP C 219    48.260   8.547  20.446  1.00 47.85
ATOM  3340  OH2 TIP C 220    -0.925  31.171  41.173  1.00 36.99
ATOM  3341  OH2 TIP C 221    41.791  22.878   0.132  1.00 56.14
ATOM  3342  OH2 TIP C 222     7.088  25.685  41.540  1.00 47.43
ATOM  3343  OH2 TIP C 223    24.815   4.785  13.582  1.00 47.96
ATOM  3344  OH2 TIP C 224    40.690   4.520  15.174  1.00 48.76
```

FIG. 1BBB

```
ATOM   3345  OH2 TIP C 225     10.029  32.425  18.562  1.00 36.30
ATOM   3346  OH2 TIP C 226     22.346  37.737  48.941  1.00 34.15
ATOM   3347  OH2 TIP C 227     16.274  17.012  19.693  1.00 27.63
ATOM   3348  OH2 TIP C 228     35.332  13.692  20.375  1.00 37.59
ATOM   3349  OH2 TIP C 229     41.228  36.673  22.908  1.00 51.58
ATOM   3350  OH2 TIP C 230     17.416  42.030  50.226  1.00 47.63
ATOM   3351  OH2 TIP C 231     18.428  39.213  52.835  1.00 40.43
ATOM   3352  OH2 TIP C 232     42.243  43.386  25.548  1.00 48.60
ATOM   3353  OH2 TIP C 233     14.081  18.701   0.364  1.00 32.87
ATOM   3354  OH2 TIP C 234     41.421  41.332  28.531  1.00 54.67
ATOM   3355  OH2 TIP C 235     42.772  36.396  11.892  1.00 41.24
ATOM   3356  OH2 TIP C 236     13.068  13.733  28.653  1.00 42.66
ATOM   3357  OH2 TIP C 237     10.850  26.738   7.811  1.00 40.46
ATOM   3358  OH2 TIP C 238     16.253  20.926  45.776  1.00 44.60
ATOM   3359  OH2 TIP C 239     32.681  31.139  43.220  1.00 42.20
ATOM   3360  OH2 TIP C 240     56.267  22.254   9.280  1.00 52.44
ATOM   3361  OH2 TIP C 241     12.553  25.304   9.942  1.00 38.77
ATOM   3362  OH2 TIP C 242     50.727   9.516  16.775  1.00 33.38
ATOM   3363  OH2 TIP C 243     31.871  41.347   0.512  1.00 47.78
ATOM   3364  OH2 TIP C 244     10.008  45.092  37.807  1.00 39.52
ATOM   3365  OH2 TIP C 245     14.551  39.030   6.708  1.00 44.26
ATOM   3366  OH2 TIP C 246     26.955  18.903  -5.135  1.00 42.54
ATOM   3367  OH2 TIP C 247     39.916  22.478  18.854  1.00 33.22
ATOM   3368  OH2 TIP C 248     40.431  40.824  22.426  1.00 35.58
ATOM   3369  OH2 TIP C 249     52.081  23.408  10.759  1.00 42.53
ATOM   3370  OH2 TIP C 250     12.078  16.710  24.149  1.00 32.37
ATOM   3371  OH2 TIP C 251     54.111  15.908   8.256  1.00 44.58
ATOM   3372  OH2 TIP C 252     33.950  12.827  -1.753  1.00 27.02
ATOM   3373  OH2 TIP C 253     -0.775  26.703  40.353  1.00 43.64
ATOM   3374  OH2 TIP C 254      1.937  33.711  40.561  1.00 42.67
ATOM   3375  OH2 TIP C 255      8.008  24.066  18.824  1.00 51.45
ATOM   3376  OH2 TIP C 256     11.765  27.465   3.635  1.00 47.34
ATOM   3377  OH2 TIP C 257     27.863  43.878   9.233  1.00 32.44
ATOM   3378  OH2 TIP C 258     18.655  30.114   4.303  1.00 33.13
ATOM   3379  OH2 TIP C 259     21.592  19.085  -3.960  1.00 39.86
ATOM   3380  OH2 TIP C 260     41.876  24.067  25.906  1.00 26.34
ATOM   3381  OH2 TIP C 261     46.651  10.240   2.171  1.00 44.38
ATOM   3382  OH2 TIP C 262     32.536  15.827  32.477  1.00 43.28
ATOM   3383  OH2 TIP C 263     12.479  39.205  50.359  1.00 47.33
ATOM   3384  OH2 TIP C 264      0.850  27.980  38.316  1.00 43.45
ATOM   3385  OH2 TIP C 265     49.605   7.356  18.061  1.00 66.01
ATOM   3386  OH2 TIP C 266     30.177  40.365  -3.235  1.00 44.45
ATOM   3387  OH2 TIP C 267     39.818  12.364   0.512  1.00 48.84
ATOM   3388  OH2 TIP C 268     38.149  44.716  27.884  1.00 51.18
ATOM   3389  OH2 TIP C 269     37.156  37.062  30.528  1.00 35.17
ATOM   3390  OH2 TIP C 270     51.808   7.097  12.435  1.00 51.69
ATOM   3391  OH2 TIP C 271     54.351  12.626  12.471  1.00 47.45
ATOM   3392  OH2 TIP C 272     50.835  31.155  13.092  1.00 55.05
ATOM   3393  OH2 TIP C 273     12.159  35.313  52.133  1.00 52.38
ATOM   3394  OH2 TIP C 274     21.002  44.489  13.037  1.00 39.70
ATOM   3395  OH2 TIP C 275     37.936  23.627  34.221  1.00 48.56
ATOM   3396  OH2 TIP C 276     45.844  30.935  31.365  1.00 43.24
ATOM   3397  OH2 TIP C 277     38.831  48.015  15.554  1.00 49.83
ATOM   3398  OH2 TIP C 278      5.630  28.150  44.576  1.00 48.10
ATOM   3399  OH2 TIP C 279      8.600  24.000  45.727  1.00 49.27
ATOM   3400  OH2 TIP C 280     54.276  20.854   7.807  1.00 36.02
ATOM   3401  OH2 TIP C 281      3.544  34.696  46.365  1.00 43.63
ATOM   3402  OH2 TIP C 282     24.214  46.264  46.163  1.00 48.04
ATOM   3403  OH2 TIP C 283      7.099  32.072  19.549  1.00 54.97
ATOM   3404  OH2 TIP C 284     36.469  22.374  41.355  1.00 52.17
ATOM   3405  OH2 TIP C 285     34.660  13.757  23.756  1.00 45.46
ATOM   3406  OH2 TIP C 286     28.516  42.981   5.402  1.00 53.58
```

FIG. 1CCC

```
ATOM   3407  OH2 TIP C 287     35.579   4.929  12.012  1.00 52.07
ATOM   3408  OH2 TIP C 288     22.974  49.682  24.299  1.00 53.67
ATOM   3409  OH2 TIP C 289      3.725  31.464  46.354  1.00 46.43
ATOM   3410  OH2 TIP C 290     27.340  39.594  -2.191  1.00 56.89
ATOM   3411  OH2 TIP C 291     33.413  34.856  32.335  1.00 31.78
ATOM   3412  OH2 TIP C 292     43.340   7.715   8.063  1.00 43.53
ATOM   3413  OH2 TIP C 293     28.243  21.392  -4.937  1.00 38.33
ATOM   3414  OH2 TIP C 294     49.389  26.590  35.796  1.00 45.66
ATOM   3415  OH2 TIP C 295     28.948  15.824  33.796  1.00 52.48
ATOM   3416  OH2 TIP C 296     27.347  13.383  37.207  1.00 48.27
ATOM   3417  OH2 TIP C 297     38.485  26.090  36.901  1.00 48.92
ATOM   3418  OH2 TIP C 298     12.120  20.265  11.506  1.00 50.10
ATOM   3419  OH2 TIP C 299     36.480  36.306  38.613  1.00 50.38
ATOM   3420  OH2 TIP C 300     31.471  16.463  35.507  1.00 38.37
ATOM   3421  OH2 TIP C 301     42.889   5.274   2.358  1.00 33.49
ATOM   3422  OH2 TIP C 302     23.548  44.173  32.246  1.00 39.09
ATOM   3423  OH2 TIP C 303     13.465  43.978  13.054  1.00 52.67
ATOM   3424  OH2 TIP C 304     25.133  43.053   4.111  1.00 52.03
ATOM   3425  OH2 TIP C 305     33.587  24.652  39.392  1.00 49.48
ATOM   3426  OH2 TIP C 306     39.063  28.353   1.979  1.00 47.89
ATOM   3427  OH2 TIP C 307     49.357  35.834  12.150  1.00 49.22
ATOM   3428  OH2 TIP C 308     27.159  46.386  33.347  1.00 49.50
ATOM   3429  OH2 TIP C 309      9.510  21.769  39.704  1.00 47.95
ATOM   3430  OH2 TIP C 310     34.885  32.959  39.205  1.00 51.26
ATOM   3431  OH2 TIP C 311     30.980   6.002   9.747  1.00 56.02
ATOM   3432  OH2 TIP C 312     43.802  34.511  14.853  1.00 41.89
ATOM   3433  OH2 TIP C 313     36.834   4.382   5.254  1.00 39.04
ATOM   3434  OH2 TIP C 314     12.453  30.429  47.461  1.00 47.60
ATOM   3435  OH2 TIP C 315     39.685  40.144  30.944  1.00 54.68
ATOM   3436  OH2 TIP C 316     45.982  20.840  31.078  1.00 47.99
ATOM   3437  OH2 TIP C 317     32.815  36.023  42.050  1.00 45.07
ATOM   3438  OH2 TIP C 318     17.877  37.802  -3.699  1.00 56.30
ATOM   3439  OH2 TIP C 319     53.681   9.633  16.525  1.00 55.34
ATOM   3440  OH2 TIP C 320     21.577  43.070  52.229  1.00 49.54
ATOM   3441  OH2 TIP C 321      6.139  45.122  36.565  1.00 44.40
ATOM   3442  OH2 TIP C 322     34.695  13.561  26.782  1.00 45.99
ATOM   3443  OH2 TIP C 323     17.990  33.946  -9.976  1.00 56.88
ATOM   3444  OH2 TIP C 324     25.587  50.416  28.268  1.00 52.75
ATOM   3445  OH2 TIP C 325     27.744  42.608  42.266  1.00 44.66
ATOM   3446  OH2 TIP C 326     48.357  32.815  33.851  1.00 57.98
ATOM   3447  OH2 TIP C 327     61.047  18.004  17.692  1.00 51.30
ATOM   3448  OH2 TIP C 328     17.327  11.069  11.972  1.00 48.28
ATOM   3449  OH2 TIP C 329     59.624  17.562  20.598  1.00 44.37
ATOM   3450  OH2 TIP C 330     40.644  39.227  19.932  1.00 37.57
ATOM   3451  OH2 TIP C 331     12.920  31.214  52.942  1.00 51.07
ATOM   3452  OH2 TIP C 332     37.639   0.847  19.561  1.00 49.44
ATOM   3453  OH2 TIP C 333     34.243  38.790  -3.251  1.00 54.21
ATOM   3454  OH2 TIP C 334     24.216  47.874   6.983  1.00 50.90
ATOM   3455  OH2 TIP C 335     15.324  34.797   6.670  1.00 45.25
ATOM   3456  OH2 TIP C 336     18.474  15.525  21.402  1.00 34.12
ATOM   3457  OH2 TIP C 337     40.048   8.873  26.818  1.00 49.89
ATOM   3458  OH2 TIP C 338     32.472  13.331  20.523  1.00 29.86
ATOM   3459  OH2 TIP C 339     57.778  14.167  30.422  1.00 49.76
ATOM   3460  OH2 TIP C 340     46.651  35.476  13.375  1.00 56.48
ATOM   3461  OH2 TIP C 341     15.427  13.237   3.552  1.00 57.25
ATOM   3462  OH2 TIP C 342     40.349  38.972   3.722  1.00 65.27
ATOM   3463  OH2 TIP C 343      8.685  28.945  15.205  1.00 59.60
ATOM   3464  OH2 TIP C 344     11.958  41.585  22.587  1.00 37.18
ATOM   3465  OH2 TIP C 345      9.054  20.498  28.914  1.00 42.95
ATOM   3466  OH2 TIP C 346     20.086  20.088  46.913  1.00 42.03
ATOM   3467  OH2 TIP C 347     40.370  35.093   2.009  1.00 49.35
ATOM   3468  OH2 TIP C 348     41.948   4.327  12.147  1.00 50.59
```

FIG. 1DDD

| ATOM | 3469 | OH2 | TIP | C | 349 | 23.518 | 45.701 | 40.287 | 1.00 | 39.79 |
| --- | --- | --- | --- | --- | --- | --- | --- | --- | --- | --- |
| ATOM | 3470 | OH2 | TIP | C | 350 | 19.169 | 37.474 | 4.786 | 1.00 | 44.67 |
| ATOM | 3471 | OH2 | TIP | C | 351 | 32.946 | 39.184 | 41.062 | 1.00 | 57.56 |
| ATOM | 3472 | OH2 | TIP | C | 352 | 37.578 | 47.817 | 18.421 | 1.00 | 51.80 |
| ATOM | 3473 | OH2 | TIP | C | 353 | 15.391 | 43.820 | 7.645 | 1.00 | 58.15 |
| ATOM | 3474 | OH2 | TIP | C | 354 | 38.205 | 17.257 | 33.401 | 1.00 | 55.84 |
| ATOM | 3475 | OH2 | TIP | C | 355 | 43.224 | 1.565 | 14.606 | 1.00 | 41.12 |
| ATOM | 3476 | OH2 | TIP | C | 356 | 18.704 | 51.623 | 28.487 | 1.00 | 61.11 |
| ATOM | 3477 | OH2 | TIP | C | 357 | 46.033 | 5.813 | 0.173 | 1.00 | 43.43 |
| ATOM | 3478 | OH2 | TIP | C | 358 | 51.950 | 27.722 | 14.408 | 1.00 | 45.00 |
| ATOM | 3479 | OH2 | TIP | C | 359 | 46.825 | 2.427 | 15.714 | 1.00 | 52.68 |
| ATOM | 3480 | OH2 | TIP | C | 360 | 17.624 | 50.111 | 20.315 | 1.00 | 39.65 |
| ATOM | 3481 | O | HOH | C | 361 | 27.534 | 15.877 | 26.687 | 1.00 | 20.00 |
| ATOM | 3482 | O | HOH | C | 362 | 28.946 | 16.344 | 30.514 | 1.00 | 20.00 |
| END | | | | | | | | | | |

FIG. 1EEE

SEQUENCE LISTING

<160> NUMBER OF SEQ ID NOS: 15

<210> SEQ ID NO 1
<211> LENGTH: 501
<212> TYPE: PRT
<213> ORGANISM: Homo sapiens

<400> SEQUENCE: 1

Met Ala Gln Ala Leu Pro Trp Leu Leu Leu Trp Met Gly Ala Gly Val
 1               5                  10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg

```
                355                 360                 365
Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
                420                 425                 430

Gly Pro Phe Val Thr Leu Asp Met Glu Asp Cys Gly Tyr Asn Ile Pro
            435                 440                 445

Gln Thr Asp Glu Ser Thr Leu Met Thr Ile Ala Tyr Val Met Ala Ala
    450                 455                 460

Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
            500

<210> SEQ ID NO 2
<211> LENGTH: 695
<212> TYPE: PRT
<213> ORGANISM: Homo sapiens

<400> SEQUENCE: 2

Met Leu Pro Gly Leu Ala Leu Leu Leu Ala Ala Trp Thr Val Trp
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220
```

-continued

```
Val Val Glu Val Ala Glu Glu Val Ala Glu Val Glu Glu Glu
225                 230                 235                 240

Glu Ala Asp Asp Asp Glu Asp Glu Asp Gly Asp Glu Val Glu Glu
            245                 250                 255

Glu Ala Glu Glu Pro Tyr Glu Glu Ala Thr Glu Arg Thr Thr Ser Ile
                260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
        290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
                340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
        370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
        450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
        530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
                580                 585                 590

Glu Val Lys Met Asp Ala Glu Phe Arg His Asp Ser Gly Tyr Glu Val
        595                 600                 605

His His Gln Lys Leu Val Phe Phe Ala Glu Asp Val Gly Ser Asn Lys
        610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
```

```
                    645                 650                 655
His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695
```

```
<210> SEQ ID NO 3
<211> LENGTH: 9
<212> TYPE: PRT
<213> ORGANISM: Artificial Sequence
<220> FEATURE:
<223> OTHER INFORMATION: APP inhibitor peptide
<220> FEATURE:
<221> NAME/KEY: VARIANT
<222> LOCATION: 5
<223> OTHER INFORMATION: Xaa = Sta = Statine

<400> SEQUENCE: 3

Ser Glu Val Asn Xaa Val Ala Glu Phe
 1               5

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
gctctagaac ccagcacggc atccggctg                                       29

<210> SEQ ID NO 5
<211> LENGTH: 42
<212> TYPE: DNA
<213> ORGANISM: Artificial Sequence
<220> FEATURE:
<223> OTHER INFORMATION: Primer

<400> SEQUENCE: 5
ccaagcatgc ggccgcaata ggctatggtc atgagggttg ac                        42

<210> SEQ ID NO 6
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 6

Ser Glu Val Asn Leu Asp Ala Glu Phe Arg
 1               5                  10

<210> SEQ ID NO 7
<211> LENGTH: 390
<212> TYPE: PRT
<213> ORGANISM: Homo sapiens

<400> SEQUENCE: 7

Gly Ser Phe Val Glu Met Val Asp Asn Leu Arg Gly Lys Ser Gly Gln
 1               5                  10                  15

Gly Tyr Tyr Val Glu Met Thr Val Gly Ser Pro Pro Gln Thr Leu Asn
            20                  25                  30
```

Ile Leu Val Asp Thr Gly Ser Ser Asn Phe Ala Val Gly Ala Ala Pro
        35                  40                  45

His Pro Phe Leu His Arg Tyr Tyr Gln Arg Gln Leu Ser Ser Thr Tyr
    50                  55                  60

Arg Asp Leu Arg Lys Gly Val Tyr Val Pro Tyr Thr Gln Gly Lys Trp
65                  70                  75                  80

Glu Gly Glu Leu Gly Thr Asp Leu Val Ser Ile Pro His Gly Pro Asn
                85                  90                  95

Val Thr Val Arg Ala Asn Ile Ala Ala Ile Thr Glu Ser Asp Lys Phe
            100                 105                 110

Phe Ile Asn Gly Ser Asn Trp Glu Gly Ile Leu Gly Leu Ala Tyr Ala
        115                 120                 125

Glu Ile Ala Arg Pro Asp Asp Ser Leu Glu Pro Phe Phe Asp Ser Leu
    130                 135                 140

Val Lys Gln Thr His Val Pro Asn Leu Phe Ser Leu Gln Leu Cys Gly
145                 150                 155                 160

Ala Gly Phe Pro Leu Asn Gln Ser Glu Val Leu Ala Ser Val Gly Gly
                165                 170                 175

Ser Met Ile Ile Gly Ile Asp His Ser Leu Tyr Thr Gly Ser Leu
            180                 185                 190

Trp Tyr Thr Pro Ile Arg Arg Glu Trp Tyr Tyr Glu Val Ile Ile Val
        195                 200                 205

Arg Val Glu Ile Asn Gly Gln Asp Leu Lys Met Asp Cys Lys Glu Tyr
    210                 215                 220

Asn Tyr Asp Lys Ser Ile Val Asp Ser Gly Thr Thr Asn Leu Arg Leu
225                 230                 235                 240

Pro Lys Lys Val Phe Glu Ala Ala Val Lys Ser Ile Lys Ala Ala Ser
                245                 250                 255

Ser Thr Glu Lys Phe Pro Asp Gly Phe Trp Leu Gly Glu Gln Leu Val
            260                 265                 270

Cys Trp Gln Ala Gly Thr Thr Pro Trp Asn Ile Phe Pro Val Ile Ser
        275                 280                 285

Leu Tyr Leu Met Gly Glu Val Thr Asn Gln Ser Phe Arg Ile Thr Ile
    290                 295                 300

Leu Pro Gln Gln Tyr Leu Arg Pro Val Glu Asp Val Ala Thr Ser Gln
305                 310                 315                 320

Asp Asp Cys Tyr Lys Phe Ala Ile Ser Gln Ser Ser Thr Gly Thr Val
                325                 330                 335

Met Gly Ala Val Ile Met Glu Gly Phe Tyr Val Val Phe Asp Arg Ala
            340                 345                 350

Arg Lys Arg Ile Gly Phe Ala Val Ser Ala Cys His Val His Asp Glu
        355                 360                 365

Phe Arg Thr Ala Ala Val Glu Gly Pro Phe Val Thr Leu Asp Met Glu
    370                 375                 380

Asp Cys Gly Tyr Asn Ile
385                 390

<210> SEQ ID NO 8
<211> LENGTH: 390
<212> TYPE: PRT
<213> ORGANISM: Homo sapiens

<400> SEQUENCE: 8

Ser Phe Val Glu Met Val Asp Asn Leu Arg Gly Lys Ser Gly Gln Gly
1               5                   10                  15

Tyr Tyr Val Glu Met Thr Val Gly Ser Pro Pro Gln Thr Leu Asn Ile
            20                  25                  30

Leu Val Asp Thr Gly Ser Ser Asn Phe Ala Val Gly Ala Ala Pro His
        35                  40                  45

Pro Phe Leu His Arg Tyr Tyr Gln Arg Gln Leu Ser Ser Thr Tyr Arg
    50                  55                  60

Asp Leu Arg Lys Gly Val Tyr Val Pro Tyr Thr Gln Gly Lys Trp Glu
65                  70                  75                  80

Gly Glu Leu Gly Thr Asp Leu Val Ser Ile Pro His Gly Pro Asn Val
                85                  90                  95

Thr Val Arg Ala Asn Ile Ala Ala Ile Thr Glu Ser Asp Lys Phe Phe
            100                 105                 110

Ile Asn Gly Ser Asn Trp Glu Gly Ile Leu Gly Leu Ala Tyr Ala Glu
        115                 120                 125

Ile Ala Arg Pro Asp Asp Ser Leu Glu Pro Phe Phe Asp Ser Leu Val
    130                 135                 140

Lys Gln Thr His Val Pro Asn Leu Phe Ser Leu Gln Leu Cys Gly Ala
145                 150                 155                 160

Gly Phe Pro Leu Asn Gln Ser Glu Val Leu Ala Ser Val Gly Gly Ser
                165                 170                 175

Met Ile Ile Gly Gly Ile Asp His Ser Leu Tyr Thr Gly Ser Leu Trp
            180                 185                 190

Tyr Thr Pro Ile Arg Arg Glu Trp Tyr Tyr Glu Val Ile Ile Val Arg
        195                 200                 205

Val Glu Ile Asn Gly Gln Asp Leu Lys Met Asp Cys Lys Glu Tyr Asn
    210                 215                 220

Tyr Asp Lys Ser Ile Val Asp Ser Gly Thr Thr Asn Leu Arg Leu Pro
225                 230                 235                 240

Lys Lys Val Phe Glu Ala Ala Val Lys Ser Ile Lys Ala Ala Ser Ser
                245                 250                 255

Thr Glu Lys Phe Pro Asp Gly Phe Trp Leu Gly Glu Gln Leu Val Cys
            260                 265                 270

Trp Gln Ala Gly Thr Thr Pro Trp Asn Ile Phe Pro Val Ile Ser Leu
        275                 280                 285

Tyr Leu Met Gly Glu Val Thr Asn Gln Ser Phe Arg Ile Thr Ile Leu
    290                 295                 300

Pro Gln Gln Tyr Leu Arg Pro Val Glu Asp Val Ala Thr Ser Gln Asp
305                 310                 315                 320

Asp Cys Tyr Lys Phe Ala Ile Ser Gln Ser Ser Thr Gly Thr Val Met
                325                 330                 335

Gly Ala Val Ile Met Glu Gly Phe Tyr Val Val Phe Asp Arg Ala Arg
            340                 345                 350

Lys Arg Ile Gly Phe Ala Val Ser Ala Cys His Val His Asp Glu Phe
        355                 360                 365

Arg Thr Ala Ala Val Glu Gly Pro Phe Val Thr Leu Asp Met Glu Asp
    370                 375                 380

Cys Gly Tyr Asn Ile Pro
385                 390

<210> SEQ ID NO 9
<211> LENGTH: 150
<212> TYPE: PRT
<213> ORGANISM: Homo sapiens

<400> SEQUENCE: 9

```
Gly Ser Phe Val Glu Met Val Asp Asn Leu Arg Gly Lys Ser Gly Gln
  1               5                  10                  15
Gly Tyr Tyr Val Glu Met Thr Val Gly Ser Pro Pro Gln Thr Leu Asn
             20                  25                  30
Ile Leu Val Asp Thr Gly Ser Ser Asn Phe Ala Val Gly Ala Ala Pro
         35                  40                  45
His Pro Phe Leu His Arg Tyr Tyr Gln Arg Gln Leu Ser Ser Thr Tyr
 50                  55                  60
Arg Asp Leu Arg Lys Gly Val Tyr Val Pro Tyr Thr Gln Gly Lys Trp
 65                  70                  75                  80
Glu Gly Glu Leu Gly Thr Asp Leu Val Ser Ile Pro His Gly Pro Asn
                 85                  90                  95
Val Thr Val Arg Ala Asn Ile Ala Ala Ile Thr Glu Ser Asp Lys Phe
            100                 105                 110
Phe Ile Asn Gly Ser Asn Trp Glu Gly Ile Leu Gly Leu Ala Tyr Ala
        115                 120                 125
Glu Ile Ala Arg Pro Asp Asp Ser Leu Glu Pro Phe Phe Asp Ser Leu
130                 135                 140
Val Lys Gln Thr His Val
145                 150
```

<210> SEQ ID NO 10
<211> LENGTH: 240
<212> TYPE: PRT
<213> ORGANISM: Homo sapiens

<400> SEQUENCE: 10

```
Pro Asn Leu Phe Ser Leu Gln Leu Cys Gly Ala Gly Phe Pro Leu Asn
  1               5                  10                  15
Gln Ser Glu Val Leu Ala Ser Val Gly Gly Ser Met Ile Ile Gly Gly
             20                  25                  30
Ile Asp His Ser Leu Tyr Thr Gly Ser Leu Trp Tyr Thr Pro Ile Arg
         35                  40                  45
Arg Glu Trp Tyr Tyr Glu Val Ile Ile Val Arg Val Glu Ile Asn Gly
 50                  55                  60
Gln Asp Leu Lys Met Asp Cys Lys Glu Tyr Asn Tyr Asp Lys Ser Ile
 65                  70                  75                  80
Val Asp Ser Gly Thr Thr Asn Leu Arg Leu Pro Lys Lys Val Phe Glu
                 85                  90                  95
Ala Ala Val Lys Ser Ile Lys Ala Ala Ser Ser Thr Glu Lys Phe Pro
            100                 105                 110
Asp Gly Phe Trp Leu Gly Glu Gln Leu Val Cys Trp Gln Ala Gly Thr
        115                 120                 125
Thr Pro Trp Asn Ile Phe Pro Val Ile Ser Leu Tyr Leu Met Gly Glu
130                 135                 140
Val Thr Asn Gln Ser Phe Arg Ile Thr Ile Leu Pro Gln Gln Tyr Leu
145                 150                 155                 160
Arg Pro Val Glu Asp Val Ala Thr Ser Gln Asp Asp Cys Tyr Lys Phe
                165                 170                 175
Ala Ile Ser Gln Ser Ser Thr Gly Thr Val Met Gly Ala Val Ile Met
            180                 185                 190
Glu Gly Phe Tyr Val Val Phe Asp Arg Ala Arg Lys Arg Ile Gly Phe
        195                 200                 205
```

-continued

```
Ala Val Ser Ala Cys His Val His Asp Glu Phe Arg Thr Ala Ala Val
    210                 215                 220
Glu Gly Pro Phe Val Thr Leu Asp Met Glu Asp Cys Gly Tyr Asn Ile
225                 230                 235                 240

<210> SEQ ID NO 11
<211> LENGTH: 14
<212> TYPE: PRT
<213> ORGANISM: Homo sapiens

<400> SEQUENCE: 11

Gly Ser Phe Val Glu Met Val Asp Asn Leu Arg Gly Lys Ser
1               5                   10

<210> SEQ ID NO 12
<211> LENGTH: 6
<212> TYPE: PRT
<213> ORGANISM: Homo sapiens

<400> SEQUENCE: 12

Gly Gly Ile Asp His Ser
1               5

<210> SEQ ID NO 13
<211> LENGTH: 5
<212> TYPE: PRT
<213> ORGANISM: Homo sapiens

<400> SEQUENCE: 13

Pro Tyr Thr Gln Gly
1               5

<210> SEQ ID NO 14
<211> LENGTH: 4
<212> TYPE: PRT
<213> ORGANISM: Homo sapiens

<400> SEQUENCE: 14

Ser Ser Thr Gly
1

<210> SEQ ID NO 15
<211> LENGTH: 7
<212> TYPE: PRT
<213> ORGANISM: Homo sapiens

<400> SEQUENCE: 15

Arg Arg Glu Trp Tyr Tyr Glu
1               5
```

METHOD FOR IDENTIFYING AGENTS THAT INTERACT WITH BETA-SITE APP CLEAVING ENZYME (BACE)

This application claims the benefit of U.S. Provisional Application No. 60/234,576 filed Sep. 22, 2000.

FIELD OF THE INVENTION

The present invention relates to the three dimensional crystal structure of Beta-site APP Cleaving Enzyme (BACE), and to the use of this structure in rational drug design methods to identify agents that may interact with active sites of BACE. Such agents may represent new therapeutics in the treatment and/or prevention of Alzheimer's Disease.

BACKGROUND OF THE INVENTION

A characteristic pathology of Alzheimer's Disease is the build up of insoluble amyloid plaques in the brain. These proteinaceous plaques are composed of a 4 KDa, 42 amino acid fragment of β-Amyloid Precursor Protein (APP) and is termed Amyloid β-peptide (Aβ). The mechanism of Aβ production is hence of critical importance in understanding the onset and progress of Alzheimer's Disease. It has been shown that Aβ is derived from the proteolytic cleavage of a larger protein, β-amyloid precursor protein (APP). Two enzymes are responsible for this cleavage; first, the enzyme β-secretase cleaves APP at residue 671 (770aa isoform of APP numbering) and then γ-secretase cleaves at residue 716. More recently, the novel transmembrane aspartic protease BACE has been identified as being β-secretase. This protein is now a significant target in a therapeutic approach to Alzheimer's Disease. In rare cases of Alzheimer's Disease that are hereditary (Familial Alzheimer's Disease (FAD)) the disease phenotype has been isolated to mutations in the β-Amyloid Precursor Protein. One particular cohort, the 'Swedish mutation', exhibits a double mutation at the β-secretase cleavage site.

Based upon the role of BACE in Alzheimer's Disease, the elucidation of the three-dimensional structure of BACE, as well as its site of binding with APP, would have important implications in the treatment and/or prevention of Alzheimer's Disease and similar diseases associated with the presence of insoluble amyloid plaques composed the 42 amino acid fragment of APP in the brain.

SUMMARY OF THE INVENTION

The present invention provides a crystal of BACE complexed with an APP inhibitor peptide, as well as the three dimensional structure of BACE as derived by x-ray diffraction data of the BACE/APP inhibitor peptide crystal. Specifically, the three dimensional structure of BACE is defined by the structural coordinates shown in FIG. 1, ±a root mean square deviation from the backbone atoms of the amino acids of not more than 1.5 Å. The structural coordinates of BACE are useful for a number of applications, including, but not limited to, the visualization, identification and characterization of various active sites of BACE, and the BACE/APP inhibitor peptide complex, including the APP binding site. The active site structures may then be used to design various agents which interact with BACE, as well as BACE complexed with an APP protein or peptide, or related molecules.

The present invention is also directed to an active site of an APP binding protein or peptide, and preferably the APP peptide binding site of BACE that is elucidated and derived from the three dimensional structure of BACE as defined by the relative structural coordinates set forth in FIG. 1, ±a root mean square deviation from the backbone atoms of said amino acids of not more than 1.5 Å.

In one embodiment of the present invention, the active site of the APP binding protein or peptide, preferably the APP peptide binding site of BACE, comprises the relative structural coordinates according to FIG. 1 of residues SER71, GLY72, LEU91, ASP93, GLY95, SER96, VAL130, PRO131, TYR132, THR133, GLN134, ILE171, ILE179, ILE187, ALA188, ARG189, PRO190, TRP258, TYR259, ASP284, LYS285, ASP289, GLY291, THR292, THR293, ASN294, ARG296 and ARG368, ±a root mean square deviation from the backbone atoms of said amino acids of not more than 1.5 Å.

In another embodiment, the active site of the APP binding protein or peptide, preferably the APP peptide binding site of BACE, comprises the relative structural coordinates according to FIG. 1 of residues LYS70, SER71, GLY72, GLN73, GLY74, TYR75, LEU91, VAL92, ASP93, THR94, GLY95, SER96, SER97, ASN98, TYR129, VAL130, PRO131, TYR132, THR133, GLN134, GLY135, LYS136, TRP137, LYS168, PHE169, PHE170, ILE171, ASN172, SER174, TRP176, GLY178, ILE179, LEU180, GLY181, ALA183, TYR184, ALA185, GLU186, ILE187, ALA188, ARG189, PRO190, ASP191, ASP192, ARG256, TRP258, TYR259, TYR283, ASP284, LYS285, SER286, ILE287, VAL288, ASP289, SER290, GLY291, THR292, THR293, ASN294, LEU295, ARG296, GLY325, GLU326, ARG368, VAL370, LYS382, PHE383, ALA384, ILE385, SER386, GLN387, SER388, SER389, THR390, GLY391, THR392, VAL393, GLY395, ALA396 and ILE447, ±a root mean square deviation from the backbone atoms of said amino acids of not more than 1.5 Å.

The present invention further provides a method for identifying an agent that interacts with an active site of BACE. The method comprises the steps of: (a) determining a putative active site of BACE from a three dimensional model of BACE using the relative structural coordinates of FIG. 1, ±a root mean square deviation from the backbone atoms of the amino acids of not more than 1.5 Å; and (b) performing various computer fitting analyses to identify an agent which interacts with the putative active site.

The present invention also provides method for identifying an agent that interacts with an active site of an APP binding protein or peptide, preferably BACE. The method comprises the steps of: (a) generating a three dimensional model of an active site of an APP binding protein or peptide using the relative structural coordinates according to FIG. 1 of residues SER71, GLY72, LEU91, ASP93, GLY95, SER96, VAL130, PRO131, TYR132, THR133, GLN134, ILE171, ILE179, ILE187, ALA188, ARG189, PRO190, TRP258, TYR259, ASP284, LYS285, ASP289, GLY291, THR292, THR293, ASN294, ARG296 and ARG368, ±a root mean square deviation from the backbone atoms of said amino acids of not more than 1.5 Å; and (b) designing an agent using the three dimensional model generated in step (a).

The present invention also provides another method for identifying an agent that interacts with an active site of an APP binding protein or peptide, preferably BACE. The method comprises the steps of: (a) generating a three dimensional model of an active site of an APP binding protein or peptide using the relative structural coordinates according to FIG. 1 of residues LYS70, SER71, GLY72, GLN73, GLY74, TYR75, LEU91, VAL92, ASP93, THR94, GLY95, SER96, SER97, ASN98, TYR129, VAL130, PRO131, TYR132, THR133, GLN134, GLY135, LYS136, TRP137, LYS168, PHE169, PHE170, ILE171, ASN172, SER174, TRP176, GLY178, ILE179, LEU180, GLY181, ALA183, TYR184, ALA185, GLU186, ILE187, ALA188, ARG189, PRO190, ASP191, ASP192, ARG256, TRP258, TYR259, TYR283, ASP284, LYS285, SER286, ILE287, VAL288, ASP289, SER290, GLY291, THR292, THR293, ASN294, LEU295, ARG296, GLY325, GLU326, ARG368, VAL370, LYS382, PHE383, ALA384, ILE385, SER386, GLN387, SER388, SER389, THR390, GLY391, THR392, VAL393, GLY395, ALA396 and ILE447, ±a root mean square deviation from the backbone atoms of said amino acids of not more than 1.5 Å; and (b) designing an agent using the three dimensional model generated in step (a).

Finally, the present invention provides agents, and preferably inhibitors, identified using the foregoing methods. Small molecules or other agents which inhibit or otherwise interfere with the ability of BACE to cleave APP may be useful in the treatment and/or prevention of Alzheimer's Disease.

Additional objects of the present invention will be apparent from the description which follows.

BRIEF DESCRIPTION OF THE FIGURE

FIGS. 1A-1EEE provide the atomic structural coordinates for BACE and the APP inhibitor peptide (SEQ ID NO:7) and (SEQ ID NO:3) as derived by X-ray diffraction of a crystal of the BACE and APP inhibitor peptide complex. "Atom type" refers to the atom whose coordinates are being measured. "Residue" refers to the type of residue of which each measured atom is a part—i.e., amino acid, cofactor, ligand or solvent. The "x, y and z" coordinates indicate the Cartesian coordinates of each measured atom's location in the unit cell (Å). "Occ" indicates the occupancy factor. "B" indicates the "B-value", which is a measure of how mobile the atom is in the atomic structure ($Å^2$).

DETAILED DESCRIPTION OF THE INVENTION

As used herein, the following terms and phrases shall have the meanings set forth below:

Unless otherwise noted, "BACE" is Beta-site APP Cleaving Enzyme, and is the β-secretase enzyme that cleaves β-amyloid precursor protein (APP) at residue 671 (770aa isoform of APP numbering). After cleavage of APP by BACE, the remaining APP is cleaved at residue 716 by γ-secretase, leaving a 42 amino acid fragment of APP that is found in the proteinaceous plaques of Alzheimer's patients. The amino acid sequence of BACE preferably has the amino acid sequence deposited with Swiss Prot under accession number P56817 (SEQ ID NO:1), including conservative substitutions. As used herein, BACE also includes "BACE peptides," which are molecules having less than the complete amino acid sequence of BACE. Preferably, BACE peptides include the active site in which BACE binds to and cleaves APP. Most preferably, the BACE peptide corresponds to amino acid residues 58-447 set forth in 1A-1EEE ("$BACE_{58-447}$") (SEQ ID NO:7), including conservative substitutions.

"APP" is β-amyloid precursor protein having the amino acid sequence deposited with Swiss Prot under accession number CAA31830 (SEQ ID NO:2), including conservative substitutions. As used herein, APP also includes "APP peptides," which are molecules having less than the complete amino acid sequence of APP. Preferably, APP peptides include the active site in which APP is cleaved by BACE.

An "APP inhibitor peptide" is a peptide which inhibits binding between BACE and APP. Preferably, the APP peptide has the amino acid sequence SER-GLU-VAL-ASN-Sta-VAL-ALA-GLU-PHE (SEQ ID NO:3), where Sta is rare amino acid (S)-Statine.

An "APP binding protein or peptide" is a protein or peptide that binds APP and has a APP binding site, and includes but is not limited to BACE and BACE peptides.

Unless otherwise indicated, "protein" shall include a protein, protein domain, polypeptide or peptide.

"Structural coordinates" are the Cartesian coordinates corresponding to an atom's spatial relationship to other atoms in a molecule or molecular complex. Structural coordinates may be obtained using x-ray crystallography techniques or NMR techniques, or may be derived using molecular replacement analysis or homology modeling. Various software programs allow for the graphical representation of a set of structural coordinates to obtain a three dimensional representation of a molecule or molecular complex. The structural coordinates of the present invention may be modified form the original set provided in FIGS. 1A-1EEE by mathematical manipulation, such as by inversion of integer additions or subtractions. As such, it is recognized that the structural coordinates of the present invention are relative, and are in no way specifically limited by the actual x, y, z coordinates of FIGS. 1A-1EEE.

An "agent" shall include a protein, polypeptide, peptide, nucleic acid, including DNA or RNA, molecule, compound or drug.

"Root mean square deviation" is the square root of the arithmetic mean of the squares of the deviations from the mean, and is a way of expressing deviation or variation from the structural coordinates of BACE described herein. The present invention includes all embodiments comprising conservative substitutions of the noted amino acid residues resulting in same structural coordinates within the stated root mean square deviation.

The numbering of the amino acid residues identified in FIGS. 1A-1EEE are based on the numbering of the full length BACE protein from the start of the signal sequence. It will be obvious to the skilled practitioner that the numbering of the amino acid residues of BACE may be different than that set forth herein or may contain certain conservative amino acid substitutions that yield the same three dimensional structures as those defined in FIGS. 1A-1EEE. Corresponding amino acids and conservative substitutions in other isoforms or analogues are easily identified by visual inspection of the relevant amino acid sequences or by using commercially available homology software programs (e.g., MODELLAR, MSI, San Diego, Calif.).

"Conservative substitutions" are those amino acid substitutions which are functionally equivalent to the substituted amino acid residue, either by way of having similar polarity, steric arrangement, or by belonging to the same class as the substituted residue (e.g., hydrophobic, acidic or basic) and includes substitutions having an inconsequential effect on the three dimensional structure of BACE, with respect to the use of this structure for the identification and design of agents which interact with BACE, for molecular replacement analyses and/or for homology modeling.

As used herein, an "active site" refers to a region of a molecule or molecular complex that, as a result of its shape and charge potential, favorably interacts or associates with another agent (including, without limitation, a protein, polypeptide, peptide, nucleic acid, including DNA or RNA, molecule, compound, antibiotic or drug) via various covalent and/or non-covalent binding forces. Preferably, the active site of BACE corresponds to the site in which BACE cleaves the APP molecule.

As such, the active site of BACE may include, for example, both the actual site in which BACE binds and cleaves APP, as well as accessory binding sites adjacent or proximal to the actual binding site that nonetheless may affect the ability of BACE to bind and cleave APP, either by direct interference with the actual site of binding or by indirectly affecting the steric conformation or charge potential of the BACE molecule and thereby preventing or reducing the ability of BACE to bind to APP at the actual binding site. As used herein, an active site also includes BACE or BACE analog residues which exhibit observable NMR perturbations in the presence of a binding ligand, such as APP or an APP peptide. While such residues exhibiting observable NMR perturbations may not necessarily be in direct contact with or immediately proximate to ligand binding residues, they may be critical to BACE residues for rational drug design protocols.

The present invention is directed to a crystallized complex of BACE and an APP inhibitor peptide that effectively diffracts X-rays for the determination of the structural coordinates of the complex. As used herein, BACE preferably corresponds to $BACE_{58-447}$ as set forth in FIGS. 1A-1EEE, with the N-terminal domain consisting of amino acid residues 58-207 shown in FIGS. 1A-1EEE and the C-terminal domain consisting of amino acid residues 208-447 shown in FIGS. 1A-1EEE. The APP inhibitor peptide is preferably SER-GLU-VAL-ASN-Sta-VAL-ALA-GLU-PHE (SEQ ID NO:3).

Using the crystal complex of the present invention, X-ray diffraction data can be collected by a variety of means in order to obtain the atomic coordinates of the crystallized molecule or molecular complex. With the aid of specifically designed computer software, such crystallographic data can be used to generate a three dimensional structure of the molecule or molecular complex. Various methods used to generate and refine the three dimensional structure of a crystallized molecule or molecular structure are well known to those skilled in the art, and include, without limitation, multi-wavelength anomalous dispersion (MAD), multiple isomorphous replacement, reciprocal space solvent flattening, molecular replacement, and single isomorphous replacement with anomalous scattering (SIRAS).

Accordingly, the present invention also provides the three dimensional structure of BACE as derived by x-ray diffraction data of the BACE/APP inhibitor peptide crystal. Specifically, the three dimensional structure of BACE is defined by the structural coordinates shown in FIGS. 1A-1EEE, ±a root mean square deviation from the backbone atoms of the amino acids of not more than 1.5 Å, preferably not more than 1.0 Å, and most preferably not more than 0.5 Å. The structural coordinates of BACE are useful for a number of applications, including, but not limited to, the visualization, identification and characterization of various active sites of BACE, and the BACE/APP inhibitor peptide complex, including the APP or APP peptide binding site. The active site structures may then be used to design agents that interact with BACE, as well as BACE complexed with APP, an APP peptide or related molecules.

The present invention is also directed to an active site of an APP binding protein or peptide, preferably the APP peptide binding site of BACE, which comprises the relative structural coordinates according to FIGS. 1A-1EEE of residues SER71, GLY72, LEU91, ASP93, GLY95, SER96, VAL130, PRO131, TYR132, THR133, GLN134, ILE171, ILE179, ILE187, ALA188, ARG189, PRO190, TRP258, TYR259, ASP284, LYS285, ASP289, GLY291, THR292, THR293, ASN294, ARG296 and ARG368, ±a root mean square deviation from the backbone atoms of said amino acids of not more than 1.5 Å, preferably not more than 1.0 Å, and most preferably not more than 0.5 Å.

In another preferred embodiment, the active site of an APP binding protein or peptide, preferably the APP peptide binding site of BACE, comprises the relative structural coordinates according to FIGS. 1A-1EEE of residues LYS70, SER71, GLY72, GLY74, TYR75, LEU91, VAL92, ASP93, THR94, GLY95, SER96, SER97, ASN98, TYR129, VAL130, PRO131, TYR132, THR133, GLN134, GLY135, LYS136, TRP137, LYS168, PHE169, PHE170, ILE171, ASN172, SER174, TRP176, GLY178, ILE179, LEU180, GLY181, ALA183, TYR184, ALA185, GLU186, ILE187, ALA188, ARG189, PRO190, ASP191, ASP192, ARG256, TRP258, TYR259, TYR283, ASP284, LYS285, SER286, ILE287, VAL288, ASP289, SER290, GLY291, THR292, THR293, ASN294, LEU295, ARG296, GLY325, GLU326, ARG368, VAL370, LYS382, PHE383, ALA384, ILE385, SER386, GLN387, WER388, SER389, THR390, GLY391, THR392, VAL393, GLY395, ALA396 and ILE447, ±a root mean square deviation from the backbone atoms of said amino acids of not more than 1.5 Å, preferably not more than 1.0 Å, and most preferably not more than 0.5 Å.

Another aspect of the present invention is directed to a method for identifying an agent that interacts with an active site of BACE comprising the steps of: (a) determining an active site of BACE from a three dimensional model of BACE using the relative structural coordinates of FIGS. 1A-1EEE, ±a root mean square deviation from the backbone atoms of said amino acids of not more than 1.5 Å, preferably not more than 1.0 Å, and most preferably not more than 0.5 Å; and (b) performing computer fitting analysis to identify an agent which interacts with said active site. Computer fitting analyses utilize various computer software programs that evaluate the "fit" between the putative active site and the identified agent, by (a) generating a three dimensional model of the putative active site of a molecule or molecular complex using homology modeling or the atomic structural coordinates of the active site, and (b) determining the degree of association between the putative active site and the identified agent. Three dimensional models of the putative active site may be generated using any one of a number of methods known in the art, and include, but are not limited to, homology modeling as well as computer analysis of raw data generated using crystallographic or spectroscopy data. Computer programs used to generate such three dimensional models and/or perform the necessary fitting analyses include, but are not limited to: GRID (Oxford University, Oxford, UK), MCSS (Molecular Simulations, San Diego, Calif.), AUTODOCK (Scripps Research Institute, La Jolla, Calif.), DOCK (University of California, San Francisco, Calif.), Flo99 (Thistlesoft, Morris Township, N.J.), Ludi (Molecular Simulations, San Diego, Calif.), QUANTA (Molecular Simulations, San Diego, Calif.), SYBYL (TRIPOS, Inc., St. Louis, Mo.) and LEAP-FROG (TRIPOS, Inc., St. Louis, Mo.).

The present invention also provides a method for identifying an agent that interacts with an active site of an APP binding protein or peptide, and preferably the APP peptide binding site on BACE. The method comprises the steps of: (a) generating a three dimensional model of an active site of an APP binding protein or peptide using the relative structural coordinates according to FIGS. 1A-1EEE of residues SER71, GLY72, LEU91, ASP93, GLY95, SER96, VAL130, PRO131, TYR132, THR133, GLN134, ILE171, ILE179, ILE187, ALA188, ARG189, PRO190, TRP258, TYR259, ASP284, LYS285, ASP289, GLY291, THR292, THR293, ASN294, ARG296 and ARG368, ±a root mean square deviation from the backbone atoms of said amino acids of not more than 1.5 Å, preferably not more than 1.0 Å, and most preferably not more than 0.5 Å; and (b) designing an agent using the three dimensional model generated in step (a). In another preferred embodiment, the active site of the APP binding protein or peptide is generated using the three dimensional model defined by the relative structural coordinates according to FIGS. 1A-1EEE of residues LYS70, SER71, GLY72, GLN73, GLY74, TYR75, LEU91, VAL92, ASP93, THR94, GLY95, SER96, SER97, ASN98, TYR129, VAL130, PRO131, TYR132, THR133, GLN134, GLY135, LYS136, TRP137, LYS168, PHE169, PHE170, ILE171, ASN172, SER174, TRP176, GLY178, ILE179, LEU180, GLY181, ALA183, TYR184, ALA185, GLU186, ILE187, ALA188, ARG189, PRO190, ASP191, ASP192, ARG256, TRP258, TYR259, TYR283, ASP284, LYS285, SER286, ILE287, VAL288, ASP289, SER290, GLY291, THR292, THR293, ASN294, LEU295, ARG296, GLY325, GLU326, ARG368, VAL370, LYS382, PHE383, ALA384, ILE385, SER386, GLN387, SER388, SER389, THR390, GLY391, THR392, VAL393, GLY395, ALA396 and ILE447, ±a root mean square deviation from the backbone atoms of said amino acids of not more than 1.5 Å, preferably not more than 1.0 Å, and most preferably not more than 0.5 Å.

The effect of such an agent identified by computer fitting analyses on the APP binding protein or peptide may be further evaluated by obtaining or synthesizing the agent, and contacting the identified agent with the APP binding protein or peptide in order to determine the effect the agent has on the APP binding protein or peptide. Preferably, the APP binding protein or peptide is BACE (or a BACE peptide), and the agent is a potential inhibitor of binding between BACE (or a BACE peptide) and APP (or an APP peptide). Therefore, in the preferred embodiment, the agent is contacted with BACE (or a BACE peptide) in the presence of APP (or a APP peptide), to determine the ability of the agent to inhibit binding between BACE (or the BACE peptide) and APP (or the APP peptide). Depending upon the action of the agent on the active site, the agent may act either as an inhibitor or activator of the BACE/APP binding. Assays may be performed and the results analyzed to determine whether the agent is an inhibitor (i.e., the agent may reduce or prevent binding affinity between BACE and APP), an activator (i.e., the agent may increase binding affinity between BACE and APP), or has no effect on the interaction between BACE and APP. Agents identified using the foregoing methods, and preferably inhibitors of BACE cleavage of APP, may then be tested as therapeutics in the treatment and/or prevention of Alzheimer's Disease, and other diseases that are also characterized by the presence of the 42 amino acid fragment of APP in the proteinaceous plaques of the brain.

Various molecular analysis and rational drug design techniques are further disclosed in U.S. Pat. Nos. 5,834,228, 5,939,528 and 5,865,116, as well as in PCT Application No. PCT/US98/16879, ; published WO 99/09148, the contents of which are hereby incorporated by reference.

Finally, the present invention is also directed to the agents, and preferably the inhibitors, identified using the foregoing methods. Such agents may be a protein, polypeptide, peptide, nucleic acid, including DNA or RNA, molecule, compound, or drug, and preferably are small molecules that effectively inhibit binding between BACE and APP or an APP peptide. Such molecules may be useful in treating, preventing or inhibiting progression of Alzheimer's Disease.

The present invention may be better understood by reference to the following non-limiting Example. The following Example is presented in order to more fully illustrate the preferred embodiments of the invention, and should in no way be construed as limiting the scope of the present invention.

EXAMPLE 1

A. Methods

Cloning of Human BACE1. Human polyA+ mRNA from whole brain (Clontech) was converted to cDNA by random-priming using Thermoscript RT-PCR System, according to the manufacturer's protocol (Lifetechnologies). This cDNA was amplified by PCR using the forward and reverse primers, 5' GCTCTAGAACCCAGC ACGGCATCCGGCTG 3' (SEQ ID NO:4) (XbaI site indicated by underlined sequence; nts. 517-537 in accession no. AF190725) and 5' CCAAGCAT-GCGGCCGCAATAGGCTATGGTCA TGAGGGTTGAC 3' (SEQ ID NO:5) (NotI site indicated by underlined sequence; nts. 1809-1833; bold "A" indicates additional nucleotide to permit in-frame translation of the Fc chimera; see below), respectively. PCR was accomplished using Expand Long Polymerase kit according to the manufacturer's conditions (Roche Biochemicals; buffer #3), with PCR cycling consisting of an initial denaturing step at 95° C. for 3 mm, 30-40 cycles of denaturation at 94° C. for 30 sec, annealing at 65° C. for 30 sec, elongation at 68° C. for 1 mm 30 sec, followed by a final elongation at 68° C. for 5 mm. The PCR products were run on a 1% agarose gel. The appropriate band was cut out of the gel, purified by Quantum Prep Freeze'N Squeeze DNA Extraction Columns (Bio-Rad), and cloned into the SpeI/NotI sites of the mammalian expression vector, pED/Fc (Kaufman, R J et al., 1991, Nucl. Acids. Res. 19:4485-4490).

An intermediate construct contained the honey bee meletin secretory leader fused to the prodomain and coding region of BACE1, just upstream to the predicted transmembrane domain of BACE1 (Vassar, R. et al., 1999, Science 286:735-741). The absence of the predicted hydrophobic transmembrane domain in this construct would permit soluble secreted BACE.Fc protein to be extracted from the conditioned medium. Downstream of BACE1 was an engineered enterokinase cleavage site followed by sequence encoding the Fc portion of immunoglobulin IgG. The final construct contained the BACE1.FC gene, flanked by SalI and EcoRI in pED/Fc, cloned into the SalI/EcoRI sites of the mammalian expression vector, pHTop, a derivative of pED, in which the majority of the adenovirus major late promoter was replaced by six repeats of a bacterial tetracycline operator (described in Gossen et al, 1992, PNAS, 89:5547-5551). Sequencing of the BACE1.Fc recombinant gene was accomplished by BigDye terminator dideoxy sequencing using an ABI3700. Sequence analyses was accomplished using DNAstar software package.

Expression of Human BACE1. The vector, pHTOP, with the BACE1.Fc insert, contains the dihydrofolate reductase gene and when introduced in the cell line CHO/A2 (see description below) functions very efficiently and high expressers can be selected by isolating cells surviving in high methotrexate concentrations. The CHO/A2 cell line is derived from CHO DUKX B11 (Urlaub and Chasin, 1980, PNAS USA 77:4216-4220) by stably integrating a transcriptional activator (tTA), a fusion protein between the Tet repressor and the herpes virus VP16 transcriptional domain (Gossen et al). A CHO cell line expressing extracellular BACE1.Fc was established by transfecting (lipofection) pHTopBACE1.Fc into CHO/A2 cells and selecting clones in 0.02 and 0.05 µM methotrexate. The conditioned media from multiple clones were screened by Western blot using a (mouse) anti-human IgG.Fc HRP antibody. The same clones were also metabolically labeled with 35 S (met/cys). The best clone, determined by virtue of its high expression, was one which resulted from 0.05 μM MIX selection and was chosen to be scaled up for roller bottle conditioned media production (4 Liters). The conditioned media was then used for purification. The expressed protein has residues 22-460 and nine extra-residues at the C-terminal (an artefact from cloning and remains of the EK cleavage site).

Purification of BACE1. For the purification of BACE the 102 liters of conditioned media was used. During purification the activity of the enzyme was estimated at room temperature by continuously monitoring the fluorescent intensity for 5-10 min. at 420 nm (ext −320 nm) Abz-Ser-Glu-Val-Asn-Leu-Asp-Ala-Glu-Phe-Arg-Dpa (SEQ ID NO:6) (Abz:=Amino benzoic acid, Dpa=9,10-diphenylanthracene) as the substrate. The reaction mixture contained 20 .mu.M of substrate, different amounts of enzyme in 0.5 ml of 20 mM Tris-HCl pH 8.0 and 100 mM NaCl. The concentrated material of conditioned media (1.6 1) was applied to column (2.8.times.12 cm) containing ImmunoPure Immobilized Protein A agarose (Pierce, Ill., USA) equilibrated in PBS buffer. The speed of application was 2 mL/min. The column was washed with 1 liter of PBS buffer and the BACE-Fc protein was eluted by ImmunoPure IgG Elution Buffer (Pierce, Ill., USA). The fractions containing protein were immediately neutralized by 1 M Tris-HCl to pH 8.0.

The obtained protein material was treated with Enterokinase at 25° C. The ratio of BACE-Fc to Enterokinase was 3000:1 and the time of reaction was 3 hrs. The reaction was stopped by removing Enterokinase from reaction mixture by applying the protein to a column (1×5 cm) containing soybean trypsin inhibitor agarose (Sigma, Mo., USA) equilibrated in 20 mM Tris-HCL pH 8.0 containing 100 mM NaCl (speed was 1 ml/min). The flow through material contained BACE and cleaved Fc. Cleaved Fc was removed from BACE by flowing through a protein A column equilibrated in 20 mM Tris-HCl pH 8.0.

BACE was partially de-glycosylated using PNGase F (New England Labs., Mass., USA). 8-9 μg of PNGase was added to 1 mg of BACE and the incubation was carried at 37° C. for 16 hrs. The additional 5-6 μg of PNGase was added to each mg of BACE and incubation was continued for another 4 hrs. The purified BACE was separated from PNGase by HPLC size-exclusion chromatography using 21.5×0 cm G-3000SW column (TosoHaas, Pa., USA) equilibrated in 20 mM tris-HCL pH 8.0 containing 200 mM NaCl. (Speed of elution was 3 ml/min). The purified BACE was concentrated and used for crystallization experiments.

N-terminal sequencing of purified BACE reveals a mixture of protein species, with the major sample having the processing domain cleaved and beginning at residue 47 (all numbering refers to full length BACE; accession code: A59090) and a minor sample which had not been cleaved beginning at residue 22. A smaller sample with sequence MTIAY was also detected.

Crystallization. The crystals were grown using the hanging drop vapour diffusion method. The protein was concentrated to mg/ml in 20 mM Tris pH 7.5, 200 mM sodium chloride. Inhibitor peptide sequence is SEVNStaVAEF (SEQ ID NO:3), where Sta is the rare amino acid (S)-Statine. It was concentrated to 100 mM in 100% DMSO and mixed with concentrated protein in a two-fold peptide excess to form the complex. 1 μl of complex was added to 1 μl of well solution containing 100 mM Sodium Cacodylate pH6.5, 25% PEG8K, 300 mM lithium sulphate. Plate-like crystal clusters grew within one week to dimensions of 200 μm times.400 μm times 75 μm. Single crystals were transferred to a stabilizing, cryoprotectant solution which contained the well solution plus 25% Glycerol for a brief, 10 second, soak and then frozen in liquid nitrogen. X-ray diffraction crystals had space group 1222, and unit cell parameters a=86.627, b=130.861, c=130.729, and $\alpha=\beta=\gamma=90°$.

B. Results

Structure Determination and Overall Fold. Full length BACE was expressed in CHO cells as a fc fusion protein and, after purification, cleavage and partial deglycosylation, complexed with peptide inhibitor and crystallized. Crystals diffracted to 2.3 Å and the structure was solved using the technique of molecular replacement. The search model used was derived from cod atlantic Pepsin and contained 63% of the final number of atoms. The density modified maps obtained using a poly-alanine version of the search model (39% of the final atoms) provided sufficient information to build all but 12 amino acids. The final model contains residues from 59 to 448 (SEQ ID NO:8) (using full length numbering), all 9 residues of the statine inhibitor and 360 water molecules. Of the four predicted N-linked glycosylation sites only two have interpretable electron density.

The overall shape of the BACE protein is spherical and is composed of two distinct domains, an N-terminal (58-207) (SEQ ID NO:9) and a C-terminal (208-447) (SEQ ID NO:10). With the first thirteen amino acids (58-71) (SEQ ID NO:11) being packed against residues 238-243 (SEQ ID NO:12). There is a significant cleft-like channel across one surface of the interface between the domains. This contains the inhibitor peptide and conserved aspartic acid motifs that define the active sites of aspartic proteases.

The N-terminal domain is composed of a single .alpha.-helix preceeding the loop joining the two domains and thirteen β-strands. The larger C-terminal domain has a total of seventeen β-strands and three α-helices. The overall topology is characterised by an eight stranded antiparallel interdomain β-sheet. This central sheet comprises the majority of the active site residues including the two conserved aspartates (one from each domain: 93 and 289). Asp93 and Asp289 define the position of a pseudo two-fold axis for the central β-sheet. Outside of this symmetry the two domains differ significantly. The N-terminal domain has an extra two strands extending the central sheet. In addition, there are two anti-parallel β-sheets above and below the central sheet composed of three and four β-strands respectively. Residues from the upper sheet (131-135 (SEQ ID NO:13)) fold over the active site aspartates and form a 'flap' over the centre of the peptide binding cleft.

The C-terminal domain contains two lobes in addition to the strands which from the central β-sheet. These are weakly homologous to known aspartic protease structures. The binding pocket for the P1' and P3' positions are instead derived from three β-turns 388-391 (SEQ ID NO:14), 284-286 and 255-261 (SEQ ID NO:15).

There are a total of six cysteine residues in BACE. Each of these is involved in a disulphide interaction. The pattern of disulphide crosslinking, Cys278-Cys443, Cys380-Cys330, Cys420-Cys216 are unique in the aspartic proteases known to date.

A novel aspartic protease. The first attempts to study the relationship of function to structure of an Apartic proteases began in the 1930s with Pepsin. Since then this rich field of research has been successfully applied to the design of clinically used inhibitors in only one system; HIV protease. The reasons for this are related more to the validity of the pharmacological target than the efficacy of inhibitors. β-secretase has been described as a novel protease and has been shown to be linked to the onset and progression of Alzheimer's disease.

From a gross viewpoint the overall fold and domain organization is very similar to that of a canonical aspartic protease. The comparison at a more detailed level reveals a significant number of differences. The active site is characterized by two aspartic residues surrounded by a conserved set of hydrogen bonds termed a 'fireman's grip'. This is reproduced in the β-secretase structure presented here. The characteristic flap which wraps over the active site in pepsin is absent from the C-terminal domain in a manner analogous to cathepsin D. In β-secretase the critical main chain amide hydrogen bond to the carboxyl group of statine is maintained by Thr133 from this flap. The amide of the statine makes a hydrogen bond to the carboxyl group of Gly95, emphasizing that the statine residue occupies both the P1 and P1' position.

Enzyme Mechanism. It has been shown that β-secretase cleavage is dependent on proximity to the cell membrane. Both β-secretase and its substrate APP have putative transmembrane regions. Our expressed BACE construct finishes one amino acid before the predicted transmembrane region. The final residue in the current structure is Ile447, thirteen residues away from the beginning of the putative transmembrane domain. In the current crystal structure Ile447 is only 6 Å away from the P3 Glutamic acid of the inhibitor suggesting a role for the remaining C-terminal residues in the enzyme mechanism. The Statine residue of the inhibitor peptide is bound at the S1 position within the active site. The position of the C-3 hydroxyl group, coplanar to and within hydrogen bonding distance of both aspartate 93 and 289 carboxyl groups, confirms that the rare amino acid mimics the tetrahedral transition state i.e the intermediate of peptide-bond hydrolysis. The distance between the oxygen atoms of Asp93 and Asp289 is 2.8 Å, strongly suggesting a shared proton atom and a classic aspartic protease pK profile for these side-chains and a common enzyme mechanism to other known aspartic proteases.

Inhibitor binding. The inhibitor peptide binds in an extended form along a 20 Å groove formed at the interface between the domains. The conserved catalytic aspartic residues lie at the middle of this groove. The bound peptide consists of 8 amino acids plus a statine amino acid at position 5. There is contiguous electron density for the whole peptide. The statine based inhibitor used in this study has been show to inhibit the β-secretase enzyme with nanomolar efficiency. The peptide sequence is based on the P10 to P4' APP751 Swedish family mutation. This mutation of a Lys-Asn at the P2 position and Met-Leu at the P1 position is strongly correlated to the early onset of Alzheimer's disease. The inhibitor peptide utilizes Statine's Leucyl like side-chain to explore this interaction. Due to the di-peptide nature of Statine the P1' position of the substrate is shifted to P2' leaving an empty S1' pocket. The β-secretase enzyme appears to have a novel preference for an apartate or glutamate at the P1' position whereas other aspartic proteases show a preference for hydrophobic residues. This unusual preference for a negatively charged P1' amino acid is explained by the guanadinium group of Arg189 forming part of the putative S1' pocket. Even at the acidic pH optima of BACE the arginine side chain would form a positively charged environment for the possibly protonated carboxyl side-chain atoms.

The S1 and S3 binding pockets are a contiguous, hydrophobic pocket formed by the side-chain of residues Tyr132, Phe169, Ile171, Trp176, Ile179 and main chain atoms of Gly74, and Gln73. This packing of inhibitor P1 and P3 side chains has been seen in previous aspartic protease complexes.

The canonical APP cleavage site for b-secretase appears to have a preference for a small hydrophobic residues at the P2' position. The side chain of the valine residue bound in the putative S2' site of β-secretase appears to not make any significant interactions with the protein, its main chain however forms a tight set of hydrogen bonds to the backbone carboxyl of Gly 95 and the sidechain OH of Tyr259. In turn, Tyr259 is held rigidly in place by an edge-pi interaction with Trp258, which packs against the guanadinium group of Arg256.

Swedish mutation. Autosomal dominant mutations identified on the β-amyloid precursor protein have been correlated to early-onset cases of Alzheimer's disease. These have been shown to cluster around the three canonical cleavage sites. A double (the so-called Swedish) mutation of Lys670-Met671 (770aa isoform of APP numbering) to Asn-Leu causes an increase in the overall quantity of Aβ detectable in the plasma and in the medium of cultured fibroblasts from carriers of the Swedish mutation. These two amino acids lie at the P2 and P1 positions of the β-secretase active site. The statine based inhibitor used here is based on this Swedish mutation. A methionine at position P1 would clearly be accommodated but would loose the van Der Waal's complentarity exhibited by the statine side-chain to Leu90 and Ile178. The Cε atom of the methione would make supplement the hydrophobic interaction to Phe169.

Table 1

Residues of BACE Within 4 Å of Peptide Inhibitor SER71, GLY72, LEU91, ASP93, GLY95, SER96, VAL130, PRO131, TYR132, THR133, GLN134, ILE171, ILE179, ILE187, ALA188, ARG189, PRO190, TRP258, TYR259, ASP284, LYS285, ASP289, GLY291, THR292, THR293, ASN294, ARG296, ARG368

Residues of BACE Within 8 Å of Peptide Inhibitor LYS70, SER71, GLY72, GLN73, GLY74, TYR75, LEU91, VAL92, ASP93, THR94, GLY95, SER96, SER97, ASN98, TYR129, VAL130, PRO131, TYR132, THR133, GLN134, GLY135, LYS136, TRP137, LYS168, PHE169, PHE170, ILE171, ASN172, SER174, TRP176, GLY178, ILE179, LEU180, GLY181, ALA183, TYR184, ALA185, GLU186, ILE187, ALA188, ARG189, PRO190, ASP191, ASP192, ARG256, TRP258, TYR259, TYR283, ASP284, LYS285, SER286, ILE287, VAL288, ASP289, SER290, GLY291, THR292, THR293, ASN294, LEU295, ARG296, GLY325, GLU326, ARG368, VAL370, LYS382, PHE383, ALA384, ILE385, SER386, GLN387, SER388, SER389, THR390, GLY391, THR392, VAL393, GLY395, ALA396, ILE447

All publications mentioned herein above, whether to issued patents, pending applications, published articles, deposited sequences, or otherwise, are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for identifying a candidate agent that interacts with or binds to a beta-amyloid precursor protein (APP) binding site of Beta-site APP Cleaving Enzyme (BACE), the method comprising:

(a) utilizing the relative three-dimensional structural coordinates of a complex of a BACE peptide and an APP inhibitor peptide according to FIGS. 1A-1EEE, ±a root mean square deviation from the backbone atoms of the amino acid residues in the complex not more than 1.5 Å to generate a three-dimensional representation of the complex, wherein:

(i) the BACE peptide in the complex comprises the amino acid sequence of residues 58-447 of SEQ ID NO: 1, and (ii) the APP inhibitor peptide in the complex comprises the amino acid sequence SEVNStaVAEF (SEQ ID NO:3), wherein Sta is (S)-statine;

(b) identifying the amino acid residues forming the APP binding site of the BACE peptide from the three-dimensional representation in step (a), wherein the APP-binding site comprises the relative structural coordinates according to FIGS. 1A-1EEE of amino acid residues LYS70, SER71, GLY72, GLN73, GLY74, TYR75, LEU91, VAL92, ASP93, THR94, GLY95, SER96, SER97, ASN98, TYR129, VAL130, PRO131, TYR132, THR133, GLN134, GLY135, LYS136, TRP137, LYS168, PHE169, PHE170, ILE171, ASN172, SER174, TRP176, GLY178, ILE179, LEU180, GLY181, ALA183, TYR184, ALA185, GLU186, ILE187, ALA188, ARG189, PRO190, ASP191, ASP192, ARG256, TRP258, TYR259, TYR283, ASP284, LYS285, SER286, ILE287, VAL288, ASP289, SER290, GLY291, THR292, THR293, ASN294, LEU295, ARG296, GLY325, GLU326, ARG368, VAL370, LYS382, PHE383, ALA384, ILE385, SER386, GLN387, SER388, SER389, THR390, GLY391, THR392, VAL393, GLY395, ALA396, and ILE447, ±a root mean square deviation from the backbone atoms of said amino acid residues of not more than 1.5 Å ;

(c) generating a three-dimensional model of the APP binding site of BACE;
(d) employing said three-dimensional model from step (c) to identify said candidate agent;
(e) obtaining said candidate agent; and
(f) contacting in vitro or in vivo said candidate agent with BACE to determine the ability of said candidate agent to interact or bind to BACE, whereby the detection of the ability of said candidate agent to interact or bind to BACE identifies said candidate agent.

2. The method of claim 1, wherein the ±root mean square deviation from the backbone atoms of said amino acid residues in the complex is not more than 1.0 Å.

3. The method of claim 1, wherein the ±root mean square deviation from the backbone atoms of said amino acid residues in the complex is not more than 0.5 Å.

4. The method of claim 1, wherein step (d) comprises determining the degree of association between the candidate agent and the three dimensional model of the APP-binding site of BACE.

5. The method of claim 1, wherein the contacting of the candidate agent with BACE comprises determining the effect the agent has on BACE aspartic protease activity.

6. The method of claim 5, wherein the candidate agent is a potential inhibitor of binding between BACE and APP or an APP peptide.

7. The method of claim 6, further comprising contacting the candidate agent with BACE in the presence of APP or the APP peptide.

8. A method for identifying a candidate agent that interacts with or binds to a beta-amyloid precursor protein (APP) binding site of Beta-site APP Cleaving Enzyme (BACE), the method comprising:
(a) utilizing the relative three-dimensional structural coordinates of a complex of a BACE peptide and an APP inhibitor peptide according to FIGS. 1A-1EEE, ±a root mean square deviation from the backbone atoms of the amino acid residues in the complex not more than 1.5 Å, to generate a three-dimensional representation of the complex, wherein the BACE peptide in the complex comprises the amino acid sequence of residues 58-447 of SEQ ID NO: 1, and the APP inhibitor peptide in the complex comprises the amino acid sequence SEVNStaVAEF (SEQ ID NO:3), wherein Sta is (S)-statine;
(b) identifying the amino acid residues forming the APP binding site of the BACE peptide from the three-dimensional representation in step (a), wherein the APP-binding site comprises the relative structural coordinates according to FIGS. 1A-1EEE of amino acid residues LYS70, SER71, GLY72, GLN73, GLY74, TYR75, LEU91, VAL92, ASP93, THR94, GLY95, SER96, SER97, ASN98, TYR129, VAL130, PRO131, TYR132, THR133, GLN134, GLY135, LYS136, TRP137, LYS168, PHE169, PHE170, ILE171, ASN172, SER174, TRP176, GLY178, ILE179, LEU180, GLY181, ALA183, TYR184, ALA185, GLU186, ILE187, ALA188, ARG189, PRO190, ASP191, ASP192, ARG256, TRP258, TYR259, TYR283, ASP284, LYS285, SER286, ILE287, VAL288, ASP289, SER290, GLY291, THR292, THR293, ASN294, LEU295, ARG296, GLY325, GLU326, ARG368, VAL370, LYS382, PHE383, ALA384, ILE385, SER386, GLN387, SER388, SER389, THR390, GLY391, THR392, VAL393, GLY395, ALA396, and ILE447, ±a root mean square deviation from the backbone atoms of said amino acid residues of not more than 1.5 Å ;

(c) generating a three-dimensional model of the APP binding site of BACE;
(d) employing said three-dimensional model from step (c) to identify said candidate agent;
(e) synthesizing said candidate agent; and
(f) contacting in vitro or in vivo said candidate agent with BACE to determine the ability of said candidate agent to interact or bind to BACE, whereby the detection of the ability of said candidate agent to interact or bind to BACE identifies said candidate agent.

9. The method of claim 8, wherein the ±root mean square deviation from the backbone atoms of said amino acid residues in the complex is not more than 1.0 Å.

10. The method of claim 8, wherein the root mean square deviation from the backbone atoms of said amino acid residues in the complex is not more than 0.5 Å.

11. The method of claim 8, wherein step (d) comprises determining the degree of association between the candidate agent and the three dimensional model of the APP-binding site of BACE.

12. The method of claim 8, wherein the contacting of the candidate agent with BACE comprises determining the effect the agent has on BACE aspartic protease activity.

13. The method of claim 12, wherein the candidate agent is a potential inhibitor of binding between BACE and APP or an APP peptide.

14. The method of claim 13, further comprising contacting the candidate agent with BACE in the presence of APP or an APP peptide.

15. A method for identifying a candidate agent that interacts with or binds to a beta-amyloid precursor protein (APP) binding site of Beta-site APP Cleaving Enzyme (BACE), the method comprising:
(a) forming a co-crystal of a BACE peptide in complex with an APP inhibitor peptide, wherein said co-crystal has space group I222, and unit cell parameters a=86.627 Å, b=130.861 Å, c=130.729 Å, and α=β=γ=90° and subjecting the co-crystal to X-ray diffraction and collecting data sufficient to determine the three-dimensional coordinates of said complex, wherein:
(i) the BACE peptide in the co-crystal comprises the amino acid sequence of residues 58-447 of SEQ ID NO: 1, and
(ii) the APP inhibitor peptide in the co-crystal comprises the amino acid sequence SEVNStaVAEF (SEQ ID NO:3), wherein Sta is (S)-statine;
(b) utilizing the relative three-dimensional structural coordinates of the complex of a BACE peptide and an APP inhibitor peptide according to FIGS. 1A-1EEE, ±a root mean square deviation from the backbone atoms of the amino acid residues in the complex not more than 1.5 Å, to generate a three-dimensional representation of the complex,
(c) identifying the amino acid residues forming the APP binding site of the BACE peptide from the three-dimensional representation in step (a), wherein the APP-binding site comprises the relative structural coordinates according to FIGS. 1A-1EEE of amino acid residues LYS70, SER71, GLY72, GLN73, GLY74, TYR75, LEU91, VAL92, ASP93, THR94, GLY95, SER96, SER97, ASN98, TYR129, VAL130, PRO131, TYR132, THR133, GLN134, GLY135, LYS136, TRP137, LYS168, PHE169, PHE170, ILE171, ASN172, SER174, TRP176, GLY178, ILE179, LEU180, GLY181, ALA183, TYR184, ALA185, GLU186, ILE187, ALA188, ARG189, PRO190, ASP191, ASP192, ARG256, TRP258, TYR259, TYR283, ASP284, LYS285, SER286, ILE287, VAL288, ASP289, SER290, GLY291, THR292, THR293, ASN294, LEU295, ARG296, GLY325, GLU326, ARG368, VAL370, LYS382, PHE383, ALA384, ILE385, SER386, GLN387, SER388, SER389, THR390, GLY391, THR392, VAL393, GLY395, ALA396, and ILE447, ±a root mean square deviation from the backbone atoms of said amino acid residues of not more than 1.5 Å;
(d) generating a three-dimensional model of the APP binding site of BACE;
(e) employing said three-dimensional model from step (d) to identify said candidate agent;
(f) obtaining said candidate agent; and
(g) contacting in vitro or in vivo said candidate agent with BACE to determine the ability of said candidate agent to interact or bind to BACE, whereby the detection of the ability of said candidate agent to interact or bind to BACE identifies said candidate agent.

16. A method for identifying a candidate agent that interacts with or binds to a beta-amyloid precursor protein (APP) binding site of Beta-site APP Cleaving Enzyme (BACE), the method comprising:
(a) utilizing the relative three-dimensional structural coordinates of a complex of a BACE peptide and an APP inhibitor peptide according to FIGS. 1A-1EEE, ±a root mean square deviation from the backbone atoms of the amino acid residues in the complex not more than 1.5 Å, to generate a three-dimensional representation of the complex, wherein the BACE peptide in the complex comprises the amino acid sequence of residues 58-447 of SEQ ID NO: 1, and the APP inhibitor peptide in the complex comprises the amino acid sequence SEVNStaVAEF (SEQ ID NO:3), wherein Sta is (S)-statine;
(b) identifying the amino acid residues forming the APP binding site of the BACE peptide from the three-dimensional representation in step (a), wherein the APP-binding site comprises the relative structural coordinates according to FIGS. 1A-1EEE of amino acid residues LYS70, SER71, GLY72, GLN73, GLY74, TYR75, LEU91, VAL92, ASP93, THR94, GLY95, SER96, SER97, ASN98, TYR129, VAL130, PRO131, TYR132, THR133, GLN134, GLY135, LYS136, TRP137, LYS168, PHE169, PHE170O, ILE171, ASN172, SER174, TRP176, GLY178, ILE179, LEU180, GLY181, ALA183, TYR184, ALA185, GLU186, ILE187, ALA188, ARG189, PRO190, ASP191, ASP192, ARG256, TRP258, TYR259, TYR283, ASP284, LYS285, SER286, ILE287, VAL288, ASP289, SER290, GLY291, THR292, THR293, ASN294, LEU295, ARG296, GLY325, GLU326, ARG368, VAL370, LYS382, PHE383, ALA384, ILE385, SER386, GLN387, SER388, SER389, THR390, GLY391, THR392, VAL393, GLY395, ALA396, and ILE447, ±a root mean square deviation from the backbone atoms of said amino acid residues of not more than 1.5 Å;
(c) generating a three-dimensional model of the APP binding site of BACE;
(d) employing said three-dimensional model from step (c) to identify said candidate agent;
(e) obtaining said candidate agent; and
(f) contacting said candidate agent with the APP-binding site of the BACE to determine the ability of said candidate agent to interact or bind to BACE, whereby the detection of the ability of said candidate agent to interact or bind to the APP-binding site of the BACE identifies said candidate agent.

\* \* \* \* \*